US008535912B2

(12) United States Patent
Sonoda

(10) Patent No.: US 8,535,912 B2
(45) Date of Patent: Sep. 17, 2013

(54) CHIMERIC FIBROBLAST GROWTH FACTORS WITH ALTERED RECEPTOR SPECIFICITY

(75) Inventor: Junichiro Sonoda, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 28 days.

(21) Appl. No.: 12/905,776

(22) Filed: Oct. 15, 2010

(65) Prior Publication Data

US 2011/0104152 A1 May 5, 2011

Related U.S. Application Data

(60) Provisional application No. 61/252,074, filed on Oct. 15, 2009.

(51) Int. Cl.
| *A61K 38/18* | (2006.01) |
| *C07K 14/50* | (2006.01) |
| *C07K 16/22* | (2006.01) |
| *C12N 5/10* | (2006.01) |
| *C12N 15/18* | (2006.01) |
| *C12N 15/63* | (2006.01) |

(52) U.S. Cl.
USPC ....... 435/69.7; 435/320.1; 435/325; 435/243; 514/9.1; 530/387.9; 530/388.1; 530/399

(58) Field of Classification Search
None
See application file for complete search history.

(56) References Cited

U.S. PATENT DOCUMENTS

| 3,773,919 A | 11/1973 | Boswell et al. |
| 4,179,337 A | 12/1979 | Davis et al. |
| 4,275,149 A | 6/1981 | Litman et al. |
| 4,301,144 A | 11/1981 | Iwashita et al. |
| 4,399,216 A | 8/1983 | Axel et al. |
| 4,485,045 A | 11/1984 | Regen |
| 4,496,689 A | 1/1985 | Mitra |
| 4,544,545 A | 10/1985 | Ryan et al. |
| 4,640,835 A | 2/1987 | Shimizu et al. |
| 4,657,760 A | 4/1987 | Kung et al. |
| 4,670,417 A | 6/1987 | Iwasaki et al. |
| 4,676,980 A | 6/1987 | Segal et al. |
| 4,791,192 A | 12/1988 | Nakagawa et al. |
| 4,816,567 A | 3/1989 | Cabilly et al. |
| 4,943,529 A | 7/1990 | Van den Berg et al. |
| 4,946,783 A | 8/1990 | Beckwith et al. |
| 5,010,182 A | 4/1991 | Brake et al. |
| 5,013,556 A | 5/1991 | Woodle et al. |
| 5,206,344 A | 4/1993 | Katre et al. |
| 5,225,212 A | 7/1993 | Martin et al. |
| 5,364,934 A | 11/1994 | Drayna et al. |
| 5,428,130 A | 6/1995 | Capon et al. |
| 5,545,806 A | 8/1996 | Lonberg et al. |
| 5,545,807 A | 8/1996 | Surnai et al. |
| 5,569,825 A | 10/1996 | Lonberg et al. |
| 5,625,126 A | 4/1997 | Lonberg et al. |
| 5,631,144 A | 5/1997 | Lemoine et al. |
| 5,633,425 A | 5/1997 | Lonberg et al. |
| 5,654,010 A | 8/1997 | Johnson et al. |
| 5,661,016 A | 8/1997 | Lonberg et al. |
| 7,576,190 B2 | 8/2009 | Glaesner et al. |
| 2007/0042395 A1* | 2/2007 | Botstein et al. .............. 435/6 |
| 2007/0248604 A1* | 10/2007 | Desnoyers et al. ........ 424/136.1 |
| 2009/0192087 A1 | 7/2009 | Glass et al. |
| 2010/0323954 A1 | 12/2010 | Li et al. |

FOREIGN PATENT DOCUMENTS

| CA | 2 019 559 C | 12/1990 |
| EP | 0 036 776 A2 | 9/1981 |
| EP | 0 036 776 A3 | 9/1981 |
| EP | 0 073 657 A1 | 3/1983 |
| EP | 0 117 058 A2 | 8/1984 |
| EP | 0 117 058 A3 | 8/1984 |
| EP | 0 117 058 B1 | 8/1984 |
| EP | 0 117 060 A2 | 8/1984 |
| EP | 0 117 060 A3 | 8/1984 |
| EP | 0 139 383 A1 | 5/1985 |
| EP | 0 183 070 A2 | 6/1986 |
| EP | 0 183 070 A3 | 6/1986 |
| EP | 0 183 070 B1 | 6/1986 |
| EP | 0 244 234 A2 | 11/1987 |
| EP | 0 308 936 B1 | 3/1989 |
| EP | 0 362 179 A2 | 4/1990 |
| EP | 0 394 538 A1 | 10/1990 |
| EP | 0 402 226 A1 | 12/1990 |
| EP | 0 404 097 A2 | 12/1990 |
| GB | 2 211 504 A | 7/1989 |
| WO | WO-87/05330 A1 | 9/1987 |
| WO | WO-89/05859 A1 | 6/1989 |
| WO | WO-90/10048 A1 | 9/1990 |

(Continued)

OTHER PUBLICATIONS

Anderson, W.F. et al. (May 8, 1992). "Human Gene Therapy," *Science* 256:808-813.

Aplin, J.D. et al. (May 1981). "Preparation, Properties, and Applications of Carbohydrate Conjugates of Proteins and Lipids," *CRC Crit. Rev. Biochem* pp. 259-306.

Ballance, D.J. et al. (Apr. 15, 1983). "Transformation of *Aspergillus nidulans* by the Orotidine-5'-Phosphate Decarboxylase Gene of *Neurospora crassa*," *Biochem. Biophys. Res. Commun.* 112(1):284-289.

Beach, D. et al. (Mar. 12, 1981). "High-Frequency Tranformation of the Fission Yeast *Schizosaccharomyces pombe*," *Nature* 290:140-142.

(Continued)

*Primary Examiner* — Christine J Saoud
(74) *Attorney, Agent, or Firm* — Morrison & Foerster LLP

(57) ABSTRACT

The present invention is directed to novel chimeric fibroblast growth factor (FGF) polypeptides, novel DNA encoding chimeric FGF polypeptides, and to the recombinant production of chimeric FGF polypeptides, and to methods, compositions and assays utilizing chimeric FGF polypeptides for the therapeutic treatment of metabolic-related disorders and other conditions, and for producing pharmaceutically active compositions including chimeric FGF polypeptides, the compositions having therapeutic and pharmacologic properties including those associated with the treatment of metabolic-related disorders and other conditions.

29 Claims, 28 Drawing Sheets

(56) References Cited

FOREIGN PATENT DOCUMENTS

| WO | WO-90/10448 A2 | 9/1990 |
|---|---|---|
| WO | WO-90/13641 A1 | 11/1990 |
| WO | WO-90/13646 A1 | 11/1990 |
| WO | WO-91/00357 A1 | 1/1991 |
| WO | WO-91/00360 A1 | 1/1991 |
| WO | WO-91/06629 A1 | 5/1991 |
| WO | WO-92/20373 A1 | 11/1992 |
| WO | WO-93/08829 A1 | 5/1993 |
| WO | WO-93/11161 A1 | 6/1993 |
| WO | WO-94/11026 A2 | 5/1994 |
| WO | WO-94/11026 A3 | 5/1994 |
| WO | WO-94/11026 C1 | 5/1994 |
| WO | WO-96/07399 A1 | 3/1996 |
| WO | WO-96/27011 A1 | 9/1996 |
| WO | WO-96/40072 A2 | 12/1996 |
| WO | WO-96/40072 A3 | 12/1996 |
| WO | WO-97/03692 A1 | 2/1997 |

OTHER PUBLICATIONS

Beauloye, V. et al.(Mar. 2002). "Impairment of Liver GH Receptor Signaling by Fasting," *Endocrinology* 143(3):792-800.

Boerner, et al. (Jul. 1, 1991). "Production of Antigen-Specific Human Monoclonal Antibodies From in Vitro-Primed Human Splenocytes," *J. Immunol.* 147(1):86-95.

Brennan, M. et al. (Jul. 5,1985). "Preparation of Bispecific Antibodies by Chemical Recombination of Monoclonal Immunoglobulin $G_1$ Fragments," *Science* 229(4708):81-83.

Caron, P.C. et al. (Oct. 1, 1992). "Engineered Humanized Dimeric Forms of IgG are More Effective Antibodies," *J. Exp. Med.* 176(4):1191-1195.

Case, M.E. et al. (Oct. 1979). "Efficient transformation of *Neurospora crassa* by Utilizing Hybrid Plasmid DNA," *Proc.Natl. Acad. Sci. USA* 76(10):5259-5263.

Carter, P. et al. (1985). "Improved Oligonudeotide Site-Directed Rautagenesis Using M13 Vectors," *Nucl. Acids Res.* 13:4431-4443.

Chang, A.C.et al. (Oct. 19, 1978). "Phenotypic Expression in *E. coli* of a DNA Sequence Coding for Mouse Dihydrofolate Reductase," *Nature* 275:617-624.

Chothia, C. (1976). "The Nature of the Accessible and Buried Surfaces in Proteins," *J. Mol. Biol.* 105(1):1-12.

Cunningham, B.C. et al. (Jun. 2, 1989). "High-Resolution Epitope Mapping of hGH-Receptor Interactions by Alanine-Scanning Mutagenesis," *Science* 244(4908):1081-1085.

David, G.S. et al. (Feb. 26, 1974). "Protein Iodination with Solid State Lactoperoxidase," *Biochemistry* 13(5):1014-1021.

De Boer, H.A. et al. (Jan. 1983). "The *tac* Promoter: A Functional Hybrid Derived From the *trp* and *lac* Promoters," *Proc. Natl. Acad. Sci. USA* 80(1):21-25.

De Louvencourt, L. et al. (May 1983). "Transformation of *Kluyveromyces lactis* by Killer Plasmid DNA," *J. Bacteriol.* 154(2):737-742.

Desnoyers, L.R. et al. (2008, e-pub. Jun. 25, 2007), "Targeting FGF19 Inhibits Tumor Growth in Colon Cancer Xenograft and FGF19 Transgenic Hepatocellular Carcinoma Models," *Oncogene* 27:85-97.

Dzau, V.J. et al. (1993). "Gene Therapy for Cardiovascular Disease," *Trends in Biotechnology* 11(5):205-210.

Edge, A.S. et al. (Nov. 15, 1981). "Deglycosylation of Gglycoproteins by Trifluoromethanesulfonic Acid," *Anal. Biochem.* 118(1)131-137.

Epstein, D.A. et al. (Jun. 1985). "Biological Activity of Liposome-Encapsulated Murine Interferon γ is Mediated by a Cell Membrane Receptor," *Proc. Natl. Acad. Sci. USA* 81(11):3688-3692.

Evan. G.I. et al. (Dec. 1985). "Isolation of Monoclonal Antibodies Specific for Human c-*myc* Proto-Oncogene Product," *Molecular and Cellular Biology* 5(12):3610-3616.

Field, J. et al. (May 1988). "Purification of a *RAS*-Responsive Adenylyl Cyclase Complex from *Saccharomyces cerevisiae* by Use of an Epitope Addition Method," *Mol. Cell. Biol.* 8(5):2159-2165.

Fishwild, D.M. et al. (Jul. 1996). "High-Avidity Human IgGK Monoclonal Antibodies From a Novel Strain of Minilocus Transgenic Mice," *Nature Biotechnology* 14(7):845-851.

Fleer, R. et al. (Oct. 1991). "Stable Multicopy Vectors for High-Level Secretion of Recombinant Human Serum Albumin by *Kluyveromyces* Yeasts," *Bio/Technology* 9(10):968-975.

Fu, L. et al. (Jun. 2004, e-pub. Feb. 19, 2004). "Fibroblast Growth Factor 19 Increases Metabolic Rate and Reverses Dietary and Leptin-Deficient Diabetes," *Endocrinology* 145(6):2594-2603.

Gething, M-J. et al. (Oct. 22, 1981). "Cell-Surface Expression of Influenza Haemagglutinin From a Cloned DNA Copy of the RNA Gene," *Nature* 293(5834):620-625.

Goeddel, D.V. (Oct. 18, 1979). "Direct Expression in *Escherichia coli* of a DNA Sequence Coding for Human Growth Hormone," *Nature* 281:544-548.

Goeddel, D.V. et al. (1980). "Synthesis of human fibroblast interferon by *E. coli*," *Nucleic Acis Res.* 8(18):4057-4074.

Graham, F.L. et al. (Apr. 1973). "A New Technique for the Assay of Infectivity of Human Adenovirus 5 DNA," *Virology* 52(2):456-467.

Graham, F.L. et al. (Jul. 1977). "Characteristics of a Human Cell Line Transformed by DNA From Human Adenovirus Type 5," *J. Gen. Virol.* 36(1):59-72.

Gruber, M. et al. (1994). "Efficient Tumor Cell Lysis Mediated by a Bispecific Single Chain Antibody Expressed in *Escherichia coli*," *J. Immunol.* 152:5368-5374.

Hess, B. et al. (1968). "Cooperation of Glycolytic Enzymes," *J. Adv. Enzyme Reg.* 7:149-167.

Hitzeman et al. (Dec. 25, 1980). "Isolation and characterization of the Yeast 3-Phosphoglycerokinase gene (PGK) by an immunological screening Technique," *J. Biol. Chem.* 255(24):12073-12080.

Holland, M.J. et al. (1978). "Isolation and Identification of Yeast Messenger Ribonucleic Acids Coding for Enolase, Glyceraldehyde-3-Phosphate Dehydrogenase, and Phosphoglycerate Kinase," *Biochemistry* 17(23):4900-4907.

Holliger, P. et al. (Jul. 15, 1993). "Diabodies: Small Bivalent and Bispecific Antibody Fragments," *Proc. Natl. Acad. Sci. USA* 90(14):6444-6448.

Hopp, T.P. et al. (Oct. 1992). "A Short Polypeptide Marker Sequence Useful for Recombinant Protein Identification and Purification," *BioTechnology* 6:1204-1210.

Hoogenboom, H.R. et al. (1991). "By-passing Immunisation. Human Antibodies From Synthetic Repertoires of Germline $V_H$ Gene Segments Rearranged in Vitro," *J. Mol. Biol.* 227:381-388.

Hora, M.S. et al. (Aug. 1990). "Controlled Release of Interleukin-2 From Biodegradable Microspheres," *Bio/Technology* 8:755-758.

Hsiao, C-L. et al. (Aug. 1979). "High-Frequency Transformation of Yeast by Plasmids Containing the Cloned Yeast *ARG4* Gene," *Proc. Natl. Acad. Sci. USA* 76(8):3829-3833.

Hunter, W.M. et al. (May 5, 1962). "Preparation of Iodine-131 Labelled Human Growth Hormone of High Specific Activity," *Nature* 194(4827):495-496.

Hwang, K.J. et al. (Jul. 1980). "Hepatic Uptake and Degradation of Unilamellar Sphingomyelin/Cholesterol Liposomes: a Kinetic Study," *Proc. Natl. Acad. Sci. USA* 77(7):4030-4034.

Inagaki, T. et al. (Jul. 2008). "Inhibition of Growth Hormone Signaling by the Fasting-Induced Hormone FGF21," *Cell Metabolism* 8(1):77-83.

Johnson. O.L. et al. (Jul. 1996). "A Month-Long Effect From a Single Injection of Microencapsulated Human Growth Hormone," *Nat. Med.* 2(7):795-799.

Jones, E.W (Jan. 1977). "Proteinase Mutants of *Saccharomyces cerevisiae*," *Genetics* 85(1)23-33.

Jones, P.T. et al. (May 29, 1986). "Replacing the Complementarity-Determining Regions in a Human Antibody with Those from a Mouse," *Nature* 321:522-525.

Kelley, J.M. et al. (Feb. 1985). "Tranformation of *Aspergillus niger* by the *amdS* Gene of *Aspergillus nidulans*," *EMBO J.* 4(2):475-479.

Keown, W.A. et al. (1990). "Methods for Introducing DNA Into Mammalian Cells," *Methods in Enzymology* 185:527-537.

Kharitonenkov, A. et al. (Jun. 2005). "FGF-21 as a Novel Metabolic Regulator," *J. Clin. Invest.* 115(6):1627-1635.

Kingman, A.J. et al. (1979). "Replication in *Saccharomyces cerevisiae* of Plasmid pBR313 Carrying DNA From the Yeast *trp1* Region," *Gene* 7:141-152.

Köhler, G. et al. (Aug. 7, 1975). "Continuous Cultures of Fused Cells Secreting Antibody of Predefined Specificity," *Nature* 256(5517):495-497.

Kostelny. S.A. et al. (Mar. 1, 1992). "Formation of a Bispecific Antibody by the Use of Leucine Zippers," *J. Immunol.* 148(5);1547-1533.

Kozbor, D. et al. (Dec. 1984). "A Human Hybrid Myeloma for Production of Human Monoclonal Antibodies," *J. Immunol.* 133(6):3001-3005.

Lonberg, N. et al. (Apr. 28, 1994). "Antigen-Specific Human Antibodies from Mice Comprising Four Distinct Genetic Modifications," *Nature* 368(6474):856-859.

Lonberg, N. et al. (1995). "Human Antibodies From Transgenic Mice," *Intern. Rev. Immunol.* 13(1):65-93.

Lutz-Freyermuth, C. et al. (Aug. 1990). "Quantitative Determination that One of two Potential RNA-Binding Domains of the a Protein Component of the U1 Small Nuclear Ribonucleoprotein Complex Binds With High Affinity to Stem-Loop II of U1 RNA," *Proc. Natl. Acad. Sci. USA* 87:6393-6397.

Mansour, S.L. et al. (Nov. 24, 1988). "Disruption of the Proto-Oncogene *int-2* in Mouse Embryo-Derived Stem Cells: a General Strategy for Targeting Mutations to Non-Selectable Genes," *Nature* 336(6197):348-352.

Mantei, N. et al. (Sep. 6, 1979). "Rabbit β-Globin mRNA Production in Mouse L Cells Transformed with Cloned Rabbit β-Globin Chromosomal DNA," *Nature* 281(5726):40-46.

Marasco. W.A. et al. (Aug. 1993). "Design, Intracellular Expression, and Activity of a Human Anti-Human Immunodeficiency Virus Type 1 gp120 Single-Chain Antibody," *Proc. Natl. Acad. Sci. USA* 90:7889-7893.

Marks, J.D. et al. (Dec. 5, 1991). "By-Passing Immunization. Human Antibodies From V-Gene Libraries Displayed on Phage," *J. Mol. Biol.* 222(3):581-597.

Marks, J.D. et al. (Jul. 1992). "By-Passing Immunization: Building High Affinity Human Antibodies by Chain Shuffling," *Bio/Technology* 10(7):779-783.

Martin, G.A. et al. (Jan. 10, 1992). "GAP Domains Responsible for Ras p21-Dependent Inhibition of Muscarinic Atrial $K^+$ Channel Currents," *Science* 255(5041):192-194.

Martin, F.J. et al. (Jan. 10, 1982). "Irreversible Coupling of Immunoglobulin Fragments to Preformed Vesicles. An improved Method for Liposome Targeting," *J. Biol. Chem.* 257(1):286-288.

Mather, J.P. (Aug. 1980). "Establishment and Characterization of two Distinct Mouse Testicular Epithelial Cell Lines," *Biol. Reprod.* 23(1):243-252.

Merrifield, R.B. (Jul. 20, 1963). "Solid Phase Peptide Synthesis. I. The Synthesis of a Tetrapeptide," J. Am. Chem. Soc. 85(14):2149-2154.

Milstein, C. et al. (Oct. 6, 1983). "Hybrid Hybridomas and Their Use in Immunohistochemistry," *Nature* 305(5934):537-540.

Morrison, S.L. (Apr. 28, 1994). "Immunology. Success in Specification," *Nature* 368(6474):812-813.

Munson, P.J. et al. (Sep. 1, 1980). "Ligand: A Versatile Computerized Approach for Characterization of Ligand-Binding Systems," *Anal. Biochem.* 107(1):220-239.

Neuberger, M. (Jul. 1996). "Generating High-Avidity Human Mabs in Mice," *Nature Biotechnology* 14(7):826.

Nicholes, K. et al. (Jun. 2002). "A Mouse Model of Hepatocellular Carcinoma: Ectopic Expression of Fibroblast Growth Factor 19 in Skeletal Muscle of Transgenic Mice," *Am J Pathol* 160(6):2295-2307.

Nygren, H. (May 1982). "Conjugation of Horseradish Peroxidase to Fab Fragments With Different Homobifunctional and Heterobifunctional Cross-Linking Reagents. A Comparative Study," *J. Histochem. and Cytochem.* 30(5):407-412.

Paborsky, L.R. et al. (May 6, 1990). "Mammalian Cell Transient Expression of Tissue Factor for the Production of Antigen," *Protein Engineering* 3(6):547-553.

Pain, D. et al. (1981). "Preparation of Protein A-Peroxidase Monoconjugate Using a Heterobifunctional Reagent, and its Use in Enzyme Immunoassays," *J. Immunol. Meth.* 40(2):219-230.

Presta, L.G. (1992). "Antibody Engineering," *Curr. Op. Struct. Biol.* 2:593-596.

Riechmann, L et al. (Mar. 24, 1988). "Reshaping Human Antibodies for Therapy," *Nature* 332(6162):323-327.

Shalaby, M.R. et al. (Jan. 1, 1992). "Development of Humanized Bispecific Antibodies Reactive with Cytotoxic Lymphocytes and Tumor Cells Overexpressing the *HER2* Protooncogene," *J. Exp. Med.* 175(1):217-225.

Shaw, C.H. et al. (1983). "A General Method for the Transfer of Cloned Genes to Plant Cells," *Gene* 23(3):315-330.

Shopes, B. (May 1, 1992). "A Genetically Engineered Human IgG Mutant with Enhanced Cytolytic Activity," J. Immunol. 148(9):2918-2922.

Skinner, R.H. et al. (Aug. 5, 1991). "Use of the Glu-Glu-Phe C-Terminal Epitope for Rapid Purification of the Catalytic Domain of Normal and Mutant *ras* GTPase-Activating Proteins," *J. Biol. Chem.* 266(22):14163-14166.

Sojar, H.T. et al. (Nov. 15, 1987). "A Chemical Method for the Deglycosylation of Proteins," *Arch. Biochem. Biophys.* 259(1):52-57.

Sreekrishna, K. et al. (1988). "High Level Expression of Heterologous Proteins in Methylotrophic Yeast *Pichia pastoris*," *J. Basic Microbiol.* 28(4):265-278.

Stedman, C. et al. (Mar. 2004, Dec. 17, 2003). "Feed-Forward Regulation of Bile Acid Detoxification by CYP3A4: Studies in Humanized Transgenic Mice," *J. Biol. Chem.* 279(12):11336-11343.

Stein, C.A. et al. (May 15, 1988). "Oligodeoxynucleotides as Inhibitors of Gene Expression: A Review," *Cancer Res.* 48:2659-2688.

Stevenson, G.T. et al. (Mar. 1989). "A Chimeric Antibody With Dual Fc Regions (*bis*FabFc) Prepared by Manipulations at the IgG Hinge," *Anti-Cancer Drug Design* 3(4):219-230.

Stinchcomb, D.T. et al. (Nov. 1, 1979). "Isolation and Characterisation of a Yeast Chromosomal Replicator," *Nature* 282(5734):39-43.

Suresh, M.R. et al. (1986). "Bispecific Monoclonal Antibodies From Hybrid Hybridomas," Chapter 17 in *Methods of Enzymology*, Academic Press, Inc., 121:210-228.

Thissen, J.P. et al. (Feb. 1994). "Nutritional Regulation of the Insulin-Like Growth Factors," *Endocr. Rev.* 15(1):80-101.

Thomas, P.S. (Sep. 1980). Hybridization of Denatured RNA and Small DNA Fragments Transferred to Nitrocellulose, *Proc. Natl. Acad. Sci. USA* 77(9):5201-5205.

Thotakura, n. R. et al. (1987). "Enzymatic Deglycosylation of Glycoproteins," *Meth. Enzymol.* 138:350-359.

Tilburn, J. et al. (Dec. 1983). "Transformation by Integration in *Aspergillus nidulans*," *Gene* 26(2-3):205-221.

Tomlinson, E. et al. (May 2002). "Transgenic Mice Expressing Human Fibroblast Growth Factor-19 Display Increased Metabolic Rate and Decreased Adiposity," *Endocrinology* 143(5):1741-1747.

Traunecker, a. et al. (Dec. 1991). "Bispecific Single Chain Molecules (Janusins) Target Cytotoxic Lymphocytes on HIV Infected Cells," *EMBO J.* 10(12):3655-3659.

Tschemper, G. et al. (1980). "Sequence of a Yeast DNA Fragment Containing a Chromosomal Recplicator and the *TRP1* Gene," *Gene* 10:157-166.

Tutt, A. et al. (Jul. 1, 1991). "Trispecific F(ab')3 Derivatives that Use Cooperative Signaling via the TCR/CD3 Complex and CD2 to Activate and Redirect Resting Cytotoxic T cells," *J. Immunol.* 147(1):60-69.

Urlaub, G. et al. (Jul. 1980). "Isolation of Chinese Hamster Cell Mutants Deficient in Dihydrofolate Reductase Activity," *Proc. Natl. Acad. Sci. USA*. 77(7):4216-4220.

Van Den Berg, J.A. et al. (Feb. 1990). "*Kluyveromyces* as a Host for Heterologous Gene Expression: Expression and Secretion of Prochymosin," *Bio/Technology* 8(2):135-139.

Van Der Krol, A.R. et al. (Nov./Dec. 1988). "Modulation of Eukaryotic Gene Expression by Complementary RNA or DNA Sequences," *Bio/Techniques* 6(10):958-976.

Van Solingen, P. et al. (May 1977). "Fusion of Yeast Spheroplasts," *J. Bact.* 130(2):946-947.

Verhoeyen, M. et al. (Mar. 25, 1988). "Reshaping Human Antibodies: Grafting an Antilysozyme Activity," *Science* 239(4847):1534-1536.

Vitetta, E.S. et al. (Nov. 20, 1987). "Redesigning Nature's Poisons to Create Anti-Tumor Reagents," *Science* 238(4830):1098-1104.

Wagner, E. et al. (May 1990). "Transferrin-Polycation Conjugates as Carriers for DNA Uptake into Cells," *Proc. Natl. Acad. Sci. USA* 87(9):3410-3414.

Wells, J.A. et al. (1985). "Cassette Mutagenesis: an Efficient Method for Generation of Multiple Mutations at Defined Sites," *Gene* 34(2-3):315-323.

Wells, J.A. et al. (1986). "Importance of Hydogen-Bond Formation in Stablilizing the Transition State of Subtilisin," *Philos. Trans. R. Soc. London Ser A* 317:415-428.

Weinstein, M. et al. (Sep. 1998, e-pub. Aug. 25, 1998). "FGFR-3 and FGFR-4 Function Cooperatively to Direct Alveogenesis in the Murine Lung," *Development* 125(18):3615-3623.

Wolff, E.A. et al. (Jun. 1, 1993). "Monoclonal Antibody Homodimers: Enhanced Antitumor Activity in Nude Mice," *Cancer Research* 53(11):2560-2565.

Wu, G.Y. et al. (Apr. 5, 1987). "Receptor-Mediated in vitro Gene Transformation by a Soluble DNA Carrier System," *J. Biol. Chem.* 262(10):4429-4432.

Wu, X. et al. (Nov. 28, 2008, e-pub. Oct. 1, 2008). "C-Terminal Tail of FGF19 Determines Its Specificity Toward Klotho Co-Receptors," *Journal of Biological Chemistry* 283(48):33304-33309.

Yasuda, K. (1993). "Long-Acting Pharaceutical Interferon," *Biomed. Ther.* 27(10):1221-1223, Translation of the Abstract Only.

Yelton, M.M. et al. (Mar. 1984). "Transformation of *Aspergillus nidulans* by using a *trpC* plasmid," *Proc. Natl. Acad. Sci. USA* 81(5):1470-1474.

Yie, J. et al. (2009, e-pub. Dec. 4, 2008). "FGF21 N- and C-Termini Play Different Roles in Receptor Interaction and Activation," *FEBS Letters* 583:19-24.

Zamecnik, P.C. et al. (Jun. 1986). "Inhibition of Replication and Expression of Human T-cell Lymphotropic Virus Type III in Cultured cells by Exogenous Synthetic Oligonucleotides Complementary to Viral RNA," *Proc. Natl. Acad. Sci. USA* 83(12):4143-4146.

Zoller, M.J. et al. (Oct. 25, 1982). "Oligonucleotide-Directed Mutagenesis Using M13-Derived Vectors: an Efficient and General Procedure for the Production of Point Mutations in any Fragment of DNA." *Nuci. Acids Res.* 10(20):6487-6500.

Kurosu et al., "Tissue-specific expression of betaKlotho and fibroblast growth factor (FGF) receptor isoforms determines metabolic activity of FGF19 and FGF21." J Biol Chem. 282(37):26687-95 (Sep. 2007).

* cited by examiner

FIG. 1

SEQ ID NO: 1   - hFGF19 (194 aa)

```
  1    RPLAF SDAGP HVHYG WGDPI RLRHL YTSGP HGLSS CFLRI RADGV VDCAR
 51    GQSAH SLLEI KAVAL RTVAI KGVHS VRYLC MGADG KMQGL LQYSE EDCAF
101    EEEIR PDGYN VYRSE KHRLP VSLSS AKQRQ LYKNR GFLPL SHFLP MLPMV
151    PEEPE DLRGH LESDM FSSPL ETDSM DPFGL VTGLE AVRSP SFEK
```

SEQ ID NO: 3 - Pre-hFGF19 (216 aa)

```
  1    MRSGC VVVHV WILAG LWLAV AG
 23    RPLAF SDAGP HVHYG WGDPI RLRHL YTSGP HGLSS CFLRI RADGV VDCAR
 74    GQSAH SLLEI KAVAL RTVAI KGVHS VRYLC MGADG KMQGL LQYSE EDCAF
123    EEEIR PDGYN VYRSE KHRLP VSLSS AKQRQ LYKNR GFLPL SHFLP MLPMV
174    PEEPE DLRGH LESDM FSSPL ETDSM DPFGL VTGLE AVRSP SFEK
```

FIG. 2

SEQ ID NO: 2  - hFGF21 (181 aa)

```
  1 HPIPD SSPLL QFGGQ VRQRY LYTDD AQQTE AHLEI REDGT VGGAA DQSPE
 51 SLLQL KALKP GVIQI LGVKT SRFLC QRPDG ALYGS LHFDP EACSF RELLL
101 EDGYN VYQSE AHGLP LHLPG NKSPH RDPAP RGPAR FLPLP GLPPA LPEPP
151 GILAP QPPDV GSSDP LSMVG PSQGR SPSYA S
```

SEQ ID NO: 4 - Pre-hFGF21 (209 aa)

```
  1 MDSDE TGFEH SGLWV SVLAG LLLGA CQA
 29 HPIPD SSPLL QFGGQ VRQRY LYTDD AQQTE AHLEI REDGT VGGAA DQSPE
 79 SLLQL KALKP GVIQI LGVKT SRFLC QRPDG ALYGS LHFDP EACSF RELLL
129 EDGYN VYQSE AHGLP LHLPG NKSPH RDPAP RGPAR FLPLP GLPPA LPEPP
179 GILAP QPPDV GSSDP LSMVG PSQGR SPSYA S
```

|   | | 293 | R1c | R4 |
|---|---|---|---|---|
| A | hFGF21-f | + | + | − |
| B | | + | + | − |
| C | | + | + | − |
| D | | + | + | +/− |
| E | | + | + | +/− |
| F | | + | + | + |
| G | | + | + | + |
| H | | + | + | + |
| I | | +/− | | |
| J | | − | | |
| K | | + | + | + |
| L | hFGF19-f | + | + | + |

FIG. 11

|   |         |                                                      | 293/KLB | L6/R4+KLB |
|---|---------|------------------------------------------------------|---------|-----------|
| A | hFGF21: | HPIPDSSPLLQFGGQVRQRYLYTDDAQ QTEAHLEIREDG..            | +       | —         |
| B | hFGF19: | RPLAFSDAGPHVHYGWGDPIRLRHLYTSGPHGLSSCFLRIRADG..        | +       | +         |
| C |         | HPIPDSSPHVHYGWGDPIRLRHLYTSGPHGLSSCFLRIRADG..          | +       | +         |
| D |         | HPIPDSSPLLQFGGQVRQRYLYTSGPHGLSSCFLRIRADG..            | +       | +/-       |
| E |         | HPIPDSSPLLQFGGQVRQRYLYTDDPHGLSSCFLRIRADG..            | +       | +/-       |
| F |         | HPIPDSSPLLQFGGQVRQRYLYTDDAQ LSSCFLRIRADG..            | +       | —         |
| G |         | HPIPDSSPLLQFGGQVRQRYLYTDDAQ QTSCFLRIRADG..            | +       | —         |
| H |         | HPIPDSSPLLQFGGQVRQRYLYTDDAQ QTEAFLRIRADG..            | —       | NT        |

*FIG. 13*

|   |   | 293/KLB | L6/KLB+ R1c | R4 |
|---|---|---|---|---|
| hFGF21: | HPIPDSSPLLQFGGQVRQRYLYTDDAQ_QTEAHLEIREDG... | + | + | − |
| hFGF19: | RPLAFSDAGPHVHYGWDPIRLRHLYTSGPHGLSSCFLRIRADG... | + | + | + |
| A | HPIPDSSPLLQFGGQVRQRYLYTSGPHGLSSCFLRIRADG... | + | + | +/− |
| B | HPIPDSSPLLQFGGQVRQRYLYTDDPHGLSSCFLRIRADG... | + | + | +/− |
| C | HPIPDSSPLLQFGGQVRQRYLYTDDAQ_LSSCFLRIRADG... | + | + | − |
| D | HPIPDSSPLLQFGGQVRQRYLYTDDAQ_QTSCFLRIRADG... | + | + | − |
| E | HPIPDSSPLLQFGGQVRQRYLYTDDAQ_QTEAFLRIRADG... | − | NT | NT |
| F | RPLAFSDAGPLLQFGGQVRQRYLYTSGPHGLSSCFLRIRADG... | + | + | +/− |
| G | RPLAFSDAGPLLQFGGQVRQRYLYTDDPHGLSSCFLRIRADG... | +/− | NT | NT |
| H | RPLAFSDAGPLLQFGGQVRQRYLYTDDAQGLSSCFLRIRADG... | − | NT | NT |
| I | RPLAFSDAGPLLQFGGQVRQRYLYTDDAQ_LSSCFLRIRADG... | − | NT | NT |
| J | RPLAFSDAGPLLQFGGQVRQRYLYTDDAQ_QTSCFLRIRADG... | − | NT | NT |
| K | RPLAFSDAGPLLQFGGQVRQRYLYTDDAQ_QTEAFLRIRADG... | − | NT | NT |
| L | RPLAFSDAGPLLQFGGQVRQRYLYTDDAQ_QTEAHLEIREDG... | + | + | − |

FIG. 14

FIG. 18
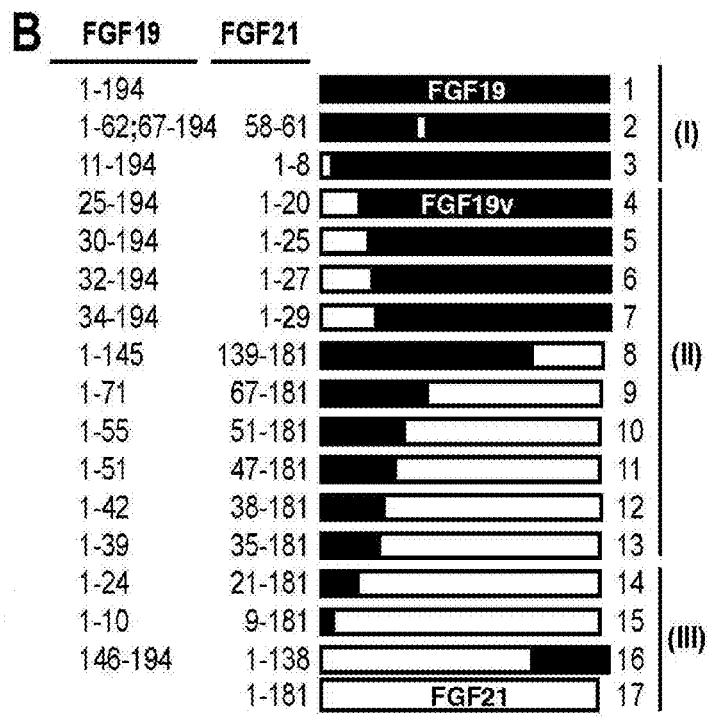
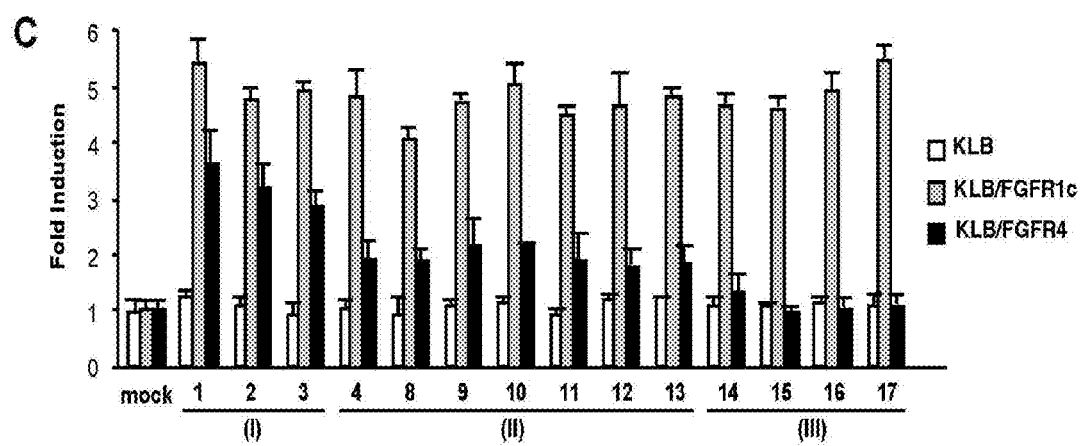

*FIG. 18*
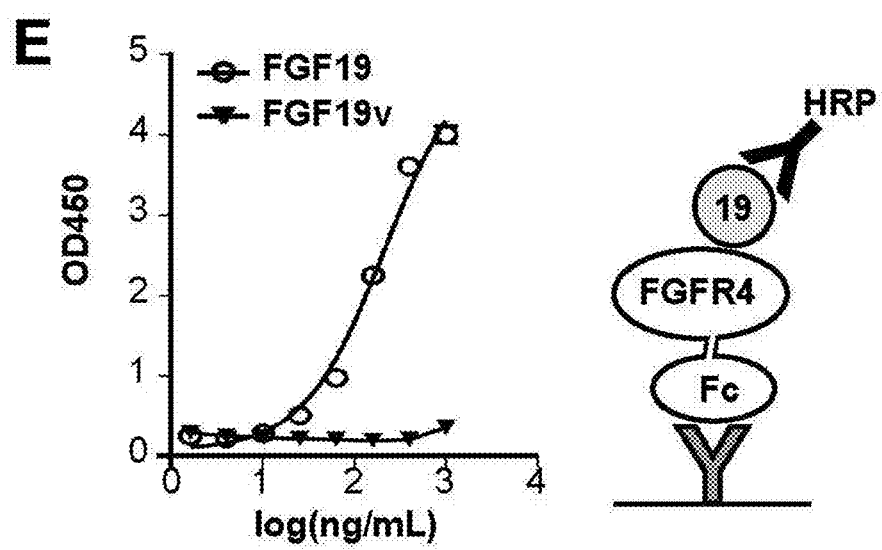
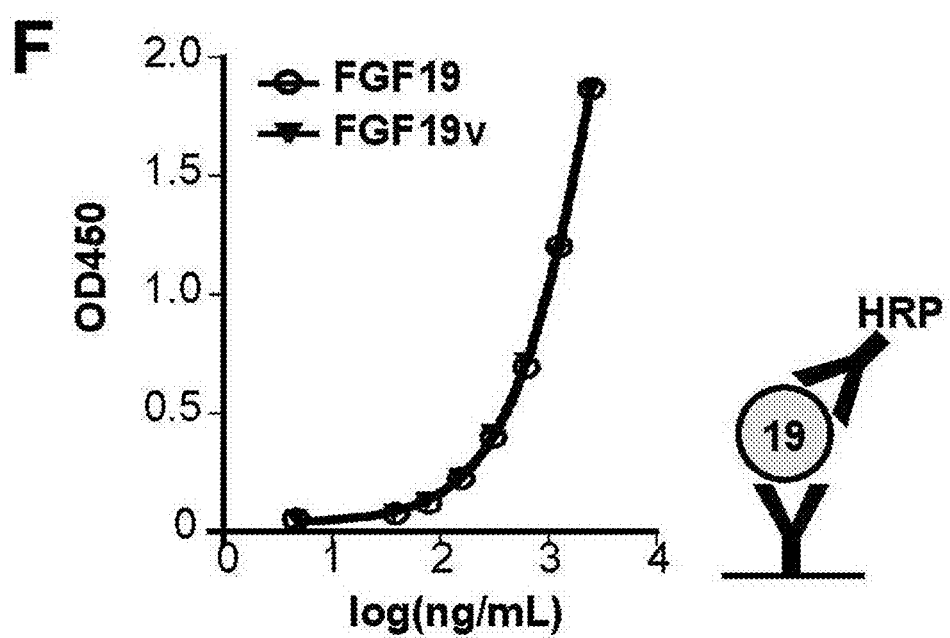

FIG. 21
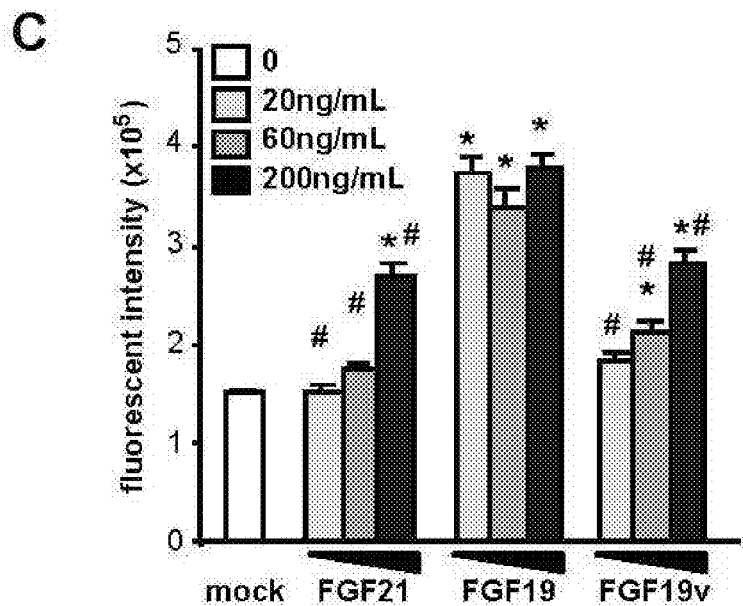
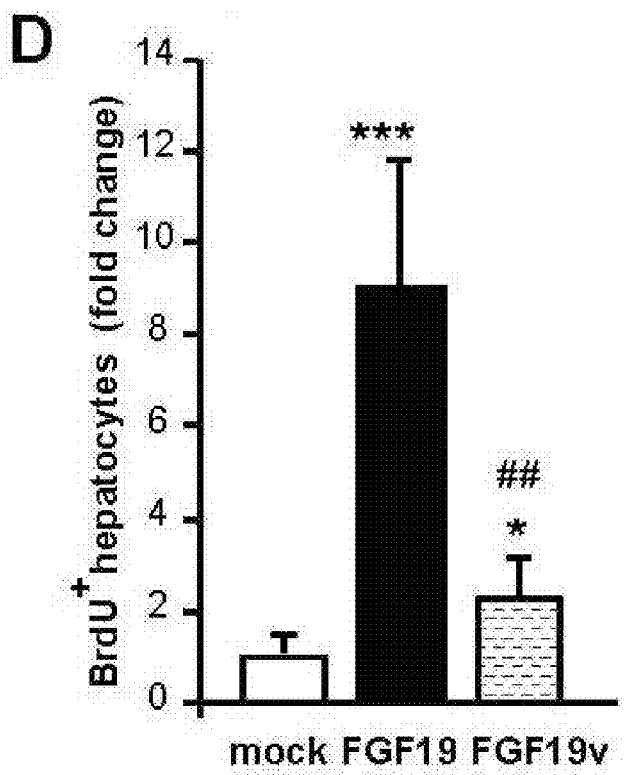

FIG. 22
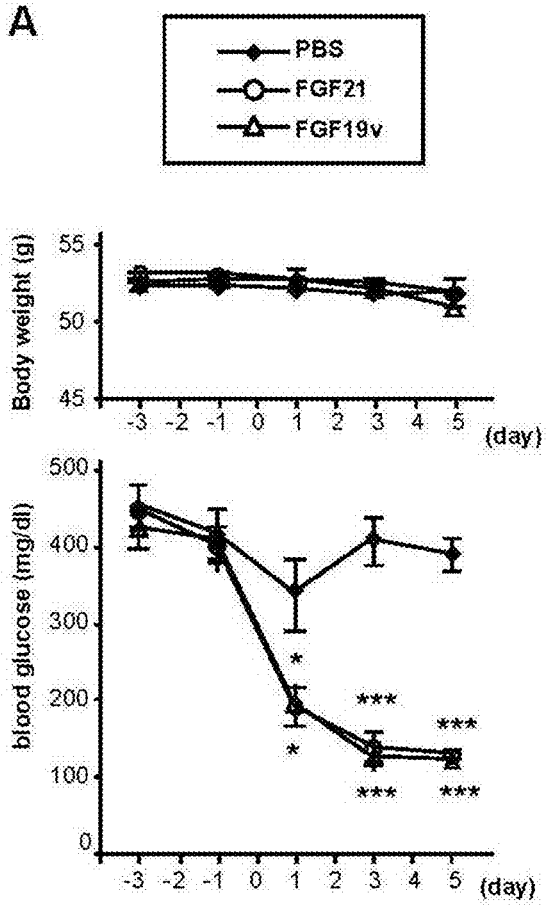
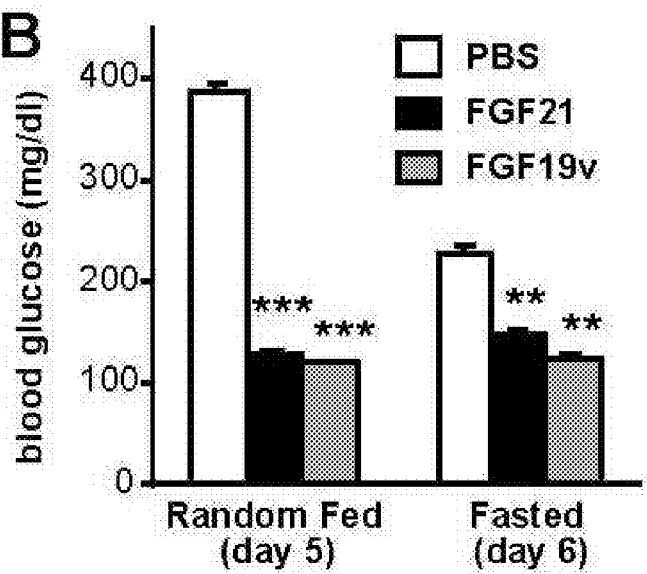

*FIG. 22*
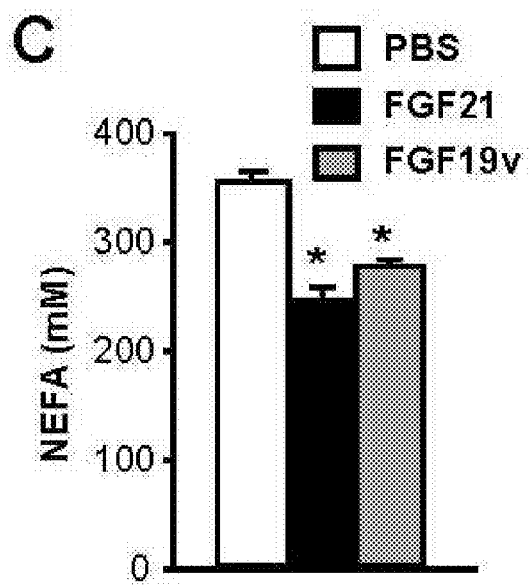
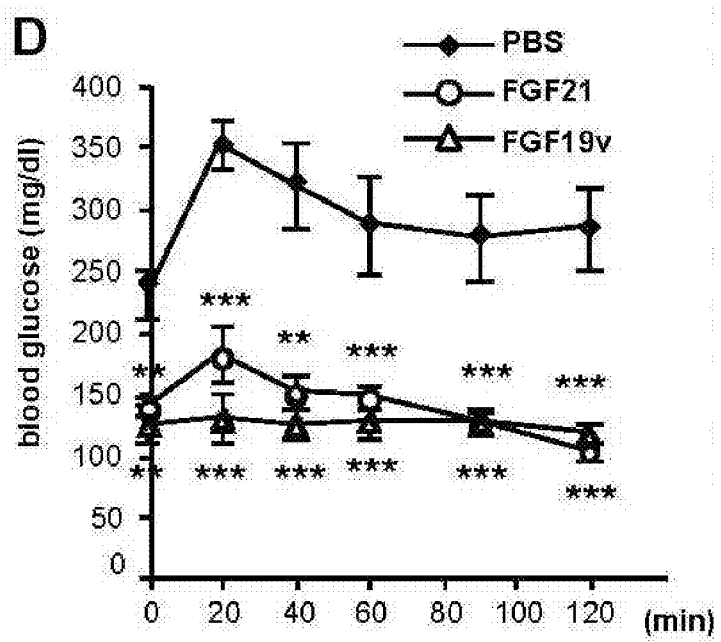

CHIMERIC FIBROBLAST GROWTH FACTORS WITH ALTERED RECEPTOR SPECIFICITY

CROSS-REFERENCE TO RELATED APPLICATIONS

This application claims priority benefit to U.S. Provisional Application Ser. No. 61/252,074, filed Oct. 15, 2009, the entirety of which is hereby incorporated by reference.

FIELD OF THE INVENTION

The present invention relates generally to novel polypeptides designated herein as chimeric fibroblast growth factor (FGF) polypeptides, novel DNA encoding chimeric FGF polypeptides, and to the recombinant production of chimeric FGF polypeptides, and to methods, compositions and assays utilizing chimeric FGF polypeptides for the therapeutic treatment of metabolic-related disorders and other conditions, and for producing pharmaceutically active compositions including chimeric FGF polypeptides, the compositions having therapeutic and pharmacologic properties including those associated with the treatment of metabolic-related disorders and other conditions.

BACKGROUND OF THE INVENTION

The family of fibroblast growth factors (FGF) includes the FGF19 subfamily, which consists of human FGF21, FGF23 and FGF19 and mouse FGF15. Unlike other members of the FGF family, which typically act on their tissue of origin in a paracrine manner, members of the FGF19 subfamily act on specific distal tissues in an endocrine manner. The effects of FGF family members are the result of their heparin-dependent binding to one or more members of the FGF receptor tyrosine kinase (FGFR) family. This family of receptors includes four members each having a tyrosine kinase domain, FGFR1, FGFR2, FGFR3 and FGFR4, as well as two splice variants each of FGFR1, FGFR2 and FGFR3. These splice variants, which occur in exon 3 of FGFR1, FGFR2 and FGFR3, are designated as "b" and "c" variants (i.e., FGFR1b, FGFR2b, FGFR3c, FGFR1c, FGFR2c and FGFR3c, which are also known as FGFR1(III)b, FGFR2(III)b, FGFR3(III)c, FGFR1(III)c, FGFR2(III)c and FGFR3(III)c, respectively).

Members of the FGF19 subfamily have been implicated in regulating a variety of tissue-specific metabolic processes in mammals. Of particular interest is FGF19, which has been shown to target and have effects on both adipocytes and hepatocytes. For example, mice treated with recombinant human FGF19 (rhFGF19), despite being on a high-fat diet, show increased metabolic rates, increased lipid oxidation, a lower respiratory quotient and weight loss. Moreover, such mice showed lower serum levels of leptin, insulin, cholesterol and triglycerides, and normal levels of blood glucose despite the high-fat diet and without appetite diminishment. Obese mice that lacked leptin but included a FGF19 transgene showed weight loss, lowered cholesterol and triglycerides, and did not develop diabetes. Obese, diabetic mice that lack leptin, when injected with rhFGF19, showed reversal of their metabolic characteristics in the form of weight loss and lowered blood glucose. (Fu, L. et al., *Endocrinology* 145(6), 2594-2603 (2004); Tomlinson, E. et al., *Endocrinology* 143 (5), 1741-1747 (2002)).

Another member of the FGF19 subfamily, FGF21, is expressed primarily by the liver and has metabolic effects similar to that of FGF19, such as increased metabolism via its effects on adipose tissue, weight loss, lowered blood glucose levels, and resistance to obesity and diabetes. (Kharitonenkov, A. et al., *J Clin Invest* 115(6), 1627-1635 (2005)). FGF21-transgenic mice were also resistant to diet-induced obesity. Moreover, in diabetic rodent models, FGF21 administration lowered blood glucose and triglyceride levels.

FGF21 has been also shown to have a role in regulating the growth hormone (GH) pathway. The anabolic effects of GH are mediated by insulin-like growth factor 1 (IGF-1), which is primarily produced by the liver. GH induces IGF-1 transcription, thereby increasing its circulating levels, via activation of the Janus kinase 2 (JAK2) by the GH receptor. Activated JAK2 phosphorylates members of the signal transducers and activators of transcription (STAT) family which, when phosphorylated, undergo nuclear translocation and bind to regulatory elements of target genes, including those of IGF-1. In particular, STAT5, in its phosphorylated form, has been shown to have a prominent role in this response.

The effects of GH on IGF-1 levels appear to be countered by starvation or fasting—conditions that result in lower levels of IGF-1 transcription and circulating IGF-1. (Thissen, J. P. et al., *Endocr. Rev.* 15, 80-101 (1994)). These effects on IGF-1 may be due to reduced levels of phosphorylated STAT5. In particular, fasted rats injected with GH have lower levels of hepatic phosphorylated STAT5 than non-fasted rats. (Beauloye, V. et al., *Endocrinology* 143, 792-800 (2002)). FGF21, which is induced in the liver under starvation or fasting conditions, may mediate this effect. FGF21-transgenic mice have been shown to have lowered levels of IGF-1 and phosphorylated STAT5. (Inagaki, T. et al., *Cell Metabolism* 8, 77-83 (2008)).

The metabolic effects of FGF19 and FGF21 are effected via their binding to the FGFR1c, FGFR2c and FGFR3c receptors, of which the binding to FGFR1c and FGFR2c are the most significant. Furthermore, binding of FGF19 and FGF21 to these receptors require the co-receptor Klotho-beta. Despite the prevalence of these FGFR receptors, the metabolic effects of FGF19 and FGF21 are made adipocyte-specific due to this requirement for the Klotho-beta co-receptor, which has tissue-specific localization.

FGF19 has also been shown to have effects that are distinct from FGF21. For example, FGF19 has been shown to regulate bile production by the liver via its liver-specific effects. In response to postprandial bile-production, FGF19 negatively regulates bile production by repressing transcription of the cholesterol 7-alpha-hydroxylase gene (CYP7A1), a rate limiting enzyme in the synthesis of bile acids, and by stimulating the filling of the gall bladder. In addition, FGF19 appears to have liver mitogenic effects that are not observed with respect to FGF21. For example, FGF19 transgenic mice develop hepatic adenocarcinoma due to increased proliferation and dysplasia of hepatocytes, and rhFGF19-treated mice exhibit hepatocyte proliferation of hepatocytes. (Nicholes, K. et al., *Am J Pathol* 160, 2295-2307 (2000).)

These additional activities of FGF19 appear to be mediated via its binding to FGFR4. FGF19 can bind FGFR4 in both a Klotho-beta-dependent and -independent manner. Although FGF21 has also been shown to bind FGFR4 in a Klotho-beta-dependent manner, no efficient signaling results from the binding of FGF21 to FGFR4.

There is a need to develop new therapies for the treatment of metabolic-related disorders such as diabetes, obesity, high blood sugar, and other related disorders. There is also a need to develop new therapies for such metabolic-related disorders in which the undesired growth or proliferation potential (e.g., tumorigenic potential) of such a therapy is eliminated or reduced. There is also a need to develop new therapies for such metabolic-related disorders in which the potential for growth hormone resistance of such a therapy is eliminated or reduced.

BRIEF SUMMARY OF THE INVENTION

In a first aspect, the present invention provides a chimeric human fibroblast growth factor 19 (hFGF19) polypeptide. In some embodiments of the present invention, the sequence of the chimeric polypeptide includes a C-terminal portion that includes a C-terminal portion of the hFGF19 polypeptide sequence, and an N-terminal portion that includes an N-terminal portion of the hFGF21 polypeptide sequence. In certain embodiments, the C-terminal portion of the hFGF19 polypeptide sequence is from about 45 to about 185 residues in length and the N-terminal portion of the hFGF21 polypeptide sequence is from about 7 to about 140 residues in length.

In another embodiment of the present invention, a chimeric hFGF19 polypeptide is provided in which the sequence of the polypeptide includes a C-terminal portion that includes a C-terminal portion of the hFGF21 polypeptide sequence, and an N-terminal portion that includes an N-terminal portion of the hFGF19 polypeptide sequence. In some embodiments, the C-terminal portion of the hFGF21 polypeptide sequence is from about 8 to about 145 residues in length, and the N-terminal portion of the hFGF19 polypeptide sequence is from about 45 to about 175 residues in length.

In another embodiment of the present invention, a chimeric hFGF19 polypeptide is provided in which the sequence of the chimeric polypeptide includes a first polypeptide sequence having at least a certain sequence identity to the sequence of hFGF19 polypeptide, and wherein a portion of the first polypeptide sequence is substituted with a portion of a second polypeptide sequence, the second polypeptide sequence having at least a certain sequence identity to the sequence of hFGF21 polypeptide, such that the substituted portion of the first polypeptide sequence is from about 3 to about 185 residues in length.

In some embodiments of the present invention, a chimeric hFGF19 polypeptide is provided in which the sequence of the chimeric polypeptide includes a first polypeptide sequence having at least a certain sequence identity to the sequence of hFGF19 polypeptide, and wherein a portion of the first polypeptide sequence is substituted with more than one portion of a second polypeptide sequence, the second polypeptide sequence having at least a certain sequence identity to the sequence of hFGF21 polypeptide. In some embodiments, the chimeric hFGF19 polypeptide comprises a substitution of the β1-β2 loop of the first polypeptide, a substitution of the β10-β12 segment of the first polypeptide, and/or a substitution of the five residues WGDPI (SEQ ID NO:287) of the first polypeptide with the β1-β2 loop of the second polypeptide, the β10-β12 segment of the second polypeptide, and/or the corresponding sequence GQV of the second polypeptide.

In certain embodiments of the present invention, the chimeric hFGF19 polypeptide comprises the sequence (SEQ ID NO: 5)
HPIPDSSPLLQFGGQVRQRYLYTSGPHGLSSCFLRIRADGVVDCARGQ

SAHSLLEIKAVALRTVAIKGVHSVRYLCMGADGKMQGLLQYSEEDCAF

EEEIRPDGYNVYRSEKHRLPVSLSSAKQRQLYKNRGFLPLSHFLPMLP

MVPEEPEDLRGHLESDMFSSPLETDSMDPFGLVTGLEAVRSPSFEK.

In certain embodiments, the chimeric hFGF19 polypeptide of the present invention is fused to a second polypeptide, the second polypeptide is the Fc portion of an immunoglobulin, an analog of the Fc portion of an immunoglobulin and one or more fragments of the Fc portion of an immunoglobulin. In certain embodiments, the immunoglobulin is selected from the group consisting of: IgG-1, IgG-2, IgG-3, IgG-4, IgA-1, IgA-2, IgE, IgD and IgM. In some embodiments, the Fc portion is human or humanized. In some embodiments, the C-terminus of the chimeric hFGF19 polypeptide is fused to the N-terminus of the second polypeptide. In some embodiments, the C-terminus of the chimeric hFGF19 polypeptide is fused to the N-terminus of the second polypeptide via a linker, the linker is selected from the group consisting of: a [Gly]$_n$ linker, a [Gly$_3$Ser]m linker and a [Gly$_4$Ser]m linker, wherein n is an integer from 1-30 and m is an integer from 1-6.

The present invention includes chimeric hFGF19 polypeptides that have a physiological half-life that is at least or about the same as native hFGF19. The present invention includes chimeric hFGF19 polypeptides that have a physiological half-life that is at least or about the same as native hFGF21.

In certain embodiments, the chimeric hFGF19 polypeptide does not substantially activate FGFR4 in either a Klotho-beta independent or Klotho-beta dependent manner. In certain embodiments, the chimeric hFGF19 polypeptide activates FGFR1c in a Klotho-beta dependent manner.

In certain embodiments, the chimeric hFGF19 polypeptide when administered to an individual does not reduce the lean mass of the individual. In certain embodiments, the chimeric hFGF19 polypeptide when administered to an individual does not substantially reduce the lean mass of the individual. In certain embodiments, the chimeric hFGF19 polypeptide when administered to an individual does not reduce the bone density of the individual. In certain embodiments, the chimeric hFGF19 polypeptide when administered to an individual does not substantially reduce the bone density of the individual. In certain embodiments, the chimeric hFGF19 polypeptide when administered to an individual does not reduce the cardiac capacity of the individual. In certain embodiments, the chimeric hFGF19 polypeptide when administered to an individual does not substantially reduce the cardiac capacity of the individual.

In certain embodiments, the chimeric hFGF19 polypeptide does not reduce or does not substantially reduce the amount of phosphorylated STAT5 polypeptide in vivo. In certain embodiments, the chimeric hFGF19 polypeptide when administered to an individual does not reduce or does not substantially reduce the amount of phosphorylated STAT5 polypeptide in the individual. In certain embodiments when the chimeric hFGF19 polypeptide is administered to an individual, the amount of phosphorylated STAT5 polypeptide is reduced in the individual but this amount of phosphorylated STAT5 polypeptide is greater than the amount of phosphorylated STAT5 polypeptide upon administration of native hFGF21 to the individual. In certain embodiments when the chimeric hFGF19 polypeptide is administered to an individual, the amount of phosphorylated STAT5 polypeptide is any of: from 100% to 5%, from 100% to 10%, from 100% to 20%, from 100% to 30%, from 100% to 40%, from 100% to 50%, from 100% to 60%, from 100% to 70%, from 100% to 80%, from 100% to 90% or from 100% to 95%, of the amount of phosphorylated STAT5 polypeptide in the individual without such administration. In certain embodiments when the chimeric hFGF19 polypeptide is administered to an individual, the reduction in the amount of phosphorylated STAT5 polypeptide is less than reduction in the amount of phosphorylated STAT5 polypeptide upon administration of native hFGF21. For example, the reduction of phosphorylated STAT5 polypeptide when the chimeric hFGF19 polypeptide is administered to an individual is by any of: from 0% to 5%, from 0% to 10%, from 0% to 20%, from 0% to 30%, from 0% to 40%, from 0% to 50%, from 0% to 60%, from 0% to 70%, from 0% to 80%, from 0% to 90% or from 0% to 95%, of the reduction in the amount of phosphorylated STAT5 polypeptide upon administration of native hFGF21.

In certain embodiments, the chimeric hFGF19 polypeptide does not reduce or does not substantially reduce the amount of circulating insulin-like growth factor 1 (IGF-1) in vivo. In certain embodiments, the chimeric hFGF19 polypeptide when administered to an individual does not reduce or does not substantially reduce the amount of circulating IGF-1 in the individual. In certain embodiments when the chimeric hFGF19 polypeptide is administered to an individual, the amount of circulating IGF-1 is reduced but this amount of circulating IGF-1 is greater than the amount of circulating IGF-1 upon administration of native hFGF21 to the individual. In certain embodiments when the chimeric hFGF19 polypeptide is administered to an individual, the amount of circulating IGF-1 is any of: from 100% to 5%, from 100% to 10%, from 100% to 20%, from 100% to 30%, from 100% to 40%, from 100% to 50%, from 100% to 60%, from 100% to 70%, from 100% to 80%, from 100% to 90% or from 100% to 95%, of the amount of circulating IGF-1 in the individual without such administration. In certain embodiments when the chimeric hFGF19 polypeptide is administered to an individual, the reduction in the amount of circulating IGF-1 is less than reduction in the amount of circulating IGF-1 upon administration of native hFGF21. For example, the reduction of circulating IGF-1 when the chimeric hFGF19 polypeptide is administered to an individual is by any of: from 0% to 5%, from 0% to 10%, from 0% to 20%, from 0% to 30%, from 0% to 40%, from 0% to 50%, from 0% to 60%, from 0% to 70%, from 0% to 80%, from 0% to 90% or from 0% to 95%, of the reduction in the amount of circulating IGF-1 upon administration of native hFGF21.

In another aspect, the present invention provides a pharmaceutical composition comprising a therapeutically effective amount of a chimeric hFGF19 polypeptide of the present invention; and an acceptable pharmaceutical carrier.

In another aspect, the present invention provides methods of treating an individual exhibiting one or more of obesity, type 1 diabetes, type 2 diabetes, high blood glucose, metabolic syndrome, atherosclerosis, hypercholesterolemia, stroke, osteoporosis, osteoarthritis, degenerative joint disease, muscle atrophy, sarcopenia, decreased lean body mass, baldness, wrinkles, increased fatigue, decreased stamina, decreased cardiac function, immune system dysfunction, cancer, Parkinson's disease, senile dementia, Alzheimer's disease and decreased cognitive function, the method comprising administering to the individual a therapeutically effective amount of the pharmaceutical composition of the present invention.

In another aspect, the present invention provides a method of lowering the blood glucose of an individual in need of such treatment, the method comprising administering to the individual a therapeutically effective amount of the pharmaceutical composition of the present invention.

In another aspect, the present invention provides an isolated nucleic acid molecule comprising DNA having at least an 80%, at least a 90%, at least a 95% or at least a 99% sequence identity to a DNA molecule encoding a polypeptide having amino acid residues from about 1 to about 190 of SEQ ID NO:5, or the complement thereof.

In another aspect, the present invention provides a isolated nucleic acid molecule comprising the sequence: CACCCCATCCCTGACTCCAGTCCTCTC-CTGCAATTCGGGGGCCAAGTCCGGCAGCGGTA CCTCTACACCTCCGGC-CCCCACGGGCTCTCCAGCTGCTTCCT-GCGCATCCGTGCCGACGG CGTCGTGGACT-GCGCGCGGGGCCAGAGCGCGCACAGTTTGCTGGA GATCAAGGCAGTC GCTCTGCGGACCGTGGCCAT-CAAGGGCGTGCACAGCGTGCGGTAC-CTCTGCATGGGCGC CGACGGCAAGATG-CAGGGGCTGCTTCAGTACTCGGAGGAAGACTGTGC TTTCGAGGAG GAGATCCGCCCAGATGGCTACAAT-GTGTACCGATCCGAGAAGCACCGCCTCCCGGTCTC CCTGAGCAGTGCCAAACAGCGGCAGCTG-TACAAGAACAGAGGCTTTCTTCCACTCTCTC ATTTCCTGCCCATGCTGCCCATGGTC-CCAGAGGAGCCTGAGGACCTCAGGGGCCACTTG GAATCTGACATGTTCTCTTCGCCCCTG-GAGACCGACAGCATGGACCCATTTGGGCTTGTC ACCGGACTGGAGGCCGTGAGGAGTC-CCAGCTTTGAGAAG (SEQ ID NO:7), or a portion thereof.

In certain embodiments, a isolated nucleic acid of the present invention further comprises a sequence encoding the amino acid residues corresponding to a Fc portion of an immunoglobulin.

In another aspect, the present invention provides an expression system comprising the nucleic acid molecule of the present invention. In another aspect, the present invention provides a host cell comprising an expression system or nucleic acid of the present invention.

In another aspect, the present invention provides an isolated polypeptide encoded by a nucleic acid molecule of the present invention.

In another aspect, the present invention provides a process for producing an isolated polypeptide comprising culturing a host cell of the present invention under conditions suitable for expression of the encoded polypeptide and recovering the encoded polypeptide from the cell culture.

In another aspect, the present invention provides an isolated polypeptide produced by a process of the present invention.

BRIEF DESCRIPTION OF THE DRAWINGS

FIG. 1 shows the amino acid sequence of human FGF19 polypeptide (SEQ ID NO:1) and human pre-FGF19 polypeptide (SEQ ID NO:3);

FIG. 2 shows the amino acid sequence of human FGF21 polypeptide (SEQ ID NO:2) and human pre-FGF21 polypeptide (SEQ ID NO:4);

FIG. 10-14 shows exemplary results of a receptor specificity assay using chimeric FGF19 polypeptides of the present invention.

FIG. 17A shows glucose level of FGF19 or PBS treated wildtype ("WT") and FGFR4 knockout ("KO") mice in glucose tolerance test. *$p<0.05$. $p<0.01$. p value for area under the curve (AUC) was $p<0.02$ (WT) and $p<0.005$ (KO). N=6~8. FIG. 17B shows various metabolic parameters (body weight (g), liver/BW ratio (%), serum insulin (ng/mL), serum beta-hydroxybutyrate ("BHB") (mg/L), serum lactate (mg/dl), and serum triglyceride (mg/dl)) in FGF19 or PBS treated WT and FGFR4KO mice at euthanasia on day 7. Mice were euthanized and the serum was prepared after 3 hr fast. N=6~8. FIG. 17C shows serum BA composition analysis in FGF19 or PBS treated WT and FGFR4KO mice. Only major BA species are shown. CA: cholic acid, DCA: deoxycholic acid, MCA: muricholic acid, T-: taurine conjugated. FIG. 17D shows relative expression of various hepatic genes (Egr-1, c-Fos, AFP, Cyp7a1, Cyp8b, Cyp27a1, Cyp7b, and GK) in FGF19 or PBS treated WT and FGFR4KO mice determined by real-time qPCR. N=6-8. p values for FIGS. 17B-17D are: $<0.05$, $<0.005$ (PBS vs FGF19), #$<0.05$, ##$<0.005$ (WT vs FGFR4KO).

FIG. 18A shows the relative firefly luciferase activity normalized by renilla luciferase activity (shown as relative luciferase unit ("RLU")) from a GAL-Elk1 luciferase assay using rat L6 cells transfected with KLB and FGFR1c or FGFR4 and incubated with media containing increasing concentrations of FGF19 (O) or FGF21(▲). FIG. 18B shows drawings (to scale) of FGF19 (top), FGF21 (bottom), and various chimeric proteins with amino acid composition at left. Based on the results of GAL-Elk1 assays shown in FIG. 18C, each chimera was classified into class (I), (II) or (III) as indicated at right. Chimeras which did not exhibit an equivalent FGFR1c activity to FGF21 or FGF19 when conditioned medium was used are not shown here. FIG. 18C shows the activation of FGFR1c or FGFR4 in a GAL-Elk-1 assay using L6 cells cotransfected with KLB and/or FGFR (FGFR1c or FGFR4) and incubated with conditioned medium from 293 cells transiently transfected with various FGF constructs (see FIG. 18B for amino acid compositions for FGF constructs used). The results are shown as a fold induction over control media conditioned with mock transfected cells. FIG. 18D shows the fold induction for FGFR activation in a GAL-Elk1 luciferase assay using rat L6 cells transfected with FGFR1c, FGFR4+KLB, or FGFR4 and incubated with media containing increasing concentrations of purified FGF19 (O) or FGF19v (▼) (the construct #4 in FIGS. 18B and 18C). FIG. 18E shows solid phase binding assay results for FGF19 and FGF19v to FGFR4 fused to Fc fragment. The schematic diagram for the experiments is shown at right. FIG. 18F shows that the anti-FGF19 antibody used in FIG. 18E recognized FGF19 and FGF19v at indistinguishable affinity (control ELISA experiment). The schematic diagram for the experiments is shown at right.

FIG. 21A shows relative expression of various genes (c-Fos, Egr-1, GK, SHP, and Cyp7a1) in FVB mice injected (via tail vein) with FGF21, FGF19, or FGF19v at 1 mg/kg or PBS control. p values: *$<0.05$, $<0.01$, *$<0.001$ (vs PBS). At 4 hours post-injection, hepatic mRNA was prepared from each mouse and subjected to real-time qPCR analysis for the indicated genes. FIG. 21B shows relative expression of various genes (c-Fos, Egr-1, GK, SHP, and Cyp7a1) in WT or FGFR4KO (KO) mice (N=5-7) i.p. injected with FGF21 or FGF19 at 1 mg/kg or PBS control. Overnight fasted mice were i.p. injected with FGF protein or PBS control. At 4 hours post-injection, hepatic mRNA was prepared from each mouse and subjected to real-time qPCR analysis for the indicated genes. p values: *$<0.05$, $<0.01$, *$<0.001$. FIG. 21C shows the proliferation of HepG2 cells treated with FGF21, FGF19, or FGF19v at various concentrations (10 ng/mL, 60 ng/mL, and 200 ng/mL) measured by the fluorescent intensity ($\times 10^5$) in an anchorage independent cell growth assay. Proliferation of HepG2 cells in soft agar was estimated based on conversion of Resazurin (Alamer Blue), a non-fluorescent indicator dye, to resorufin. FIG. 21D shows fold change of BrdU hepatocytes in FVB mice infused with FGF19 or FGF19v. N=6, *$p<0.01$, ***$p<5E-5$ (vs PBS), ##$p<0.0002$ (vs FGF19). FVB mice were implanted with an osmotic pump to continuously infuse indicated FGF protein at 1 ng/hr (~0.8 mg/kg/day) (day 0). The mice also received daily injection of 1 mg/kg/day FGF protein (q.d.) and 30 mg/kg/day BrdU (b.i.d.) starting day 1. On day 7, livers were dissected out and subjected to anti-BrdU staining. The results are shown as a fold induction over mock treated animals for the number of BrdU positive hepatocytes per area analyzed. FIG. 21E shows representative images for the study shown in FIG. 21C. FIG. 21F shows relative expression of various genes (c-Fos, Egr-1, AFP, GK, Cyp7a1 and Cyp8b) in mice used in FIGS. 21D and 21E. N=6. *$p<0.05$, $p<0.005$, *$p<0.001$ (vs PBS), #$p<0.05$, ##$p<0.005$ (vs FGF19).

FIG. 22A shows body weight (g) and blood glucose (mg/dl) in ob/ob mice infused by osmotic pump with 1 ng/hr FGF21 or FGF19v (0.4 mg/kg/day) or PBS control (N=7). The osmotic pump was implanted on day 0. FIG. 22B shows blood glucose levels (mg/dl) in ob/ob mice infused with FGF21, FGF19v or PBS control at random fed condition and after overnight fast. FIG. 22C shows serum non-esterified fatty acids ("NEFA") levels in ob/ob mice infused with FGF21, FGF19v or PBS control on day 8. FIG. 22D shows glucose tolerance test results conducted in ob/ob mice infused with FGF21, FGF19v or PBS control on day 6. Mice were overnight fasted and i.p. injected with 1 g/kg glucose at t=0. FIG. 22E shows organ/body weight ratio (%) in ob/ob mice infused with FGF21, FGF19v or PBS control on day 8. FIG. 22F shows relative expression of various genes (AFP, IGFBP2, SCD-1, Cyp7A, Cyp8B, UCP-1, MCAD, and SREBP-1c) from various tissues (liver, brown adipose tissue ("BAT"), and white adipose tissue ("WAT")) in ob/ob mice infused with FGF21, FGF19v or PBS control determined by qPCR. p values: *<0.05, <0.005, *<0.0005 (vs PBS control).

DETAILED DESCRIPTION OF THE INVENTION

Figure 3:
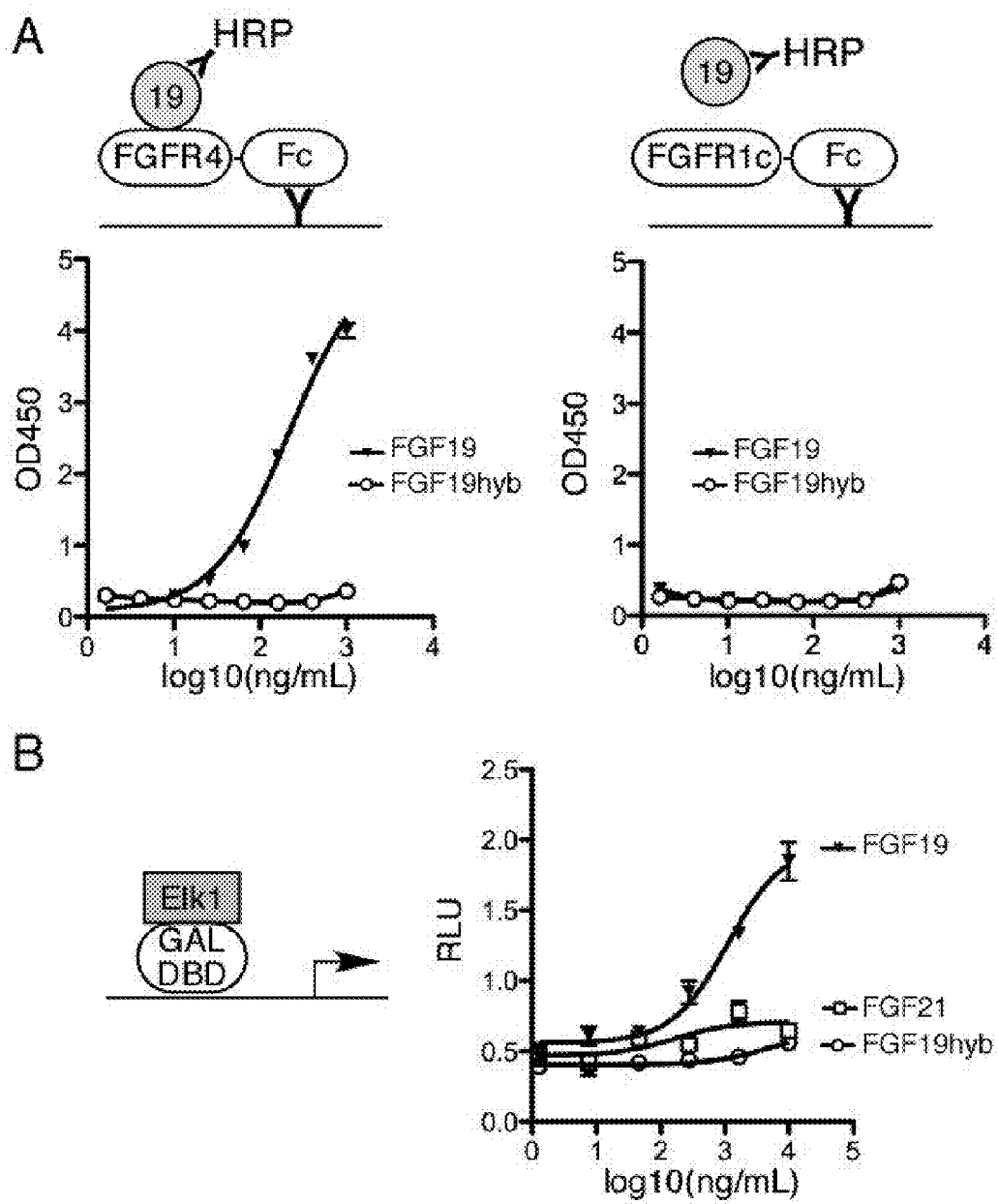
FIG. 3 shows exemplary results of a receptor binding assay using chimeric FGF19 polypeptides of the present invention.

The present invention provides novel chimeric FGF19 polypeptides. In some embodiments of the present invention, a chimeric FGF19 polypeptide sequence includes a portion of a FGF19 polypeptide sequence and a portion of a FGF21 polypeptide sequence. In certain preferred embodiments, the FGF19 polypeptide is processed human FGF19 (hFGF19) polypeptide whose sequence is defined in SEQ ID NO:1. In certain preferred embodiments, the FGF21 polypeptide is processed human FGF21 (hFGF21) polypeptide whose sequence is defined in SEQ ID NO:2. In another aspect, the present invention provides novel chimeric FGF19 polypeptides that are further fused to an immunoglobulin domain, such as the Fc domain.

In another aspect, the present invention provides novel chimeric FGF19 polypeptides that have altered receptor specificity. In certain preferred embodiments, a chimeric FGF19 polypeptide of the present invention does not substantially activate FGFR4 in a Klotho-beta-dependent or -independent manner. In certain embodiments, a chimeric FGF19 polypeptide of the present invention does activate at least one of FGFR1c, FGFR2c or FGFR3c in a Klotho-beta-dependent manner.

In some embodiments, a chimeric FGF19 polypeptide of the present invention may have one or more of the following advantageous features: the polypeptide does not substantially induce hepatocyte proliferation in an individual upon administration, the polypeptide does not substantially induce growth hormone resistance in an individual upon administration, the polypeptide does not include a residue that is polymorphic in the population, the polypeptide has an in vivo physiological half-life that is at least or about the same as native FGF19 polypeptide (such as native hFGF19 polypeptide), the polypeptide has an in vivo physiological half-life that is at least or about the same as native FGF21 polypeptide (such as native hFGF21 polypeptide), the polypeptide does not substantially reduce lean mass in an individual upon administration, the polypeptide does not substantially reduce bone density in an individual upon administration, and the polypeptide does not reduce substantially cardiac capacity in an individual upon administration.

Further advantageous features of a chimeric FGF19 polypeptide of the present invention may include one or more of following: the polypeptide reduces the blood glucose in an individual in an individual in need of such treatment; the polypeptide activates at least one of FGFR1c, FGFR2c or FGFR3c in a Klotho-beta-dependent manner; the polypeptide does not substantially activate FGFR4 in a Klotho-beta-dependent manner; the polypeptide does not substantially activate FGFR4 in a Klotho-beta-independent manner; the polypeptide does not reduce or does not substantially reduce the amount of phosphorylated STAT5 polypeptide in an individual upon administration; the polypeptide when administered to an individual the amount of phosphorylated STAT5 polypeptide in the individual is reduced but this amount of phosphorylated STAT5 polypeptide is greater than the amount of phosphorylated STAT5 polypeptide upon administration of native hFGF21 to the individual; the polypeptide when administered to an individual the reduction in the amount of phosphorylated STAT5 polypeptide in the individual is less than reduction in the amount of phosphorylated STAT5 polypeptide upon administration of native hFGF21 in the individual; the polypeptide does not reduce or does not substantially reduce the amount of circulating IGF-1 polypeptide in an individual upon administration; the polypeptide when administered to an individual the amount of circulating IGF-1 in the individual is reduced but this amount of circulating IGF-1 is greater than the amount of circulating IGF-1 upon administration of native hFGF21 to the individual; the polypeptide when administered to an individual the reduction in the amount of circulating IGF-1 in the individual is less than reduction in the amount of circulating IGF-1 upon administration of native hFGF21 in the individual; and the polypeptide does not reduce or does not substantially reduce the amount of circulating IGF-1 polypeptide in an individual having a normal or supranormal amount of GH.

In certain embodiments, a chimeric FGF19 polypeptide of the present invention has the advantageous features of activating at least one of FGFR1c, FGFR2c or FGFR3c in a Klotho-beta-dependent manner, and does not substantially activate FGFR4 in a Klotho-beta-dependent or -independent manner. In certain embodiments, a chimeric FGF19 polypeptide of the present invention has the advantageous features of activating at least one of FGFR1c, FGFR2c or FGFR3c in a Klotho-beta-dependent manner, does not substantially activate FGFR4 in a Klotho-beta-dependent or -independent manner, and reduces the amount of phosphorylated STAT5 polypeptide in an individual but this amount of phosphorylated STAT5 polypeptide is greater than the amount of phosphorylated STAT5 polypeptide upon administration of native hFGF21 to the individual. In certain embodiments, a chimeric FGF19 polypeptide of the present invention has the advantageous features of activating at least one of FGFR1c, FGFR2c or FGFR3c in a Klotho-beta-dependent manner, and does not substantially activate FGFR4 in a Klotho-beta-dependent or -independent manner, and does not include a residue that is polymorphic in the population. In certain embodiments, a chimeric FGF19 polypeptide of the present invention has the advantageous features of activating at least one of FGFR1c, FGFR2c or FGFR3c in a Klotho-beta-dependent manner, does not substantially activate FGFR4 in a Klotho-beta-dependent or -independent manner, reduces the amount of phosphorylated STAT5 polypeptide in an individual but this amount of phosphorylated STAT5 polypeptide is greater than the amount of phosphorylated STAT5 polypeptide upon administration of native hFGF21 to the individual and does not include a residue that is polymorphic in the population.

In another aspect, the present invention provides novel chimeric FGF19 polypeptides that have altered receptor specificity. In certain preferred embodiments, a chimeric FGF19 polypeptide of the present invention does not substantially activate FGFR4 in a Klotho-beta-dependent or -independent manner. In certain embodiments, a chimeric FGF19 polypeptide of the present invention does activate at least one of FGFR1c, FGFR2c or FGFR3c in a Klotho-beta-dependent manner.

In another aspect, the chimeric FGF19 polypeptide does not effect growth hormone resistance activity in an individual compared to the growth hormone resistance effected by native FGF21. In another aspect, the chimeric FGF19 polypeptide does not effect substantial growth hormone resistance activity in an individual compared to the growth hormone resistance effected by native FGF21. In certain embodiments, the chimeric FGF19 polypeptide does not reduce or does not substantially reduce the amount of phosphorylated STAT5 polypeptide in an individual. In certain embodiments when the chimeric hFGF19 polypeptide is administered to an individual, the amount of phosphorylated STAT5 polypeptide is reduced in the individual but this amount of phosphorylated STAT5 polypeptide is greater than the amount of phosphorylated STAT5 polypeptide upon administration of native hFGF21 to the individual. In certain embodiments when the chimeric hFGF19 polypeptide is administered to an individual, the reduction in the amount of phosphorylated STAT5 polypeptide is less than reduction in the amount of phosphorylated STAT5 polypeptide upon administration of native hFGF21. In certain embodiments, the chimeric FGF19 polypeptide does not reduce or does not substantially reduce the amount of circulating insulin-like growth factor 1 (IGF-1). In certain embodiments when the chimeric hFGF19 polypeptide is administered to an individual, the amount of circulating IGF-1 is reduced but this amount of circulating IGF-1 is greater than the amount of circulating IGF-1 upon administration of native hFGF21 to the individual. In certain embodiments when the chimeric hFGF19 polypeptide is administered to an individual, the reduction in the amount of circulating IGF-1 is less than reduction in the amount of circulating IGF-1 upon administration of native hFGF21.

In another aspect, the present invention provides novel isolated nucleic acid molecules having a sequence that encodes a chimeric FGF19 polypeptide of the present invention, novel expression systems that include a nucleic acid molecule of the present invention, and host cells that include a inventive nucleic acid molecule or an inventive expression system.

In another aspect, the present invention includes antibodies that can specifically bind a chimeric FGF19 polypeptide of the present invention.

In another aspect, the present invention provides pharmaceutical compositions that include a chimeric FGF19 polypeptide of the present invention and a pharmaceutically-acceptable carrier.

In another aspect, the present invention provides methods of treating an individual for a metabolic-related disorder by administering a chimeric FGF19 polypeptide of the present invention, or a suitable pharmaceutical formulation thereof. In another aspect, the present invention provides methods for effecting at least one or more of the following effects in an individual: lowering blood glucose, reducing obesity, increasing metabolic rate, increasing lipid oxidation, reducing weight, lower serum levels of glucose, leptin, insulin, cholesterol and/or triglycerides, treating diabetes, and other metabolic effects, wherein such effects are by administering to the individual a therapeutic amount of an inventive chimeric FGF19 polypeptide or pharmaceutical formulation thereof.

I. Chimeric FGF19 Polypeptides with N-Terminal FGF21 Polypeptide Sequences

In an aspect of the present invention, a chimeric FGF19 polypeptide sequence includes a C-terminal portion and an N-terminal portion. The N-terminal portion of the chimeric FGF19 polypeptide sequence includes an N-terminal portion of a FGF21 polypeptide sequence and the C-terminal portion of the chimeric FGF19 polypeptide sequence includes a C-terminal portion of a FGF19 polypeptide sequence. In some embodiments of the foregoing, the C-terminal portion of a FGF19 polypeptide sequence and the N-terminal portion of the chimeric FGF21 polypeptide sequence are contiguously joined. In some embodiments of the foregoing, the C-terminal portion of a FGF19 polypeptide sequence and the N-terminal portion of the chimeric FGF21 polypeptide sequence are contiguously joined by overlapping the 1, 2, 3 or more residues in common between the two portions. In some alternative embodiments, the C-terminal portion of a FGF19 polypeptide sequence and the N-terminal portion of the chimeric FGF21 polypeptide sequence have an intervening spacer of 1, 2, 3, 4, 5 or more amino residues.

In certain preferred embodiments, the FGF19 polypeptide is human FGF19 (hFGF19) polypeptide whose sequence is defined in SEQ ID NO:1 (FIG. 1). In some embodiments, the C-terminal portion of the hFGF19 polypeptide sequence is from about 45 to about 185 residues in length, expressly including the sequence lengths of the hFGF19 C-terminal portions shown in Table 1. In some embodiments, the C-terminal portion of the chimeric FGF19 polypeptide sequence includes a C-terminal portion of a polypeptide sequence that has at least 80%, at least 85%, at least 90%, at least 95%, at least 97% or at least 99% amino acid sequence identity to the hFGF19 polypeptide sequence. In some embodiments, the FGF19 polypeptide is pre-processed human FGF19 (hFGF19) polypeptide, which includes its signal sequence and whose sequence is defined in SEQ ID NO:3 (FIG. 1).

In certain preferred embodiments, the FGF21 polypeptide is human FGF21 (hFGF21) polypeptide whose sequence is defined in SEQ ID NO:2 (FIG. 2). In some embodiments, the N-terminal portion of the hFGF21 polypeptide sequence is from about 7 to about 140 residue in length, expressly including the sequence lengths of the hFGF19 N-terminal portions shown in Table 2. In some embodiments, the N-terminal portion of the chimeric FGF19 polypeptide sequence includes a N-terminal portion of a polypeptide sequence that has at least 80%, at least 85%, at least 90%, at least 95%, at least 97% or at least 99% amino acid sequence identity to the hFGF21 polypeptide sequence. In some embodiments, the FGF21 polypeptide is pre-processed human FGF21 (hFGF21) polypeptide, which includes its signal sequence and whose sequence is defined in SEQ ID NO:4 (FIG. 2).

As used herein, a C-terminal portion, an N-terminal portion, a substituted portion or a substituting portion of a polypeptide sequence, such as that of the hFGF19 or hFGF21 polypeptide sequences, has a first position and a final position. These positions correspond to positions in the polypeptide sequence from which the portion is referenced. Thus, the sequence of a defined portion is the contiguous sequence of amino acids that begins at or about the position in the polypeptide sequence that corresponds to the first position, and ends at or about the position in the polypeptide sequence that corresponds to the final position. In some embodiments, the final position of a C-terminal portion of a polypeptide corresponds to or about the final residue of the polypeptide. In some embodiments, the first position of an N-terminal portion of a polypeptide corresponds to or about the first residue of the polypeptide.

Examples of C-terminal portions of hFGF19 polypeptide sequence referred to in the present invention include, without limitation, those that have a first position that correspond to or about any one of positions 10, 11, 25, 26, 27, 28, 30, 33, 35, 37, 40, 41, 42, 43, 44, 45, 52, 53, 54, 56, 57, 58, 59, 72, 73, 74, 79, 80, 81, 143, 144, 145 or 146 of SEQ ID NO:1. Each exemplary C-terminal portion also has a final position that corresponds to or about position 194 of SEQ ID NO:1. Table 1 shows the polypeptide sequences of exemplary C-terminal portions of hFGF19. Other analogous portions of hFGF19 are also contemplated herein.

TABLE 1

Exemplary C-Terminal Portions of hFGF19 Polypeptide Sequence

| Name | Amino Acid Sequence (N-C) | SEQ ID NO |
|---|---|---|
| hFGF19-C10 | PHVHYGWGDPIRLRHLYTSGPHGLSSCFLRIRADGVVDCARGQSAHSLLEIKA VALRTVAIKGVHSVRYLCMGADGKMQGLLQYSEEDCAFEEEIRPDGYNVYR SEKHRLPVSLSSAKQRQLYKNRGFLPLSHFLPMLPMVPEEPEDLRGHLESDMF SSPLETDSMDPFGLVTGLEAVRSPSFEK | 8 |
| hFGF19-C11 | HVHYGWGDPIRLRHLYTSGPHGLSSCFLRIRADGVVDCARGQSAHSLLEIKAV ALRTVAIKGVHSVRYLCMGADGKMQGLLQYSEEDCAFEEEIRPDGYNVYRSE KHRLPVSLSSAKQRQLYKNRGFLPLSHFLPMLPMVPEEPEDLRGHLESDMFSS PL ETDSMDPFGLVTGLEAVRSPSFEK | 9 |
| hFGF19-C25 | LYTSGPHGLSSCFLRIRADGVVDCARGQSAHSLLEIKAVALRTVAIKGVHSVR YLCMGADGKMQGLLQYSEEDCAFEEEIRPDGYNVYRSEKHRLPVSLSSAKQR QLYKNRGFLPLSHFLPMLPMVPEEPEDLRGHLESDMFSSPLETDSMDPFGLVT GLEAVRSPSFEK | 10 |
| hFGF19-C26 | YTSGPHGLSSCFLRIRADGVVDCARGQSAHSLLEIKAVALRTVAIKGVHSVRY LCMGADGKMQGLLQYSEEDCAFEEEIRPDGYNVYRSEKHRLPVSLSSAKQRQ LYKNRGFLPLSHFLPMLPMVPEEPEDLRGHLESDMFSSPL ETDSMDPFGLVTGLEAVRSPSFEK | 11 |
| hFGF19-C27 | TSGPHGLSSCFLRIRADGVVDCARGQSAHSLLEIKAVALRTVAIKGVHSVRYL CMGADGKMQGLLQYSEEDCAFEEEIRPDGYNVYRSEKHRLPVSLSSAKQRQ LYKNRGFLPLSHFLPMLPMVPEEPEDLRGHLESDMFSSPL ETDSMDPFGLVTGLEAVRSPSFEK | 12 |
| hFGF19-C28 | SGPHGLSSCFLRIRADGVVDCARGQSAHSLLEIKAVALRTVAIKGVHSVRYLC MGADGKMQGLLQYSEEDCAFEEEIRPDGYNVYRSEKHRLPVSLSSAKQRQ LYKNRGFLPLSHFLPMLPMVPEEPEDLRGHLESDMFSSPL ETDSMDPFGLVTGLEAVRSPSFEK | 13 |
| hFGF19-C30 | PHGLSSCFLRIRADGVVDCARGQSAHSLLEIKAVALRTVAIKGVHSVRYLCM GADGKMQGLLQYSEEDCAFEEEIRPDGYNVYRSEKHRLPVSLSSAKQRQLYK NRGFLPLSHFLPMLPMVPEEPEDLRGHLESDMFSSPLETDSMDPFGLVTGLEA VRSPSFEK | 14 |
| hFGF19-C33 | LSSCFLRIRADGVVDCARGQSAHSLLEIKAVALRTVAIKGVHSVRYLCMGAD GKMQGLLQYSEEDCAFEEEIRPDGYNVYRSEKHRLPVSLSSAKQRQLYKNRG FLPLSHFLPMLPMVPEEPEDLRGHLESDMFSSPLETDSMDPFGLVTGLEAVRSP SFEK | 15 |
| hFGF19-C35 | SCFLRIRADGVVDCARGQSAHSLLEIKAVALRTVAIKGVHSVRYLCMGADGK MQGLLQYSEEDCAFEEEIRPDGYNVYRSEKHRLPVSLSSAKQRQLYKNRGFLP LSHFLPMLPMVPEEPEDLRGHLESDMFSSPLETDSMDPFGLVTGLEAVRSPSFE K | 16 |
| hFGF19-C37 | FLRIRADGVVDCARGQSAHSLLEIKAVALRTVAIKGVHSVRYLCMGADGKM QGLLQYSEEDCAFEEEIRPDGYNVYRSEKHRLPVSLSSAKQRQLYKNRGFLPL SHFLPMLPMVPEEPEDLRGHLESDMFSSPLETDSMDPFGLVTGLEAVRSPSFE K | 17 |
| hFGF19-C40 | IRADGVVDCARGQSAHSLLEIKAVALRTVAIKGVHSVRYLCMGADGKMQGL LQYSEEDCAFEEEIRPDGYNVYRSEKHRLPVSLSSAKQRQLYKNRGFLPLSHF LPMLPMVPEEPEDLRGHLESDMFSSPLETDSMDPFGLVTGLEAVRSPSFEK | 18 |
| hFGF19-C41 | RADGVVDCARGQSAHSLLEIKAVALRTVAIKGVHSVRYLCMGADGKMQGLL QYSEEDCAFEEEIRPDGYNVYRSEKHRLPVSLSSAKQRQLYKNRGFLPLSHFL PMLPMVPEEPEDLRGHLESDMFSSPLETDSMDPFGLVTGLEAVRSPSFEK | 19 |
| hFGF19-C42 | ADGVVDCARGQSAHSLLEIKAVALRTVAIKGVHSVRYLCMGADGKMQGLLQ YSEEDCAFEEEIRPDGYNVYRSEKHRLPVSLSSAKQRQLYKNRGFLPLSHFLP MLPMVPEEPEDLRGHLESDMFSSPLETDSMDPFGLVTGLEAVRSPSFEK | 20 |
| hFGF19-C43 | DGVVDCARGQSAHSLLEIKAVALRTVAIKGVHSVRYLCMGADGKMQGLLQY SEEDCAFEEEIRPDGYNVYRSEKHRLPVSLSSAKQRQLYKNRGFLPLSHFLPM LPMVPEEPEDLRGHLESDMFSSPLETDSMDPFGLVTGLEAVRSPSFEK | 21 |
| hFGF19-C44 | GVVDCARGQSAHSLLEIKAVALRTVAIKGVHSVRYLCMGADGKMQGLLQYS EEDCAFEEEIRPDGYNVYRSEKHRLPVSLSSAKQRQLYKNRGFLPLSHFLPML PMVPEEPEDLRGHLESDMFSSPLETDSMDPFGLVTGLEAVRSPSFEK | 22 |
| hFGF19-C45 | VVDCARGQSAHSLLEIKAVALRTVAIKGVHSVRYLCMGADGKMQGLLQYSE EDCAFEEEIRPDGYNVYRSEKHRLPVSLSSAKQRQLYKNRGFLPLSHFLPMLP MVPEEPEDLRGHLESDMFSSPLETDSMDPFGLVTGLEAVRSPSFEK | 23 |

TABLE 1-continued

Exemplary C-Terminal Portions of hFGF19 Polypeptide Sequence

| Name | Amino Acid Sequence (N-C) | SEQ ID NO |
|---|---|---|
| hFGF19-C52 | QSAHSLLEIKAVALRTVAIKGVHSVRYLCMGADGKMQGLLQYSEEDCAFEEE IRPDGYNVYRSEKHRLPVSLSSAKQRQLYKNRGFLPLSHFLPMLPMVPEEPED LRGHLESDMFSSPLETDSMDPFGLVTGLEAVRSPSFEK | 24 |
| hFGF19-C53 | SAHSLLEIKAVALRTVAIKGVHSVRYLCMGADGKMQGLLQYSEEDCAFEEEI RPDGYNVYRSEKHRLPVSLSSAKQRQLYKNRGFLPLSHFLPMLPMVPEEPEDL RGHLESDMFSSPLETDSMDPFGLVTGLEAVRSPSFEK | 25 |
| hFGF19-C54 | AHSLLEIKAVALRTVAIKGVHSVRYLCMGADGKMQGLLQYSEEDCAFEEEIR PDGYNVYRSEKHRLPVSLSSAKQRQLYKNRGFLPLSHFLPMLPMVPEEPEDLR GHLESDMFSSPLETDSMDPFGLVTGLEAVRSPSFEK | 26 |
| hFGF19-C56 | SLLEIKAVALRTVAIKGVHSVRYLCMGADGKMQGLLQYSEEDCAFEEEIRPD GYNVYRSEKHRLPVSLSSAKQRQLYKNRGFLPLSHFLPMLPMVPEEPEDLRG HLESDMFSSPLETDSMDPFGLVTGLEAVRSPSFEK | 27 |
| hFGF19-C57 | LLEIKAVALRTVAIKGVHSVRYLCMGADGKMQGLLQYSEEDCAFEEEIRPDG YNVYRSEKHRLPVSLSSAKQRQLYKNRGFLPLSHFLPMLPMVPEEPEDLRGHL ESDMFSSPLETDSMDPFGLVTGLEAVRSPSFEK | 28 |
| hFGF19-C58 | LEIKAVALRTVAIKGVHSVRYLCMGADGKMQGLLQYSEEDCAFEEEIRPDGY NVYRSEKHRLPVSLSSAKQRQLYKNRGFLPLSHFLPMLPMVPEEPEDLRGHLE SDMFSSPLETDSMDPFGLVTGLEAVRSPSFEK | 29 |
| hFGF19-C59 | EIKAVALRTVAIKGVHSVRYLCMGADGKMQGLLQYSEEDCAFEEEIRPDGYN VYRSEKHRLPVSLSSAKQRQLYKNRGFLPLSHFLPMLPMVPEEPEDLRGHLES DMFSSPLETDSMDPFGLVTGLEAVRSPSFEK | 30 |
| hFGF19-C72 | GVHSVRYLCMGADGKMQGLLQYSEEDCAFEEEIRPDGYNVYRSEKHRLPVS LSSAKQRQLYKNRGFLPLSHFLPMLPMVPEEPEDLRGHLESDMFSSPL ETDSMDPFGLVTGLEAVRSPSFEK | 31 |
| hFGF19-C73 | VHSVRYLCMGADGKMQGLLQYSEEDCAFEEEIRPDGYNVYRSEKHRLPVSLS SAKQRQLYKNRGFLPLSHFLPMLPMVPEEPEDLRGHLESDMFSSPL ETDSMDPFGLVTGLEAVRSPSFEK | 32 |
| hFGF19-C74 | HSVRYLCMGADGKMQGLLQYSEEDCAFEEEIRPDGYNVYRSEKHRLPVSLSS AKQRQLYKNRGFLPLSHFLPMLPMVPEEPEDLRGHLESDMFSSPL ETDSMDPFGLVTGLEAVRSPSFEK | 33 |
| hFGF19-C79 | LCMGADGKMQGLLQYSEEDCAFEEEIRPDGYNVYRSEKHRLPVSLSSAKQRQ LYKNRGELPLSHFLPMLPMVPEEPEDLRGHLESDMESSPL ETDSMDPFGLVTGLEAVRSPSFEK | 34 |
| hFGF19-C80 | CMGADGKMQGLLQYSEEDCAFEEEIRPDGYNVYRSEKHRLPVSLSSAKQRQ LYKNRGELPLSHFLPMLPMVPEEPEDLRGHLESDMESSPLETDSMDPFGLVTG LEAVRSPSFEK | 35 |
| hFGF19-C81 | MGADGKMQGLLQYSEEDCAFEEEIRPDGYNVYRSEKHRLPVSLSSAKQRQ LYKNRGELPLSHFLPMLPMVPEEPEDLRGHLESDMFSSPLETDSMDPFGLVTG LEAVRSPSFEK | 36 |
| hFGF19-C143 | FLPMLPMVPEEPEDLRGHLESDMFSSPLETDSMDPFGLVTGLEAVRSPSFEK | 37 |
| hFGF19-C144 | LPMLPMVPEEPEDLRGHLESDMFSSPLETDSMDPFGLVTGLEAVRSPSFEK | 38 |
| hFGF19-C145 | PMLPMVPEEPEDLRGHLESDMFSSPLETDSMDPFGLVTGLEAVRSPSFEK | 39 |
| hFGF19-C146 | MLPMVPEEPEDLRGHLESDMFSSPLETDSMDPFGLVTGLEAVRSPSFEK | 40 |

Examples of N-terminal portions of hFGF21 polypeptide sequence referred to in the present invention include, without limitation, those that have a final position that correspond to or about any one of positions 7, 8, 20, 21, 22, 23, 25, 27, 29, 31, 34, 35, 36, 37, 38, 39, 46, 47, 48, 50, 51, 52, 53, 66, 67, 68, 73, 74, 75, 135, 136, 137 and 138 of SEQ ID NO:2. Each exemplary N-terminal portion also has a first position that corresponds to or about position 1 of SEQ ID NO:2. Table 2 shows a list of exemplary N-terminal portions of hFGF21. Other analogous portions of hFGF21 are also contemplated herein.

TABLE 2

Exemplary N-Terminal Portions of hFGF21 Polypeptide Sequence

| Name | Amino Acid Sequence (N-C) | SEQ ID NO |
|---|---|---|
| hFGF21-N7 | HPIPDSS | 41 |
| hFGF21-N8 | HPIPDSSP | 42 |
| hFGF21-N20 | HPIPDSSPLLQFGGQVRQRY | 43 |
| hFGF21-N21 | HPIPDSSPLLQFGGQVRQRYL | 44 |
| hFGF21-N22 | HPIPDSSPLLQFGGQVRQRYLY | 45 |
| hFGF21-N23 | HPIPDSSPLLQFGGQVRQRYLYT | 46 |
| hFGF21-N25 | HPIPDSSPLLQFGGQVRQRYLYTDD | 47 |
| hFGF21-N27 | HPIPDSSPLLQFGGQVRQRYLYTDDAQ | 48 |
| hFGF21-N29 | HPIPDSSPLLQFGGQVRQRYLYTDDAQQT | 49 |
| hFGF21-N31 | HPIPDSSPLLQFGGQVRQRYLYTDDAQQTEA | 50 |
| hFGF21-N34 | HPIPDSSPLLQFGGQVRQRYLYTDDAQQTEAHLE | 51 |
| hFGF21-N35 | HPIPDSSPLLQFGGQVRQRYLYTDDAQQTEAHLEI | 52 |
| hFGF21-N36 | HPIPDSSPLLQFGGQVRQRYLYTDDAQQTEAHLEIR | 53 |
| hFGF21-N37 | HPIPDSSPLLQFGGQVRQRYLYTDDAQQTEAHLEIRE | 54 |
| hFGF21-N38 | HPIPDSSPLLQFGGQVRQRYLYTDDAQQTEAHLEIRED | 55 |
| hFGF21-N39 | HPIPDSSPLLQFGGQVRQRYLYTDDAQQTEAHLEIREDG | 56 |
| hFGF21-N46 | HPIPDSSPLLQFGGQVRQRYLYTDDAQQTEAHLEIREDGTVGGAAD | 57 |
| hFGF21-N47 | HPIPDSSPLLQFGGQVRQRYLYTDDAQQTEAHLEIREDGTVGGAADQ | 58 |
| hFGF21-N48 | HPIPDSSPLLQFGGQVRQRYLYTDDAQQTEAHLEIREDGTVGGAADQS | 59 |
| hFGF21-N50 | HPIPDSSPLLQFGGQVRQRYLYTDDAQQTEAHLEIREDGTVGGAADQSPE | 60 |
| hFGF21-N51 | HPIPDSSPLLQFGGQVRQRYLYTDDAQQTEAHLEIREDGTVGGAADQSPES | 61 |
| hFGF21-N52 | HPIPDSSPLLQFGGQVRQRYLYTDDAQQTEAHLEIREDGTVGGAADQSPESL | 62 |
| hFGF21-N53 | HPIPDSSPLLQFGGQVRQRYLYTDDAQQTEAHLEIREDGTVGGAADQSPESLL | 63 |
| hFGF21-N66 | HPIPDSSPLLQFGGQVRQRYLYTDDAQQTEAHLEIREDGTVGGAADQSPESLLQLKALKPGVIQIL | 64 |
| hFGF21-N67 | HPIPDSSPLLQFGGQVRQRYLYTDDAQQTEAHLEIREDGTVGGAADQSPESLLQLKALKPGVIQILG | 65 |
| hFGF21-N68 | HPIPDSSPLLQFGGQVRQRYLYTDDAQQTEAHLEIREDGTVGGAADQSPESLLQLKALKPGVIQILGV | 66 |
| hFGF21-N73 | HPIPDSSPLLQFGGQVRQRYLYTDDAQQTEAHLEIREDGTVGGAADQSPESLLQLKALKPGVIQILGVKTSRF | 67 |
| hFGF21-N74 | HPIPDSSPLLQFGGQVRQRYLYTDDAQQTEAHLEIREDGTVGGAADQSPESLLQLKALKPGVIQILGVKTSRFL | 68 |
| hFGF21-N75 | HPIPDSSPLLQFGGQVRQRYLYTDDAQQTEAHLEIREDGTVGGAADQSPESLLQLKALKPGVIQILGVKTSRFLC | 69 |
| hFGF21-N135 | HPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPAR | 70 |
| hFGF21-N136 | HPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARF | 71 |

TABLE 2-continued

Exemplary N-Terminal Portions of hFGF21 Polypeptide Sequence

| Name | Amino Acid Sequence (N-C) | SEQ ID NO |
|---|---|---|
| hFGF21-N137 | HPIPDSSPLLQFGGQVRQRYLYTDDAQQTEAHLEIREDGTVGGAADQS PESLLQLKALKPGVIQILGVKTSRFLCQRPDGALYGSLHFDPEACSFRE LLLEDGYNVYQSEAHGLPLHLPGNKSPHRDPAPRGPARFL | 72 |
| hFGF21-N138 | HPIPDSSPLLQFGGQVRQRYLYTDDAQQTEAHLEIREDGTVGGAADQS PESLLQLKALKPGVIQILGVKTSRFLCQRPDGALYGSLHFDPEACSFRE LLLEDGYNVYQSEAHGLPLHLPGNKSPHRDPAPRGPARFLP | 73 |

It is intended that a C-terminal, N-terminal or any other portion of a polypeptide sequence defined herein may independently and optionally include one to five or more additional or fewer residues at the defined first or final position. For example, a C-terminal portion of a polypeptide having a first position at or about residue 100 may, independently, (i) optionally include 1, 2, 3, 4, 5 or more additional residues N-terminal to the residue at position 100, (ii) optionally include 1, 2, 3, 4, 5 or more additional residues C-terminal to the final residue, (iii) optionally begin at a position 1, 2, 3, 4, 5 or more residues C-terminal to the residue at position 100 or (iv) optionally end at a position 1, 2, 3, 4, 5 or more residues N-terminal to the final residue. If present, one or more of the additional residues may or may not be the same as the residues at the corresponding position in the polypeptide.

In some embodiments of a chimeric FGF19 polypeptide of the present invention, the N-terminal portion of its sequence includes a sequence that is selected from the N-terminal portions of the hFGF21 polypeptide sequence listed in Table 2, and the C-terminal portion of its sequence includes a sequence that is selected from among the C-terminal portions of the hFGF19 polypeptide sequence listed in Table 1. In some embodiments, the selected hFGF21 N-terminal portion and the selected hFGF19 C-terminal portion are selected independently with respect to each other. In some embodiments, the hFGF21 N-terminal sequence portion and the hFGF19 C-terminal sequence portion are selected such that the C-terminus of the N-terminal sequence portion and the N-terminus end of the C-terminal sequence portion have at least 1, at least 2 or at least 3 or more residues in common. In some embodiments, the sequence of the chimeric FGF19 polypeptide comprises a sequence in which the C-terminal portion of a FGF19 polypeptide sequence and the N-terminal portion of the chimeric FGF21 polypeptide sequence are contiguous without intervening amino acids therebetween. In some embodiments of the foregoing, the sequence of the chimeric FGF19 polypeptide comprises a sequence in which the C-terminal portion of a FGF19 polypeptide sequence and the N-terminal portion of the chimeric FGF21 polypeptide sequence are contiguously joined by overlapping the 1, 2, 3 or more residues in common between the two portions. In some alternative embodiments, the sequence of the chimeric FGF19 polypeptide comprises a sequence in which includes the C-terminal portion of a FGF19 polypeptide sequence and the N-terminal portion of the chimeric FGF21 polypeptide sequence, and further includes an intervening spacer therebetween of 1, 2, 3, 4, 5 or more amino residues.

Exemplary sequences of chimeric FGF19 polypeptides of the present invention are shown in Table 3, wherein its N-terminal portion includes an N-terminal portion of a hFGF21 polypeptide sequence and its C-terminal portion includes a C-terminal portion of a hFGF19 polypeptide sequence.

TABLE 3

Exemplary Chimeric FGF19 Polypeptide Sequences

| Name | Amino Acid Sequence (N-C) | SEQ ID NO |
|---|---|---|
| cFGF21/19-1 | HPIPDSSPHVHYGWGDPIRLRHLYTSGPHGLSSCFLRIRADGVVDCARGQSAHSLLEIKAVALRTVAIKGVHSVRYLCMGADGKMQGLLQYSEEDCAFEEEIRPDGYNVYRSEKHRLPVSLSSAKQRQLYKNRGFLPLSHFLPMLPMVPEEPEDLRGHLESDMFSSPLETDSMDPFGLVTGLEAVRSPSFEK | 74 |
| cFGF21/19-2 | HPIPDSSPLLQFGGQVRQRYLYTSGPHGLSSCFLRIRADGVVDCARGQSAHSLLEIKAVALRTVAIKGVHSVRYLCMGADGKMQGLLQYSEEDCAFEEEIRPDGYNVYRSEKHRLPVSLSSAKQRQLYKNRGFLPLSHFLPMLPMVPEEPEDLRGHLESDMFSSPL ETDSMDPFGLVTGLEAVRSPSFEK | 5 |
| cFGF21/19-3 | HPIPDSSPLLQFGGQVRQRYLYTDDPHGLSSCFLRIRADGVVDCARGQSAHSLLEIKAVALRTVAIKGVHSVRYLCMGADGKMQGLLQYSEEDCAFEEEIRPDGYNVYRSEKHRLPVSLSSAKQRQLYKNRGFLPLSHFLPMLPMVPEEPEDLRGHLESDMFSSPLETDSMDPFGLVTGLEAVRSPSFEK | 75 |
| cFGF21/19-4 | HPIPDSSPLLQFGGQVRQRYLYTDDAQLSSCFLRIRADGVVDCARGQSAHSLLEIKAVALRTVAIKGVHSVRYLCMGADGKMQGLLQYSEEDCAFEEEIRPDGYNVYRSEKHRLPVSL | 76 |

TABLE 3-continued

Exemplary Chimeric FGF19 Polypeptide Sequences

| Name | Amino Acid Sequence (N-C) | SEQ ID NO |
|---|---|---|
| | SSAKQRQLYKNRGFLPLSHFLPMLPMVPEEPEDLRGHLESDMFSSP LETDSMDPFGLVTGLEAVRSPSFEK | |
| cFGF21/19-5 | HPIPDSSPLLQFGGQVRQRYLYTDDAQQT SCFLRIRADGVVDCARGQSAHSLLEIKAVALRTVAIKGVHSVRYLC MGADGKMQGLLQYSEEDCAFEEEIRPDGYNVYRSEKHRLPVSLSS AKQRQLYKNRGFLPLSHFLPMLPMVPEEPEDLRGHLESDMFSSPLE TDSMDPFGLVTGLEAVRSPSFEK | 77 |
| cFGF21/19-6 | HPIPDSSPLLQFGGQVRQRYLYTDDAQQTEA FLRIRADGVVDCARGQSAHSLLEIKAVALRTVAIKGVHSVRYLCM GADGKMQGLLQYSEEDCAFEEEIRPDGYNVYRSEKHRLPVSLSSAK QRQLYKNRGFLPLSHFLPMLPMVPEEPEDLRGHLESDMFSSPLETD SMDPFGLVTGLEAVRSPSFEK | 78 |
| cFGF21/19-7 | HPIPDSSPLLQFGGQVRQRYLYTDDAQQTEAHLE IRADGVVDCARGQSAHSLLEIKAVALRTVAIKGVHSVRYLCMGAD GKMQGLLQYSEEDCAFEEEIRPDGYNVYRSEKHRLPVSLSSAKQRQ LYKNRGFLPLSHFLPMLPMVPEEPEDLRGHLESDMFSSPLETDSMD PFGLVTGLEAVRSPSFEK | 79 |
| cFGF21/19-8 | HPIPDSSPLLQFGGQVRQRYLYTDDAQQTEAHLEIRE DGVVDCARGQSAHSLLEIKAVALRTVAIKGVHSVRYLCMGADGK MQGLLQYSEEDCAFEEEIRPDGYNVYRSEKHRLPVSLSSAKQRQLY KNRGFLPLSHFLPMLPMVPEEPEDLRGHLESDMFSSPLETDSMDPF GLVTGLEAVRSPSFEK | 80 |
| cFGF21/19-9 | HPIPDSSPLLQFGGQVRQRYLYTDDAQQTEAHLEIREDGTVGG AAD QSAHSLLEIKAVALRTVAIKGVHSVRYLCMGADGKMQGLLQYSEE DCAFEEEIRPDGYNVYRSEKHRLPVSLSSAKQRQLYKNRGFLPLSH FLPMLPMVPEEPEDLRGHLESDMFSSPLETDSMDPFGLVTGLEAVR SPSFEK | 81 |
| cFGF21/19-10 | HPIPDSSPLLQFGGQVRQRYLYTDDAQQTEAHLEIREDGTVGG AADQSPE SLLEIKAVALRTVAIKGVHSVRYLCMGADGKMQGLLQYSEEDCAF EEEIRPDGYNVYRSEKHRLPVSLSSAKQRQLYKNRGFLPLSHFLPM LPMVPEEPEDLRGHLESDMFSSPLETDSMDPFGLVTGLEAVRSPSFE K | 82 |
| cFGF21/19-11 | HPIPDSSPLLQFGGQVRQRYLYTDDAQQTEAHLEIREDGTVGG AADQSPESLLQLKALKPGVIQIL GVHSVRYLCMGADGKMQGLLQYSEEDCAFEEEIRPDGYNVYRSEK HRLPVSLSSAKQRQLYKNRGFLPLSHFLPMLPMVPEEPEDLRGHLE SDMFSSPL ETDSMDPFGLVTGLEAVRSPSFEK | 83 |
| cFGF21/19-12 | HPIPDSSPLLQFGGQVRQRYLYTDDAQQTEAHLEIREDGTVGG AADQSPESLLQLKALKPGVIQILGVKTSRF LCMGADGKMQGLLQYSEEDCAFEEEIRPDGYNVYRSEKHRLPVSL SSAKQRQLYKNRGFLPLSHFLPMLPMVPEEPEDLRGHLESDMFSSP LETDSMDPFGLVTGLEAVRSPSFEK | 84 |
| cFGF21/19-13 | HPIPDSSPLLQFGGQVRQRYLYTDDAQQTEAHLEIREDGTVGG AADQSPESLLQLKALKPGVIQILGVKTSRFLCQRPDGALYGSLH FDPEACSFRELLLEDGYNVYQSEAHGLPLHLPGNKSPHRDPAPR GPAR FLPMLPMVPEEPEDLRGHLESDMFSSPLETDSMDPFGLVTGLEAVR SPSFEK | 85 |

II. Chimeric FGF19 Polypeptides with C-Terminal FGF21 Polypeptide Sequences

In a second aspect of the present invention, a chimeric FGF19 polypeptide sequence includes a C-terminal portion and an N-terminal portion. The N-terminal portion of the chimeric FGF19 polypeptide sequence includes a N-terminal portion of a FGF19 polypeptide sequence and the C-terminal portion of the chimeric FGF19 polypeptide sequence includes an C-terminal portion of a FGF21 polypeptide sequence. In some embodiments of the foregoing, the C-terminal portion of a FGF21 polypeptide sequence and the N-terminal portion of the chimeric FGF19 polypeptide sequence are contiguously joined. In some embodiments of the foregoing, the C-terminal portion of a FGF21 polypeptide sequence and the N-terminal portion of the chimeric FGF19 polypeptide sequence are contiguously joined by overlapping the 1, 2, 3 or more residues in common between the two portions. In some alternative embodiments, the C-terminal portion of a FGF21 polypeptide sequence and the N-terminal portion of the chimeric FGF19 polypeptide sequence have an intervening spacer of 1, 2, 3, 4, 5 or more amino residues.

In certain preferred embodiments, the FGF19 polypeptide is human FGF19 (hFGF19) polypeptide whose sequence is defined in SEQ ID NO:1. In some embodiments, the N-terminal portion of the hFGF19 polypeptide sequence is from about 45 to about 175 residues in length, expressly including the sequence lengths of the hFGF19 N-terminal portions shown in Table 4. In some embodiments, the N-terminal portion of the chimeric FGF19 polypeptide sequence includes a N-terminal portion of a polypeptide sequence that has at least 80%, at least 85%, at least 90%, at least 95%, at least 97% or at least 99% amino acid sequence identity to the hFGF19 polypeptide sequence.

In certain preferred embodiments, the FGF21 polypeptide is human FGF21 (hFGF21) polypeptide whose sequence is defined in SEQ ID NO:2. In some embodiments, the C-terminal portion of the hFGF21 polypeptide sequence is from about 8 to about 145 residues in length, expressly including the sequence lengths of the hFGF19 C-terminal portions shown in Table 5. In some embodiments, the C-terminal portion of the chimeric FGF21 polypeptide sequence includes a C-terminal portion of a polypeptide sequence that has at least 80%, at least 85%, at least 90%, at least 95%, at least 97% or at least 99% amino acid sequence identity to the hFGF21 polypeptide sequence.

Examples of N-terminal portions of hFGF19 polypeptide sequence referred to in the present invention include, without limitation, those that have a final position that correspond to or about any one of positions 9, 10, 24, 25, 26, 27, 39, 40, 41, 42, 43, 44, 51, 52, 53, 55, 56, 57, 58, 71, 72, 73, 78, 79, 80, 142, 143, 144 and 145 of SEQ ID NO:1. Each exemplary N-terminal portion also has a final position that corresponds to or about position 1 of SEQ ID NO:1. Table 4 shows the polypeptide sequences of exemplary N-terminal portions of hFGF19. Other analogous portions of hFGF19 are also contemplated herein.

TABLE 4

Exemplary N-Terminal Portions of hFGF19 Polypeptide Sequence

| Name | Amino Acid Sequence (N-) | SEQ ID NO |
|---|---|---|
| hFGF19-N9 | RPLAFSDAG | 86 |
| hFGF19-N10 | RPLAFSDAGP | 87 |
| hFGF19-N24 | RPLAFSDAGPHVHYGWGDPIRLRH | 88 |
| hFGF19-N25 | RPLAFSDAGPHVHYGWGDPIRLRHL | 89 |
| hFGF19-N26 | RPLAFSDAGPHVHYGWGDPIRLRHLY | 90 |
| hFGF19-N27 | RPLAFSDAGPHVHYGWGDPIRLRHLYT | 91 |
| hFGF19-N39 | RPLAFSDAGPHVHYGWGDPIRLRHLYTSGPHGLSSCFLR | 92 |
| hFGF19-N40 | RPLAFSDAGPHVHYGWGDPIRLRHLYTSGPHGLSSCFLRI | 93 |
| hFGF19-N41 | RPLAFSDAGPHVHYGWGDPIRLRHLYTSGPHGLSSCFLRIR | 94 |
| hFGF19-N42 | RPLAFSDAGPHVHYGWGDPIRLRHLYTSGPHGLSSCFLRIRA | 95 |
| hFGF19-N43 | RPLAFSDAGPHVHYGWGDPIRLRHLYTSGPHGLSSCFLRIRAD | 96 |
| hFGF19-N44 | RPLAFSDAGPHVHYGWGDPIRLRHLYTSGPHGLSSCFLRIRADG | 97 |
| hFGF19-N51 | RPLAFSDAGPHVHYGWGDPIRLRHLYTSGPHGLSSCFLRIRADGVVDCARG | 98 |
| hFGF19-N52 | RPLAFSDAGPHVHYGWGDPIRLRHLYTSGPHGLSSCFLRIRADGVVDCARGQ | 99 |
| hFGF19-N53 | RPLAFSDAGPHVHYGWGDPIRLRHLYTSGPHGLSSCFLRIRADGVVDCARGQS | 100 |
| hFGF19-55 | RPLAFSDAGPHVHYGWGDPIRLRHLYTSGPHGLSSCFLRIRADGVVDCARGQSAH | 101 |
| hFGF19-N56 | RPLAFSDAGPHVHYGWGDPIRLRHLYTSGPHGLSSCFLRIRADGVVDCARGQSAHS | 102 |
| hFGF19-N57 | RPLAFSDAGPHVHYGWGDPIRLRHLYTSGPHGLSSCFLRIRADGVVDCARGQSAHSL | 103 |

TABLE 4-continued

Exemplary N-Terminal Portions of hFGF19 Polypeptide Sequence

| Name | Amino Acid Sequence (N-) | SEQ ID NO |
|---|---|---|
| hFGF19-N58 | RPLAFSDAGPHVHYGWGDPIRLRHLYTSGPHGLSSCFLRIRADGVVDCARGQSAHSLL | 104 |
| hFGF19-N71 | RPLAFSDAGPHVHYGWGDPIRLRHLYTSGPHGLSSCFLRIRADGVVDCARGQSAHSLLEIKAVALRTVAIK | 105 |
| hFGF19-N72 | RPLAFSDAGPHVHYGWGDPIRLRHLYTSGPHGLSSCFLRIRADGVVDCARGQSAHSLLEIKAVALRTVAIKG | 106 |
| hFGF19-N73 | RPLAFSDAGPHVHYGWGDPIRLRHLYTSGPHGLSSCFLRIRADGVVDCARGQSAHSLLEIKAVALRTVAIKGV | 107 |
| hFGF19-N78 | RPLAFSDAGPHVHYGWGDPIRLRHLYTSGPHGLSSCFLRIRADGVVDCARGQSAHSLLEIKAVALRTVAIKGVHSVRY | 108 |
| hFGF19-N79 | RPLAFSDAGPHVHYGWGDPIRLRHLYTSGPHGLSSCFLRIRADGVVDCARGQSAHSLLEIKAVALRTVAIKGVHSVRYL | 109 |
| hFGF19-N80 | RPLAFSDAGPHVHYGWGDPIRLRHLYTSGPHGLSSCFLRIRADGVVDCARGQSAHSLLEIKAVALRTVAIKGVHSVRYLC | 110 |
| hFGF19-N142 | RPLAFSDAGPHVHYGWGDPIRLRHLYTSGPHGLSSCFLRIRADGVVDCARGQSAHSLLEIKAVALRTVAIKGVHSVRYLCMGADGKMQGLLQYSEEDCAFEEEIRPDGYNVYRSEKHRLPVSLSSAKQRQLYKNRGFLPLSH | 111 |
| hFGF19-N143 | RPLAFSDAGPHVHYGWGDPIRLRHLYTSGPHGLSSCFLRIRADGVVDCARGQSAHSLLEIKAVALRTVAIKGVHSVRYLCMGADGKMQGLLQYSEEDCAFEEEIRPDGYNVYRSEKHRLPVSLSSAKQRQLYKNRGFLPLSHF | 112 |
| hFGF19-N144 | RPLAFSDAGPHVHYGWGDPIRLRHLYTSGPHGLSSCFLRIRADGVVDCARGQSAHSLLEIKAVALRTVAIKGVHSVRYLCMGADGKMQGLLQYSEEDCAFEEEIRPDGYNVYRSEKHRLPVSLSSAKQRQLYKNRGFLPLSHFL | 113 |
| hFGF19-N145 | RPLAFSDAGPHVHYGWGDPIRLRHLYTSGPHGLSSCFLRIRADGVVDCARGQSAHSLLEIKAVALRTVAIKGVHSVRYLCMGADGKMQGLLQYSEEDCAFEEEIRPDGYNVYRSEKHRLPVSLSSAKQRQLYKNRGFLPLSHFLP | 114 |

Examples of C-terminal portions of hFGF21 polypeptide sequence referred to in the present invention include, without limitation, those that have a final position that correspond to or about any one of positions 8, 9, 21, 22, 23, 24, 35, 36, 37, 38, 39, 40, 47, 48, 49, 51, 52, 53, 54, 67, 68, 69, 146, 147, 148 and 149 of SEQ ID NO:2. Each exemplary C-terminal portion also has a final position that corresponds to or about position 181 of SEQ ID NO:2. Table 5 shows a list of exemplary C-terminal portions of hFGF21. Other analogous portions of hFGF21 are also contemplated herein.

TABLE 5

Exemplary C-Terminal Portions of hFGF21 Polypeptide Sequence

| Name | Amino Acid Sequence (N-C) | SEQ ID NO |
|---|---|---|
| hFGF21-C8 | PLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS | 115 |
| hFGF21-C9 | LLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS | 116 |
| hFGF21-C21 | LYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS | 117 |
| hFGF21-C22 | YTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS | 118 |

TABLE 5-continued

Exemplary C-Terminal Portions of hFGF21 Polypeptide Sequence

| Name | Amino Acid Sequence (N-C) | SEQ ID NO |
|---|---|---|
| hFGF21-C23 | TDDAQQTEAHLEIREDGTVGGAADQSPESLLQLKALKPGVIQILGV KTSRFLCQRPDGALYGSLHFDPEACSFRELLLEDGYNVYQSEAHGL PLHLPGNKSPHRDPAPRGPARFLPLPGLPPALPEPPGILAPQPPDVGSS SDPLSMVGPSQGRSPSYAS | 119 |
| hFGF21-C24 | DDAQQTEAHLEIREDGTVGGAADQSPESLLQLKALKPGVIQILGVK TSRFLCQRPDGALYGSLHFDPEACSFRELLLEDGYNVYQSEAHGLP LHLPGNKSPHRDPAPRGPARFLPLPGLPPALPEPPGILAPQPPDVGSS DPLSMVGPSQGRSPSYAS | 120 |
| hFGF21-C35 | IREDGTVGGAADQSPESLLQLKALKPGVIQILGVKTSRFLCQRPDGA LYGSLHFDPEACSFRELLLEDGYNVYQSEAHGLPLHLPGNKSPHRD PAPRGPARFLPLPGLPPALPEPPGILAPQPPDVGSSDPLSMVGPSQGR SPSYAS | 121 |
| hFGF21-C36 | REDGTVGGAADQSPESLLQLKALKPGVIQILGVKTSRFLCQRPDGA LYGSLHFDPEACSFRELLLEDGYNVYQSEAHGLPLHLPGNKSPHRD PAPRGPARFLPLPGLPPALPEPPGILAPQPPDVGSSDPLSMVGPSQGR SPSYAS | 122 |
| hFGF21-C37 | EDGTVGGAADQSPESLLQLKALKPGVIQILGVKTSRFLCQRPDGAL YGSLHFDPEACSFRELLLEDGYNVYQSEAHGLPLHLPGNKSPHRDP APRGPARFLPLPGLPPALPEPPGILAPQPPDVGSSDPLSMVGPSQGRS PSYAS | 123 |
| hFGF21-C38 | DGTVGGAADQSPESLLQLKALKPGVIQILGVKTSRFLCQRPDGALY GSLHFDPEACSFRELLLEDGYNVYQSEAHGLPLHLPGNKSPHRDPA PRGPARFLPLPGLPPALPEPPGILAPQPPDVGSSDPLSMVGPSQGRSP SYAS | 124 |
| hFGF21-C39 | GTVGGAADQSPESLLQLKALKPGVIQILGVKTSRFLCQRPDGALYG SLHFDPEACSFRELLLEDGYNVYQSEAHGLPLHLPGNKSPHRDPAP RGPARFLPLPGLPPALPEPPGILAPQPPDVGSSDPLSMVGPSQGRSPS YAS | 125 |
| hFGF21-C40 | TVGGAADQSPESLLQLKALKPGVIQILGVKTSRFLCQRPDGALYGS LHFDPEACSFRELLLEDGYNVYQSEAHGLPLHLPGNKSPHRDPAPR GPARFLPLPGLPPALPEPPGILAPQPPDVGSSDPLSMVGPSQGRSPSY AS | 126 |
| hFGF21-C47 | QSPESLLQLKALKPGVIQILGVKTSRFLCQRPDGALYGSLHFDPEAC SFRELLLEDGYNVYQSEAHGLPLHLPGNKSPHRDPAPRGPARFLPLP GLPPALPEPPGILAPQPPDVGSSDPLSMVGPSQGRSPSYAS | 127 |
| hFGF21-C48 | SPESLLQLKALKPGVIQILGVKTSRFLCQRPDGALYGSLHFDPEACS FRELLLEDGYNVYQSEAHGLPLHLPGNKSPHRDPAPRGPARFLPLP GLPPALPEPPGILAPQPPDVGSSDPLSMVGPSQGRSPSYAS | 128 |
| hFGF21-C49 | PESLLQLKALKPGVIQILGVKTSRFLCQRPDGALYGSLHFDPEACSF RELLLEDGYNVYQSEAHGLPLHLPGNKSPHRDPAPRGPARFLPLPG LPPALPEPPGILAPQPPDVGSSDPLSMVGPSQGRSPSYAS | 129 |
| hFGF21-C51 | SLLQLKALKPGVIQILGVKTSRFLCQRPDGALYGSLHFDPEACSFRE LLLEDGYNVYQSEAHGLPLHLPGNKSPHRDPAPRGPARFLPLPGLP PALPEPPGILAPQPPDVGSSDPLSMVGPSQGRSPSYAS | 130 |
| hFGF21-C52 | LLQLKALKPGVIQILGVKTSRFLCQRPDGALYGSLHFDPEACSFREL LLEDGYNVYQSEAHGLPLHLPGNKSPHRDPAPRGPARFLPLPGLPP ALPEPPGILAPQPPDVGSSDPLSMVGPSQGRSPSYAS | 131 |
| hFGF21-C53 | LQLKALKPGVIQILGVKTSRFLCQRPDGALYGSLHFDPEACSFRELL LEDGYNVYQSEAHGLPLHLPGNKSPHRDPAPRGPARFLPLPGLPPA LPEPPGILAPQPPDVGSSDPLSMVGPSQGRSPSYAS | 132 |
| hFGF21-C54 | QLKALKPGVIQILGVKTSRFLCQRPDGALYGSLHFDPEACSFRELLL EDGYNVYQSEAHGLPLHLPGNKSPHRDPAPRGPARFLPLPGLPPAL PEPPGILAPQPPDVGSSDPLSMVGPSQGRSPSYAS | 133 |
| hFGF21-C67 | GVKTSRFLCQRPDGALYGSLHFDPEACSFRELLLEDGYNVYQSEAH GLPLHLPGNKSPHRDPAPRGPARFLPLPGLPPALPEPPGILAPQPPDV GSSDPLSMVGPSQGRSPSYAS | 134 |
| hFGF21-C68 | VKTSRFLCQRPDGALYGSLHFDPEACSFRELLLEDGYNVYQSEAHG LPLHLPGNKSPHRDPAPRGPARFLPLPGLPPALPEPPGILAPQPPDVG SSDPLSMVGPSQGRSPSYAS | 135 |

TABLE 5-continued

Exemplary C-Terminal Portions of hFGF21 Polypeptide Sequence

| Name | Amino Acid Sequence (N-C) | SEQ ID NO |
|---|---|---|
| hFGF21-C69 | KTSRFLCQRPDGALYGSLHFDPEACSFRELLLEDGYNVYQSEAHGL PLHLPGNKSPHRDPAPRGPARFLPLPGLPPALPEPPGILAPQPPDVGS SDPLSMVGPSQGRSPSYAS | 136 |
| hFGF21-C74 | LCQRPDGALYGSLHFDPEACSFRELLLEDGYNVYQSEAHGLPLHLP GNKSPHRDPAPRGPARFLPLPGLPPALPEPPGILAPQPPDVGSSDPLS MVGPSQGRSPSYAS | 137 |
| hFGF21-C75 | CQRPDGALYGSLHFDPEACSFRELLLEDGYNVYQSEAHGLPLHLPG NKSPHRDPAPRGPARFLPLPGLPPALPEPPGILAPQPPDVGSSDPLSM VGPSQGRSPSYAS | 138 |
| hFGF21-C76 | QRPDGALYGSLHFDPEACSFRELLLEDGYNVYQSEAHGLPLHLPGN KSPHRDPAPRGPARFLPLPGLPPALPEPPGILAPQPPDVGSSDPLSMV GPSQGRSPSYAS | 139 |
| hFGF21-C146 | FLPLPGLPPALPEPPGILAPQPPDVGSSDPLSMVGPSQGRSPSYAS | 140 |
| hFGF21-C147 | LPLPGLPPALPEPPGILAPQPPDVGSSDPLSMVGPSQGRSPSYAS | 141 |
| hFGF21-C148 | PLPGLPPALPEPPGILAPQPPDVGSSDPLSMVGPSQGRSPSYAS | 142 |
| hFGF21-C149 | LPGLPPALPEPPGILAPQPPDVGSSDPLSMVGPSQGRSPSYAS | 143 |

In some embodiments of a chimeric FGF19 polypeptide of the present invention, the N-terminal portion of its sequence includes a sequence that is selected from the hFGF19 polypeptide sequence portions listed in Table 4, and the C-terminal portion of its sequence includes a sequence that is selected from among the hFGF21 polypeptide sequence portions listed in Table 5. In some embodiments, the selected hFGF19 N-terminal portion and the selected hFGF21 C-terminal portion are selected independently with respect to each other. In some embodiments, the hFGF19 N-terminal sequence portion and the hFGF21 C-terminal sequence portion are selected such that the C-terminus of the N-terminal sequence portion and the N-terminus end of the C-terminal sequence portion have at least 1, at least 2 or at least 3 or more residues in common. In some embodiments, the sequence of the chimeric FGF19 polypeptide comprises a sequence in which the N-terminal portion of a FGF19 polypeptide sequence and the C-terminal portion of the chimeric FGF21 polypeptide sequence are contiguous without intervening amino acids therebetween. In some embodiments, the sequence of the chimeric FGF19 polypeptide comprises a sequence in which the N-terminal portion of a FGF19 polypeptide sequence and the C-terminal portion of the chimeric FGF21 polypeptide sequence are contiguously joined by overlapping the 1, 2, 3 or more residues in common between the two portions. In some alternative embodiments, the sequence of the chimeric FGF19 polypeptide comprises a sequence in which includes the N-terminal portion of a FGF19 polypeptide sequence and the C-terminal portion of the chimeric FGF21 polypeptide sequence, and further includes an intervening spacer therebetween of 1, 2, 3, 4, 5 or more amino residues.

Exemplary sequences of chimeric FGF19 polypeptides of the present invention are shown in Table 6, wherein its N-terminal portion includes an N-terminal portion of a hFGF19 polypeptide sequence and its C-terminal portion includes a C-terminal portion of a hFGF21 polypeptide sequence.

TABLE 6

Exemplary Chimeric FGF19 Polypeptide Sequences

| Name | Amino Acid Sequence (N-C) | SEQ ID NO |
|---|---|---|
| cFGF19/21-1 | RPLAFSDAG<br>PLLQFGGQVRQRYLYTDDAQQTEAHLEIREDGTVGGAADQSPESL LQLKALKPGVIQILGVKTSRFLCQRPDGALYGSLHFDPEACSFRELL LEDGYNVYQSEAHGLPLHLPGNKSPHRDPAPRGPARFLPLPGLPPA LPEPPGILAPQPPDVGSSDPLSMVGPSQGRSPSYAS | 144 |
| cFGF19/21-2 | RPLAFSDAGPHVHYGWGDPIRLRH<br>LYTDDAQQTEAHLEIREDGTVGGAADQSPESLLQLKALKPGVIQIL GVKTSRFLCQRPDGALYGSLHFDPEACSFRELLLEDGYNVYQSEAH GLPLHLPGNKSPHRDPAPRGPARFLPLPGLPPALPEPPGILAPQPPDV GSSDPLSMVGPSQGRSPSYAS | 145 |
| cFGF19/21-3 | RPLAFSDAGPHVHYGWGDPIRLRHLYTSGPHGLSSCFLR<br>IREDGTVGGAADQSPESLLQLKALKPGVIQILGVKTSRFLCQRPDGA LYGSLHFDPEACSFRELLLEDGYNVYQSEAHGLPLHLPGNKSPHRD | 146 |

TABLE 6-continued

Exemplary Chimeric FGF19 Polypeptide Sequences

| Name | Amino Acid Sequence (N-C) | SEQ ID NO |
|---|---|---|
| | PAPRGPARFLPLPGLPPALPEPPGILAPQPPDVGSSDPLSMVGPSQGR SPSYAS | |
| cFGF19/21-4 | RPLAFSDAGPHVHYGWGDPIRLRHLYTSGPHGLSSCFLRIRA DGTVGGAADQSPESLLQLKALKPGVIQILGVKTSRFLCQRPDGALY GSLHFDPEACSFRELLLEDGYNVYQSEAHGLPLHLPGNKSPHRDPA PRGPARFLPLPGLPPALPEPPGILAPQPPDVGSSDPLSMVGPSQGRSP SYAS | 147 |
| cFGF19/21-5 | RPLAFSDAGPHVHYGWGDPIRLRHLYTSGPHGLSSCFLRIRADG VVDCARG QSPESLLQLKALKPGVIQILGVKTSRFLCQRPDGALYGSLHFDPEAC SFRELLLEDGYNVYQSEAHGLPLHLPGNKSPHRDPAPRGPARFLPLP GLPPALPEPPGILAPQPPDVGSSDPLSMVGPSQGRSPSYAS | 148 |
| cFGF19/21-6 | RPLAFSDAGPHVHYGWGDPIRLRHLYTSGPHGLSSCFLRIRADG VVDCARGQSAH SLLQLKALKPGVIQILGVKTSRFLCQRPDGALYGSLHFDPEACSFRE LLLEDGYNVYQSEAHGLPLHLPGNKSPHRDPAPRGPARFLPLPGLP PALPEPPGILAPQPPDVGSSDPLSMVGPSQGRSPSYAS | 149 |
| cFGF19/21-7 | RPLAFSDAGPHVHYGWGDPIRLRHLYTSGPHGLSSCFLRIRADG VVDCARGQSAHSLLEIKAVALRTVAIK GVKTSRFLCQRPDGALYGSLHFDPEACSFRELLLEDGYNVYQSEAH GLPLHLPGNKSPHRDPAPRGPARFLPLPGLPPALPEPPGILAPQPPDV GSSDPLSMVGPSQGRSPSYAS | 150 |
| cFGF19/21-8 | RPLAFSDAGPHVHYGWGDPIRLRHLYTSGPHGLSSCFLRIRADG VVDCARGQSAHSLLEIKAVALRTVAIKGVHSVRY LCQRPDGALYGSLHFDPEACSFRELLLEDGYNVYQSEAHGLPLHLP GNKSPHRDPAPRGPARFLPLPGLPPALPEPPGILAPQPPDVGSSDPLS MVGPSQGRSPSYAS | 151 |
| cFGF19/21-9 | RPLAFSDAGPHVHYGWGDPIRLRHLYTSGPHGLSSCFLRIRADG VVDCARGQSAHSLLEIKAVALRTVAIKGVHSVRYLCMGADGK MQGLLQYSEEDCAFEEEIRPDGYNVYRSEKHRLPVSLSSAKQR QLYKNRGFLPLSH FLPLPGLPPALPEPPGILAPQPPDVGSSDPLSMVGPSQGRSPSYAS | 152 |
| cFGF19/21-10 (Construct 8 shown in FIG. 18B) | RPLAFSDAGPHVHYGWGDPIRLRHLYTSGPHGLSSCFLRIRADG VVDCARGQSAHSLLEIKAVALRTVAIKGVHSVRYLCMGADGK MQGLLQYSEEDCAFEEEIRPDGYNVYRSEKHRLPVSLSSAKQR QLYKNRGFLPLSHFLP LPGLPPALPEPPGILAPQPPDVGSSDPLSMVGPSQGRSPSYAS | 271 |
| cFGF19/21-11 (Construct 9 shown in FIG. 18B) | RPLAFSDAGPHVHYGWGDPIRLRHLYTSGPHGLSSCFLRIRADG VVDCARGQSAHSLLEIKAVALRTVAIKGV KTSRFLCQRPDGALYGSLHFDPEACSFRELLLEDGYNVYQSE AHGLPLHLPGNKSPHRDPAPRGPARFLPLPGLPPALPEPPGILAPQPP DVGSSDPLSMVGPSQGRSPSYAS | 272 |
| cFGF19/21-12 (Construct 10 shown in FIG. 18B) | RPLAFSDAGPHVHYGWGDPIRLRHLYTSGPHGLSSCFLRIRADG VVDCARGQSAHSLL QLKALKPGVIQILGVKTSRFLCQRPDGALYGSLHFDPEACSFRELLL EDGYNVYQSEAHGLPLHLPGNKSPHRDPAPRGPARFLPLPGLPPAL PEPPGILAPQPPDVGSSDPLSMVGPSQGRSPSYAS | 273 |
| cFGF19/21-13 (Construct 11 shown in FIG. 18B) | RPLAFSDAGPHVHYGWGDPIRLRHLYTSGPHGLSSCFLRIRADG VVDCARGQS PESLLQLKALKPGVIQILGVKTSRFLCQRPDGALYGSLHFDPEACSF RELLLEDGYNVYQSEAHGLPLHLPGNKSPHRDPAPRGPARFLPLPG LPPALPEPPGILAPQPPDVGSSDPLSMVGPSQGRSPSYAS | 274 |
| cFGF19/21-14 (Construct 12 shown in FIG. 18B) | RPLAFSDAGPHVHYGWGDPIRLRHLYTSGPHGLSSCFLRIRADG TVGGAADQSPESLLQLKALKPGVIQILGVKTSRFLCQRPDGALYGS LHFDPEACSFRELLLEDGYNVYQSEAHGLPLHLPGNKSPHRDPAPR GPARFLPLPGLPPALPEPPGILAPQPPDVGSSDPL SMVGPSQGRSPSYAS | 275 |
| cFGF19/21-15 (Construct 13 shown in FIG. 18B) | RPLAFSDAGPHVHYGWGDPIRLRHLYTSGPHGLSSCFLRIR EDGTVGGAADQSPESLLQLKALKPGVIQILGVKTSRFLCQRPDGAL YGSLHFDPEACSFRELLLEDGYNVYQSEAHGLPLHLPGNKSPHRDP APRGPARFLPLPGLPPALPEPPGILAPQPPDVGSSDPLSMVGPSQGRS PSYAS | 276 |

TABLE 6-continued

Exemplary Chimeric FGF19 Polypeptide Sequences

| Name | Amino Acid Sequence (N-C) | SEQ ID NO |
|---|---|---|
| cFGF19/21-16 (Construct 14 shown in FIG. 18B) | RPLAFSDAGPHVHYGWGDPIRLRHLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS | 277 |
| cFGF19/21-17 (Construct 15 shown in FIG. 18B) | RPLAFSDAGPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS | 278 |

III. Chimeric FGF19 Polypeptides with Substituting FGF21 Polypeptide Sequences In a third aspect of the present invention, a chimeric FGF19 polypeptide sequence includes a first polypeptide sequence in which a portion of first polypeptide sequence is substituted with a portion of a second polypeptide sequence. In preferred embodiments, the first polypeptide is human FGF19 (hFGF19) polypeptide whose sequence is defined in SEQ ID NO:1. In some embodiments, the first polypeptide sequence is a polypeptide sequence that has at least 80%, at least 85%, at least 90%, at least 95%, at least 97% or at least 99% amino acid sequence identity to the hFGF19 polypeptide sequence.

In certain preferred embodiments, the second polypeptide is human FGF21 (hFGF21) polypeptide whose sequence is defined in SEQ ID NO:2. In some embodiments, the FGF21 polypeptide sequence is a polypeptide sequence that has at least 80%, at least 85%, at least 90%, at least 95%, at least 97% or at least 99% amino acid sequence identity to the hFGF21 polypeptide sequence.

In some embodiments, the sequence of the chimeric FGF19 polypeptide includes a hFGF19 polypeptide sequence in which the portion to be substituted is from a group that include, without limitation, portions that have (i) a first position that corresponds to or about any one of positions 1, 10, 11, 17, 18, 21, 22, 25, 26, 27, 28, 40, 41, 42, 43, 44, 45, 52, 53, 54, 56, 57, 58, 59, 63, 72, 73, 74, 79, 80, 81, 143, 144, 145 and 146 in SEQ ID NO:1, and (ii) a final position that corresponds to or about any one of positions 9, 10, 24, 25, 26, 27, 29, 31, 32, 34, 36, 39, 40, 41, 42, 43, 44, 51, 52, 53, 55, 56, 57, 58, 66, 71, 72, 73, 78, 79, 80, 142, 143, 144, 145 and 194 in SEQ ID NO:1, such that the final position is C-terminal to the first position and the positions are selected independently. Table 7 shows a list of exemplary portions of the hFGF19 polypeptide sequence that are to be substituted for a portion of the hFGF21 polypeptide sequence.

TABLE 7

Exemplary Substituted Portions of the hFGF19 Polypeptide Sequence

| Name | Amino Acid Sequence (N-C) | SEQ ID NO |
|---|---|---|
| hFGF19-S10-27 | PHVHYGWGDPIRLRHLYT | 153 |
| hFGF19-S10-29 | PHVHYGWGDPIRLRHLYTSG | 154 |
| hFGF19-S10-31 | PHVHYGWGDPIRLRHLYTSGPH | 155 |
| hFGF19-S10-32 | PHVHYGWGDPIRLRHLYTSGPHG | 156 |
| hFGF19-S10-34 | PHVHYGWGDPIRLRHLYTSGPHGLS | 157 |
| hFGF19-S10-36 | PHVHYGWGDPIRLRHLYTSGPHGLSSC | 158 |
| hFGF19-S10-41 | PHVHYGWGDPIRLRHLYTSGPHGLSSCFLRIR | 159 |
| hFGF19-S10-44 | PHVHYGWGDPIRLRHLYTSGPHGLSSCFLRIRADG | 160 |
| hFGF19-S10-52 | PHVHYGWGDPIRLRHLYTSGPHGLSSCFLRIRADGVVDCARGQS | 161 |
| hFGF19-S10-58 | PHVHYGWGDPIRLRHLYTSGPHGLSSCFLRIRADGVVDCARGQSAHSLL | 162 |
| hFGF19-S10-73 | PHVHYGWGDPIRLRHLYTSGPHGLSSCFLRIRADGVVDCARGQSAHSLLEIKAVALRTVAIKGV | 163 |
| hFGF19-S17-27 | GDPIRLRHLYT | 164 |
| hFGF19-S17-29 | GDPIRLRHLYTSG | 165 |
| hFGF19-S17-31 | GDPIRLRHLYTSGPH | 166 |
| hFGF19-S17-32 | GDPIRLRHLYTSGPHG | 167 |
| hFGF19-S17-34 | GDPIRLRHLYTSGPHGLS | 168 |
| hFGF19-S17-36 | GDPIRLRHLYTSGPHGLSSC | 169 |
| hFGF19-S21-27 | RLRHLYT | 170 |
| hFGF19-S21-29 | RLRHLYTSG | 171 |

TABLE 7-continued

Exemplary Substituted Portions of the hFGF19 Polypeptide Sequence

| Name | Amino Acid Sequence (N-C) | SEQ ID NO |
|---|---|---|
| hFGF19-S21-31 | RLRHLYTSGPH | 172 |
| hFGF19-S21-32 | RLRHLYTSGPHG | 173 |
| hFGF19-S21-34 | RLRHLYTSGPHGLS | 174 |
| hFGF19-S21-36 | RLRHLYTSGPHGLSSC | 175 |
| hFGF19-S25-41 | LYTSGPHGLSSCFLRIR | 176 |
| hFGF19-S25-44 | LYTSGPHGLSSCFLRIRADG | 177 |
| hFGF19-S25-52 | LYTSGPHGLSSCFLRIRADGVVDCARGQS | 178 |
| hFGF19-S25-58 | LYTSGPHGLSSCFLRIRADGVVDCARGQSAHSLL | 179 |
| hFGF19-S25-73 | LYTSGPHGLSSCFLRIRADGVVDCARGQSAHSLLEIKAVALRTVAIKGV | 180 |
| hFGF19-S63-66 | VALR | 181 |

The substituted portion of the hFGF19 polypeptide sequence is substituted with a portion of the hFGF21 polypeptide sequence. Exemplary substituting portions of the hFGF21 polypeptide sequence include, without limitation, portions that have (i) a first position that corresponds to or about any one of positions 1, 8, 9, 13, 14, 17, 18, 21, 22, 23, 24, 35, 36, 37, 38, 39, 40, 47, 48, 49, 51, 52, 53, 54, 58, 67, 68, 69, 74, 75, 76, 136, 137, 138 and 139 in SEQ ID NO:2, and (ii) a final position that corresponds to or about any one of positions 7, 8, 20, 21, 22, 23, 24, 25, 27, 29, 31, 34, 35, 36, 37, 38, 39, 46, 47, 48, 50, 51, 52, 53, 61, 66, 67, 68, 73, 74, 75, 135, 136, 137, 138 and 181 in SEQ ID NO:2, such that the final position is C-terminal to the first position and the positions are selected independently. Table 8 shows a list of exemplary portions of hFGF21 polypeptide sequence that are to substitute for a portion of the hFGF19 polypeptide sequence.

TABLE 8

Exemplary Substituting Portions From hFGF21 Polypeptide Sequence

| Name | Amino Acid Sequence (N-C) | SEQ ID NO |
|---|---|---|
| hFGF21-S8-23 | PLLQFGGQVRQRYLYT | 182 |
| hFGF21-S8-25 | PLLQFGGQVRQRYLYTDD | 183 |
| hFGF21-S8-27 | PLLQFGGQVRQRYLYTDDAQ | 184 |
| hFGF21-S8-29 | PLLQFGGQVRQRYLYTDDAQQT | 185 |
| hFGF21-S8-31 | PLLQFGGQVRQRYLYTDDAQQTEA | 186 |
| hFGF21-S8-36 | PLLQFGGQVRQRYLYTDDAQQTEAHLEIR | 187 |
| hFGF21-S8-39 | PLLQFGGQVRQRYLYTDDAQQTEAHLEIREDG | 188 |
| hFGF21-S8-48 | PLLQFGGQVRQRYLYTDDAQQTEAHLEIREDGTVGGAADQS | 189 |
| hFGF21-S8-53 | PLLQFGGQVRQRYLYTDDAQQTEAHLEIREDGTVGGAADQSPESLL | 190 |
| hFGF21-S8-68 | PLLQFGGQVRQRYLYTDDAQQTEAHLEIREDGTVGGAADQSPESLLQLKALKPGV | 191 |
| hFGF21-S13-23 | GGQVRQRYLYT | 192 |
| hFGF21-S13-25 | GGQVRQRYLYTDD | 193 |
| hFGF21-S13-27 | GGQVRQRYLYTDDAQ | 194 |
| hFGF21-S13-29 | GGQVRQRYLYTDDAQQT | 195 |
| hFGF21-S13-31 | GGQVRQRYLYTDDAQQTEA | 196 |
| hFGF21-S17-23 | RQRYLYT | 197 |
| hFGF21-S17-25 | RQRYLYTDD | 198 |
| hFGF21-S17-27 | RQRYLYTDDAQ | 199 |
| hFGF21-S17-29 | RQRYLYTDDAQQT | 200 |
| hFGF21-S17-31 | RQRYLYTDDAQQTEA | 201 |
| hFGF21-S21-36 | LYTDDAQQTEAHLEIR | 202 |
| hEGF21-S21-39 | LYTDDAQQTEAHLEIREDG | 203 |
| hEGF21-S21-48 | LYTDDAQQTEAHLEIREDGTVGGAADQS | 204 |
| hEGF21-S21-53 | LYTDDAQQTEAHLEIREDGTVGGAADQSPESLL | 205 |
| hEGF21-S21-68 | LYTDDAQQTEAHLEIREDGTVGGAADQSPESLLQLKALKPGV | 206 |
| hFGF21-S58-62 | LKPG | 207 |

In some embodiments, a chimeric FGF19 polypeptide includes the polypeptide sequence of hFGF19 with a portion of its sequence, such as a sequence selected from the hFGF19 polypeptide sequence portions listed in Table 7, substituted with a portion of the hFGF21 polypeptide sequence, such as the sequence portions listed in Table 8. In some embodiments, the selected hFGF19 N-terminal portion and the selected hFGF21 C-terminal portion are selected independently with respect to each other. In some embodiments, the hFGF19 portion to be substituted includes the N-terminal residue of the hFGF19 polypeptide. In some embodiments, the hFGF19 portion to be substituted includes the C-terminal residue of the hFGF19 polypeptide. In some embodiments, the substituting hFGF21 portion includes the N-terminal residue of the hFGF21 polypeptide. In some embodiments, the substituting hFGF21 portion includes the C-terminal residue of the hFGF21 polypeptide. In some embodiments, the hFGF19 portion to be substituted includes the N-terminal residue of the hFGF19 polypeptide, and the substituting hFGF21 portion also includes the N-terminal residue of the hFGF21 polypeptide. In some embodiments, the hFGF19 portion to be substituted includes the C-terminal residue of the hFGF19 polypeptide, and the substituting hFGF21 portion also includes the C-terminal residue of the hFGF21 polypeptide.

In some embodiments, the hFGF19 sequence portion and the hFGF21 sequence portion are selected such that at least one of their respective corresponding ends (e.g., the N-terminal end of the hFGF19 portion and the N-terminal end of the hFGF21 portion, the C-terminal end of the hFGF19 portion and the C-terminal end of the hFGF21 portion, or both) have at least 1, at least 2 or at least 3 or more residues in common at said corresponding ends. In some embodiments, the sequence of the chimeric FGF19 polypeptide comprises a sequence in which the substituting portion of the hFGF21 polypeptide sequence is contiguous with the remaining hFGF19 polypeptide sequence by overlapping the 1, 2, 3 or more residues in common between the two portions.

In some embodiments, the sequence of the chimeric FGF19 polypeptide comprises a sequence in which the portion of the hFGF21 polypeptide sequence is substituted in the hFGF19 polypeptide sequence such that the hFGF19 and hFGF21 polypeptide sequences are contiguous and without additional, intervening amino acids therebetween. In some alternative embodiments, the sequence of the chimeric FGF19 polypeptide comprises a sequence in which the portion of the hFGF21 polypeptide sequence is substituted in the hFGF19 polypeptide sequence such that the chimeric FGF19 polypeptide sequence further includes an intervening spacer therebetween of 1, 2, 3, 4, 5 or more amino residues between the hFGF19 and hFGF21 sequences.

Exemplary sequences of chimeric FGF19 polypeptides of the present invention are shown in Table 9, in which a portion of hFGF19 is substituted with a portion of hFGF21.

TABLE 9

Exemplary Chimeric FGF19 Polypeptide Sequences

| Name | Amino Acid Sequence (N-C) | SEQ ID NO |
|---|---|---|
| cFGF19/21/19-1 | RPLAFSDAGPLLQFGGQVRQRYLYTSGPHGLSSCFLRIRADGVVDCARGQSAHSLLEIKAVALRTVAIKGVHSVRYLCMGADGKMQGLLQYSEEDCAFEEEIRPDGYNVYRSEKHRLPVSLSSAKQRQLYKNRGFLPLSHFLPMLPMVPEEPEDLRGHLESDMFSSPLETDSMDPFGLVTGLEAVRSPSFEK | 208 |
| cFGF19/21/19-2 | RPLAFSDAGPLLQFGGQVRQRYLYTDDPHGLSSCFLRIRADGVVDCARGQSAHSLLEIKAVALRTVAIKGVHSVRYLCMGADGKMQGLLQYSEEDCAFEEEIRPDGYNVYRSEKHRLPVSLSSAKQRQLYKNRGFLPLSHFLPMLPMVPEEPEDLRGHLESDMFSSPLETDSMDPFGLVTGLEAVRSPSFEK | 209 |
| cFGF19/21/19-3 | RPLAFSDAGPLLQFGGQVRQRYLYTDDAQGLSSCFLRIRADGVVDCARGQSAHSLLEIKAVALRTVAIKGVHSVRYLCMGADGKMQGLLQYSEEDCAFEEEIRPDGYNVYRSEKHRLPVSLSSAKQRQLYKNRGFLPLSHFLPMLPMVPEEPEDLRGHLESDMFSSPLETDSMDPFGLVTGLEAVRSPSFEK | 210 |
| cFGF19/21/19-4 | RPLAFSDAGPLLQFGGQVRQRYLYTDDAQLSSCFLRIRADGVVDCARGQSAHSLLEIKAVALRTVAIKGVHSVRYLCMGADGKMQGLLQYSEEDCAFEEEIRPDGYNVYRSEKHRLPVSLSSAKQRQLYKNRGFLPLSHFLPMLPMVPEEPEDLRGHLESDMFSSPLETDSMDPFGLVTGLEAVRSPSFEK | 211 |
| cFGF19/21/19-5 | RPLAFSDAGPLLQFGGQVRQRYLYTDDAQQTSCFLRIRADGVVDCARGQSAHSLLEIKAVALRTVAIKGVHSVRYLCMGADGKMQGLLQYSEEDCAFEEEIRPDGYNVYRSEKHRLPVSLSSAKQRQLYKNRGFLPLSHFLPMLPMVPEEPEDLRGHLESDMFSSPLETDSMDPFGLVTGLEAVRSPSFEK | 212 |
| cFGF19/21/19-6 | RPLAFSDAGPLLQFGGQVRQRYLYTDDAQQTEAFLRIRADGVVDCARGQSAHSLLEIKAVALRTVAIKGVHSVRYLCMGADGKMQGLLQYSEEDCAFEEEIRPDGYNVYRSEKHRLPVSLSSAKQRQLYKNRGFLPLSHFLPMLPMVPEEPEDLRGHLESDMFSSPLETDSMDPFGLVTGLEAVRSPSFEK | 213 |
| cFGF19/21/19-7 | RPLAFSDAGPLLQFGGQVRQRYLYTDDAQQTEAHLEIRADGVVDCARGQSAHSLLEIKAVALRTVAIKGVHSVRYLCMGADGKMQGLLQYSEEDCAFEEEIRPDGYNVYRSEKHRLPVSLSSAKQRQLYKNRGFLPLSHFLPMLPMVPEEPEDLRGHLESDMFSSPLETDSMDPFGLVTGLEAVRSPSFEK | 214 |
| cFGF19/21/19-8 | RPLAFSDAGPLLQFGGQVRQRYLYTDDAQQTEAHLEIREDGVVDCARGQSAHSLLEIKAVALRTVAIKGVHSVRYLCMGADGKMQGLLQYSEEDCAFEEEIRPDGYNVYRSEKHRLPVSLSSAKQRQLYKNRGFLPLS | 215 |

TABLE 9-continued

Exemplary Chimeric FGF19 Polypeptide Sequences

| Name | Amino Acid Sequence (N-C) | SEQ ID NO |
|---|---|---|
| | HFLPMLPMVPEEPEDLRGHLESDMFSSPLETDSMDPFGLVTGLEAVR SPSFEK | |
| cFGF19/21/19-9 | RPLAFSDAGPLLQFGGQVRQRYLYTDDAQQTEAHLEIREDGTVGGA ADQSAHSLLEIKAVALRTVAIKGVHSVRYLCMGADGKMQGLLQYS EEDCAFEEEIRPDGYNVYRSEKHRLPVSLSSAKQRQLYKNRGFLPLS HFLPMLPMVPEEPEDLRGHLESDMFSSPLETDSMDPFGLVTGLEAVR SPSFEK | 216 |
| cFGF19/21/19-10 | RPLAFSDAGPLLQFGGQVRQRYLYTDDAQQTEAHLEIREDGTVGGA ADQSPESLLEIKAVALRTVAIKGVHSVRYLCMGADGKMQGLLQYSE EDCAFEEEIRPDGYNVYRSEKHRLPVSLSSAKQRQLYKNRGFLPLSH FLPMLPMVPEEPEDLRGHLESDMFSSPLETDSMDPFGLVTGLEAVRS PSFEK | 217 |
| cFGF19/21/19-11 | RPLAFSDAGPLLQFGGQVRQRYLYTDDAQQTEAHLEIREDGTVGGA ADQSPESLLQLKALKPGVIQILGVHSVRYLCMGADGKMQGLLQYSE EDCAFEEEIRPDGYNVYRSEKHRLPVSLSSAKQRQLYKNRGFLPLSH FLPMLPMVPEEPEDLRGHLESDMFSSPLETDSMDPFGLVTGLEAVRS PSFEK | 218 |
| cFGF19/21/19-12 | RPLAFSDAGPHVHYGWGGQVRQRYLYTSGPHGLSSCFLRIRADGVV DCARGQSAHSLLEIKAVALRTVAIKGVHSVRYLCMGADGKMQGLL QYSEEDCAFEEEIRPDGYNVYRSEKHRLPVSLSSAKQRQLYKNRGFL PLSHFLPMLPMVPEEPEDLRGHLESDMFSSPLETDSMDPFGLVTGLE AVRSPSFEK | 219 |
| cFGF19/21/19-13 | RPLAFSDAGPHVHYGWGGQVRQRYLYTDDPHGLSSCFLRIRADGVV DCARGQSAHSLLEIKAVALRTVAIKGVHSVRYLCMGADGKMQGLL QYSEEDCAFEEEIRPDGYNVYRSEKHRLPVSLSSAKQRQLYKNRGFL PLSHFLPMLPMVPEEPEDLRGHLESDMFSSPLETDSMDPFGLVTGLE AVRSPSFEK | 220 |
| cFGF19/21/19-14 | RPLAFSDAGPHVHYGWGGQVRQRYLYTDDAQGLSSCFLRIRADGV VDCARGQSAHSLLEIKAVALRTVAIKGVHSVRYLCMGADGKMQGL LQYSEEDCAFEEEIRPDGYNVYRSEKHRLPVSLSSAKQRQLYKNRGF LPLSHFLPMLPMVPEEPEDLRGHLESDMFSSPLETDSMDPFGLVTGL EAVRSPSFEK | 221 |
| cFGF19/21/19-15 | RPLAFSDAGPHVHYGWGGQVRQRYLYTDDAQLSSCFLRIRADGVV DCARGQSAHSLLEIKAVALRTVAIKGVHSVRYLCMGADGKMQGLL QYSEEDCAFEEEIRPDGYNVYRSEKHRLPVSLSSAKQRQLYKNRGFL PLSHFLPMLPMVPEEPEDLRGHLESDMFSSPLETDSMDPFGLVTGLE AVRSPSFEK | 222 |
| cFGF19/21/19-16 | RPLAFSDAGPHVHYGWGGQVRQRYLYTDDAQQTSCFLRIRADGVV DCARGQSAHSLLEIKAVALRTVAIKGVHSVRYLCMGADGKMQGLL QYSEEDCAFEEEIRPDGYNVYRSEKHRLPVSLSSAKQRQLYKNRGFL PLSHFLPMLPMVPEEPEDLRGHLESDMFSSPLETDSMDPFGLVTGLE AVRSPSFEK | 223 |
| cFGF19/21/19-17 | RPLAFSDAGPHVHYGWGGQVRQRYLYTDDAQQTEAFLRIRADGVV DCARGQSAHSLLEIKAVALRTVAIKGVHSVRYLCMGADGKMQGLL QYSEEDCAFEEEIRPDGYNVYRSEKHRLPVSLSSAKQRQLYKNRGFL PLSHFLPMLPMVPEEPEDLRGHLESDMFSSPLETDSMDPFGLVTGLE AVRSPSFEK | 224 |
| cFGF19/21/19-18 | RPLAFSDAGPHVHYGWGDPIRQRYLYTSGPHGLSSCFLRIRADGVVD CARGQSAHSLLEIKAVALRTVAIKGVHSVRYLCMGADGKMQGLLQ YSEEDCAFEEEIRPDGYNVYRSEKHRLPVSLSSAKQRQLYKNRGFLP LSHFLPMLPMVPEEPEDLRGHLESDMFSSPLETDSMDPFGLVTGLEA VRSPSFEK | 225 |
| cFGF19/21/19-19 | RPLAFSDAGPHVHYGWGDPIRQRYLYTDDPHGLSSCFLRIRADGVV DCARGQSAHSLLEIKAVALRTVAIKGVHSVRYLCMGADGKMQGLL QYSEEDCAFEEEIRPDGYNVYRSEKHRLPVSLSSAKQRQLYKNRGFL PLSHFLPMLPMVPEEPEDLRGHLESDMFSSPLETDSMDPFGLVTGLE AVRSPSFEK | 226 |
| cFGF19/21/19-20 | RPLAFSDAGPHVHYGWGDPIRQRYLYTDDAQGLSSCFLRIRADGVV DCARGQSAHSLLEIKAVALRTVAIKGVHSVRYLCMGADGKMQGLL QYSEEDCAFEEEIRPDGYNVYRSEKHRLPVSLSSAKQRQLYKNRGFL PLSHFLPMLPMVPEEPEDLRGHLESDMFSSPLETDSMDPFGLVTGLE AVRSPSFEK | 227 |

TABLE 9-continued

Exemplary Chimeric FGF19 Polypeptide Sequences

| Name | Amino Acid Sequence (N-C) | SEQ ID NO |
|---|---|---|
| cFGF19/21/19-21 | RPLAFSDAGPHVHYGWGDPIRQRYLYTDDAQLSSCFLRIRADGVVDCARGQSAHSLLEIKAVALRTVAIKGVHSVRYLCMGADGKMQGLLQYSEEDCAFEEEIRPDGYNVYRSEKHRLPVSLSSAKQRQLYKNRGFLPLSHFLPMLPMVPEEPEDLRGHLESDMFSSPLETDSMDPFGLVTGLEAVRSPSFEK | 228 |
| cFGF19/21/19-22 | RPLAFSDAGPHVHYGWGDPIRQRYLYTDDAQQTSCFLRIRADGVVDCARGQSAHSLLEIKAVALRTVAIKGVHSVRYLCMGADGKMQGLLQYSEEDCAFEEEIRPDGYNVYRSEKHRLPVSLSSAKQRQLYKNRGFLPLSHFLPMLPMVPEEPEDLRGHLESDMFSSPLETDSMDPFGLVTGLEAVRSPSFEK | 229 |
| cFGF19/21/19-23 | RPLAFSDAGPHVHYGWGDPIRQRYLYTDDAQQTEAFLRIRADGVVDCARGQSAHSLLEIKAVALRTVAIKGVHSVRYLCMGADGKMQGLLQYSEEDCAFEEEIRPDGYNVYRSEKHRLPVSLSSAKQRQLYKNRGFLPLSHFLPMLPMVPEEPEDLRGHLESDMFSSPLETDSMDPFGLVTGLEAVRSPSFEK | 230 |
| cFGF19/21/19-24 | RPLAFSDAGPHVHYGWGDPIRLRHLYTDDAQQTEAHLEIRADGVVDCARGQSAHSLLEIKAVALRTVAIKGVHSVRYLCMGADGKMQGLLQYSEEDCAFEEEIRPDGYNVYRSEKHRLPVSLSSAKQRQLYKNRGFLPLSHFLPMLPMVPEEPEDLRGHLESDMFSSPLETDSMDPFGLVTGLEAVRSPSFEK | 231 |
| cFGF19/21/19-25 | RPLAFSDAGPHVHYGWGDPIRLRHLYTDDAQQTEAHLEIREDGVVDCARGQSAHSLLEIKAVALRTVAIKGVHSVRYLCMGADGKMQGLLQYSEEDCAFEEEIRPDGYNVYRSEKHRLPVSLSSAKQRQLYKNRGFLPLSHFLPMLPMVPEEPEDLRGHLESDMFSSPLETDSMDPFGLVTGLEAVRSPSFEK | 232 |
| cFGF19/21/19-26 | RPLAFSDAGPHVHYGWGDPIRLRHLYTDDAQQTEAHLEIREDGTVGGAADQSAHSLLEIKAVALRTVAIKGVHSVRYLCMGADGKMQGLLQYSEEDCAFEEEIRPDGYNVYRSEKHRLPVSLSSAKQRQLYKNRGFLPLSHFLPMLPMVPEEPEDLRGHLESDMFSSPLETDSMDPFGLVTGLEAVRSPSFEK | 233 |
| cFGF19/21/19-27 | RPLAFSDAGPHVHYGWGDPIRLRHLYTDDAQQTEAHLEIREDGTVGGAADQSPESLLEIKAVALRTVAIKGVHSVRYLCMGADGKMQGLLQYSEEDCAFEEEIRPDGYNVYRSEKHRLPVSLSSAKQRQLYKNRGFLPLSHFLPMLPMVPEEPEDLRGHLESDMFSSPLETDSMDPFGLVTGLEAVRSPSFEK | 234 |
| cFGF19/21/19-28 | RPLAFSDAGPHVHYGWGDPIRLRHLYTDDAQQTEAHLEIREDGTVGGAADQSPESLLQLKALKPGVIQILGVHSVRYLCMGADGKMQGLLQYSEEDCAFEEEIRPDGYNVYRSEKHRLPVSLSSAKQRQLYKNRGFLPLSHFLPMLPMVPEEPEDLRGHLESDMFSSPLETDSMDPFGLVTGLEAVRSPSFEK | 235 |
| cFGF19/21/19-29 | RPLAFSDAGPHVHYGWGDPIRLRHLYTSGPHGLSSCFLRIRADGVVDCARGQSAHSLLEIKALKPGTVAIKGVHSVRYLCMGADGKMQGLLQYSEEDCAFEEEIRPDGYNVYRSEKHRLPVSLSSAKQRQLYKNRGFLPLSHFLPMLPMVPEEPEDLRGHLESDMFSSPLETDSMDPFGLVTGLEAVRSPSFEK | 236 |

In some embodiments of any of the chimeric hFGF19, the chimeric hFGF19 polypeptide includes a first polypeptide sequence having at least a certain sequence identity to the sequence of hFGF19 polypeptide, and wherein a portion of the first polypeptide sequence is substituted with more than one portion of a second polypeptide sequence, the second polypeptide sequence having at least a certain sequence identity to the sequence of hFGF21 polypeptide. In some embodiments, the chimeric hFGF19 polypeptide further comprises a substitution of the β1-β2 loop of the first polypeptide, a substitution of the β10-β12 segment of the first polypeptide, and/or a substitution of the five residues WGDPI (SEQ ID NO:287) of the first polypeptide with the β1-β2 loop of the second polypeptide, the β10-β12 segment of the second polypeptide, and/or the corresponding sequence GQV of the second polypeptide. In some embodiments, the chimeric hFGF19 polypeptide further comprises a substitution of the β1-β2 loop (amino acid residues 50-57 of FGF19 (SGPHGLSS (SEQ ID NO:288)) of FGF19 with the β1-β2 loop (amino acid residues 51-57 of FGF21 (DDAQQTE (SEQ ID NO:289)) of FGF21. In some embodiments, the chimeric hFGF19 polypeptide further comprises a substitution of the β10-β12 segment (amino acid residues 146-162 of FGF19 (SSAKQRQLYKNRGFLPL (SEQ ID NO:290)) of FGF19 with the β10-β12 segment (amino acid residues 147-161 of FGF21 (PGNKSPHRDPAPRGP (SEQ ID NO:291)) of FGF21. In some embodiments, the chimeric hFGF19 polypeptide further comprises a substitution of amino acid residues 38-42 (WGDPI (SEQ ID NO:287)) of FGF19 with amino acid residues 41-43 (GQV) of FGF21.

Chimeric FGF19 polypeptides of the present invention, and particularly pharmaceutically active compositions thereof and methods of using said chimeric FGF19 polypeptides in therapeutic treatment of one or more of the diseases, conditions, etc. listed or described herein or known in the art have certain advantages over the use of either native FGF19 (e.g., hFGF19) or native FGF21 (e.g., hFGF21).

In some embodiments, chimeric FGF19 polypeptides may be less immunogenic than one or both of their native parental FGFs. A native FGF19 and/or FGF21 (such as hFGF19 or hFGF21) may be present in the population in more than one allelic variation, wherein there is at least one amino acid residue that is different between the allelic forms. For example, hFGF21 is known to have a polymorphism at position 146 in the mature form, where this is residue can be leucine (as in FIG. 2 and SEQ ID NO:2) or proline in different alleles. Such polymorphism may limit the usefulness of native hFGF21 as a therapeutic composition. For example, administering a FGF19 polypeptide to an individual, wherein the individual's endogenous FGF19 has a different sequence than the administered FGF19, may result in an immune response by the individual to the administered hFGF21. Thus, in some embodiments, a chimeric FGF19 polypeptide of the present invention may include a portion of the hFGF21 polypeptide sequence and a portion of the hFGF19 polypeptide sequence, wherein both portions include only portions of the respective polypeptide sequences that are non-polymorphic. This can be accomplished by, for example, substituting a polymorphic sequence portion of one FGF with the analogous, non-polymorphic portion of the other FGF polypeptide. For example, a chimeric FGF19 polypeptide of the present invention, such as cFGF21/19-2 (cf. Table 3) that includes a portion of hFGF21 but does not include position 146 lacks the polymorphism at this position. In this manner, chimeric FGF19 polypeptides of the present invention may be advantageously less immunogenic, and thus may be advantageously more suitable for administration in a wide range of individuals.

In some embodiments, chimeric FGF19 polypeptides may be less tumorigenic than one or both of their corresponding native FGFs. In particular, chimeric FGF19 polypeptides may be less tumorigenic than native hFGF19. Native hFGF19, as discussed hereinabove, demonstrates potential tumorigenic activity via its binding to FGFR4. This tumorigenic activity appears separable from hFGF19's metabolic effects, which, like hFGF21, are effected via Klotho-beta-dependent binding to FGFR1c, FGFR2c and/or FGFR3c. In some embodiments, chimeric FGF19 polypeptides of the present invention include a portion of the hFGF19 polypeptide sequence that does not include the FGFR4-effector motif, and are instead substituted with a corresponding sequence from hFGF21. In some embodiments, chimeric FGF19 polypeptides of the present invention no longer substantially binds to and/or substantially activates FGFR4. In some embodiments, chimeric FGF19 polypeptides of the present invention no longer substantially binds to and/or substantially activates a receptor, such as FGFR4, in a Klotho-beta-independent manner. In this manner, chimeric FGF19 polypeptides of the present invention may be advantageously less tumorigenic, and thus may be advantageously more suitable for administration in a wide range of individuals.

In some embodiments, chimeric FGF19 polypeptides may not effect growth hormone (GH) resistance, or demonstrate substantially less GH resistance activity, than one or both of their corresponding native FGFs. In some embodiments, chimeric FGF19 polypeptides may have less GH resistance activity than native FGF21, such as native hFGF21. GH normally has growth and metabolic effects that are mediated by insulin-like growth factor 1 (IGF-1). The binding of GH to its receptor results in activation of Janus kinase 2 (JAK2), which then phosphorylates the STAT5 protein. Phosphorylated STAT5 is translocated to the nucleus and binds to gene regulatory response elements that promote IGF-1 expression.

GH's effects can be blunted in individuals by increased levels of FGF21, or by prolonged starvation or fasting, which also increases levels of FGF21. The effects of GH resistance in individuals include energy conservation, increased torpor, decreased body temperature, decreased physical activity, growth inhibition, loss of lean mass, and induction of ketone body synthesis. Native hFGF21 effects GH resistance by, for example, reducing the level of IGF-1 that is normally induced by GH. Without being bound by theory, this GH resistance activity of hFGF21 may be mediated by its ability to reduce the amount of phosphorylated STAT5 polypeptide and, as a result, reduce the translocation of the phosphorylated STAT5 to the nucleus and thus reduce the expression of IGF-1, thereby resisting the effects of GH.

In some embodiments, chimeric FGF19 polypeptides of the present invention do not reduce or do not substantially reduce the amount of phosphorylated STAT5 polypeptide. In this manner, chimeric FGF19 polypeptides of the present invention may demonstrate less or substantially no GH resistance activity, and thus may be advantageously more suitable for administration in a wide range of individuals.

In some embodiments, chimeric FGF19 polypeptides do not substantially promote anchorage-independent growth of cells. In some embodiments, chimeric FGF19 polypeptides may not substantially promote increased metabolic activity and/or the proliferation of cells in an environment requiring anchorage-independent growth. In some embodiments, chimeric FGF19 polypeptides may promote anchorage-independent growth of cells to an extent that is less than the corresponding anchorage-independent growth promotion of native FGF19. In some embodiments, chimeric FGF19 polypeptides may promote increased metabolic activity and/or the proliferation of cells in an environment requiring anchorage-independent growth to an extent that is less than the corresponding effect of native FGF19. As anchorage-independent growth is one of the defining characteristics of transformed cells, such chimerical FGF19 polypeptides of the present invention that do not promote anchorage-independent growth of cells, or do not substantially promote increased metabolic activity and/or the proliferation of cells in an environment requiring anchorage-independent growth, may be less able to promote or increase differentially the growth and/or metabolic activity of transformed cells, and thus may be advantageously more suitable for administration in a wide range of individuals.

IV. Definitions

The terms "FGF19 polypeptide", "FGF19 protein" and "FGF19" when used herein encompass a polypeptide having an amino acid sequence that is the same as the native sequence of a member of the fibroblast growth factor 19 family. Members of such family include the 194-amino acid sequence of human FGF19 (hFGF19) as provided by SEQ ID NO:1 and in FIG. 1. An FGF19 polypeptide can be isolated from nature or can be produced by recombinant and/or synthetic means. An FGF19 polypeptide specifically encompasses naturally-occurring truncated or secreted forms, naturally-occurring variant forms (e.g., alternatively spliced forms) and naturally-occurring allelic variants of the FGF19. An FGF19 polypeptide also specifically encompasses both unprocessed and processed forms of FGF19 such as, for example, the 216-amino acid sequence of the pre-human FGF19 polypeptide as provided by SEQ ID NO:3 and in FIG. 1.

The terms "FGF21 polypeptide", "FGF21 protein" and "FGF21" when used herein encompass a polypeptide having an amino acid sequence that is the same as the native sequence of a member of the fibroblast growth factor 21 family. Members of such family include the 181-amino acid sequence of human FGF21 (hFGF21) as provided by SEQ ID NO:2 and in FIG. 2. An FGF21 polypeptide can be isolated from nature or can be produced by recombinant and/or synthetic means. An FGF21 polypeptide specifically encompasses naturally-occurring truncated or secreted forms, naturally-occurring variant forms (e.g., alternatively spliced forms) and naturally-occurring allelic variants of the FGF21. An FGF21 polypeptide also specifically encompasses both unprocessed and processed forms of FGF21 such as, for example, the 209-amino acid sequence of the pre-human FGF21 polypeptide as provided by SEQ ID NO:4 and in FIG. 2.

The terms "FGF polypeptide" and "FGF protein" when used herein encompass a polypeptide having the native sequence of a member of the FGF family, such as human FGF1, FGF2, FGF3, FGF4, FGF5, FGF6, FGF7, FGF8, FGF9, FGF10, FGF11, FGF12, FGF13, FGF14, FGF16, FGF17, FGF18, FGF19, FGF20, FGF21, FGF22, FGF23, and mammalian homologues thereof. A native sequence of a given FGF polypeptide can be isolated from nature or can be produced by recombinant and/or synthetic means. The native sequence of a given FGF specifically encompasses naturally-occurring truncated or secreted forms, naturally-occurring variant forms (e.g., alternatively spliced forms), naturally-occurring allelic variants thereof, and both unprocessed and processed forms of FGF.

The terms "chimeric polypeptide" and "chimeric protein" when used herein encompass a polypeptide having a sequence that includes at least a portion of a full-length sequence of first polypeptide sequence and at least a portion of a full-length sequence of a second polypeptide sequence, wherein the first and second polypeptides are different polypeptides. A chimeric polypeptide also encompasses polypeptides that include two or more non-contiguous portions derived from the same polypeptide. A chimeric polypeptide also encompasses polypeptides having at least one substitution, wherein the chimeric polypeptide includes a first polypeptide sequence in which a portion of the first polypeptide sequence has been substituted by a portion of a second polypeptide sequence.

The term "portion," when used herein with respect to a given polypeptide sequence, refers to a contiguous length of the given polypeptide's sequence that is shorter than the given polypeptide's full-length sequence. A portion of a given polypeptide may be defined by its first position and its final position, in which the first and final positions each correspond to a position in the sequence of the given polypeptide, wherein the sequence position corresponding to the first position is situated N-terminal to the sequence position corresponding to the final position, and whereby the sequence of the portion is the contiguous sequence of amino acids in the given polypeptide that begins at the sequence position corresponding to the first position and ending at the sequence position corresponding to the final position. A portion may also be defined by reference to a position in the given polypeptide sequence and a length of residues relative to the referenced position, whereby the sequence of the portion is a contiguous sequence of amino acids in the given polypeptide that has the defined length and that is located in the given polypeptide in reference to the defined position.

The term "N-terminal portion" of a given polypeptide sequence is a contiguous length of the given polypeptide sequence that begins at or near the N-terminal residue of the given polypeptide sequence. An N-terminal portion of the given polypeptide can be defined by a length. Similarly, the term "C-terminal portion" of a given polypeptide sequence is a contiguous length of the given polypeptide sequence that ends at or near the C-terminal residue of the given polypeptide sequence. An C-terminal portion of the given polypeptide can be defined by a length.

The terms "chimeric FGF polypeptide" and "chimeric FGF protein" when used herein encompass a polypeptide having a sequence that includes at least a portion of a first FGF polypeptide sequence and a portion of a second FGF polypeptide sequence, wherein the first and the second FGF polypeptides are different from each other. A chimeric FGF polypeptide also encompasses polypeptides that include two or more non-contiguous portions derived from the same FGF polypeptide. A chimeric FGF polypeptide also encompasses polypeptides having at least one substitution, wherein the chimeric FGF polypeptide includes a first FGF polypeptide sequence in which a portion of the first FGF polypeptide sequence has been substituted by a portion of a second FGF polypeptide sequence.

The terms "chimeric FGF19 polypeptide" and "chimeric FGF19 protein" when used herein encompass a chimeric FGF polypeptide having a sequence that includes at least a portion of a FGF19 polypeptide sequence and a portion of a second polypeptide sequence. For example, a chimeric FGF19 polypeptide encompasses polypeptides in which the second polypeptide sequence is a FGF21 polypeptide sequence.

A chimeric FGF19 polypeptide also encompasses polypeptides that include two or more non-contiguous portions derived from a FGF19 polypeptide sequence. A chimeric FGF19 polypeptide also encompasses polypeptides having at least one substitution, wherein the chimeric FGF19 polypeptide sequence includes a FGF19 polypeptide sequence in which a portion of the FGF19 polypeptide sequence has been substituted by a portion of a second polypeptide sequence. In such cases, a chimeric FGF19 polypeptide expressly encompasses polypeptides in which the substituting portion is a portion of a FGF21 polypeptide sequence.

A chimeric FGF19 polypeptide also encompasses a polypeptide whose sequence consists only of portions derived from either a FGF19 polypeptide sequence or a second polypeptide sequence, such as a FGF21 polypeptide sequence. Unless otherwise stated, a chimeric FGF19 polypeptide is not limited to, nor does it imply unless otherwise indicated, the respective order or locations of the FGF19 polypeptide sequence with respect to any other sequence portions within the chimeric FGF19 polypeptide sequence.

"Percent (%) amino acid sequence identity" with respect to a given polypeptide sequences identified herein is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by a given sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"Percent (%) nucleic acid sequence identity" with respect to a polypeptide-encoding nucleic acid sequences identified herein is defined as the percentage of nucleotides in a candidate sequence that are identical with the nucleotides in the polypeptide-encoding nucleic acid sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

For purposes-herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z where W is the number of nucleotides scored as identical matches by a given sequence alignment program in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

"Isolated," when used to describe the various polypeptides disclosed herein, means polypeptide that has been identified and separated and/or recovered from a component of its natural environment. Preferably, the isolated polypeptide is free of association with all components with which it is naturally associated. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the polypeptide's natural environment will not be present. Ordinarily, however, isolated polypeptide will be prepared by at least one purification step.

An "isolated" nucleic acid molecule encoding a polypeptide is a nucleic acid molecule that is identified and separated from at least one contaminant nucleic acid molecule with which it is ordinarily associated in the natural source of the polypeptide-encoding nucleic acid. Preferably, the isolated nucleic is free of association with all components with which it is naturally associated. An isolated polypeptide-encoding nucleic acid molecule is other than in the form or setting in which it is found in nature. Isolated nucleic acid molecules therefore are distinguished from the polypeptide-encoding nucleic acid molecule as it exists in natural cells. However, an isolated nucleic acid molecule encoding a polypeptide includes polypeptide-encoding nucleic acid molecules contained in cells that ordinarily express polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single monoclonal antibodies (including agonist, antagonist, and neutralizing antibodies), antibody compositions with polyepitopic specificity, single chain antibodies, and fragments of antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

With regard to the binding of an polypeptide, antibody, oligopeptide or other organic molecule to a target molecule or cognate receptor, the term "specific binding" or "specifically binds to" or is "specific for" a particular polypeptide or an epitope on a particular polypeptide target or cognate receptor means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target or cognate receptor as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-11}$) M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide or cognate receptor without substantially binding to any other polypeptide or polypeptide epitope or receptor.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficol/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to chimeric FGF19 polypeptide which retains at least one biological and/or immunological activity of native or naturally-occurring FGF19 polypeptide and/or FGF21 polypeptide, particularly native or naturally-occurring hFGF19 polypeptide and/or hFGF21 polypeptide. "Biological" activity refers to a biological function (either inhibitory, stimulatory or cooperative) caused by a native or naturally-occurring FGF19 polypeptide and/or FGF21 polypeptide other than the ability to induce the production of an antibody against an antigenic epitope possessed by a native or naturally-occurring FGF19 polypeptide and/or FGF21 polypeptide. "Biological" activity may also refer to a cellular or biochemical function of native or naturally-occurring FGF19 polypeptide and/or FGF21 polypeptide, such as the ability to bind to one or more of its respective cognate receptors. "Immunological" activity refers to the ability to induce the production of an antibody against an antigenic epitope possessed by a native or naturally-occurring FGF19 polypeptide and/or FGF21 polypeptide. A preferred biological activity includes any one or more of the following exemplary activities: increases metabolism (or metabolic rate) in an individual, decreases body weight of an individual, decreases adiposity in an individual, decreases glucose uptake into adipocytes, increases leptin release from adipocytes, decreases triglycerides in an individual, decreases free fatty acids in an individual, Klotho-beta-dependent binding to a cognate FGF receptor, and Klotho-beta-independent binding to a cognate FGF receptor. It is understood that some of the activities of FGF19 and/or FGF21 polypeptides are directly induced by the polypeptide and some are indirectly induced, however, each are the result of the presence of FGF19 and/or FGF21 polypeptide and would not otherwise have the result in the absence of the polypeptide.

The term "antagonist" is used in the broadest sense, and includes any molecule that partially or fully blocks, inhibits, or neutralizes a biological activity of a native or chimeric polypeptide disclosed herein. In a similar manner, the term "agonist" is used in the broadest sense and includes any molecule that mimics a biological activity of a native or chimeric polypeptide disclosed herein. Suitable agonist or antagonist molecules specifically include agonist or antagonist antibodies or antibody fragments, fragments or amino acid sequence variants of native polypeptides, peptides, small organic molecules, etc. Methods for identifying agonists or antagonists of a polypeptide may comprise contacting a polypeptide with a candidate agonist or antagonist molecule and measuring a detectable change in one or more biological activities normally associated with the polypeptide.

As used herein, "treatment" or "treating" is an approach for obtaining beneficial or desired results including clinical results. For purposes of this invention, beneficial or desired clinical results include, but are not limited to, one or more of the following: decreasing one or more symptoms resulting from the disease, diminishing the extent of the disease, stabilizing the disease (e.g., preventing or delaying the worsening of the disease), delay or slowing the progression of the disease, ameliorating the disease state, decreasing the dose of one or more other medications required to treat the disease, and/or increasing the quality of life.

As used herein, "delaying" the progression means to defer, hinder, slow, retard, stabilize, and/or postpone development of the disease. This delay can be of varying lengths of time, depending on the history of the disease and/or individual being treated.

In some embodiments, the methods of treatment described herein ameliorate (e.g., reduce incidence of, reduce duration of, reduce or lessen severity of) of one or more symptoms of the disease.

A "symptom" is any morbid phenomenon or departure from the normal in structure, function, or sensation, experienced by the individual.

An "effective amount" of a polypeptide, antibody, agonist, or antagonist thereof as disclosed herein is an amount sufficient to carry out a specifically stated purpose. An "effective amount" may be determined empirically and in a routine manner, in relation to the stated purpose.

The term "therapeutically effective amount" refers to an amount of an antibody, polypeptide, or other drug effective to "treat" a disease or disorder in an individual or mammal. See the definition herein of "treating".

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

"Individual" is any mammal, preferably a human.

"Obesity" refers to a condition whereby a mammal has a Body Mass Index (BMI), which is calculated as weight (kg) per height (meters), of at least 25.9. Conventionally, those persons with normal weight have a BMI of 19.9 to less than 25.9. The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficient individuals, normal variant short stature, Turner's syndrome, and other pathological conditions showing reduced metabolic activity or a decrease in resting energy expenditure as a percentage of total fat-free mass, e.g., children with acute lymphoblastic leukemia.

"Conditions related to obesity" refer to conditions which are the result of or which are exasperated by obesity, such as, but not limited to dermatological disorders such as infections, varicose veins, Acanthosis nigricans, and eczema, exercise intolerance, diabetes mellitus, insulin resistance, hypertension, hypercholesterolemia, cholelithiasis, osteoarthritis, orthopedic injury, thromboembolic disease, cancer, and coronary (or cardiovascular) heart disease, particular those cardiovascular conditions associated with high triglycerides and free fatty acids in an individual.

Administration "in combination with" or "in conjunction with" one or more further therapeutic agents includes simultaneous, concurrent, consecutive and sequential administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_{H1}$). Each Fab fragment is monovalent with respect to antigen binding, i.e., it has a single antigen-binding site. Pepsin treatment of an antibody yields a single large $F(ab')_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_{H1}$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the VH and VL domains of antibody, wherein these domains are present in a single polypeptide chain. Preferably, the Fv polypeptide further comprises a polypeptide linker between the VH and VL domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP Patent Publication 0404097; PCT International Patent Publication WO 93/11161; and Hollinger et al., *Proc. Natl. Acad. Sci. USA*, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a chimeric FGF19 polypeptide or antibody thereto) to a mammal. The components of the liposome are commonly arranged in a bilayer formation, similar to the lipid arrangement of biological membranes.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

V. Chimeric FGF19 Variants

In addition to the chimeric FGF19 polypeptides described herein, it is contemplated that chimeric FGF19 variant polypeptides (or "chimeric FGF19 variants") can be prepared. Chimeric FGF19 variants can be prepared by introducing appropriate nucleotide changes into a DNA encoding a chimeric or native FGF19 or FGF21 polypeptide, and/or by synthesis of the desired chimeric FGF19 variant. Those skilled in the art will appreciate that amino acid changes may alter post-translational processes of the chimeric FGF19 variant, such as changing the number or position of glycosylation sites or altering the membrane anchoring characteristics.

Variations in chimeric FGF19 polypeptides of the present invention or in various domains thereof can be made, for example, using any of the techniques and guidelines for conservative and non-conservative mutations set forth, for instance, in U.S. Pat. No. 5,364,934. Variations may be a substitution, deletion or insertion of one or more codons encoding the chimeric FGF19 polypeptide that results in a change in the amino acid sequence of the chimeric FGF19 polypeptide. The variations may be with respect to one or more codons encoding the chimeric FGF19 polypeptide that is derived from native FGF19 or FGF21 polypeptide. Optionally the variation is by substitution of at least one amino acid with any other amino acid in one or more of the domains of the chimeric FGF19 polypeptide. Guidance in determining which amino acid residue may be inserted, substituted or deleted without adversely affecting the desired activity may be found by comparing the sequence of the chimeric FGF19 polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Chimeric FGF19 polypeptide fragments ("or chimeric FGF19 fragments") are provided herein. Such fragments may be truncated at the N-terminus or C-terminus, or may lack internal residues, for example, when compared with a full length native protein. Certain fragments lack amino acid residues that are not essential for a desired biological activity of the chimeric FGF19 polypeptide.

Chimeric FGF19 fragments may be prepared by any of a number of conventional techniques. Desired peptide fragments may be chemically synthesized. An alternative approach involves generating chimeric FGF19 fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, chimeric FGF19 polypeptide fragments share at least one biological and/or immunological activity with a native FGF19 polypeptide, such as hFGF19 polypeptide shown in FIG. 1 (SEQ ID NO:1) or the native FGF21 polypeptide, such as hFGF21 shown in FIG. 2 (SEQ ID NO:2).

In particular embodiments, conservative substitutions of interest are shown in Table 10 under the heading of preferred substitutions. If such substitutions result in a change in biological activity, then more substantial changes, denominated exemplary substitutions in Table 10, or as further described below in reference to amino acid classes, are introduced and the products screened.

TABLE 10

Preferred Amino Acid Residue Substitutions

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the chimeric FGF19 polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the DNA encoding the chimeric FGF19 variant polypeptide.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, Science, 244: 1081-1085 (1989)]. Alanine is also typically preferred because it is the most common amino acid. Further, it is frequently found in both buried and exposed positions [Creighton, The Proteins, (W.H. Freeman & Co., N.Y.); Chothia, J. Mol. Biol., 150:1 (1976)]. If alanine substitution does not yield adequate amounts of variant, an isoteric amino acid can be used.

VI. Modifications of Chimeric FGF19

Covalent modifications of chimeric FGF19 polypeptide are included within the scope of this invention. One type of covalent modification includes reacting targeted amino acid residues of a chimeric FGF19 polypeptide with an organic derivatizing agent that is capable of reacting with selected side chains or the N- or C-terminal residues of the chimeric FGF19 polypeptide. Derivatization with bifunctional agents is useful, for instance, for cross-linking chimeric FGF19 polypeptide to a water-insoluble support matrix or surface for use in the method for purifying antibodies, and vice-versa. Commonly used cross-linking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, Proteins: Structure and Molecular Properties, W.H. Freeman & Co., San Francisco, pp. 79-86 (1983)], acetylation of the N-terminal amine, and amidation of any C-terminal carboxyl group.

Another type of covalent modification of the chimeric FGF19 polypeptide included within the scope of this invention comprises altering the glycosylation pattern of the polypeptide. "Altering the native glycosylation pattern" is intended for purposes herein to mean deleting one or more carbohydrate moieties found in the corresponding native FGF19 polypeptide and/or FGF21 polypeptide sequence (either by removing the underlying glycosylation site or by deleting the glycosylation by chemical and/or enzymatic means), and/or adding one or more glycosylation sites that are not present in the native FGF19 polypeptide and/or FGF21 polypeptide sequence. In addition, the phrase includes qualitative changes in the glycosylation of the native proteins, involving a change in the nature and proportions of the various carbohydrate moieties present.

Addition of glycosylation sites to the chimeric FGF19 polypeptide may be accomplished by altering the amino acid sequence. The alteration may be made, for example, by the addition of, or substitution by, one or more serine or threonine residues to the chimeric FGF19 polypeptide (for O-linked glycosylation sites). The chimeric FGF19 polypeptide amino acid sequence may optionally be altered through changes at the DNA level, particularly by mutating the DNA encoding the chimeric FGF19 polypeptide at preselected bases such that codons are generated that will translate into the desired amino acids.

Another means of increasing the number of carbohydrate moieties on the chimeric FGF19 polypeptide is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259-306 (1981).

Removal of carbohydrate moieties present on the chimeric FGF19 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification of chimeric FGF19 polypeptide comprises linking the chimeric FGF19 polypeptide to one of a variety of nonproteinaceous polymers, e.g., polyethylene glycol (PEG), polypropylene glycol, or polyoxyalkylenes, in the manner set forth in U.S. Pat. No. 4,640, 835; 4,496,689; 4,301,144; 4,670,417; 4,791,192 or 4,179, 337.

The chimeric FGF19 polypeptide of the present invention may also be modified by fusing the chimeric FGF19 polypeptide fused to another, heterologous polypeptide or amino acid sequence.

In one embodiment, such a chimeric molecule comprises a fusion of the chimeric FGF19 polypeptide with a tag polypeptide which provides an epitope to which an anti-tag antibody can selectively bind. The epitope tag is generally placed at the amino- or carboxyl-terminus of the chimeric FGF19 polypeptide. The presence of such epitope-tagged forms of the chimeric FGF19 polypeptide can be detected using an antibody against the tag polypeptide. Also, provision of the epitope tag enables the chimeric FGF19 polypeptide to be readily purified by affinity purification using an anti-tag antibody or another type of affinity matrix that binds to the epitope tag. Various tag polypeptides and their respective antibodies are well known in the art. Examples include poly-histidine (polyhis) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology, 6: 1204-1210 (1988)]; the KT3 epitope peptide [Martin et al., Science, 255:192-194 (1992)]; an α-tubulin epitope peptide [Skinner et al., J. Biol. Chem., 266:15163-15166 (1991)]; and the T7 gene 10 protein peptide tag [Lutz-Freyermuth et al., Proc. Natl. Acad. Sci. USA, 87:6393-6397 (1990)].

In an alternative embodiment, a polypeptide of the present invention may comprise a fusion of a chimeric FGF19 polypeptide with an immunoglobulin or a particular region of an immunoglobulin. For a bivalent form of the chimeric molecule (also referred to as an "immunoadhesin"), such a fusion could be to the Fc portion of an immunoglobulin, an analog of the Fc portion of an immunoglobulin and one or more fragments of the Fc portion of an immunoglobulin. In some embodiments, the immunoglobulin is selected from the group consisting of: IgG-1, IgG-2, IgG-3, IgG-4, IgA-1, IgA-2, IgE, IgD and IgM. In some embodiments, the Fc portion is human or humanized.

In some embodiments, the C-terminus of the chimeric FGF19 polypeptide and the N-terminus of the Fc portion are fused. In some embodiments, the N-terminus of the chimeric FGF19 polypeptide and the C-terminus of the Fc portion are fused. In some embodiments, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995. In some embodiments, the C-terminus of the chimeric FGF19 polypeptide is fused to the N-terminus of the Fc portion via a linker, the linker is selected from the group consisting of: a $[Gly]_n$ linker, a $[Gly_3Ser]_m$ linker and a $[Gly_4Ser]_m$ linker, wherein n is a integer from 1-30 and m is an integer from 1-6.

VII. Uses and Methods Using Chimeric FGF19 Polypeptides

The chimeric FGF19 polypeptides and modulators thereof described herein may also be employed as therapeutic agents. The chimeric FGF19 polypeptides and modulators thereof of the present invention can be formulated according to known methods to prepare pharmaceutically useful compositions, whereby the chimeric FGF19 polypeptides hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a chimeric FGF19 polypeptide or agonist or antagonist thereof is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a chimeric FGF19 polypeptide or modulator is desired in a formulation with release characteristics suitable for the treatment of any disease or disorder requiring administration of the chimeric FGF19 polypeptide or modulator, microencapsulation is contemplated. Microencapsulation of recombinant proteins for sustained release has been successfully performed with human growth hormone (rhGH), interferon- (rhIFN-), interleukin-2, and MN rgp120. Johnson et al., Nat. Med., 2:795-799 (1996); Yasuda, Biomed. Ther., 27:1221-1223 (1993); Hora et al., Bio/Technology 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis. "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41.

The therapeutic agents and compositions comprising chimeric FGF19 polypeptide provided herein can be used in a number of applications. The applications include treating an individual with obesity or a condition associated with obesity.

In one aspect, chimeric FGF19 polypeptide is administered to an individual in need thereof in an amount effective to treat the condition. Preferably, the condition is one which requires at least one of the following to be treated: decrease in blood glucose, an increase in metabolism, a decrease in body weight, a decrease in body fat, a decrease in triglycerides, a decrease in free fatty acids, an increase in glucose release from adipocytes and/or an increase in leptin release from adipocytes. Each of these parameters can be measured by standard methods, for example, by measuring oxygen consumption to determine metabolic rate, using scales to determine weight, and measuring size to determine fat. Moreover, the presence and amount of triglycerides, free fatty acids, glucose and leptin can be determined by standard methods. The applications include treating an individual with one or more of type 1 diabetes, type 2 diabetes, high blood glucose, metabolic syndrome, atherosclerosis, hypercholesterolemia, stroke, osteoporosis, osteoarthritis, degenerative joint disease, muscle atrophy, sarcopenia, decreased lean body mass, baldness, wrinkles, increased fatigue, decreased stamina, decreased cardiac function, immune system dysfunction, cancer, Parkinson's disease, senile dementia, Alzheimer's disease and decreased cognitive function.

Chimeric FGF19 polypeptide and compositions comprising chimeric FGF19 polypeptide are preferably used in vivo. However, as discussed below, administration can be in vitro such as in the methods described below for screening for modulators of chimeric FGF19 polypeptide. Although, it is understood that modulators of chimeric FGF19 polypeptide can also be identified by the use of animal models and samples from individuals.

The present invention also includes aspects in which a chimeric FGF19 polypeptide of the present invention or a pharmaceutical composition thereof is administered to an individual in combination with a second agent, wherein the second agent is preferably a pharmacological agent. In some embodiments, the chimeric FGF19 polypeptide of the present invention or a pharmaceutical composition thereof is administered in a therapeutically effect amount in combination with a therapeutically effective amount of the second agent. In some embodiments, the chimeric FGF19 polypeptide or pharmaceutical composition thereof is administered in conjunction with the second agent, i.e., the respective periods of administration are part of a single administrative regimen. In some embodiments, the chimeric FGF19 polypeptide or pharmaceutical composition thereof and the second agent are administered concurrently, i.e., the respective periods of administration overlap each other. In some embodiments, the chimeric FGF19 polypeptide or pharmaceutical composition thereof and the second agent are administered non-concurrently, i.e., the respective periods of administration do not overlap each other. In some embodiments, the chimeric FGF19 polypeptide or pharmaceutical composition thereof and the second agent are administered sequentially, i.e., the chimeric FGF19 polypeptide or pharmaceutical composition thereof is administered prior to and/or after the administration of the second agent. In some embodiments, the chimeric FGF19 polypeptide or pharmaceutical composition thereof and the second agent are administered simultaneously as separate compositions. In some embodiments, the chimeric FGF19 polypeptide or pharmaceutical composition thereof and the second agent are administered simultaneously as part of the same compositions.

In some embodiments, the second agent is different chimeric FGF19 polypeptide of the present invention. In some embodiments, the second agent is an anti-inflammatory agent, an anti-diabetic agent, and/or cholesterol-lowering drug of the "statin" class. In some embodiments, the second active agent is insulin. In some embodiments, the insulin is rapid acting, short acting, regular acting, intermediate acting, or long acting insulin. In some embodiments, the insulin is and/or comprises Humalog, Lispro, Novolog, Apidra, Humulin, Aspart, regular insulin, NPH, Lente, Ultralente, Lantus, Glargine, Levemir, or Detemir. In some embodiments, the second active agent is a statin. In some embodiments, the statin is and/or comprises Atorvastatin (e.g., Lipitor or Torvast), Cerivastatin (e.g., Lipobay or Baycol), Fluvastatin (e.g., Lescol or Lescol), Lovastatin (e.g., Mevacor, Altocor, or Altoprev) Mevastatin, Pitavastatin (e.g., Livalo or Pitava), Pravastatin (e.g., Pravachol, Selektine, or Lipostat) Rosuvastatin (e.g., Crestor), Simvastatin (e.g., Zocor or Lipex), Vytorin, Advicor, Besylate Caduet or Simcor.

In another aspect of the present invention, a chimeric FGF19 polypeptide of the present invention or a pharmaceutical composition thereof is administered to an individual in combination with a second therapy performed on the individual, wherein the second therapy comprises a surgery. In some embodiments, the chimeric FGF19 polypeptide of the present invention or a pharmaceutical composition thereof is administered in a therapeutically effect amount in combination with the second therapy. In some embodiments, the chimeric FGF19 polypeptide or pharmaceutical composition thereof is administered in conjunction with the second therapy, i.e., the administration and the therapy are part of a single administrative regimen. In some embodiments, the chimeric FGF19 polypeptide or pharmaceutical composition thereof is administered concurrently with the second therapy, i.e., the respective periods of administration and therapy overlap each other. In some embodiments, the chimeric FGF19 polypeptide or pharmaceutical composition thereof and the second agent is administered non-concurrently with the second therapy, i.e., the respective periods of administration and therapy do not overlap each other. In some embodiments, the chimeric FGF19 polypeptide or pharmaceutical composition thereof and the second agent is administered sequentially with the second therapy, i.e., the chimeric FGF19 polypeptide or pharmaceutical composition thereof is administered prior to and/or after the second therapy. In some embodiments, the chimeric FGF19 polypeptide or pharmaceutical composition thereof and the second agent is administered simultaneously with the second therapy.

The chimeric FGF19 polypeptides described herein may also be employed as molecular weight markers for protein electrophoresis purposes.

The chimeric FGF19 polypeptides and nucleic acid molecules of the present invention may also be used for tissue typing, wherein the chimeric FGF19 polypeptides of the present invention may be differentially expressed in one tissue as compared to another. Chimeric FGF19 polypeptide nucleic acid molecules will find use for generating probes for PCR, Northern analysis, Southern analysis and Western analysis.

Chimeric FGF19 polypeptides of the present invention which bind to another protein (example, one of the FGFRs), the chimeric FGF19 polypeptide can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the chimeric FGF19 polypeptide can be used to isolate correlative ligand(s). Screening assays can be designed to find lead compounds that mimic the biological activity of a native FGF19, native FGF21, chimeric FGF19 polypeptide, or a receptor for FGF19 and/or FGF21. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

As an alternative approach for receptor identification, labeled chimeric FGF19 polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In one embodiment herein where competitive binding assays are performed, FGFR1c, FGFR2c, FGFR3c and/or FGFR4 or an antibody to chimeric FGF19 polypeptide is used as a competitor.

VIII. Antibodies to Chimeric FGF19 Polypeptide

1. Polyclonal Antibodies

The anti-chimeric FGF19 polypeptide antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the chimeric FGF19 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-chimeric FGF19 polypeptide antibodies may, alternatively, be monoclonal antibodies. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. In preferred embodiments, the anti-chimeric FGF19 polypeptide antibody specifically bind the polypeptide of the present invention. In more preferred embodiments, the specifically-binding antibody does not bind native FGF19 polypeptide or native FGF21 polypeptide.

The immunizing agent will typically include the chimeric FGF19 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, Monoclonal Antibodies: Principles and Practice, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, J. Immunol., 133:3001 (1984); Brodeur et al., Monoclonal Antibody Production Techniques and Applications, Marcel Dekker, Inc., New York, (1987) pp. 51-63].

The culture medium in which the hybridoma cells are cultured can then be assayed for the presence of monoclonal antibodies directed against chimeric FGF19 polypeptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-chimeric FGF19 polypeptide antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol. 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

4. Bispecific Antibodies

Bispecific antibodies are monoclonal, preferably human or humanized, antibodies that have binding specificities for at least two different antigens. In the present case, one of the binding specificities is for the FGF19, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')2 bispecific antibodies). Techniques for generating bispecific antibodies from antibody fragments have been described in the literature. For example, bispecific antibodies can be prepared can be prepared using chemical linkage. Brennan et al., Science 229:81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from E. coli and chemically coupled to form bispecific antibodies. Shalaby et al., J. Exp. Med. 175:217-225 (1992) describe the production of a fully humanized bispecific antibody $F(ab')_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994). Antibodies with more than two valencies are contemplated. For example, trispecific antibodies can be prepared. Tutt et al., J. Immunol. 147:60 (1991).

Exemplary bispecific antibodies may bind to two different epitopes on a given FGF19 polypeptide herein. Alternatively, an anti-chimeric FGF19 polypeptide arm may be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular FGF19 polypeptide. Bispecific antibodies may also be used to localize cytotoxic agents to cells which express a particular FGF19 polypeptide. These antibodies possess a FGF19-binding arm and an arm which binds a cytotoxic agent or a radionuclide chelator, such as EOTUBE, DPTA, DOTA, or TETA. Another bispecific antibody of interest binds the FGF19 polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med., 176: 1191-1195 (1992) and Shopes, J. Immunol., 148: 2918-2922 (1992). In one example, homodimeric antibodies with enhanced anti-tumor activity may also be prepared using heterobifunctional cross-linkers as described in Wolff et al. Cancer Research, 53: 2560-2565 (1993). Alternatively, an antibody can be engineered that has dual Fc regions and may thereby have enhanced complement lysis and ADCC capabilities. See Stevenson et al., Anti-Cancer Drug Design, 3: 219-230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria, officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the individual, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA,* 82: 3688 (1985); Hwang et al., *Proc. Natl. Acad. Sci. USA,* 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

9. Pharmaceutical Compositions of Antibodies

Antibodies specifically binding a FGF19 polypeptide identified herein, as well as other molecules identified by the screening assays disclosed hereinbefore, can be administered for the treatment of various disorders in the form of pharmaceutical compositions.

If the FGF19 polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA, 90: 7889-7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's Pharmaceutical Sciences, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

G. Uses for Antibodies

The anti-chimeric FGF19 polypeptide antibodies of the invention have various utilities. For example, anti-FGF19 antibodies may be used in diagnostic assays for chimeric FGF19 polypeptide, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, Monoclonal Antibodies: A Manual of Techniques, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., Nature, 144:945 (1962); David et al., Biochemistry, 13: 1014 (1974); Pain et al., J. Immunol. Meth., 40:219 (1981); and Nygren, J. Histochem. and Cytochem., 30:407 (1982).

Anti-chimeric FGF19 polypeptide antibodies also are useful for the affinity purification of chimeric FGF19 polypeptide from recombinant cell culture or natural sources. In this process, the antibodies against chimeric FGF19 polypeptide are immobilized on a suitable support, such a Sephadex resin or filter paper, using methods well known in the art. The immobilized antibody then is contacted with a sample containing the chimeric FGF19 polypeptide to be purified, and thereafter the support is washed with a suitable solvent that will remove substantially all the material in the sample except the chimeric FGF19 polypeptide, which is bound to the immobilized antibody. Finally, the support is washed with another suitable solvent that will release the chimeric FGF19 polypeptide from the antibody.

IX. Preparation of Chimeric FGF19 Polypeptide

The description below relates primarily to production of chimeric FGF19 polypeptide by culturing cells transformed or transfected with a vector containing nucleic acid encoding chimeric FGF19 polypeptide. It is, of course, contemplated that alternative methods, which are well known in the art, may be employed to prepare chimeric FGF19 polypeptide. For instance, the chimeric FGF19 polypeptide, or portions thereof, may be produced by direct peptide synthesis using solid-phase techniques [see, e.g., Stewart et al., Solid-Phase Peptide Synthesis, W.H. Freeman Co., San Francisco, Calif. (1969); Merrifield, J. Am. Chem. Soc., 85:2149-2154 (1963)]. In vitro protein synthesis may be performed using manual techniques or by automation; Automated synthesis may be accomplished, for instance, using an Applied Biosystems Peptide Synthesizer (Foster City, Calif.) using manufacturer's instructions. Various portions of the chimeric FGF19 polypeptide may be chemically synthesized separately and combined using chemical or enzymatic methods to produce the full-length chimeric FGF19 polypeptide.

1. Isolation of DNA Encoding Chimeric FGF19 Polypeptide cDNA fragments encoding chimeric FGF polypeptides of the present invention can be generated by using PCR methodology using cDNA encoding at least a portion of native FGF19 polypeptide and at least a portion of native FGF21 polypeptide as templates. For example, in one instance, a cDNA fragment encoding an N-terminal portion of FGF21 polypeptide and a cDNA fragment encoding a C-terminal portion of FGF19 polypeptide are separately amplified and purified by a standard procedure, such as by using PCR followed by agarose gel electrophoresis. Primer sequences are designed such that there is an 18 nucleotide overlap at the 3' end of the FGF21 cDNA fragment and 5' end of the FGF19 cDNA fragment. A second amplification using PCR is conducted using a mixture of the two cDNA fragments as templates, resulting in a cDNA that encodes a chimeric polypeptide of the FGF21 fragment and FGF19 fragment. The resulting cDNA fragment is digested with appropriate restriction enzymes, purified by agarose gel electrophoresis, and cloned into plasmid vector pRK5.sm (a pUC based plasmid vector containing CMV promoter for mammalian expression) using standard procedures. The sequence of the resulting plasmid was confirmed by the Sanger DNA sequencing method.

DNA encoding chimeric FGF19 polypeptide may be obtained from a cDNA library prepared from tissue believed to possess the FGF19 and/or FGF21 mRNA and to express it at a detectable level. Accordingly, human FGF19 and/or FGF21 DNA can be conveniently obtained from a cDNA library prepared from human tissue, such as described in the Examples. The FGF19- and/or FGF21-encoding gene may also be obtained from a genomic library or by known synthetic procedures (e.g., automated nucleic acid synthesis).

Libraries can be screened with probes (such as antibodies to the FGF19 and/or FGF21 or oligonucleotides of at least about 20-80 bases) designed to identify the gene of interest or the protein encoded by it. Screening the cDNA or genomic library with the selected probe may be conducted using standard procedures, such as described in Sambrook et al., Molecular Cloning: A Laboratory Manual (New York: Cold Spring Harbor Laboratory Press, 1989). An alternative means to isolate the gene encoding FGF19 is to use PCR methodology [Sambrook et al., supra; Dieffenbach et al., PCR Primer: A Laboratory Manual (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for chimeric FGF19 polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991) and Sambrook et al., supra.

Methods of eukaryotic cell transfection and prokaryotic cell transformation are known to the ordinarily skilled artisan, for example, CaCl$_2$, CaPO$_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., Gene, 23:315 (1983) and WO 89/05859 published 29 Jun. 1989. For mammalian cells without such cell walls, the calcium phosphate precipitation method of Graham and van der Eb, Virology, 52:456-457 (1978) can be employed. General aspects of mammalian cell host system transfections have been described in U.S. Pat. No. 4,399,216. Transformations into yeast are typically carried out according to the method of Van Solingen et al., J. Bact., 130:946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., Methods in Enzymology, 185:527-537 (1990) and Mansour et al., Nature, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for FGF19-encoding vectors. *Saccharomyces cerevisiae* is a commonly used lower eukaryotic host microorganism. Others include *Schizosaccharomyces pombe* (Beach and Nurse, Nature, 290: 140 [1981]; EP 139,383 published 2 May 1985); *Kluyveromyces* hosts (U.S. Pat. No. 4,943,529; Fleer et al., Bio/Technology, 9:968-975 (1991)) such as, e.g., *K. lactic* (MW98-8C, CBS683, CBS4574; Louvencourt et al., J. Bacteriol., 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., Bio/Technology, 8:135 (1990)), *K. thermotolerans*, and *K. marxianus; yarrowia* (EP 402, 226); *Pichia pastoris* (EP 183,070; Sreekrishna et al., J. Basic Microbiol., 28:265-278 [1988]); *Candida; Trichoderma reesia* (EP 244,234); *Neurospora crassa* (Case et al., Proc. Natl. Acad. Sci. USA, 76:5259-5263 [1979]); *Schwanniomy-* ces such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., Biochem. Biophys. Res. Commun., 112:284-289 [1983]; Tilburn et al., Gene, 26:205-221 [1983]; Yelton et al., Proc. Natl. Acad. Sci. USA, 81: 1470-1474 [1984]) and *A. niger* (Kelly and Hynes, EMB 0 J., 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, The Biochemistry of Methylotrophs, 269 (1982).

Suitable host cells for the expression of glycosylated chimeric FGF19 polypeptide are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); Chinese hamster ovary cells/−DHFR (CHO, Urlaub and Chasin, Proc. Natl. Acad. Sci. USA, 77:4216 (1980)); mouse sertoli cells (TM4, Mather, Biol. Reprod., 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding chimeric FGF19 polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The chimeric FGF19 polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the chimeric FGF19 polypeptide-encoding DNA that is inserted into the vector. The signal sequence may be the original signal sequence of FGF19 or FGF21, such as hFGF19 or hFGF21. Thus, in such embodiments, a chimeric FGF19 polypeptide of the present invention may include at least an N-terminal portion of pre-hFGF19, such as at least residues 1-22 of SEQ ID NO:3. In such embodiments, a chimeric FGF19 polypeptide of the present invention may include at least an N-terminal portion of pre-hFGF1, such as at least residues 1-28 of SEQ ID NO:4.

The signal sequence may be a prokaryotic signal sequence selected, for example, from the group of the alkaline phosphatase, penicillinase, 1pp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the FGF19-encoding nucleic acid, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980). A suitable selection gene for use in yeast is the trp1 gene present in the yeast plasmid YRp7 [Stinchcomb et al., Nature, 282:39 (1979); Kingsman et al., Gene, 7:141 (1979); Tschemper et al., Gene, 10: 157 (1980)]. The trp1 gene provides a selection marker for a mutant strain of yeast lacking the ability to grow in tryptophan, for example, ATCC No. 44076 or PEP4-1 [Jones, Genetics, 85:12 (1977)].

Expression and cloning vectors usually contain a promoter operably linked to the FGF19-encoding nucleic acid sequence to direct mRNA synthesis. Promoters recognized by a variety of potential host cells are well known. Promoters suitable for use with prokaryotic hosts include the β-lactamase and lactose promoter systems [Chang et al., Nature, 275:615 (1978); Goeddel et al., Nature, 281:544 (1979)], alkaline phosphatase, a tryptophan (trp) promoter system [Goeddel, Nucleic Acids Res., 8:4057 (1980); EP 36,776], and hybrid promoters such as the tac promoter [deBoer et al., Proc. Natl. Acad. Sci. USA, 80:21-25 (1983)]. Promoters for use in bacterial systems also will contain a Shine-Dalgarno (S.D.) sequence operably linked to the DNA encoding FGF19.

Examples of suitable promoting sequences for use with yeast hosts include the promoters for 3-phosphoglycerate kinase [Hitzeman et al., J. Biol. Chem., 255:2073 (1980)] or other glycolytic enzymes [Hess et al., J. Adv. Enzyme Reg., 7:149 (1968); Holland, Biochemistry, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate-dehydrogenase, and enzymes responsible for maltose and galactose utilization. Suitable vectors and promoters for use in yeast expression are further described in EP 73,657.

Transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the chimeric FGF19 polypeptide by higher eukaryotes may be increased by inserting an enhancer sequence into the vector Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the chimeric FGF19 polypeptide coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding chimeric FGF19 polypeptide.

Still other methods, vectors, and host cells suitable for adaptation to the synthesis of chimeric FGF19 polypeptide in recombinant vertebrate cell culture are described in Gething et al., Nature, 293:620-625 (1981); Mantei et al., Nature, 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, Proc. Natl. Acad. Sci. USA, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a chimeric FGF19 polypeptide or against a synthetic peptide based on the DNA sequences provided herein or against exogenous sequence fused to DNA encoding chimeric FGF19 polypeptide and encoding a specific antibody epitope.

5. Purification of Polypeptide

Forms of chimeric FGF19 polypeptide may be recovered from culture medium or from host cell lysates. If membrane-bound, it can be released from the membrane using a suitable detergent solution (e.g. Triton-X 100) or by enzymatic cleavage. Cells employed in expression of chimeric FGF19 polypeptide can be disrupted by various physical or chemical means, such as freeze-thaw cycling, sonication, mechanical disruption, or cell lysing agents.

It may be desired to purify chimeric FGF19 polypeptide from recombinant cell proteins or polypeptides. The following procedures are exemplary of suitable purification procedures: by fractionation on an ion-exchange, column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the chimeric FGF19 polypeptide. Various methods of protein purification may be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the particular chimeric FGF19 polypeptide produced.

X. Nucleic Acids Encoding Chimeric FGF19 Polypeptides and Their Uses

The present invention includes in another aspect nucleotide sequences (or their complement) that encode chimeric FGF19 polypeptides (or "chimeric FGF19 nucleic acids") of the present invention. Chimeric FGF19 nucleic acids of the present invention have various applications in the art of molecular biology, including uses as hybridization probes, in chromosome and gene mapping and in the generation of anti-sense RNA and DNA. Chimeric FGF19 nucleic acids will also be useful for the preparation of chimeric FGF19 polypeptides by the recombinant techniques described herein.

In some embodiments, chimeric FGF19 polypeptides may include one or more epitope tags. In some embodiments, an epitope tag is positioned at the N-terminus of the chimeric FGF19 polypeptide. In some embodiments, an epitope tag is positioned at the C-terminus of the chimeric FGF19 polypeptide. In some embodiments, an epitope tag is positioned at the N-terminus of the chimeric FGF19 polypeptide.

In some embodiments, chimeric FGF19 polypeptides may include one or more epitope tags. In some embodiments, an epitope tag is positioned at the N-terminus of the chimeric FGF19 polypeptide. In some embodiments, an epitope tag is positioned at the C-terminus of the chimeric FGF19 polypeptide. In some embodiments, an epitope tag is positioned at the N-terminus of the chimeric FGF19 polypeptide. In some embodiments, the epitope tag comprises the amino acid sequence DYKDDDDK (SEQ ID NO:279).

In an exemplary embodiment, a chimeric FGF19 nucleic acid of the present invention includes the sequence:
CACCCCATCCCTGACTCCAGTCCTCTC-
CTGCAATTCGGGGGCCAAGTCCGGCAGCGGTA
CCTCTACACCTCCGGC-
CCCCACGGGCTCTCCAGCTGCTTCCT-
GCGCATCCGTGCCGACGG CGTCGTGGACT-
GCGCGCGGGGCCAGAGCGCGCACAGTTTGCTGGA
GATCAAGGCAGTC GCTCTGCGGACCGTGGCCAT-
CAAGGGCGTGCACAGCGTGCGGTAC-
CTCTGCATGGGCGC CGACGGCAAGATG-
CAGGGGCTGCTTCAGTACTCGGAGGAAGACTGTGC
TTTCGAGGAG GAGATCCGCCCAGATGGCTACAAT-
GTGTACCGATCCGAGAAGCACCGCCTCCCGGTCTC
CCTGAGCAGTGCCAAACAGCGGCAGCTG-
TACAAGAACAGAGGCTTTCTTCCACTCTCTC
ATTTCCTGCCCATGCTGCCCATGGTC-
CCAGAGGAGCCTGAGGACCTCAGGGGCCACTTG
GAATCTGACATGTTCTCTTCGCCCCTG-
GAGACCGACAGCATGGACCCATTTGGGCTTGTC
ACCGGACTGGAGGCCGTGAGGAGTC-
CCAGCTTTGAGAAG (SEQ ID NO:7). This exemplary nucleic acid sequence encodes a polypeptide having an amino acid sequence that corresponds to the chimeric FGF19 polypeptide cFGF21/19-2, as shown in Table 3.

In another exemplary embodiment, a chimeric FGF19 nucleic acid of the present invention includes the sequence:
ATGGACTCGGACGAGACCGGGTTCGAG-
CACTCAGGgCTGTGGGTTTCTGTGCTGGCTGG TCT-
TCTGCTGGGAGCCTGCCAGGCACAC-
CCCATCCCTGACTCCAGTCCTCTCCTGCAATT
CGGGGGCCAAGTCCGGCAGCGGTACCTC-
TACACCTCCGGCCCCCACGGGCTCTCCAGCT GCT-
TCCTGCGCATCCGTGCCGACG-
GCGTCGTGGACTGCGCGCGGGGCCAGAGCGCGCAC
AGTTTGCTGGAGATCAAG-
GCAGTCGCTCTGCGGACCGTGGCCAT-
CAAGGGCGTGCACAG CGTGCGGTACCTCTG-
CATGGGCGCCGACGGCAAGATGCAGGGGCTGCTTC
AGTACTCGG AGGAAGACTGTGCTTTCGAGGAG-
GAGATCCGCCCAGATGGCTACAATGTGTACCGATCC
GAGAAGCACCGCCTCCCGGTCTCCCT-
GAGCAGTGCCAAACAGCGGCAGCTGTACAAGA
ACAGAGGCTTTCTTCCACTCTCT-
CATTTCCTGCCCATGCTGCCCATGGTC-
CCAGAGGAGC CTGAGGACCTCAGGGGCCACTTG-
GAATCTGACATGTTCTCTTCGCCCCTGGAGACCGAC
AGCATGGACCCATTTGGGCTTGTCACCG-
GACTGGAGGCCGTGAGGAGTCCCAGCTTTGA
GAAGGACTACAAAGACGATGACGACAAGTGA (SEQ ID NO:281). This exemplary nucleic acid sequence encodes a polypeptide having an amino acid sequence that includes the sequence of the chimeric FGF19 polypeptide cFGF21/19-2, as shown in Table 3. The polypeptide also includes a C-terminal epitope tag DYKDDDK (SEQ ID NO:280) and the N-terminal native signal sequence of hFGF21 polypeptide (MDSDETGFEHSGLWVSVLAGLLLGACQA; SEQ ID NO:282).

In another exemplary embodiment, a chimeric FGF19 nucleic acid of the present invention includes the sequence:
ATGCGGAGCGGGTGTGTGGTGGTCCACG-
TATGGATCCTGGCCGGCCTCTGGCTGGCCGT GGC-
CGGGCGCCCCCTCCGCCTTCTCG-
GACGCGGGGCCCCACGTGCACTACGGCTGGGGCG
ACCCCATCCGCCTGCGGCACCTGTACA-
CAGATGATGCCCAGCAGACAGAAGCCCACCTG
GAGATCAGGGAGGATGGGACG-
GTGGGGGGCGCTGCTGACCAGAGC-
CCCGAAAGTCTCC TGCAGCTGAAAGCCTTGAAGC-
CGGGGAGTTATTCAAATCTTGGGAGTCAAGACATCCA
GG TTCCTGTGCCAGCGGCCAGATGGGGC-
CCTGTATGGATCGCTCCACTTTGACCCTGAGGCC
TGCAGCTTCCGGGAGCTGCTTCTTGAG-
GACGGATACAATGTTTACCAGTCCGAAGCCCA
CGGCCTCCCGCTGCACCTGCCAGGGAA-
CAAGTCCCCACACCGGGACCCTGCACCCCGAG
GACCAGCTCGCTTCCTGCCACTACCAG-
GCCTGCCCCCGCACTCCCGGAGCCACCCGGA
ATCCTGGCCCCCCAGCCCCCGAT-
GTGGGCTCCTCGGACCCTCTGAGCATGGTGGGACC
TTCCCAGGGCCGAAGCCCCAGCTACGCT-
TCCGACTACAAGGACGACGATGACAAGTGA (SEQ ID NO:283). This exemplary nucleic acid sequence encodes a polypeptide having an amino acid sequence that includes the sequence of the chimeric FGF19 polypeptide cFGF19/21-2, as shown in Table 6. The polypeptide also includes a C-terminal epitope tag DYKDDDK (SEQ ID NO:280) and the N-terminal native signal sequence of hFGF19 polypeptide (MRSGCVVVHVWILAGLWLAVAG; SEQ ID NO:284).

In another exemplary embodiment, a chimeric FGF19 nucleic acid of the present invention includes the sequence:
ATGGAcTCGGACGAGACCGGGTTCGAG-
CACTCAGGGCTGTGGGTTTCTGTGCTGGCTGG TCT-
TCTGCTGGGAGCCTGCCAGGCACAC-
CCCATCCCTGACTCCAGTCCTCTCCTGCAATT
CGGGGGCCAAGTCCGGCAGCGGTACCTC-
TACACAGATGATGCCCAGCAGACAGAAGCC CAC-
CTGGAGATCAGGGAGGATGGGACG-
GTGGGGGGCGCTGCTGACCAGAGCCCCGAAA
GTCTCCTGCAGCTGAAAGCCTTGAAGC-
CGGGGAGTTATTCAAATCTTGGGAGTCAAGACA
TCCAGGTTCCTGTGCCAGCGGCCA-
GATGGGGCCCTGTATGGATCGCTCCACTTTGACCCT
GAGGCCTGCAGCTTCCGGGAGCTGCT-
TCTTGAGGACGGATACAATGTTTACCAGTCCGA
AGCCCACGGCCTCCCGCTGCACCTGC-
CAGGGAACAAGTCCCCACACCGGGACCCTGCAC
CCCGAGGACCAGCTCGCTTCCTTC-
CACTCTCTCATTTCCTGCCCATGCTGCCCATGGTCC
CAGAGGAGCCTGAGGACCTCAGGGGC-
CACTTGGAATCTGACATGTTCTCTTCGCCCCTG
GAGACCGACAGCATGGAC-
CCATTTGGGCTTGTCACCGGACTGGAG-
GCCGTGAGGAGTCC CAGCTTTGAGAAGGACTA-
CAAAGACGATGACGACAAGTGA (SEQ ID NO:285). This exemplary nucleic acid sequence encodes a polypeptide having an amino acid sequence that includes the sequence of the chimeric FGF19 polypeptide cFGF21/19-13, as shown in Table 5. The polypeptide also includes a C-terminal epitope tag DYKDDDK (SEQ ID NO:280) and the N-terminal native signal sequence of hFGF21 polypeptide (MDSDETGFEHSGLWVSVLAGLLLGACQA; SEQ ID NO:282).

The full-length native nucleic acid sequence of hFGF19 gene, the full-length native nucleic acid sequence of FGF21 gene, the full-length native nucleic acid sequence of a chimeric FGF19 polypeptide of the present invention, or portions thereof of any of the foregoing, may be used as hybridization probes for detecting or screening for nucleic acids that encode chimeric FGF19 polypeptides of the present invention. Optionally, the length of the probes will be about 20 to about 50 bases. By way of example, a screening method will comprise isolating the coding region of the FGF19 gene using the known DNA sequence to synthesize a selected probe of about 40 bases. Hybridization probes may be labeled by a variety of labels, including radionucleotides such as $^{32}$P or $^{35}$S, or enzymatic labels such as alkaline phosphatase coupled to the probe via avidin/biotin coupling systems. Labeled probes having a sequence complementary to that of the FGF19 gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the chimeric FGF19 nucleic acids include antisense or sense oligonucleotides comprising a singe-stranded nucleic acid sequence (either RNA or DNA) capable of binding to target chimeric FGF19 mRNA (sense) or chimeric FGF19 DNA (antisense) sequences. Antisense or sense oligonucleotides, according to the present invention, comprise a fragment of the coding region of chimeric FGF19 DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (Cancer Res. 48:2659, 1988) and van der Krol et al. (BioTechniques 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of chimeric FGF19 polypeptides. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, CaPO$_4$-mediated DNA transfection; electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The probes may also be employed in PCR techniques to generate a pool of sequences for identification of closely related chimeric FGF19 coding sequences.

Nucleic acid encoding the chimeric FGF19 polypeptide may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad. Sci. USA 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., Trends in Biotechnology 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990). For review of gene marking and gene therapy protocols see Anderson et al., Science 256, 808-813 (1992).

X. Articles of Manufacture

In another embodiment of the invention, an article of manufacture containing materials useful for treating metabolic-related disorders, conditions or symptoms as described above is provided. Preferably, the article of manufacture comprises: (a) a container comprising a composition comprising a chimeric FGF19 polypeptide described herein and a pharmaceutically acceptable carrier or diluent within the container; and (b) a package insert with instructions for administering the composition to an individual suffering from or exhibiting the metabolic-related disorders, conditions or symptoms.

In some embodiments, the individual has a metabolic-related disorders, conditions or symptoms. In some embodiments, the individual is at risk for developing a metabolic-related disorder, condition or symptom. In some embodiments, the individual has one or more characteristics selected from the group consisting of (a) waist circumference of about 102 cm or more in men and about 88 cm or more in women, (b) fasting triglycerides of about 150 mg/dL or more, (c) a fasting glucose of about 95 mg/dL or higher, and (d) high levels of oxidized LDL. In some embodiments, the individual further has inflammation associated with diabetes. In some embodiments, the individual has a blood glucose level of about 95 mg/dL or higher after an overnight fast. In some embodiments, the individual has a blood glucose level of about 126 mg/dL or higher after an overnight fast. In some embodiments, the individual has a blood glucose level of about 140 mg/dL after a two-hour oral glucose tolerance test. In some embodiments, the individual has a blood glucose level of about 200 mg/dL after a two-hour oral glucose tolerance test. In some embodiments, the individual has pre-diabetes. In some embodiments, the individual has diabetes. In some embodiments, the diabetes is selected from the group consisting of type-I diabetes, type-II diabetes, and gestational diabetes. In some embodiments, the diabetes is type-II diabetes.

The article of manufacture comprises a container and a label or package insert on or associated with the container. Suitable containers include, for example, bottles, vials, syringes, etc. The containers may be formed from a variety of materials such as glass or plastic. The container holds or contains a composition that is effective for treating the multiple sclerosis and may have a sterile access port (for example the container may be an intravenous solution bag or a vial having a stopper pierceable by a hypodermic injection needle). At least one active agent in the composition is the chimeric FGF19 polypeptide. The label or package insert indicates that the composition is used for treating metabolic-related disorders, conditions or symptoms in an individual suffering therefrom with specific guidance regarding dosing amounts and intervals of antibody and any other drug being provided. The article of manufacture may further comprise a second container comprising a pharmaceutically acceptable diluent buffer, such as bacteriostatic water for injection (BWFI), phosphate-buffered saline, Ringer's solution and dextrose solution. The article of manufacture may further include other materials desirable from a commercial and user standpoint, including other buffers, diluents, filters, needles, and syringes.

Optionally, the article of manufacture herein further comprises a container comprising a second agent other than the polypeptide for treatment and further comprising instructions on treating the mammal with such agent. In some embodiments, the second agent is an anti-inflammatory agent, an anti-diabetic agent, and/or cholesterol-lowering drug of the "statin" class. In some embodiments, the second active agent is insulin. In some embodiments, the insulin is rapid acting, short acting, regular acting, intermediate acting, or long acting insulin. In some embodiments, the insulin is and/or comprises Humalog, Lispro, Novolog, Apidra, Humulin, Aspart, regular insulin, NPH, Lente, Ultralente, Lantus, Glargine, Levemir, or Detemir. In some embodiments, the second active agent is a statin. In some embodiments, the statin is and/or comprises Atorvastatin (e.g., Lipitor or Torvast), Cerivastatin (e.g., Lipobay or Baycol), Fluvastatin (e.g., Lescol or Lescol), Lovastatin (e.g., Mevacor, Altocor, or Altoprev) Mevastatin, Pitavastatin (e.g., Livalo or Pitava), Pravastatin (e.g., Pravachol, Selektine, or Lipostat) Rosuvastatin (e.g., Crestor), Simvastatin (e.g., Zocor or Lipex), Vytorin, Advicor, Besylate Caduet or Simcor.

A "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products, etc.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of the cells identified in the following examples, and throughout the specification, by ATCC accession numbers is the American Type Culture Collection, Manassas, Va. Cells were cultured in Dulbecco's Modified Eagle Medium (DMEM) supplemented with 10% fetal bovine serum (FBS) at 37° C. under 5% $CO_2$, unless otherwise noted.

Example 1

KLB-Independent FGFR Binding Activity of Chimeric and Native FGF Polypeptides

The in vitro FGF receptor-binding activity of a chimeric FGF polypeptide of the present invention was measured using an enzyme-linked immunosorbent assay (ELISA). Referring to FIG. 3A (top), a schematic diagram of the ELISA for measuring FGF receptor (FGFR) in vitro binding activity and its corresponding control are depicted.

Monoclonal antibodies specific for human IgG-Fc fragment (Jackson ImmunoResearch, West Grove, Pa., USA) were immobilized in the wells of Maxisorp™ flat-bottom 96-well plates (Nunc, Thermo Fisher Scientific, Rochester, N.Y.) by overnight incubation with 100 µl per well of 2 µg/ml antibody solution. Each well was then incubated with either 1 µg/ml of FGFR4—Fc (a recombinant polypeptide comprising a human FGFR4 extracellular domain fused to a human $IgG_1$ Fc fragment; catalog no. 685-FR-050, R&D Systems, Inc., Minneapolis, Minn.) or 1 µg/ml FGFR1c-Fc (a recombinant polypeptide comprising a human FGFR1c extracellular domain fused to a human $IgG_1$ Fc fragment; catalog no. 658-FR-050, R&D Systems).

The surface-immobilized FGFR4-Fc or FGFR1c-Fc polypeptides were incubated for 1 hr with native human FGF19-Flag polypeptide with a C-terminal epitope tag (See FGF19-Flag in Table 10, SEQ ID NO:237) at concentrations of 1 µg/mL, 0.4 µg/mL, 0.16 µg/mL, 0.064 µg/mL, 0.0256 µg/mL, 0.004096 µg/mL or 0.0016384 µg/mL, each with 2

μg/mL heparin, to allow binding of the FGF19 polypeptide to the receptor domain. Similarly, the surface-immobilized FGFR4—Fc or FGFR1c-Fc polypeptides were incubated for 1 hr with a chimeric FGF19 polypeptide with a C-terminal epitope tag (See cFGF21/19-2/Flag in Table 10; SEQ ID NO:242) at concentrations of 1 μg/mL, 0.4 μg/mL, 0.16 μg/mL, 0.064 μg/mL, 0.0256 μg/mL, 0.004096 μg/mL or 0.0016384 μg/mL, each with 2 μg/mL heparin, to allow binding of the chimeric FGF19 polypeptide to the receptor domain. Following incubation, the amount of native or chimeric FGF19 polypeptide bound to the receptor domain at a given FGF19 polypeptide concentration was determined using biotinylated anti-human FGF19 polyclonal antibody (catalog no. BAF969, R&D Systems), streptavidin-horseradish peroxidase (HRP) (catalog no. RPN1231V, Amersham Biosciences, Pittsburgh, Pa.) and 3, 3', 5, 5'-tetramethylbenzidine substrate (catalog no. TMBE-1000, Moss, Inc., Pasadena, Md.), and by measuring concentration of the HRP-dependent product by its absorption at 450 nm. Control ELISA experiments were performed to demonstrate that the native and chimeric FGF19 polypeptides are recognized by the anti-human FGF19 polyclonal antibody with an equivalent efficiency (data not shown).

Referring to FIG. 3A, the results of the in vitro FGFR binding assay to surface-immobilized FGFR4-Fc or FGFR1c-Fc polypeptides showed that native human FGF19 polypeptide bound to FGFR4-Fc in a concentration-dependent, Klotho-beta-independent manner, but did not appreciably bind to FGFR1c-Fc. Klotho-beta-independent binding of chimeric FGFR19 polypeptide (cFGF21/19-2/Flag; SEQ ID NO:242) to either FGFR4-Fc or FGFR1c-Fc was not detected.

Referring to FIG. 3B, a schematic diagram of an assay for FGFR activation is depicted. In this assay, transiently-transfected L6 cells express an FGF receptor, such as human FGFR1c or human FGFR4, on their cell surfaces. Effective binding of a ligand to the FGF receptor can result in activation of an endogenous MAP kinase pathway, which can result in phosphorylation of a chimeric transcriptional activator having an Elk-1 activation domain and a GAL4 DNA-binding domain. The phosphorylated transcriptional activator can activate expression of a reporter gene under control of a suitable upstream activation sequence (UAS), such as the yeast GAL4 UAS. The reporter gene may encode an enzyme such as a luciferase enzyme, particularly a firefly luciferase enzyme. The L6 cells may be further transfected with a constitutively-expressed *Renilla* luciferase, which can serve as a normalization control for the inducible firefly luciferase.

In this assay, rat L6 myoblasts in a 96-well plate were transiently-transfected with an expression vector encoding a human FGFR4 polypeptide, an expression vector encoding a GAL4-Elk-1 transcriptional activator (catalog no. 219005, pFA2-Elk1, Stratagene, La Jolla, Calif.), an expression vector encoding a firefly luciferase reporter gene under control of the yeast GAL4 upstream activator (catalog no. 219050, pFR-luc, Stratagene). A vector for the constitutive expression of *Renilla* luciferase (catalog no. E2231, pRL-SV40, Promega, Madison, Wis.) was also transfected into the cells. Transfections were performed using FuGENE HD Transfection Reagent (catalog no. 04 709 705 001, Roche Applied Science, Indianapolis, Ind.) in accordance with the manufacturer's instructions.

The transfected L6 cells were cultured overnight in DMEM (prepared from Cellgro 50-013-PC, Mediatech, Inc., Manassas, Va.) containing 10% FBS (catalog no. F2442, Sigma-Aldrich, St. Louis, Mo.). The cells were then washed and cultured for an additional 6 hours in an enriched serum-free medium derived from the F12/DME 50:50 blend containing 25 mg/L porcine heparin and a given concentration of the FGF19 polypeptide. The FGF19 polypeptides that were assayed were native FGF19-Flag polypeptide (See FGF19-Flag in Table 10; SEQ ID NO:237), native FGF21-His polypeptide (See FGF21-His in Table 10; SEQ ID NO:238) and a chimeric FGF19-Flag polypeptide (See cFGF21/19-2/Flag in Table 10; SEQ ID NO:242). The cells were incubated with the polypeptide at concentrations of 10 μg/mL, 1666.7 ng/mL, 277.8 ng/mL, 46.3 ng/mL, 7.7 ng/mL, 1.3 ng/mL, 0.21 ng/mL, 0.036 ng/mL, 0.0060 ng/mL, 0.00099 ng/mL, 0.00017 ng/mL or 0.000028 ng/mL. The cells were then lysed with PLB reagent (catalog no. E1941, Promega) and luciferase activity in each well was determined using Dual-Glo Luciferase Assay System (catalog no. E2940, Promega) and EnVision Multilabel Reader (catalog no. 2103, PerkinElmer, Waltham, Mass.) in accordance with the respective manufacturers' instructions. Each firefly luciferase activity was normalized to the co-expressed *Renilla* luciferase activity, and each sample condition was performed in triplicate.

TABLE 10

Polypeptide Sequences

| Name | Amino Acid Sequence (N-C) | SEQ ID NO |
|---|---|---|
| FGF19-Flag | RPLAFSDAGPHVHYGWGDPIRLRHLYTSGPHGLSSCFLRIRADGVVDC ARGQSAHSLLEIKAVALRTVAIKGVHSVRYLCMGADGKMQGLLQYSE EDCAFEEEIRPDGYNVYRSEKHRLPVSLSSAKQRQLYKNRGELPLSHFL PMLPMVPEEPEDLRGHLESDMFSSPLETDSMDPFGL VTGLEAVRSPSFEKDYKDDDDK | 237 |
| FGF21-His | HHHHHHPIPDSSPLLQFGGQVRQRYLYTDDAQQTEAHLEIREDGTVGG AADQSPESLLQLKALKPGVIQILGVKTSRFLCQRPDGALYGSLHFDPEA CSFRELLLEDGYNVYQSEAHGLPLHLPGNKSPHRDPAPRGPARFLPLP GLPPALPEPPGILAPQPPDVGSSDPLSMVGPSQGRSPSYAS | 238 |
| FGF21-FlagC | HPIPDSSPLLQFGGQVRQRYLYTDDAQQTEAHLEIREDGTVGGAADQS PESLLQLKALKPGVIQILGVKTSRFLCQRPDGALYGSLHFDPEACSFRE LLLEDGYNVYQSEAHGLPLHLPGNKSPHRDPAPRGPARFLPLPGLPPA LPEPPGILAPQPPDVGSSDPLSMVGPSQGRSPSYASDYKDDDDK | 239 |
| FGF21-FlagN | KDYKDDDDKLEHPIPDSSPLLQFGGQVRQRYLYTDDAQQTEAHLEIRE DGTVGGAADQSPESLLQLKALKPGVIQILGVKTSRFLCQRPDGALYGS | 240 |

TABLE 10-continued

Polypeptide Sequences

| Name | Amino Acid Sequence (N-C) | SEQ ID NO |
|------|---------------------------|-----------|
| | LHFDPEACSFRELLLEDGYNVYQSEAHGLPLHLPGNKSPHRDPAPRGP ARFLPLPGLPPALPEPPGILAPQPPDVGSSDPLSMVGPSQGRSPSYAS | |
| cFGF21/19-1/Flag | HPIPDSSPHVHYGWGDPIRLRHLYTSGPHGLSSCFLRIRADGVVDCARG QSAHSLLEIKAVALRTVAIKGVHSVRYLCMGADGKMQGLLQYSEEDC AFEEEIRPDGYNVYRSEKHRLPVSLSSAKQRQLYKNRGFLPLSHFLPML PMVPEEPEDLRGHLESDMFSSPLETDSMDPFGLVTGLEAVRSPSFEKD YKDDDDK | 241 |
| cFGF21/19-2/Flag | HPIPDSSPLLQFGGQVRQRYLYTSGPHGLSSCFLRIRADGVVDCARGQS AHSLLEIKAVALRTVAIKGVHSVRYLCMGADGKMQGLLQYSEEDCAF EEEIRPDGYNVYRSEKHRLPVSLSSAKQRQLYKNRGFLPLSHFLPMLP MVPEEPEDLRGHLESDMFSSPLETDSMDPFGLVTGLEAVRSPSFEKDY KDDDDK | 242 |
| cFGF21/19-3/Flag | HPIPDSSPLLQFGGQVRQRYLYTDDPHGLSSCFLRIRADGVVDCARGQ SAHSLLEIKAVALRTVAIKGVHSVRYLCMGADGKMQGLLQYSEEDCA FEEEIRPDGYNVYRSEKHRLPVSLSSAKQRQLYKNRGFLPLSHFLPMLP MVPEEPEDLRGHLESDMFSSPLETDSMDPFGLVTGLEAVRSPSFEKDY KDDDDK | 243 |
| cFGF21/19-4/Flag | HPIPDSSPLLQFGGQVRQRYLYTDDAQLSSCFLRIRADGVVDCARGQS AHSLLEIKAVALRTVAIKGVHSVRYLCMGADGKMQGLLQYSEEDCAF EEEIRPDGYNVYRSEKHRLPVSLSSAKQRQLYKNRGFLPLSHFLPMLP MVPEEPEDLRGHLESDMFSSPLETDSMDPFGLVTGLEAVRSPSFEKDY KDDDDK | 244 |
| cFGF21/19-5/Flag | HPIPDSSPLLQFGGQVRQRYLYTDDAQQTSCFLRIRADGVVDCARGQS AHSLLEIKAVALRTVAIKGVHSVRYLCMGADGKMQGLLQYSEEDCAF EEEIRPDGYNVYRSEKHRLPVSLSSAKQRQLYKNRGFLPLSHFLPMLP MVPEEPEDLRGHLESDMFSSPLETDSMDPFGLVTGLEAVRSPSFEKDY KDDDDK | 245 |
| cFGF21/19-6/Flag | HPIPDSSPLLQFGGQVRQRYLYTDDAQQTEAFLRIRADGVVDCARGQS AHSLLEIKAVALRTVAIKGVHSVRYLCMGADGKMQGLLQYSEEDCAF EEEIRPDGYNVYRSEKHRLPVSLSSAKQRQLYKNRGFLPLSHFLPMLP MVPEEPEDLRGHLESDMFSSPLETDSMDPFGLVTGLEAVRSPSFEKDY KDDDDK | 246 |
| cFGF21/19-7/Flag | HPIPDSSPLLQFGGQVRQRYLYTDDAQQTEAHLEIRADGVVDCARGQS AHSLLEIKAVALRTVAIKGVHSVRYLCMGADGKMQGLLQYSEEDCAF EEEIRPDGYNVYRSEKHRLPVSLSSAKQRQLYKNRGFLPLSHFLPMLP MVPEEPEDLRGHLESDMFSSPLETDSMDPFGLVTGLEAVRSPSFEKDY KDDDDK | 247 |
| cFGF21/19-8/Flag | HPIPDSSPLLQFGGQVRQRYLYTDDAQQTEAHLEIREDGVVDCARGQS AHSLLEIKAVALRTVAIKGVHSVRYLCMGADGKMQGLLQYSEEDCAF EEEIRPDGYNVYRSEKHRLPVSLSSAKQRQLYKNRGFLPLSHFLPMLP MVPEEPEDLRGHLESDMFSSPLETDSMDPFGLVTGLEAVRSPSFEKDY KDDDDK | 248 |
| cFGF21/19-9/Flag | HPIPDSSPLLQFGGQVRQRYLYTDDAQQTEAHLEIREDGTVGGAAD QSAHSLLEIKAVALRTVAIKGVHSVRYLCMGADGKMQGLLQYSEEDC AFEEEIRPDGYNVYRSEKHRLPVSLSSAKQRQLYKNRGFLPLSHFLPML PMVPEEPEDLRGHLESDMFSSPLETDSMDPFGLVTGLEAVRSPSFEKD YKDDDDK | 249 |
| cFGF21/19-10/Flag | HPIPDSSPLLQFGGQVRQRYLYTDDAQQTEAHLEIREDGTVGGAADQS PESLLEIKAVALRTVAIKGVHSVRYLCMGADGKMQGLLQYSEEDCAF EEEIRPDGYNVYRSEKHRLPVSLSSAKQRQLYKNRGFLPLSHFLPMLP MVPEEPEDLRGHLESDMFSSPLETDSMDPFGLVTGLEAVRSPSFEKDY KDDDDK | 250 |
| cFGF21/19-11/Flag | HPIPDSSPLLQFGGQVRQRYLYTDDAQQTEAHLEIREDGTVGGAADQS PESLLQLKALKPGVIQILGVHSVRYLCMGADGKMQGLLQYSEEDCAFE EEIRPDGYNVYRSEKHRLPVSLSSAKQRQLYKNRGFLPLSHFLPMLPM VPEEPEDLRGHLESDMFSSPLETDSMDPFGLVTGLEAVRSPSFEKDYK DDDDK | 251 |
| cFGF21/19-12/Flag | HPIPDSSPLLQFGGQVRQRYLYTDDAQQTEAHLEIREDGTVGGAADQS PESLLQLKALKPGVIQILGVKTSRFLCMGADGKMQGLLQYSEEDCAFE EEIRPDGYNVYRSEKHRLPVSLSSAKQRQLYKNRGFLPLSHFLPMLPM VPEEPEDLRGHLESDMFSSPLETDSMDPFGLVTGLEAVRSPSFEKDYK DDDDK | 252 |

TABLE 10-continued

Polypeptide Sequences

| Name | Amino Acid Sequence (N-C) | SEQ ID NO |
|------|---------------------------|-----------|
| cFGF21/19-13/Flag | HPIPDSSPLLQFGGQVRQRYLYTDDAQQTEAHLEIREDGTVGGAADQS PESLLQLKALKPGVIQILGVKTSRFLCQRPDGALYGSLHFDPEACSFRE LLLEDGYNVYQSEAHGLPLHLPGNKSPHRDPAPRGPARFLPMLPMVPE EPEDLRGHLESDMFSSPLETDSMDPFGLVTGLEAVRSPSFEKDYKDDD DK | 253 |
| cFGF19/21-1/Flag | RPLAFSDAGPLLQFGGQVRQRYLYTDDAQQTEAHLEIREDGTVGGAA DQSPESLLQLKALKPGVIQILGVKTSRFLCQRPDGALYGSLHFDPEACS FRELLLEDGYNVYQSEAHGLPLHLPGNKSPHRDPAPRGPARFLPLPGLP PALPEPPGILAPQPPDVGSSDPLSMVGPSQGRSPSYASDYKDDDDK | 254 |
| cFGF19/21-2/Flag | RPLAFSDAGPHVHYGWGDPIRLRHLYTDDAQQTEAHLEIREDGTVGG AADQSPESLLQLKALKPGVIQILGVKTSRFLCQRPDGALYGSLHFDPEA CSFRELLLEDGYNVYQSEAHGLPLHLPGNKSPHRDPAPRGPARFLPLP GLPPALPEPPGILAPQPPDVGSSDPLSMVGPSQGRSPSYASDYKDDDDK | 255 |
| cFGF19/21-3/Flag | RPLAFSDAGPHVHYGWGDPIRLRHLYTSGPHGLSSCFLRIREDGTVGG AADQSPESLLQLKALKPGVIQILGVKTSRFLCQRPDGALYGSLHFDPEA CSFRELLLEDGYNVYQSEAHGLPLHLPGNKSPHRDPAPRGPARFLPLP GLPPALPEPPGILAPQPPDVGSSDPLSMVGPSQGRSPSYASDYKDDDDK | 256 |
| cFGF19/21-4/Flag | RPLAFSDAGPHVHYGWGDPIRLRHLYTSGPHGLSSCFLRIRADGTVGG AADQSPESLLQLKALKPGVIQILGVKTSRFLCQRPDGALYGSLHFDPEA CSFRELLLEDGYNVYQSEAHGLPLHLPGNKSPHRDPAPRGPARFLPLP GLPPALPEPPGILAPQPPDVGSSDPLSMVGPSQGRSPSYASDYKDDDDK | 257 |
| cFGF19/21-5/Flag | RPLAFSDAGPHVHYGWGDPIRLRHLYTSGPHGLSSCFLRIRADGVVDC ARGQSPESLLQLKALKPGVIQILGVKTSRFLCQRPDGALYGSLHFDPEA CSFRELLLEDGYNVYQSEAHGLPLHLPGNKSPHRDPAPRGPARFLPLP GLPPALPEPPGILAPQPPDVGSSDPLSMVGPSQGRSPSYASDYKDDDDK | 258 |
| cFGF19/21-6/Flag | RPLAFSDAGPHVHYGWGDPIRLRHLYTSGPHGLSSCFLRIRADGVVDC ARGQSAHSLLQLKALKPGVIQILGVKTSRFLCQRPDGALYGSLHFDPE ACSFRELLLEDGYNVYQSEAHGLPLHLPGNKSPHRDPAPRGPARFLPL PGLPPALPEPPGILAPQPPDVGSSDPLSMVGPSQGRSPSYASDYKDDDD K | 259 |
| cFGF19/21-7/Flag | RPLAFSDAGPHVHYGWGDPIRLRHLYTSGPHGLSSCFLRIRADGVVDC ARGQSAHSLLEIKAVALRTVAIKGVKTSRFLCQRPDGALYGSLHFDPE ACSFRELLLEDGYNVYQSEAHGLPLHLPGNKSPHRDPAPRGPARFLPL PGLPPALPEPPGILAPQPPDVGSSDPLSMVGPSQGRSPSYASDYKDDDD K | 260 |
| cFGF19/21-8/Flag | RPLAFSDAGPHVHYGWGDPIRLRHLYTSGPHGLSSCFLRIRADGVVDC ARGQSAHSLLEIKAVALRTVAIKGVHSVRYLCQRPDGALYGSLHFDPE ACSFRELLLEDGYNVYQSEAHGLPLHLPGNKSPHRDPAPRGPARFLPL PGLPPALPEPPGILAPQPPDVGSSDPLSMVGPSQGRSPSYASDYKDDDD K | 261 |
| cFGF19/21-9/Flag | RPLAFSDAGPHVHYGWGDPIRLRHLYTSGPHGLSSCFLRIRADGVVDC ARGQSAHSLLEIKAVALRTVAIKGVHSVRYLCMGADGKMQGLLQYSE EDCAFEEEIRPDGYNVYRSEKHRLPVSLSSAKQRQLYKNRGFLPLSHFL PLPGLPPALPEPPGILAPQPPDVGSSDPLSMVGPSQGRSPSYASDYKDD DDK | 262 |
| cFGF19/21/19-1/Flag | RPLAFSDAGPLLQFGGQVRQRYLYTSGPHGLSSCFLRIRADGVVDCAR GQSAHSLLEIKAVALRTVAIKGVHSVRYLCMGADGKMQGLLQYSEED CAFEEEIRPDGYNVYRSEKHRLPVSLSSAKQRQLYKNRGFLPLSHFLP MLPMVPEEPEDLRGHLESDMFSSPLETDSMDPFGLVTGLEAVRSPSFE KDYKDDDDK | 263 |
| cFGF19/21/19-2/Flag | RPLAFSDAGPLLQFGGQVRQRYLYTDDPHGLSSCFLRIRADGVVDCAR GQSAHSLLEIKAVALRTVAIKGVHSVRYLCMGADGKMQGLLQYSEED CAFEEEIRPDGYNVYRSEKHRLPVSLSSAKQRQLYKNRGFLPLSHFLP MLPMVPEEPEDLRGHLESDMFSSPLETDSMDPFGLVTGLEAVRSPSFE KDYKDDDDK | 264 |
| cFGF19/21/19-3/Flag | RPLAFSDAGPLLQFGGQVRQRYLYTDDAQGLSSCFLRIRADGVVDCAR GQSAHSLLEIKAVALRTVAIKGVHSVRYLCMGADGKMQGLLQYSEED CAFEEEIRPDGYNVYRSEKHRLPVSLSSAKQRQLYKNRGFLPLSHFLP MLPMVPEEPEDLRGHLESDMFSSPLETDSMDPFGLVTGLEAVRSPSFE KDYKDDDDK | 265 |

TABLE 10-continued

Polypeptide Sequences

| Name | Amino Acid Sequence (N-C) | SEQ ID NO |
|---|---|---|
| cFGF19/21/19-4/Flag | RPLAFSDAGPLLQFGGQVRQRYLYTDDAQLSSCFLRIRADGVVDCARG QSAHSLLEIKAVALRTVAIKGVHSVRYLCMGADGKMQGLLQYSEEDC AFEEEIRPDGYNVYRSEKHRLPVSLSSAKQRQLYKNRGFLPLSHFLPML PMVPEEPEDLRGHLESDMFSSPLETDSMDPFGLVTGLEAVRSPSFEKD YKDDDDK | 266 |
| cFGF19/21/19-5/Flag | RPLAFSDAGPLLQFGGQVRQRYLYTDDAQQTSCFLRIRADGVVDCAR GQSAHSLLEIKAVALRTVAIKGVHSVRYLCMGADGKMQGLLQYSEED CAFEEEIRPDGYNVYRSEKHRLPVSLSSAKQRQLYKNRGFLPLSHFLP MLPMVPEEPEDLRGHLESDMFSSPLETDSMDPFGLVTGLEAVRSPSFE KDYKDDDDK | 267 |
| cFGF19/21/19-6/Flag | RPLAFSDAGPLLQFGGQVRQRYLYTDDAQQTEAFLRIRADGVVDCAR GQSAHSLLEIKAVALRTVAIKGVHSVRYLCMGADGKMQGLLQYSEED CAFEEEIRPDGYNVYRSEKHRLPVSLSSAKQRQLYKNRGFLPLSHFLP MLPMVPEEPEDLRGHLESDMFSSPLETDSMDPFGLVTGLEAVRSPSFE KDYKDDDDK | 268 |
| cFGF19/21/19-29/Flag | RPLAFSDAGPHVHYGWGDPIRLRHLYTSGPHGLSSCFLRIRADGVVDC ARGQSAHSLLEIKALKPGTVAIKGVHSVRYLCMGADGKMQGLLQYSE EDCAFEEEIRPDGYNVYRSEKHRLPVSLSSAKQRQLYKNRGFLPLSHFL PMLPMVPEEPEDLRGHLESDMFSSPLETDSMDPFGLVTGLEAVRSPSFE KDYKDDDDK | 269 |

Referring again to FIG. 3B, each normalized luciferase activity is shown as an average and standard error of the mean of the three replicas. The results show that L6 cells expressing FGFR4 but not Klotho-beta, when treated with native FGF19 polypeptide, show dose-dependent activation of luciferase activity, whereas neither native FGF21 polypeptide nor chimeric FGF19 polypeptide showed such activity.

Example 2

KLB-Dependent FGFR4Binding Activity of Chimeric and Native FGF Polypeptides

In this assay, rat L6 myoblasts in a 96-well plate were transiently-transfected with an expression vector encoding either human FGFR4 polypeptide (based on NCBI Reference Sequence: NM_002011.3) or human FGFR1c polypeptide (based on NCBI Reference Sequence: NM_015850.3), an expression vector encoding Klotho-beta (KLB) polypeptide (based on NCBI Reference Sequence: NM_175737.3 fused to a C-terminal LEDYKDDDDK epitope sequence), an expression vector encoding a GAL4-Elk-1 transcriptional activator (pFA2-Elk1, Stratagene), and an expression vector encoding a firefly luciferase reporter gene under control of the yeast GAL4 upstream activator (pFR-luc, Stratagene). A vector for the constitutive expression of Renilla luciferase (pRL-SV40, Promega) was also transfected into the cells. Transfections were performed using FuGENE HD Transfection Reagent (Roche Applied Science) in accordance with the manufacturer's instructions.

The transfected L6 cells were cultured overnight in DMEM containing 10% FBS, as above. The cells were then washed and cultured for an additional 6 hours in serum-free medium containing 25 mg/L porcine heparin and a given concentration of a FGF polypeptide. The FGF polypeptides that were assayed were native human FGF19-Flag polypeptide (See FGF19-Flag in Table 10, SEQ ID NO:237), native human FGF21-His polypeptide (See FGF21-His in Table 10, SEQ ID NO:238) and a chimeric FGF19-Flag polypeptide (See cFGF21/19-2/Flag in Table 10; SEQ ID NO:242). The cells were incubated with the FGF19 polypeptide at concentrations of 500 ng/mL, 83.3 ng/mL, 13.9 ng/mL, 2.3 ng/mL, 0.39 ng/mL, 0.064 ng/mL or 0.011 ng/mL. The cells were incubated with the chimeric FGF19 polypeptide at concentrations of 2667 ng/mL, 444.4 ng/mL, 74.1 ng/mL, 12.3 ng/mL, 2.06 ng/mL, 0.34 ng/mL or 0.057 ng/mL The cells were then lysed with PLB reagent (Promega) and luciferase activity in each well was determined using Dual-Glo Luciferase Assay System (Promega) and EnVision Multilabel Reader (PerkinElmer) in accordance with the respective manufacturers' instructions. Each firefly luciferase activity was normalized to the co-expressed Renilla luciferase activity, and each sample condition was performed in triplicate.

Figure 4:
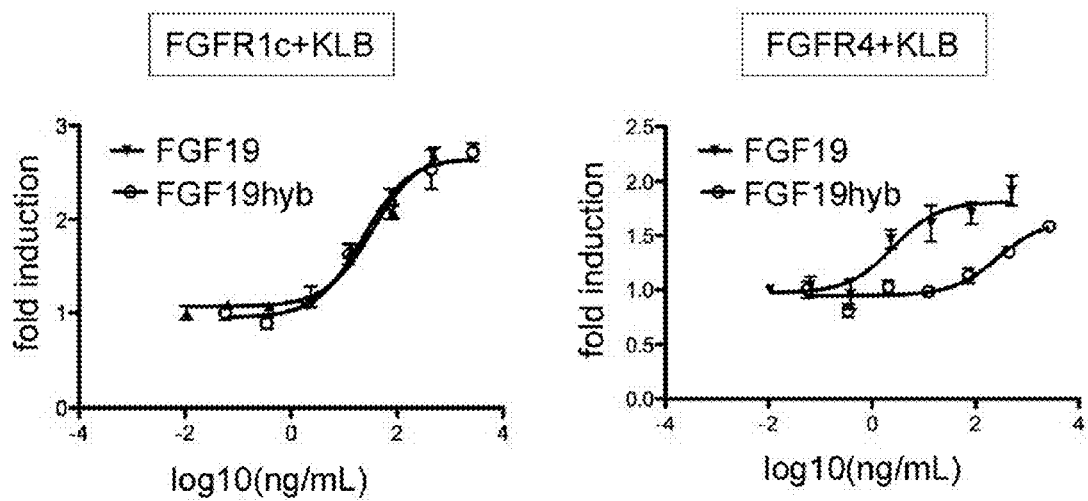
FIG. 4 shows exemplary results of a receptor binding assay using chimeric FGF19 polypeptides of the present invention.

Referring to FIG. 4, each normalized luciferase activity is shown as an average and standard error of the mean of the three replicas. The results show that native FGF19 polypeptide and chimeric FGF19 polypeptide show similar dose-dependent activation of luciferase in the presence of KLB and FGFR1c, with an $EC_{50}$ of 34.3 ng/mL and 22.7 ng/mL, respectively. In cells transformed with FGFR4 and KLB, the dose-dependent activation of luciferase activity by chimeric FGF19 polypeptide was significantly lower than that of native FGF19, with an $EC_{50}$ of 269 ng/mL and 2.6 ng/mL, respectively. The selectivity of each FGF19 polypeptide for FGFR1c and FGFR4 was estimated based on the $EC_{50}$ values calculated using Prism 5 software (GraphPad Software, La Jolla, Calif.). In this example, the chimeric FGF19 polypeptide showed a higher relative selectivity for FGFR1c over FGFR4 (based on the respective calculated $EC_{50}$ values) than the corresponding relative selectivity of native FGF19 polypeptide.

Example 3

Induction of Liver-Specific Genes by Chimeric and Native FGF Polypeptides

Figure 5:
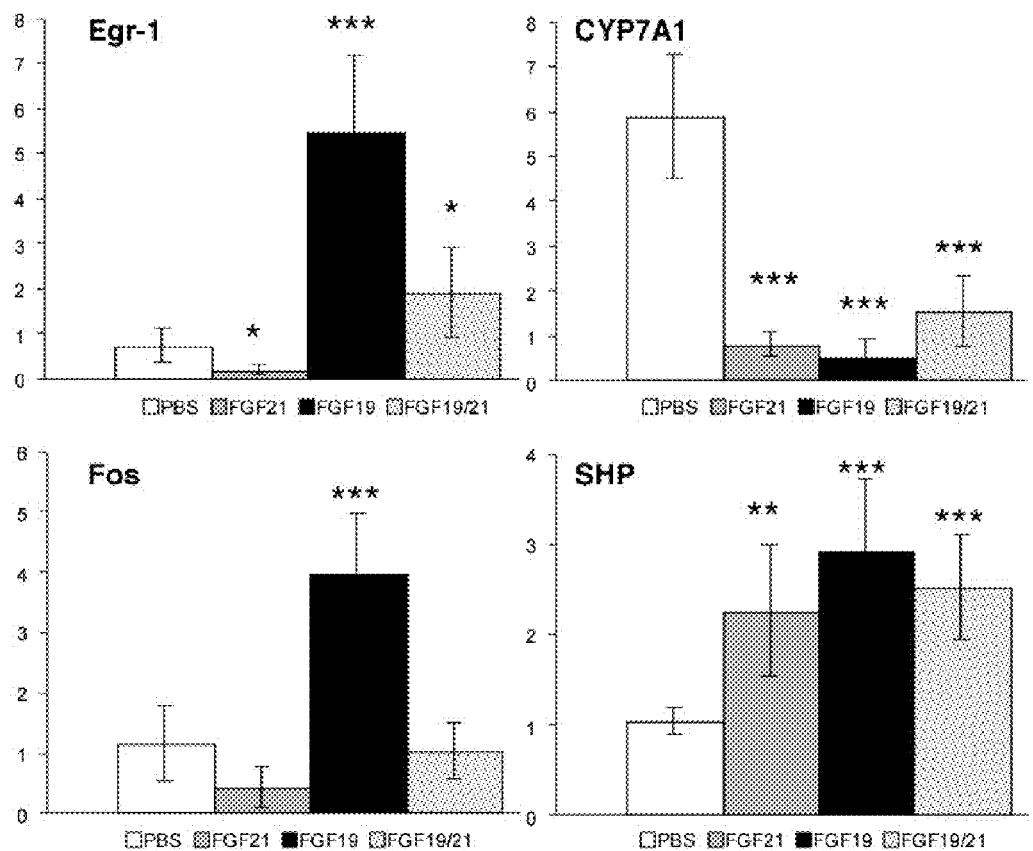
FIG. 5 shows exemplary results of a liver-specific gene expression assay using chimeric FGF19 polypeptides of the present invention.

In this example, FVB mice were fasted overnight. A sample group (n=5 or 6) of fasted mice was injected via tail vein with native human FGF19-Flag polypeptide (FGF19-Flag in Table 10, native human FGF21-His polypeptide (FGF21-His in Table 10), chimeric FGF19-Flag polypeptide (cFGF21/19-2/Flag in Table 10; SEQ ID NO:242) or phosphate-buffer saline (PBS) vehicle control. The polypeptides were provided in PBS at a dosage of 1 mg/kg. At 4 hours post-injection, liver tissue was harvested from each mouse and snap-frozen in liquid nitrogen. Total tissue RNA was isolated from the harvested liver tissue using Qiazol (catalog no. 79306, Qiagen, Germantown, Md.) and used as a template for cDNA synthesis (Quantitect Reverse Transcription Kit, catalog no. 205311, Qiagen). Following standard protocols for quantitative real-time PCR, the cDNA was quantified using SYBR Green dye (catalog no. 11760500, Invitrogen, Carlsbad, Calif.) and 7900HT Fast Real-Time PCR System (Applied BioSystems, Inc., Foster City, Calif.), with 36B4 gene as a standard. Referring to FIG. 5, the results show that levels of Egr-1 and cFos mRNA were highest in the sample injected with native FGF19 polypeptide, whereas the levels of Egr-1 and cFos mRNA were either absent or significantly lower in the samples injected with native FGF21 polypeptide or the chimeric FGF19 polypeptide. The relative levels of SHP mRNA or Cyp7A1 mRNA were comparable between the samples that were injected with the polypeptides. Levels with p values of $<0.05$, $<0.01$ and $<0.0005$ are indicated with "*", "" and "*", respectively.

Example 4

Induction of Adipocyte-Specific Genes by Chimeric and Native FGF Polypeptides

Figure 6:
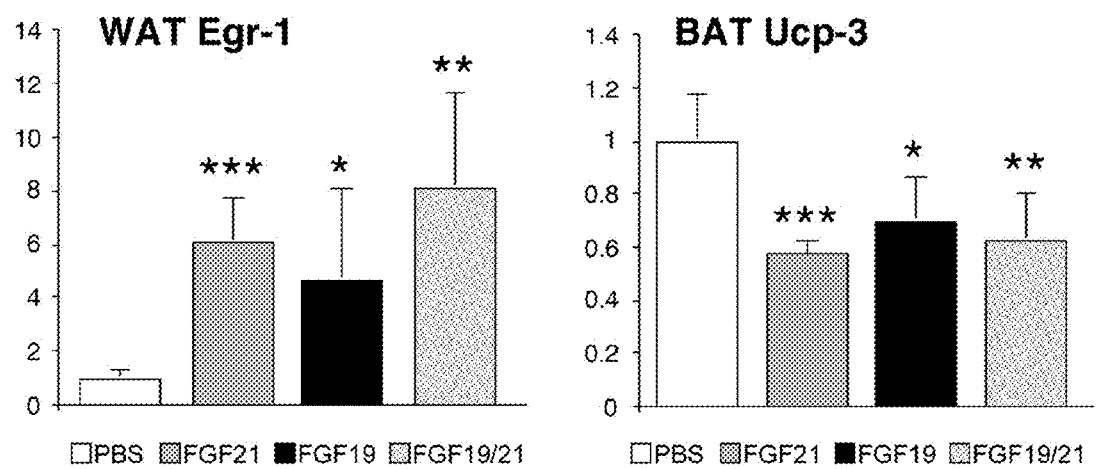
FIG. 6 shows exemplary results of a adipocyte-specific gene expression assay using chimeric FGF19 polypeptides of the present invention.

The example was performed as described in Example 3, with brown adipose tissue (BAT) and white adipose tissue (WAT) harvested at 4 hours post-injection and snap-frozen in liquid nitrogen. Referring to FIG. 6, the results show that levels of Egr-1 mRNA in WAT and UCP-3 mRNA in BAT, neither of which expresses detectable FGFR4, were similarly regulated by the FGF polypeptides used. Levels with p values of $<0.05$, $<0.01$ and $<0.001$ are indicated with "*", "" and "*", respectively.

Example 5

Reduction of Blood Glucose in Diabetic Obese Mice by Chimeric FGF19 and Native FGF21 Polypeptides In this example, 11-week-old ob/ob mice (stock#000632, The Jackson Laboratory, Bar Harbor, Me.) were subcutaneously implanted with an osmotic pump (catalog no. 2001, Alzet, Cupertino, Calif.) containing 200 µl, of native human FGF21 polypeptide (FGF21-FlagN in Table 10; 1 mg/mL in PBS), chimeric FGF19 polypeptide (cFGF21/19-2/Flag in Table 10; SEQ ID NO:242) (1 mg/mL in PBS) or vehicle control (PBS). Each sample group consisted of nine (9) mice. The osmotic pump was configured to provide polypeptide at a rate of ~0.4 mg/kg/day.

Figure 7:
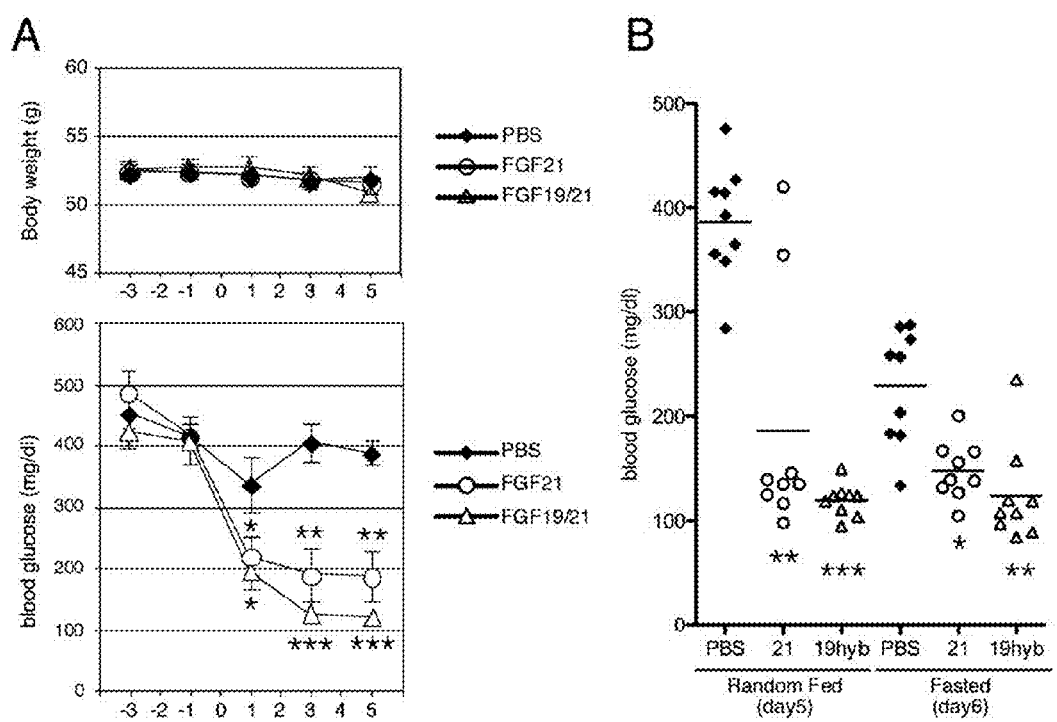
FIG. 7 shows exemplary results of a blood glucose lowering assay using chimeric FGF19 polypeptides of the present invention.

Referring to FIG. 7A, the body weight and random-fed blood glucose level of each mouse was measured beginning three (3) days prior to pump implantation until five (5) days post-implantation at the indicated time points. Blood glucose was measured using One Touch 2 Ultra Blood glucose monitoring system (LifeScan, Milpitas, Calif.). FIG. 7A shows the average body weight and blood glucose level for each sample group (levels with p values of $<0.05$, $<0.001$ and $<5\times10^{-7}$ are indicated with "*", "" and "*", respectively). On day 5, the mice were fasted overnight and the fasting blood glucose was measured in the next morning. Referring to FIG. 7B, the blood glucose levels for each mouse at days 5 and 6 (overnight fasted) are shown (levels with p values of $<0.002$, $<0.0005$ and $<5\times10^{-10}$ are indicated with "*", "" and "*", respectively). The results show that both native human FGF21 polypeptide and the chimeric FGF19 polypeptide reduced blood glucose to similar levels in these mice.

Example 6

Figure 8:
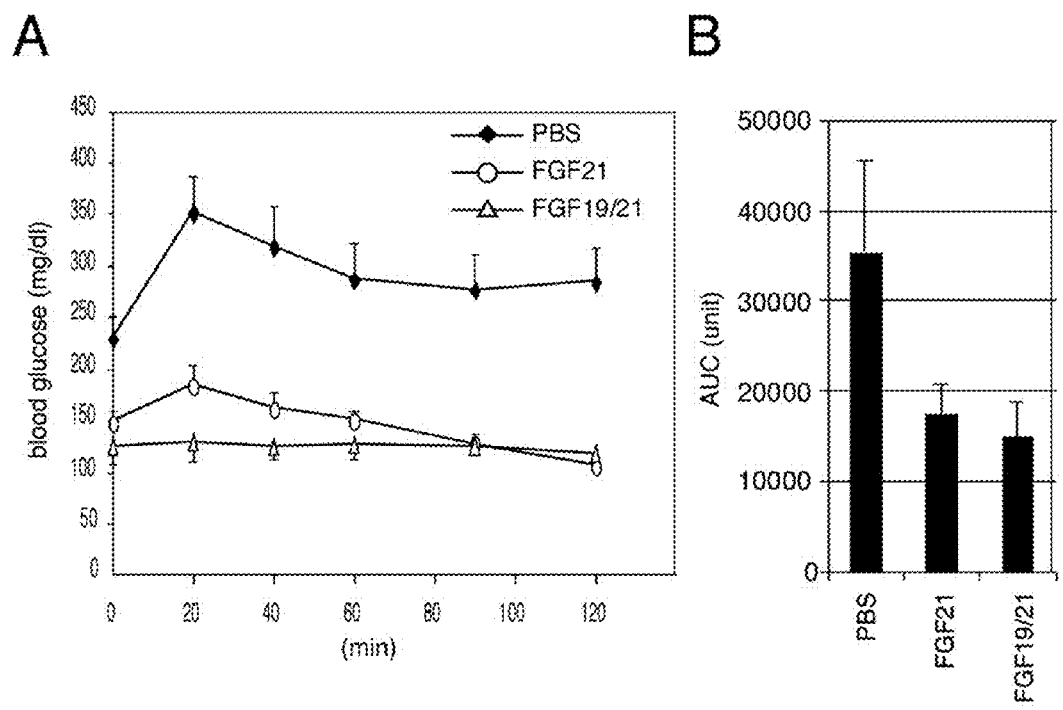
FIG. 8 shows exemplary results of a glucose tolerance test assay using chimeric FGF19 polypeptides of the present invention.

Intraperitoneal Glucose Tolerance in Diabetic Obese Mice by Chimeric FGF19 and Native FGF21Polypeptide The mice from Example 5 were injected intraperitoneally with bolus glucose in PBS (1 g/kg) following the overnight fasting on day 6 to test glucose tolerance. The bolus injection occurred at the point corresponding to time=0 in FIG. 8A. Subsequent to the bolus injection, blood glucose levels for each mouse were measured at the indicated time points, with the average blood glucose level for each sample group shown in FIG. 8A. Referring to FIG. 8B, the area under the curve (AUC) between t=0 and 120 min during the glucose tolerance test (GTT) for each animal was plotted. The p values for the sample injected with native human FGF21 polypeptide or the chimeric FGF19 polypeptide compared to the PBS control were both $<0.001$ according to student t-test. The results show that both native human FGF21 polypeptide and the chimeric FGF19 polypeptide showed similar glucose tolerance in these fasted mice.

Example 7

Activity of Native and Chimeric FGF-Fc Fusion Polypeptides

In this example, conditioned media containing a FGF-Fc fusion polypeptide is harvested from cells transfected with the corresponding expression vector. HEK293S cells were transiently transfected with an expression vector encoding native human FGF19 polypeptide fused to the N-terminus of human IgG1-Fc fragment via a 21-amino acid linker GGGGSGGGGSDYKDDDDKGRAQVT (SEQ ID NO:286), native human FGF21 polypeptide fused to the N-terminus of human IgG1-Fc fragment via a 4-amino acid linker GGGG, or human chimeric FGF19 polypeptide (cFGF21/19-2) fused to the N-terminus of human IgG1-Fc fragment via a 4-amino acid linker GGGS. Mock-transfected cells were used as a control. The cells were cultured overnight in DMEM containing 10% FBS, as above. The cells were then washed and cultured in an enriched serum-free medium derived from the F12/DME 50:50 blend for two (2) days. From each sample, conditioned medium was harvested. Equal volumes (6.5 µL) of each conditioned medium from each sample was used for immunoblot analysis using antibodies specific for the human IgG-Fc fragment. The immunoblot results are shown in FIG. 9B, which shows the presence of an Fc fragment-containing polypeptide with the expected molecular weight in the conditioned media that were harvested from the cells transformed with FGF19-Fc, FGF21-Fc and cFGF21/19-2-Fc fusion.

In this example, the conditioned media were used to demonstrate the activity of the FGF-Fc fusion polypeptides. HEK293S cells in a 96-well plate were transiently-transfected with an expression vector encoding a GAL4-Elk-1 transcriptional activator (pFA2-Elk1, Stratagene), and an expression vector encoding a firefly luciferase reporter gene under control of the yeast GAL4 upstream activator (pFR-luc, Stratagene). In some experiments, cells were also transfected with an expression vector encoding Klotho-beta (KLB) polypeptide. A vector for the constitutive expression of *Renilla* luciferase (pRL-SV40, Promega) was also transfected into the cells. Transfections were performed using FuGENE HD Transfection Reagent (Roche Applied Science) in accordance with the manufacturer's instructions.

The transfected cells were cultured overnight in DMEM containing 10% FBS, as above. The cells were then washed and cultured for an additional 6 hours in a medium made from 1 part of the conditioned medium diluted with 3 parts of an enriched serum-free medium derived from the F12/DME 50:50 blend, the final medium containing 25 mg/L porcine heparin. The cells were then lysed with PLB reagent (catalog no. E1941, Promega) and luciferase activity in each well was determined using Dual-Glo Luciferase Assay System (Promega) and EnVision Multilabel Reader (PerkinElmer) in accordance with the respective manufacturers' instructions. Each firefly luciferase activity was normalized to the co-expressed *Renilla* luciferase activity, and each sample condition was performed in triplicate.

Figure 9:
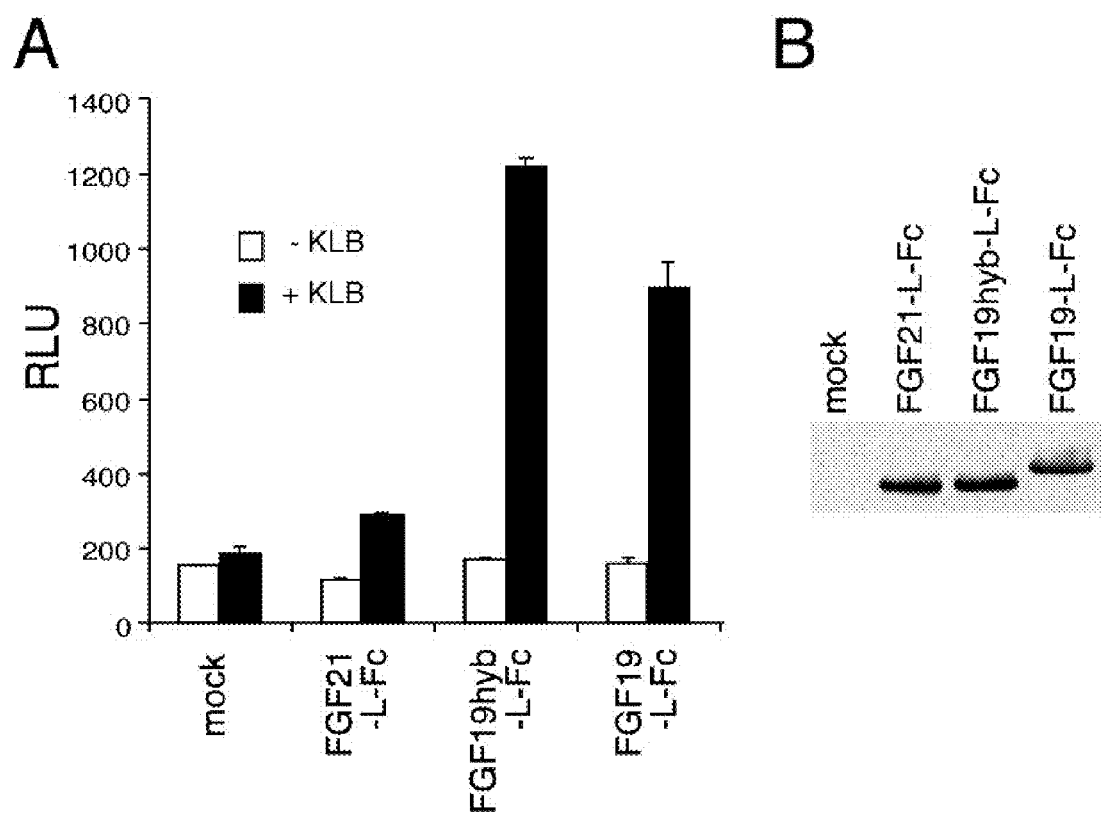
FIG. 9 shows exemplary results of an activity assay using immunoglobulin Fc fusions of chimeric FGF19 polypeptides of the present invention.

Referring to FIG. 9A, each normalized luciferase activity is shown as an average and standard error of the mean of the three replicas. The results show that the luciferase activity of the transformed HEK293S cells, with the presence of KLB, can be activated by native human FGF19-Fc polypeptide or the chimeric FGF19-Fc polypeptide in a manner similar to their respective non-Fc-fusion analogues. However, in contrast to the corresponding non-Fc-fusion analogue of native FGF21 polypeptide, the FGF21-Fc fusion polypeptide showed a substantially lower activation of firefly luciferase even with the presence of KLB.

Example 8

Receptor Specificity of Native and Chimeric FGF Polypeptides

In this example, rat L6 myoblasts in a 48-well plate were transiently-transfected with an expression vector encoding either human FGFR4 polypeptide, human FGFR1c polypeptide or a vector control. Also transfected in each cell sample were an expression vector encoding Klotho-beta (KLB) polypeptide, an expression vector encoding a GAL4-Elk-1 transcriptional activator (pFA2-Elk1, Stratagene), an expression vector encoding a firefly luciferase reporter gene under control of the yeast GAL4 upstream activator (pFR-luc, Stratagene), and vector for the constitutive expression of *Renilla* luciferase (pRL-SV40, Promega). Transfections were performed using FuGENE HD Transfection Reagent (Roche Applied Science) in accordance with the manufacturer's instructions.

The transfected L6 cells were cultured overnight in DMEM containing 10% FBS, as above. The cells were then washed and cultured for an additional 6 hours in serum-free conditioned medium (each conditioned medium was produced and harvested in accordance with Example 7, diluted for use with an equal volume of serum-free medium) containing 25 mg/L porcine heparin. The conditioned media contained either a vector control (group A in FIG. 10) (pUC-derived vector containing CMV promoter); native human FGF21-FlagC polypeptide (FGF21-FlagC in Table 10; group B in FIG. 10); native human FGF19-Flag polypeptide (FGF19-Flag in Table 10; group C in FIG. 10); a first chimeric FGF19 polypeptide having a N-terminal sequence derived from native human FGF21 (group D in FIG. 10) (cFGF21/19-13/Flag in Table 10, HPIPDSSPLLQFGGQVRQRYLYTD-DAQQTEAHLEIREDGTVGGAADQSP-ESLLQLKALKPGV IQILGVKTSRFLCQRPDGA-LYGSLHFDPEACSFRELLLEDGYNVYQSEAHGLPLHL PGNKSPH RDPAPRGPARFLPMLPMVPEEPEDL-RGHLESDMFSSPLETDSMDPFGLVTGLEAVRSPSFEK DYKDDDDK; SEQ ID NO:253); a second chimeric FGF19 polypeptide having a N-terminal sequence derived from native human FGF21 (group E in FIG. 10) (cFGF21/19-2/Flag in Table 10; HPIPDSSPLLQFGGQVRQRYLYTSGPH-GLSSCFLRIRADGVVDCARGQSAHSLLEIKAVALRT VAIKGVHSVRYLCMGADGKMQGLLQY-SEEDCAFEEEIRPDGYNVYRSEKHRLPVSLSSAKQ RQLYKNRGFLPLSHFLPMLPM-VPEEPEDLRGHLESDMFSSPLETDSMD-PFGLVTGLEAVRSP SFEKDYKDDDDK; SEQ ID NO:242) or a chimeric FGF19 polypeptide having a N-terminal sequence derived from native human FGF19 (group F in FIG. 10) (cFGF19/21-2/Flag in Table 10; RPLAFSDAG-PHVHYGWGDPIRLRHLYTDDAQQTEAHL-EIREDGTVGGAADQSPESLLQLKA LKPGVI-QILGVKTSRFLCQRPDGALYGSLHFDPEACSFRELLLE DGYNVYQSEAHGLPLHLPG NKSPHRDPAPRG-PARFLPLPGLPPALPEPPGILAPQPPD-VGSSDPLSMVGPSQGRSPSYASDYK DDDDK; SEQ ID NO:255). The cells were then lysed with PLB reagent (Promega) and luciferase activity in each well was determined using Dual-Glo Luciferase Assay System (Promega) and EnVision Multilabel Reader (PerkinElmer) in accordance with the respective manufacturers' instructions. Each firefly luciferase activity was normalized to the co-expressed *Renilla* luciferase activity, and each sample condition was performed in triplicate.

Figure 10:
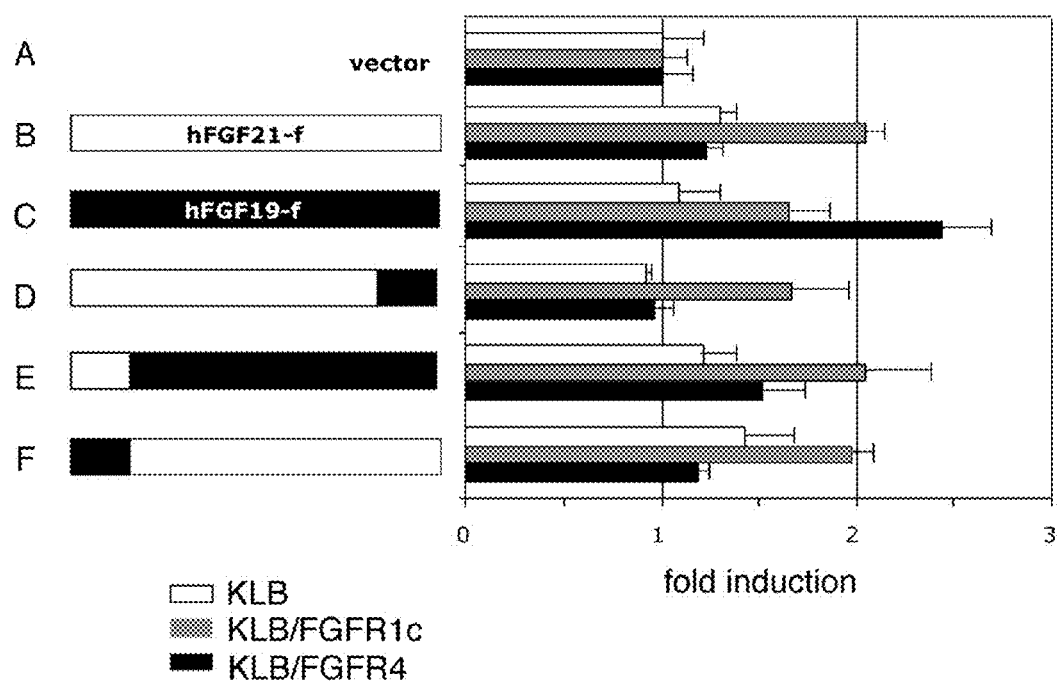

Referring to FIG. 10, each normalized luciferase activity is shown as a fold induction over the correspondingly-transfected cells in sample group A, which were incubated in control conditioned medium derived from cells transfected with vector control. Each fold induction is shown as an average and standard error of the mean of the three replicas. The results show that fold induction of normalized luciferase activity in L6 cells expressing FGFR1c was comparable between the non-control samples. However, the fold induction in L6 cells expressing FGFR4 were significantly higher in cells incubated with native FGF19 than those cells incubated with either native FGF21 or chimeric FGF19 polypeptides.

Example 9

Activity of Chimeric FGF19 Polypeptides—Part 1

In this example, chimeric FGF19 polypeptides having N-terminal domains derived from native human FGF19 polypeptide were assayed for activity. All assayed polypeptides also contained a C-terminal Flag epitope tag. HEK293S cells were transiently-transfected with an expression vector encoding Klotho-beta (KLB) polypeptide, an expression vector encoding a GAL4-Elk-1 transcriptional activator (pFA2-Elk1, Stratagene), an expression vector encoding a firefly luciferase reporter gene under control of the yeast GAL4 upstream activator (pFR-luc, Stratagene), and vector for the constitutive expression of *Renilla* luciferase (pRL-SV40, Promega). Rat L6 myoblasts were transiently-transfected with an expression vector encoding either human FGFR4 polypeptide or human FGFR1c polypeptide, an expression vector encoding Klotho-beta (KLB) polypeptide, an expression vector encoding a GAL4-Elk-1 transcriptional activator (pFA2-Elk1, Stratagene), an expression vector encoding a firefly luciferase reporter gene under control of the yeast GAL4 upstream activator (pFR-luc, Stratagene), and vector for the constitutive expression of *Renilla* luciferase (pRL-SV40, Promega). Transfections were performed using FuGENE HD Transfection Reagent (Roche Applied Science) in accordance with the manufacturer's instructions.

The transfected HEK293S and L6 cells were cultured overnight in DMEM containing 10% FBS, as above. The cells were then washed and cultured for an additional 6 hours in serum-free conditioned medium (each conditioned medium was produced and harvested in accordance with Example 7, diluted for use with an equal volume of serum-free medium) containing 25 mg/L porcine heparin. The conditioned media were harvested from cells transfected with native human FGF21-FlagC polypeptide (A in FIG. 11), chimeric FGF19 polypeptide cFGF19/21-1/Flag (cFGF19/21-1/Flag in Table 10; B in FIG. 11), chimeric FGF19 polypeptide cFGF19/21-2/Flag (cFGF19/21-2/Flag in Table 10; C in FIG. 11), chimeric FGF19 polypeptide cFGF19/21-3/Flag (cFGF19/21-3/Flag in Table 10; D in FIG. 11), chimeric FGF19 polypeptide cFGF19/21-4/Flag (cFGF19/21-4/Flag in Table 10; E in FIG. 11), chimeric FGF19 polypeptide cFGF19/21-5/Flag (cFGF19/21-5/Flag in Table 10; F in FIG. 11), chimeric FGF19 polypeptide cFGF19/21-6/Flag (cFGF19/21-6/Flag in Table 10; G in FIG. 11), chimeric FGF19 polypeptide cFGF19/21-7/Flag (cFGF19/21-7/Flag in Table 10; H in FIG. 11), chimeric FGF19 polypeptide cFGF19/21-8/Flag (cFGF19/21-8/Flag in Table 10; I in FIG. 11), chimeric FGF19 polypeptide cFGF19/21-9/Flag (cFGF19/21-9/Flag in Table 10; J in FIG. 11), chimeric FGF19 polypeptide cFGF19/21/19-29/Flag (cFGF19/21/19-29/Flag in Table 10; K in FIG. 11), or native FGF19-Flag polypeptide (L in FIG. 11).

Figure 11:
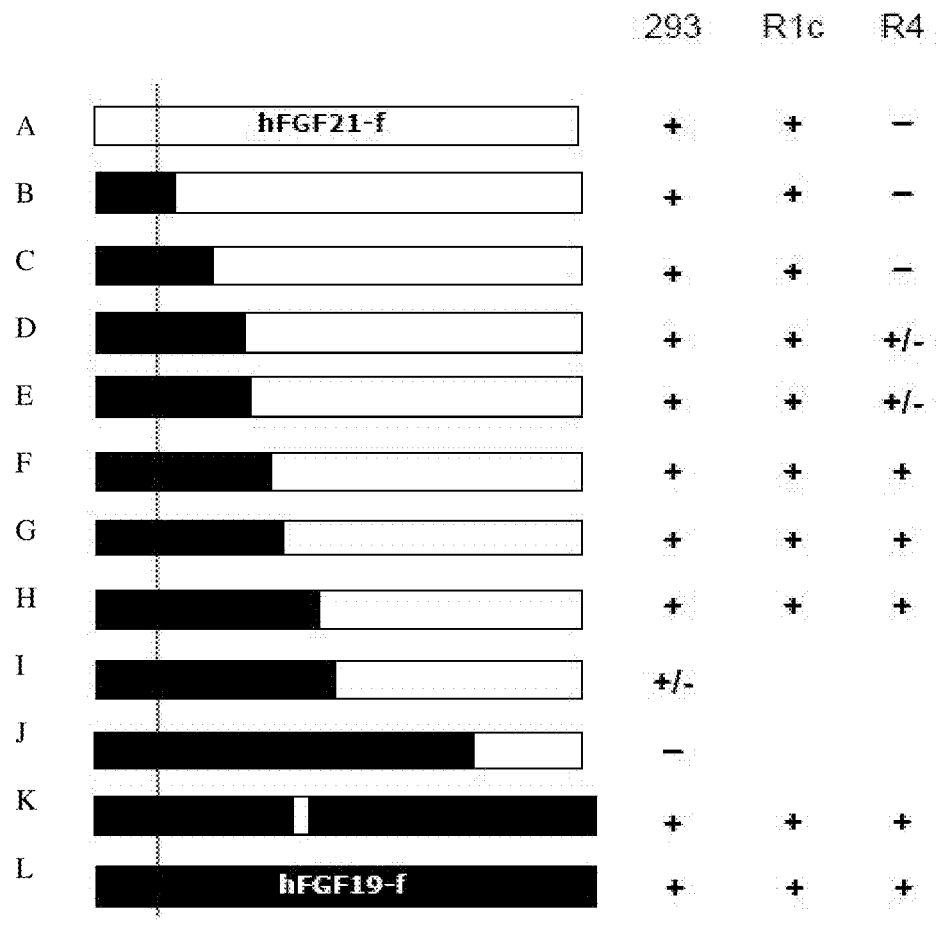

Referring to FIG. 11, the firefly luciferase activity for each sample was normalized to the co-expressed *Renilla* luciferase activity, and each sample condition was performed in triplicate. The normalized luciferase activity was compared to the activity for native human FGF19-Flag polypeptide, where "+" indicates substantially equivalent activity to that of native human FGF19-Fc fusion polypeptide, "+/−" indicates intermediate activity, and "−" indicates no detectable activity. Conditioned media that showed no detectable or intermediate activity in HEK293S cells were not tested in L6 cells.

Example 10

Activity of Chimeric FGF19 Polypeptides—Part 2

In this example, chimeric FGF19 polypeptides having N-terminal domains derived from native human FGF21 polypeptide were assayed for activity. All assayed polypeptides also contained a C-terminal Flag epitope tag. The assay was performed as described in Example 9. The conditioned media were harvested from cells transfected with native human FGF19-Flag polypeptide (FGF19-Flag in Table 10; A in FIG. 12), chimeric FGF19 polypeptide cFGF21/19-1/Flag (cFGF21/19-1/Flag in Table 10; B in FIG. 12), chimeric FGF19 polypeptide cFGF21/19-2/Flag (cFGF21/19-2/Flag in Table 10; C in FIG. 12), chimeric FGF19 polypeptide cFGF21/19-7/Flag (cFGF21/19-7/Flag in Table 10; D in FIG. 12), chimeric FGF19 polypeptide cFGF21/19-8/Flag (cFGF21/19-8/Flag in Table 10; E in FIG. 12), chimeric FGF19 polypeptide cFGF21/19-9/Flag (cFGF21/19-9/Flag in Table 10; F in FIG. 12), chimeric FGF19 polypeptide cFGF21/19-10/Flag (cFGF21/19-10/Flag in Table 10; G in FIG. 12), chimeric FGF19 polypeptide cFGF21/19-11/Flag (cFGF21/19-11/Flag in Table 10; H in FIG. 12), chimeric FGF19 polypeptide cFGF21/19-12/Flag (cFGF21/19-12/Flag in Table 10; I in FIG. 12), chimeric FGF19 polypeptide cFGF21/19-13/Flag (cFGF21/19-13/Flag in Table 10; J in FIG. 12), or native FGF21-FlagC polypeptide (FGF21-FlagC in Table 10; K in FIG. 12).

Figure 12:
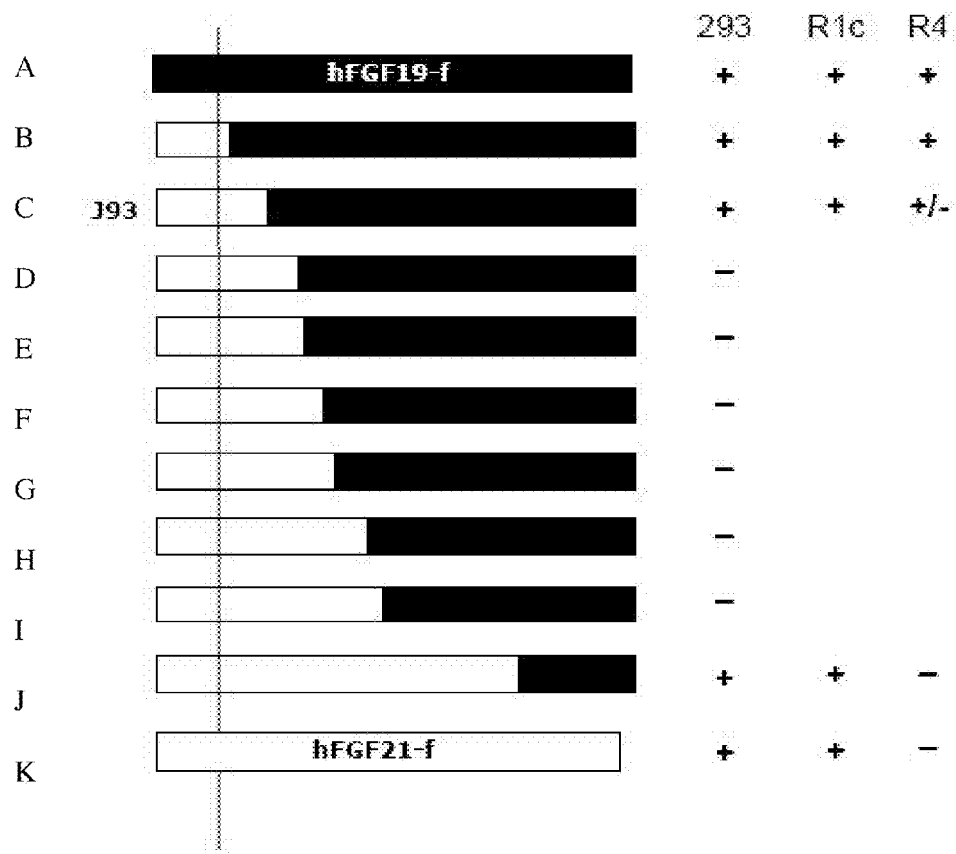

Referring to FIG. 12, the firefly luciferase activity for each sample was normalized to the co-expressed *Renilla* luciferase activity, and each sample condition was performed in triplicate. The normalized luciferase activity was compared to the activity for native human FGF19-Fc fusion polypeptide, where "+" indicates substantially equivalent activity to that of native human FGF19-Fc fusion polypeptide, "+/−" indicates intermediate activity, and "−" indicates no detectable activity. Conditioned media that showed no detectable or intermediate activity in HEK293S cells were not tested in L6 cells.

Example 11

Activity of Chimeric FGF19 Polypeptides—Part 3

In this example, chimeric FGF19 polypeptides having N-terminal domains derived from native human FGF21 polypeptide were assayed for activity. All assayed polypeptides also contained a C-terminal Flag epitope tag. The assay was performed as described in Example 9, except only the transfected HEK293S cells and the FGFR4-transfected L6 cells were used in the assay. The conditioned media were harvested from cells transfected with native human FGF21-FlagC polypeptide (FGF21-FlagC in Table 10; A in FIG. 13), native human FGF19-Flag polypeptide (FGF19-Flag in Table 10; B in FIG. 13), chimeric FGF19 polypeptide cFGF21/19-1/Flag (cFGF21/19-1/Flag in Table 10; C in FIG. 13), chimeric FGF19 polypeptide cFGF21/19-2/Flag (cFGF21/19-2/Flag in Table 10; D in FIG. 13), chimeric FGF19 polypeptide cFGF21/19-3/Flag (cFGF21/19-3/Flag in Table 10; E in FIG. 13), chimeric FGF19 polypeptide cFGF21/19-4/Flag (cFGF21/19-4/Flag in Table 10; F in FIG. 13), chimeric FGF19 polypeptide cFGF21/19-5/Flag (cFGF21/19-5/Flag in Table 10; G in FIG. 13), or chimeric FGF19 polypeptide cFGF21/19-6/Flag (cFGF21/19-6/Flag in Table 10; G in FIG. 13).

Referring to FIG. 13, the firefly luciferase activity for each sample was normalized to the co-expressed *Renilla* luciferase activity, and each sample condition was performed in triplicate. The normalized luciferase activity was compared to the activity for native human FGF19-Flag polypeptide, where "+" indicates substantially equivalent activity to that of native human FGF19-Flagn polypeptide, "+/−" indicates intermediate activity, and "−" indicates no detectable activity. Conditioned media that showed no detectable or intermediate activity in HEK293S cells were not tested in L6 cells.

FIG. 13 further shows a proposed alignment of the respective amino acid sequences of N-terminal portions of the assayed polypeptides. Selected amino acid residues which correspond to the conserved LYT and LxxIxxG motifs in each polypeptide are indicated in the alignment by outlined boxes.

Example 12

Activity of Chimeric FGF19 Polypeptides—Part 4

In this example, chimeric FGF19 polypeptides having N-terminal and internal domains derived from native human FGF21 polypeptide were assayed for activity. All assayed polypeptides also contained a C-terminal Flag epitope tag. The assay was performed as described in Example 9. The conditioned media were harvested from cells transfected with native human FGF21-FlagC polypeptide (as indicated in FIG. 14), native human FGF19-Flag polypeptide (as indicated in FIG. 14), chimeric FGF19 polypeptide cFGF21/19-2/Flag (cFGF21/19-2/Flag in Table 10; A in FIG. 14), chimeric FGF19 polypeptide cFGF21/19-3/Flag (cFGF21/19-3/Flag in Table 10; B in FIG. 14), chimeric FGF19 polypeptide cFGF21/19-4/Flag (cFGF21/19-4/Flag in Table 10; C in FIG. 14), chimeric FGF19 polypeptide cFGF21/19-5/Flag (cFGF21/19-5/Flag in Table 10; D in FIG. 14), chimeric FGF19 polypeptide cFGF21/19-6/Flag (cFGF21/19-6/Flag in Table 10; E in FIG. 14), chimeric FGF19 polypeptide cFGF19/21/19-1/Flag (cFGF19/21/19-1/Flag in Table 10; F in FIG. 14), chimeric FGF19 polypeptide cFGF19/21/19-2/Flag (cFGF19/21/19-2/Flag in Table 10; G in FIG. 14), chimeric FGF19 polypeptide cFGF19/21/19-3/Flag (cFGF19/21/19-3/Flag in Table 10; H in FIG. 14), chimeric FGF19 polypeptide cFGF19/21/19-4/Flag (cFGF19/21/19-4/Flag in Table 10; I in FIG. 14), chimeric FGF19 polypeptide cFGF19/21/19-5/Flag (cFGF19/21/19-5/Flag in Table 10; J in FIG. 14), chimeric FGF19 polypeptide cFGF19/21/19-6/Flag (cFGF19/21/19-6/Flag in Table 10; K in FIG. 14), or chimeric FGF19 polypeptide cFGF19/21-1/Flag (cFGF19/21-1/Flag in Table 10; L in FIG. 14).

Referring to FIG. 14, the firefly luciferase activity for each sample was normalized to the co-expressed *Renilla* luciferase activity, and each sample condition was performed in triplicate. The normalized luciferase activity was compared to the activity for native human FGF19-Flag polypeptide, where "+" indicates substantially equivalent activity to that of native human FGF19-Flag polypeptide, "+/−" indicates intermediate activity, and "−" indicates no detectable activity. Conditioned media that showed no detectable or intermediate activity in HEK293S cells were not tested in L6 cells.

FIG. 14 further shows a proposed alignment of the respective amino acid sequences of N-terminal portions of the assayed polypeptides. Selected amino acid residues which correspond to the conserved LYT and LxxIxxG motifs in each polypeptide are indicated in the alignment by outlined boxes.

Example 13

Reduced STAT5 Dephosphorylation By Chimeric FGF19 Polypeptides

In this example, a chimeric FGF19 polypeptide of the present invention was tested for its effect on STAT5 dephosphorylation. Five-week old male C57BL/6J mice (about 18 to 19 grams each) were subcutaneously injected in duplicate with native human FGF21-His polypeptide (catalog no. 2539-FG-025/CF, R&D Systems, Inc., Minneapolis, Minn.), chimeric FGF19-Flag polypeptide (cFGF21/19-2/Flag in Table 10; SEQ ID NO:242) or phosphate-buffered saline (PBS) carrier control. The polypeptides were solubilized in PBS and provided at a dosage of 1 mg/kg (about 20 µg polypeptide per injection) twice daily for two days. On the following morning of the third day, the mice were intraperitoneally injected with a fifth and final 1 mg/kg dose of respective polypeptide or control, and sacrificed 2 hours later. The liver was recovered from each mouse and nuclear extract was prepared from the liver using Nuclear Extraction Kit (catalog no. 10009277, Cayman Chemical, Ann Arbor, Mich.). For each nuclear extract sample, 22.5 µg of protein was resolved by SDS polyacrylamide gel electrophoresis and analyzed by immunoblotting using an antibody specific for the Stat5 protein that is phosphorylated at Tyr694 (catalog no. 9314, Cell Signaling Technology, Danvers, Mass.). A non-specific band ("NS"), which was used a loading control, is shown to be detectable at approximately the same amounts in each lane. Similar results were observed (data not shown) regarding the levels of Try694-phosphorylated-Stat5 with another monoclonal antibody specific for the Tyr694-phosphorylated-Stat5 (catalog no. 9359, Cell Signaling Technology).

Figure 15:
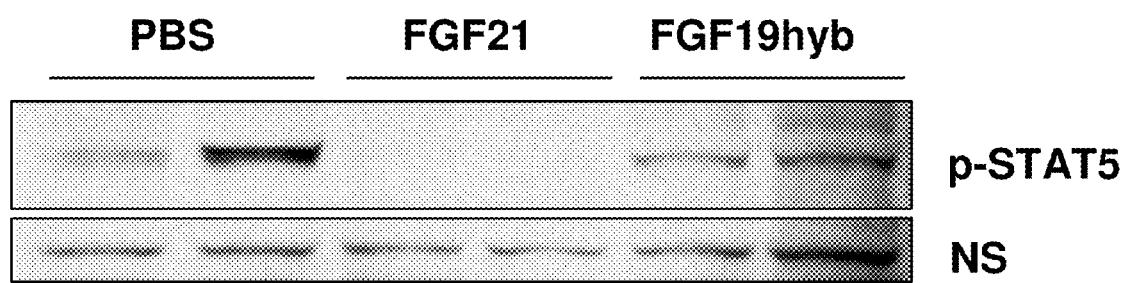
FIG. 15 shows exemplary results of using a chimeric FGF19 polypeptide of the present invention on the levels of phosphorylated-Stat5 protein.

Referring to FIG. 15, the results show Tyr694-phosphorylated Stat5 protein was not detectable in the mice that were injected with native human FGF21 polypeptide. However, mice that were injected with the chimeric FGF19 polypeptide showed significant levels of the phosphorylated Stat5 protein.

Example 14

Reduced Promotion of Anchorage-Independent Growth By Chimeric FGF19 Polypeptides In this example, a chimeric FGF19 polypeptide of the present invention was tested for its effect on anchorage-dependent growth of human hepatoma HepG2 cells, which express KLB and FGFR4. A 96-well-plate was filled with 50 µL per well of molten base agar (DMEM, 0.5% agarose and 10% FBS). After the base agar had solidified, about 670 HepG2 cells suspended in 50 µL molten top agar solution (DMEM, 0.35% agarose and 10% FBS) were added to the base agar in each well, and allowed to solidify.

Following solidification of the cell suspension, 20 µL of growth medium (DMEM and 10% FBS) was added to each well on designated day zero (0). For a given experimental sample, the growth medium further included either native human FGF19-Flag polypeptide, native human FGF21-His polypeptide (catalog no. 2539-FG-025/CF, R&D Systems, Inc., Minneapolis, Minn.), chimeric FGF19 flag-tagged polypeptide (cFGF21/19-2/Flag; SEQ ID NO:242), or no FGF polypeptide as a control. The polypeptide concentration in the growth medium that was added on day zero was either 120 ng/mL or 1200 ng/mL, so that the final concentration in each well becomes 20 ng/mL or 200 ng/mL, respectively. On each of subsequent days 2, 4, 6 and 8, an further 20 µL of growth medium was added to each well, wherein the further added growth medium to a given well contained the same FGF polypeptide as in previous applications to that well, but with one-sixth the concentration of FGF polypeptide (i.e. 20 ng/mL or 200 ng/mL) as that of the day zero amount. A subset of the sample wells were also treated with G418 protein synthesis inhibitor to provide a background fluorescence signal.

On day 9, 10 µL AlamarBlue reagent (catalog no. DAL1100, Invitrogen) was added to each sample well and the plate was further incubated for 5 hrs to assay the total metabolic activity in each well. The resulting fluorescent intensity was measured using EnVision Multilabel Reader (PerkinElmer). Five (5) replicas of each sample were tested.

Figure 16:
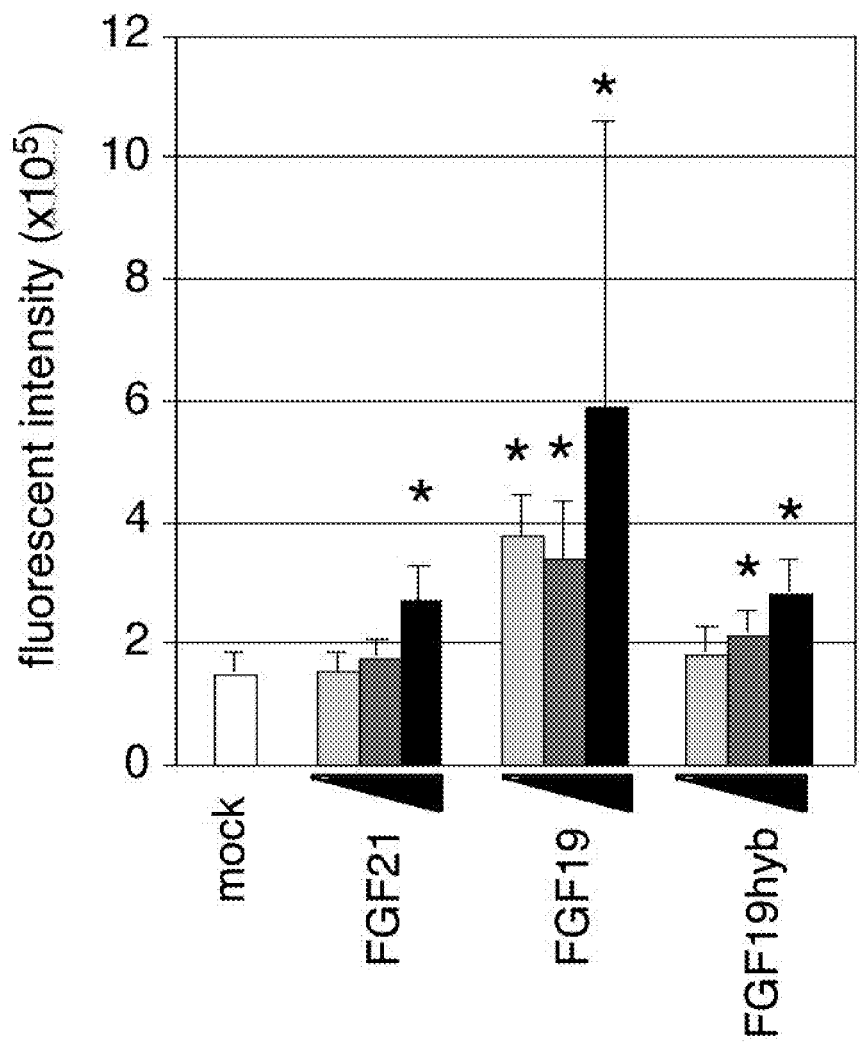
FIG. 16 shows exemplary results of using a chimeric FGF19 polypeptide of the present invention on the total metabolic activity of cells.

Referring to FIG. 16, the results are shown as fluorescent intensity above background and represent the average and standard deviation of the five (5) replicas. The results show that the total metabolic activity, as a proposed indicator of anchorage-independent growth of the cells, was promoted by the addition of native human FGF19 polypeptide, but such activity was reduced with the addition of native human FGF21 or the chimeric FGF19 polypeptides (p values<0.05 compared to mock treated samples according to student t-test).

Example 15

FGF19 Regulates Cell Proliferation, Glucose and Bile Acid Metabolism Via FGFR4-Dependent and Independent Pathways To investigate the requirement for FGFR4 in mediating FGF19 activity by using Fgfr4 deficient mice as well as a protein variant of FGF19, which is specifically impaired in its ability to activate FGFR4.

Materials and Methods

Expression of Recombinant FGF Protein.

Amino acid sequences of FGF19, FGF21, and chimeras were constructed, the drawings of the chimera constructs made are shown in FIG. 18B. The constructs with the numbering of 1-17 shown in FIG. 18B correspond to constructs comprising the amino acid sequences of SEQ ID NO:1, SEQ ID NO:270 (RPLAFSDAGPHVHYGWGDPIRLRHLYTS-GPHGLSSCFLRIRADGVVDCARGQSAHSLLEIK ALK-PGTVAIKGVHSVRYLCMGADGKM-QGLLQYSEEDCAFEEEIRPDGYNVYRSEKHRLPVS LSSAKQRQLYKNRGFLPLSHFLPMLPM-VPEEPEDLRGHLESDMFSSPLETDSMDPFGLVTGL EAVRSPSFEK), SEQ ID NO:74, SEQ ID NO:5, SEQ ID NO:75, SEQ ID NO:76, SEQ ID NO:77, SEQ ID NO:271, SEQ ID NO:272, SEQ ID NO:273, SEQ ID NO:274, SEQ ID NO:275, SEQ ID NO:276, SEQ ID NO:277, SEQ ID NO:278, SEQ ID NO:85, and SEQ ID NO:2, respectively. All the constructs shown in FIG. 18B also included signal sequences at the N-terminal end (cleaved upon secretion) and the flag tag (DYKDDDDK (SEQ ID NO:279)) at the C-terminal end.

Figure 20:
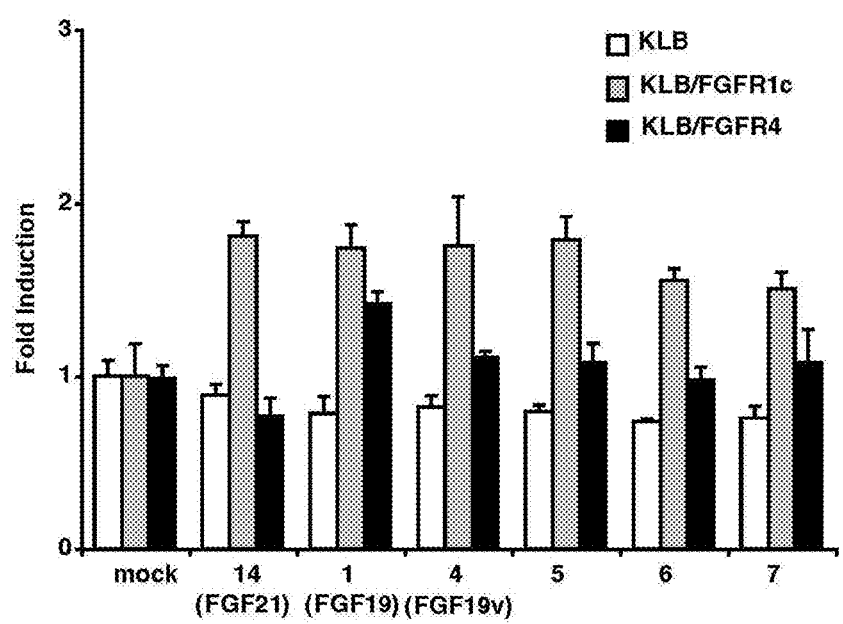
FIG. 20 shows the activation of FGFR1c or FGFR4 in a GAL-Elk-1 assay using L6 cells cotransfected with KLB and/or FGFR (FGFR1c or FGFR4) and incubated with conditioned medium from 293 cells transiently transfected with various FGF constructs shown at X-axis (see FIG. 18B for amino acid compositions of FGF constructs used). The results are shown as a fold induction over control media conditioned with mock transfected cells. The numbering indicated at X-axis corresponds to the numbering of the construct shown in FIG. 18B.

Unless otherwise noted, recombinant human FGF21, FGF19 and variants produced in transiently transfected CHO cell and purified to homogeneity in PBS were used for experiments. For some experiments, E. coli derived FGF21 (2539-FG/CF, R&D systems) were used. All the purified proteins were tested for the activity by cell based GAL-Elk1 assays prior to application for other assay. For experiments in FIGS. 18B, 18C, and 20, FGF proteins were expressed in transiently transfected HEK293 cells and fresh conditioned serum-free medium was used for assays without purification.

Luciferase Assay.

All the cells were cultured in Dulbecco's Modified Eagle Medium (DMEM) supplemented with 10% fetal bovine serum (FBS) at 37° C. under 5% CO2. Rat L6 myoblasts in a 96-well plate were transiently-transfected with expression vectors encoding Renilla luciferase (pRL-SV40, Promega), human KLB, appropriate human FGFR, GAL4-Elk-1 transcriptional activator (pFA2-Elk1, Stratagene), and firefly luciferase reporter driven GAL4 binding sites (pFR-luc, Stratagene), using FuGENE HD Transfection Reagent (Roche Applied Science). On the next day, the transfected cells were cultured for an additional 6-8 hours in serum free media containing 25 mg/L porcine heparin (Sigma) and FGF protein at a various concentrations. The cells were then lysed with PLB reagent (Promega) and luciferase activity in each well was determined using Dual-Glo Luciferase Assay System (Promega) and EnVision Multilabel Reader (PerkinElmer). Firefly luciferase activity was normalized to the co-expressed Renilla luciferase activity, and was shown as an average and standard error of the mean of the three replicas.

Anchorage Independent Cell Proliferation Assay.

A 96-well-plate was filled with 50 μL/well of 0.5% molten agarose in growth media. After the base agarose had solidified, about 670 HepG2 cells suspended in 50 μL top molten agarose solution (0.35% agarose in growth media) were added to the base agar in each well, and allowed to solidify. Following solidification, 20 μL of growth medium containing appropriate amount of FGF protein was added to each well on designated day 0. On each of subsequent days 2, 4, 6 and 8, a further 20 μL of growth medium with appropriate amount of FGF protein was added to each well. A subset of the sample wells was also treated with protein synthesis inhibitor Geneticin (invitrogen) to provide a background fluorescence signal. On day 9, 10 μL AlamarBlue reagent (Invitrogen) was added to each sample well and the plate was further incubated for 5 hrs. The resulting fluorescent intensity was measured using EnVision Multilabel Reader (PerkinElmer) and used as an indication of the total metabolic activity in each well. Five replicas of each sample were tested.

FGFR/Ligand Binding Assay.

FGFR-binding activity of FGF19 and FGF19v were measured as described in Desnoyers et al., *Oncogene* 27(1):85-97 (2008) using biotinylated anti-FGF19 antibody (BAF969, R&D systems) in the presence of 2 μg/mL heparin. Control ELSA experiments were performed using anti-FGF19 antibody (AF969, R&D systems) and biotinylated anti-FGF19 antibody (BAF969, R&D systems) to confirm that the antibody reacts to FGF19 and FGF19v in an indistinguishable manner.

Mouse Studies.

Mice were maintained in a pathogen-free animal facility at 21° C. under standard 12 hr light/12 hr dark cycle with access to chow (a standard rodent chow (Labdiet 5010, 12.7% calories from fat) or a high fat, high carbohydrate diet (Harlan Teklad TD.03584, 58.4% calories from fat) and water ad libitum. Male mice were used for all the experiments. FGFR4KO mice in C57BL/6 background were previously described Weinstein et al., *Development* 1998 125(18):3615-23 (1998). C57BL/6 mice, ob/ob mice in C57BL/6 background and FVB/NJ mice were purchased from Jackson Laboratory. For continuous infusion of FGF protein, an osmotic pump (Alzet 2001) was subcutaneously implanted. For glucose tolerance test, glucose levels were measured using One Touch Ultra glucometer. Statistics were performed by Student's t test. Values were presented as means+/−SEMs. BrdU staining was carried out as described as {Nicholes, 2002 #79} and BrdU positive hepatocytes were counted by using the Ariol automated image analysis system. All animal studies were performed under Genentech's Institutional Animal Care and Use Committee approved protocols.

Serum Analysis.

Total cholesterol, triglyceride, β-hydroxybutylate (BHB), lactate Thermo DMA) and nonesterified fatty acid (Roche) were determined by using enzymatic reactions. Serum insulin levels were determined by ELISA (crystal chem). BA composition was determined by liquid chromatography-mass spectrometry analysis as previously described Stedman et al., *J Biol. Chem.* 279(12):11336-43 (2004).

Gene Expression Analysis.

Tissue RNAs were isolated by using QIAzol reagent (Qiagen). cDNA was synthesize with the Quantitect Reverse Transcription Kit (Qiagen). For real time qPCR, samples were run in triplicate in the ABI Prism 7900HT (Applied Biosystems) by using SYBR green universal mix (Invitrogen) or by Taqman universal mix (Roche) and normalized by levels of 36B4. Pre-designed Quantitect primers for GK, SHP, Cyp8b1, IGFBP2, and AFP were obtained from Qiagen and all other primers were designed using primer express software (Applied Biosystems).

A. FGFR4 Regulates Serum Bile Acids, but not Improvement of Glucose Tolerance by Recombinant FGF19

Figure 17:
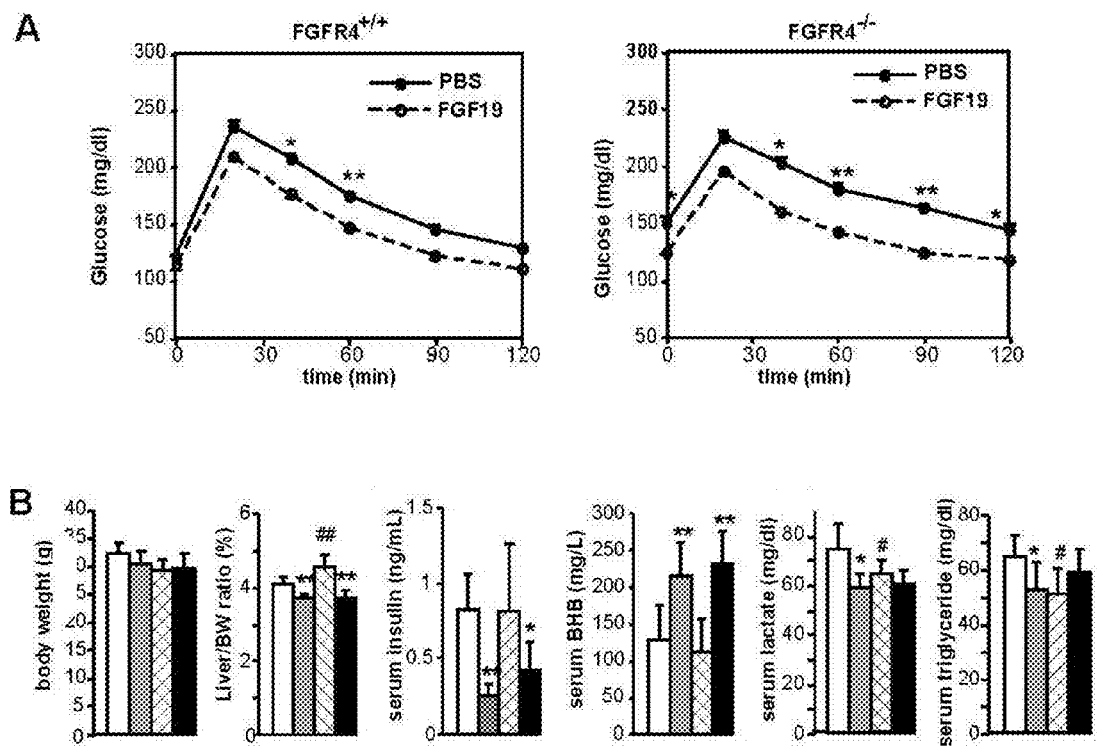
FIG. 17 shows that FGFR4 was required for bile acid ("BA") regulation but not for improvement in glucose tolerance by FGF19.
Figure 17:
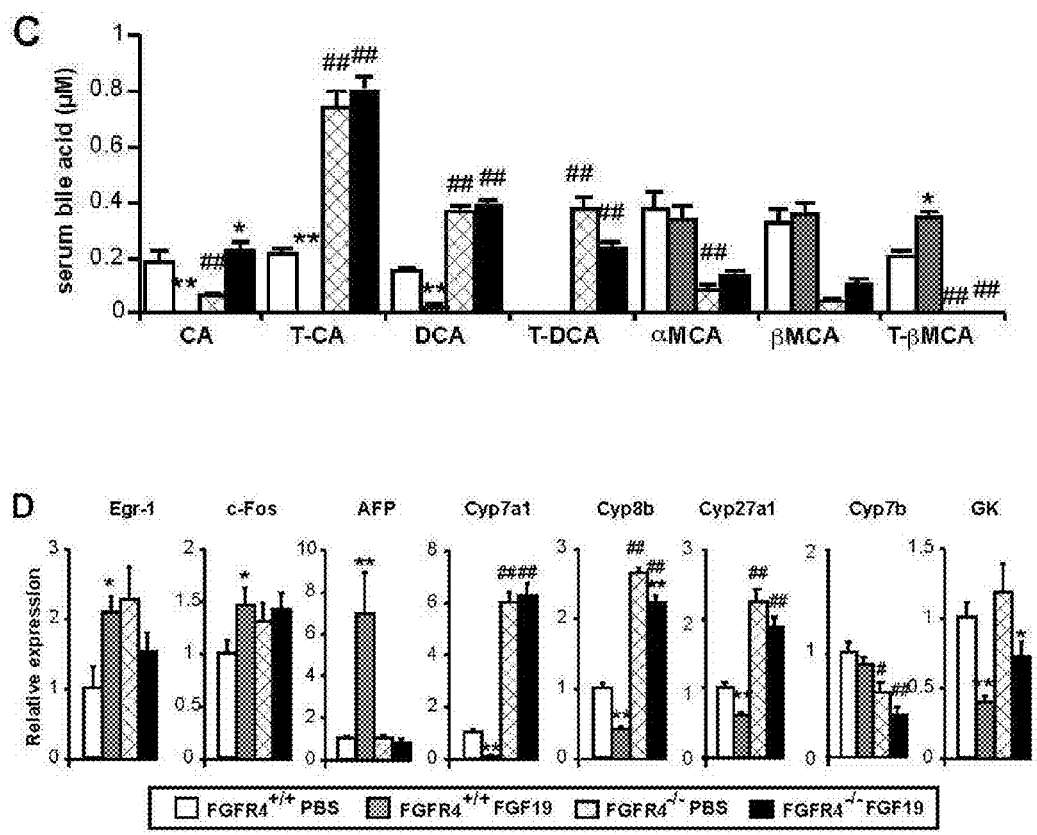

In order to determine which of the metabolic effects elicited by FGF19 are mediated by FGFR4, HFD-fed WT or Fgfr4 KO mice were treated with recombinant FGF19 or vehicle control, and metabolic phenotypes and gene expression were studied. To achieve sustained exposure to FGF19, 12 to 15 weeks old FGFR4WT and KO Mice on high fat diet for 6 weeks were implanted with an osmotic pump to continuously infuse FGF19 at 1 ng/hr. This achieved an average FGF19 serum concentration of 26 ng/ml, as determined by ELISA, which is about 50- to 250-fold higher than circulating FGF19 concentrations in humans. On day 6, overnight fasted mice were subjected to glucose tolerance test with i.p. injection of glucose at 1 g/kg. FGF19 infusion improved glucose tolerance to a similar extent both in WT and Fgfr4 KO mice (FIG. 17A), indicating that FGFR4 is dispensable for improvement in glucose tolerance in HFD-fed mice. Continuous infusion of FGF19 did not induce significant weight loss, thus the improvement glucose tolerance was independent of body weight. By day 7, FGF19 reduced liver weight and serum insulin as well as increasing ketone body (BHB) formation in both WT and Fgfr4 KO mice (FIG. 17B). FGF19 also reduced serum lactate and triglycerides in WT but not Fgfr4 KO mice (FIG. 17B), even though the latter exhibited reduced lactate and triglyceride levels prior to treatment.

To evaluate changes in BA metabolism, serum BA composition was determined by liquid chromatography-mass spectrometry (FIG. 17C). FGF19 infusion reduced free and taurine conjugated cholic acid (CA) and the CA-derived secondary bile acid deoxycholic acid in WT mice, while having minimal effect on CDCA (CDCA) metabolites. This finding is consistent with a shift of BA synthesis to the alternative (acidic) pathway, bypassing FGF19-suppressed Cyp7a1 and proceeding though Cyp7b1 (FIG. 17D). Correspondingly, loss of Fgfr4 increased basal levels of CA and its metabolites while reducing muricholic acids (hydroxylated metabolites of CDCA), indicating that FGFR4 is not only important as a regulator of bile acid synthesis, but is also a determinant of the ratio of CA to CDCA production. To determine the role of FGFR4 in regulation of hepatic gene expression, a range of hepatic mRNAs by QPCR was examined (FIG. 17D). FGF19 infusion induced expression of cell proliferation markers such as Egr-1, c-Fos, and AFP, and suppressed expression of Cyp7a1 in WT but not in Fgfr4 KO mice. In contrast, FGF19 suppressed Cyp8b1 and glucokinase (GK) in both WT and Fgfr4 KO mice, while basal expression of Cyp8b1 and Cyp27a1 levels were much higher in Fgfr4 KO compared to WT mice. Cyp8b1 is obligatory for the synthesis of cholic, but not CDCA, thus the observed changes in Cyp8b1 expression contribute to the altered balance between CA and CDCA metabolites (muricholic acids) in Fgfr4 KO mice (FIGS. 17C and D). Taken together, our findings reveal that FGFR4 is a regulator of BA synthesis and impacts on hepatocyte proliferation, but not required for the regulation of glucose utilization, insulin sensitivity, and ketone body production by FGF19.

B. Identification of FGF19 Variants with a Specific Reduction in FGFR4 Activation.

Figure 18:
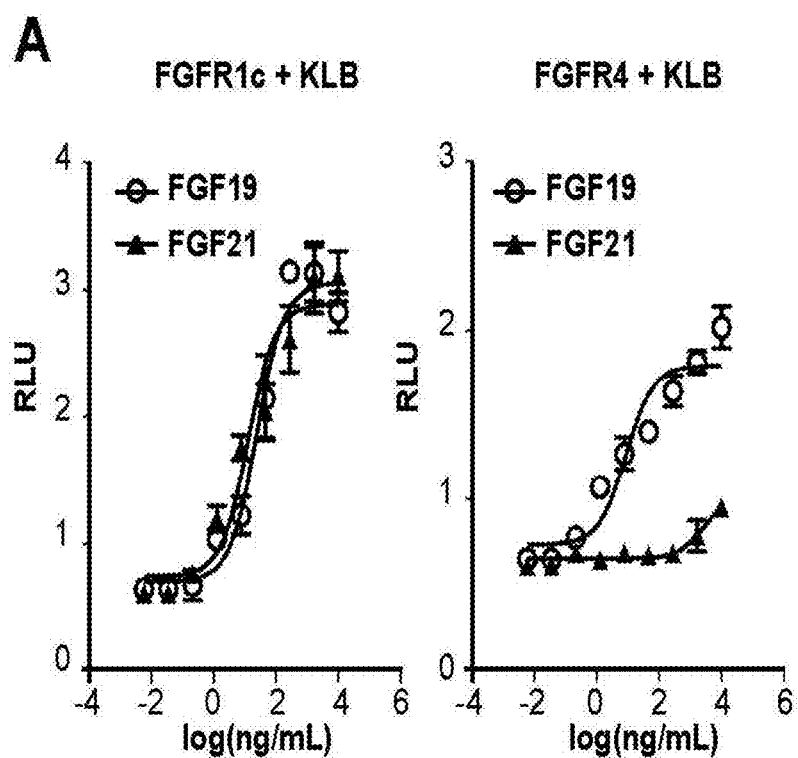
FIG. 18 shows identification of FGF19 variants with reduced FGFR4 activity.
Figure 18:
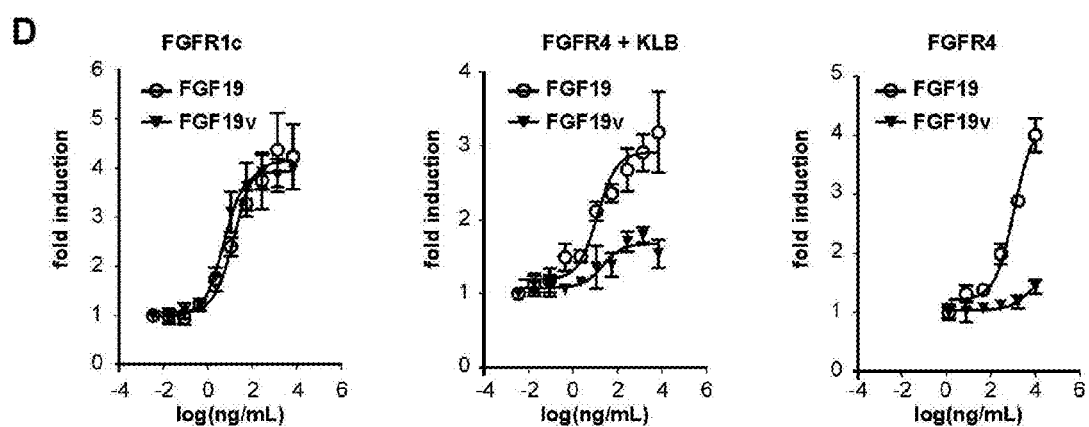
Figure 19:
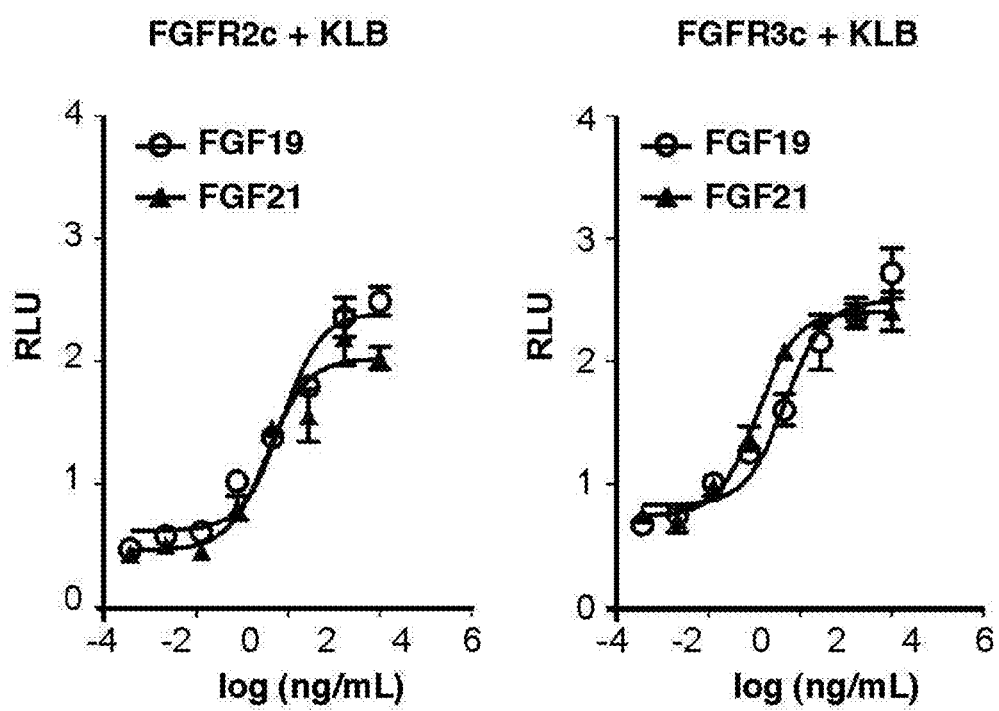
FIG. 19 shows the RLU in a GAL-Elk1 luciferase assay in rat L6 cells transfected with KLB and FGFR2c or FGFR3c and incubated with media containing increasing concentrations of FGF19 (O) or FGF21(▲). L6 cells were cotransfected with expression vectors for KLB and the indicated FGFR together with GAL-Elk1, SV40-*Renilla* Luciferase, and Gal-responsive luciferase reporter. Transfected cells were incubated with media containing increasing concentrations of FGF19 or FGF21 for 6 hours before luciferase assays. Transcriptional activation was assessed by the relative luciferase activity normalized by *Renilla* luciferase activity and expressed as relative luciferase unit (RLU). This figure shows that FGF21 and FGF19 activated FGFR2c and FGFR3c in the presence of KLB.

In order to quantitatively evaluate specific activation of FGFRs by FGF19, an FGF-responsive GAL-Elk1 luciferase reporter assay was introduced into rat L6 cells. In this assay, effective binding of a ligand to FGFR results in activation of an endogenous MAP kinase pathway, leading to activation of a chimeric transcriptional activator comprising an Elk-1 activation domain and a GAL4 DNA binding domain. L6 cells lack functional FGFR or KLB and are only responsive to FGF19 or FGF21 when cotransfected with cognate receptors. L6 cells were cotransfected with expression vectors for KLB and FGFR (FGFG1c or FGFR4) together with GAL-Elk1, SV40-renilla Luciferase, and Gal-responsive firefly luciferase reporter. Transfected cells were incubated with media containing increasing concentrations of FGF19 or FGF21 for 6 hours before luciferase assays. The results from the luciferase assay show that FGF19 and FGF21 activated FGFR1c, 2c and 3c in the presence of KLB, with similar potency and efficacy (FIGS. 18A and 19). In contrast, FGF19, but not FGF21, efficiently activated FGFR4, even in the presence of KLB (FIG. 18A). To map the signals required for FGFR4 activation, a number of chimeric constructs between FGF19 and FGF21 were generated using conserved residues to form junctions (FIG. 18B). Sequences are discussed above in the Materials and Methods section entitled Expression of recombinant FGF protein. Each FGF construct was expressed in transiently transfected HEK293 cells and the culture supernatants containing secreted chimeric FGF proteins were tested for activation of FGFR1c and/or FGFR4 in KLB-expressing L6 cells using the GAL-Elk1 reporter assay. Based on the activity of FGFR1c and FGFR4, the chimeric constructs were classified into 4 classes: high FGFR1c and FGFR4 activity (Class I, FGF19-like); high FGFR1c activity and low, but detectable FGFR4 activity (Class II); high FGFR1c activity without detectable FGFR4 activity (Class III, FGF21-like) and very low or undetectable FGFR1c and FGFR4 activity due to poor expression (Class IV) (I-III, FIGS. 18C and 20; IV not shown). This mapping indicated that the N-terminal 39 amino acids of FGF19 are sufficient to confer some FGFR4 activity when transferred to FGF21. In addition, the N-terminal 24 amino acids and the C-terminal 49 amino acids of FGF19 are necessary for full FGFR4 activity, but are not sufficient to confer FGFR4 activity when transferred to FGF21. Thus multiple signals at both the N-terminus and C-terminus of FGF19 contribute to FGFR4 activation.

One chimeric construct classified as a class II molecule, consisting of amino acids 1-20 of FGF21 and 25-194 of FGF19 (>90% identical to FGF19), was selected for large scale synthesis in CHO cells and this variant is referred to as "FGF19v". When compared with FGF19 using the luciferase reporter assay, FGF19v protein exhibited a similar dose-dependent activity to FGF19 in L6 cells cotransfected with KLB and FGFR1c (FIG. 18D). However, FGF19v activity was significantly diminished in L6 cells cotransfected with either FGFR4 alone or a combination of FGFR4 and KLB (FIG. 18D), FGF19 having been previously shown to directly bind to FGFR4 even in the absence of KLB. FGF19, but not FGF19v, exhibited dose-dependent binding activity to FGFR4 (FIGS. 18E and F).

C. FGFR4 Mediates Hepatocyte Proliferation In Vitro and In Vivo

Activity of FGF19v was further tested in vivo in comparison with FGF19 and FGF21 by intravenously injection into overnight fasted FVB mice. Livers were harvested at 4 hours post injection and hepatic mRNA expression was determined by QPCR. Genes that were acutely induced by FGF19 but not by FGF21, such as Egr-1 and c-Fos, were not efficiently induced by FGF19v, consistent with the reduced FGFR4 activity of FGF19v (FIG. 21A). FGF19v had similar activity to FGF19 or FGF21 on genes were co-regulated by FGF19 and FGF21, such as GK. Using Fgfr4 KO mice, FGFR4 contributes to the regulation of Egr-1 and c-Fos, but not GK, by FGF19 (FIG. 21B). Unexpectedly, FGF21 (as well as FGF19 and FGF19v) altered expression of SHP and Cyp7a1 (FIG. 21A), which were proposed to be major targets for FGFR4-dependent regulation by FGF19. Alterations in SHP and Cyp7a1 by FGF19 and FGF21 were observed even in Fgfr4 KO mice, indicating that with this acute treatment, both endocrine FGFs can modulate expression of these genes through an FGFR4-independent pathway (FIG. 21B).

FGF19 increased anchorage-independent proliferation of HepG2 cells in soft agar, and this effect was much less apparent for FGF19v or FGF21 proteins (FIG. 21C). To see whether FGF19v also exhibited reduced ability to induce hepatocyte proliferation in vivo, mice were infused with FGF19, FGF19v (1 ng/h) or vehicle control by osmotic minipump. In addition, 1 mg/kg/day of FGF protein was injected intraperitoneally daily for 7 days to the same mice to achieve high peak exposures. To capture intermittent proliferative events, BrdU solution (30 mg/kg) was injected twice daily for total of 13 times. Hepatocyte proliferation was determined by measuring BrdU positive hepatocytes in liver harvested on day 7. As previously reported, FGF19 treatment resulted in a dramatic increase in BrdU incorporation; however, this response was significantly blunted for FGF19v (FIGS. 21D and E). Hepatic mRNA for Egr-1, c-Fos, and the hepatocyte proliferation marker AFP were all dramatically induced by FGF19 and these inductions were largely absent for FGF19v, while regulation of GK, Cyp7a1 and Cyp8b1 did not differ between FGF19 and FGF19v (FIG. 21F).

D. FGFR4 is not Required for Amelioration of Hyperglycemia in ob/ob Mice by FGF19.

The in vitro and in vivo results described above raised the question as to whether FGF19v, a variant of FGF19 with reduced FGFR4 activity and proliferative potential, could improve hyperglycemia in diabetic animals as FGF21 does. FGF21, FGF19v (1 ng/h) or vehicle control were continuously infused subcutaneously into ob/ob mice using osmotic minipumps. While infusion did not significantly affect body weight (FIG. 22A), both FGF21 and FGF19v dramatically reduced blood glucose levels in both random fed and fasted mice (FIGS. 22A and B), reduced circulating free fatty acid levels (FIG. 22C), and improved glucose tolerance (FIG. 22D).

To visualize hepatocyte proliferation, animals were injected with BrdU 4 hours prior to sacrifice on day 7. Neither FGF21 nor FGF19v increased hepatic BrdU incorporation (not shown), rather gross liver weight was significantly reduced (FIG. 22E) and no significant change in hepatic expression of AFP mRNA was observed (FIG. 22F). Taken together, FGF19v can improve the metabolic status of obese mice without induction of hepatocyte proliferation.

A number of genes were indentied which exhibited commonly altered expression in ob/ob mice treated with FGF21 and FGF19v. In the liver, both proteins induced IGFBP2 (a recently demonstrated anti-diabetic protein), and suppressed stearoyl-Coenzyme A desaturase 1 (SCD-1; a lipogenic gene) and Cyp8b1 (the determinant of the balance between CA and CDCA production). In addition, they both induced UCP-1 (adaptive thermogenesis), SCD-1 and Medium-Chain Acyl-CoA Dehydrogenase (MCAD; mitochondrial fatty acid oxidation) in brown adipose tissue, and SREBP-1c (lipogenic transcription factor) in white adipose tissue (FIG. 22F). Thus, actions in multiple tissues could mediate the anti-diabetic effects of FGF21 and FGF19v acting through a FGFR4 independent mechanism.

Figure 21:
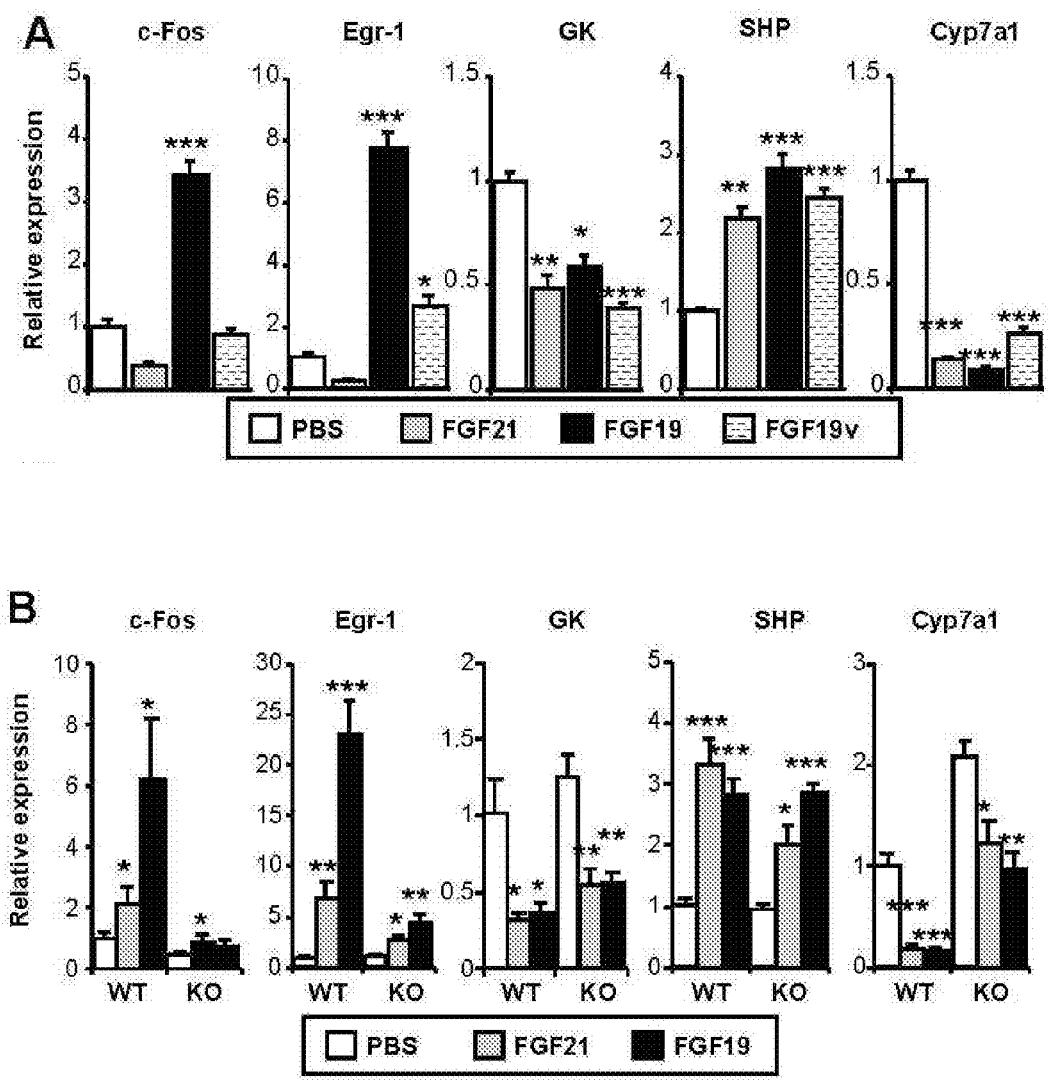
FIG. 21 shows the effects of FGF19v in chow-fed mice.
Figure 21:
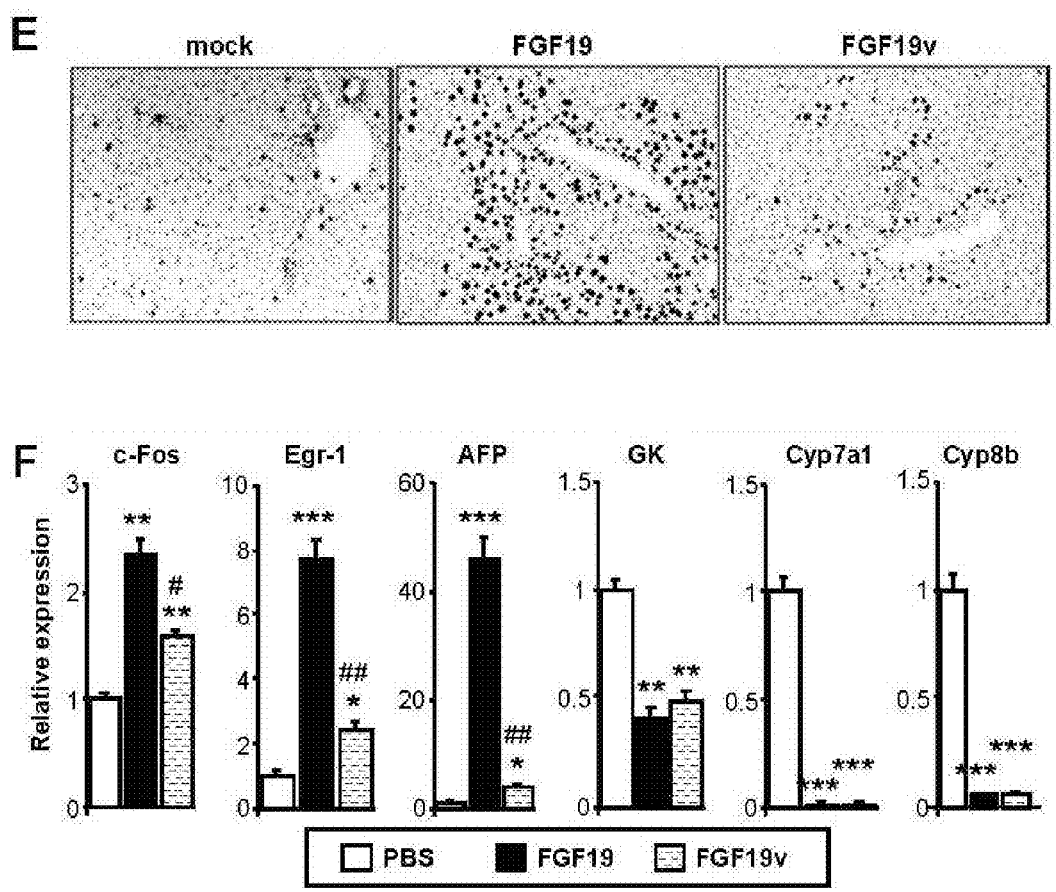
Figure 22:
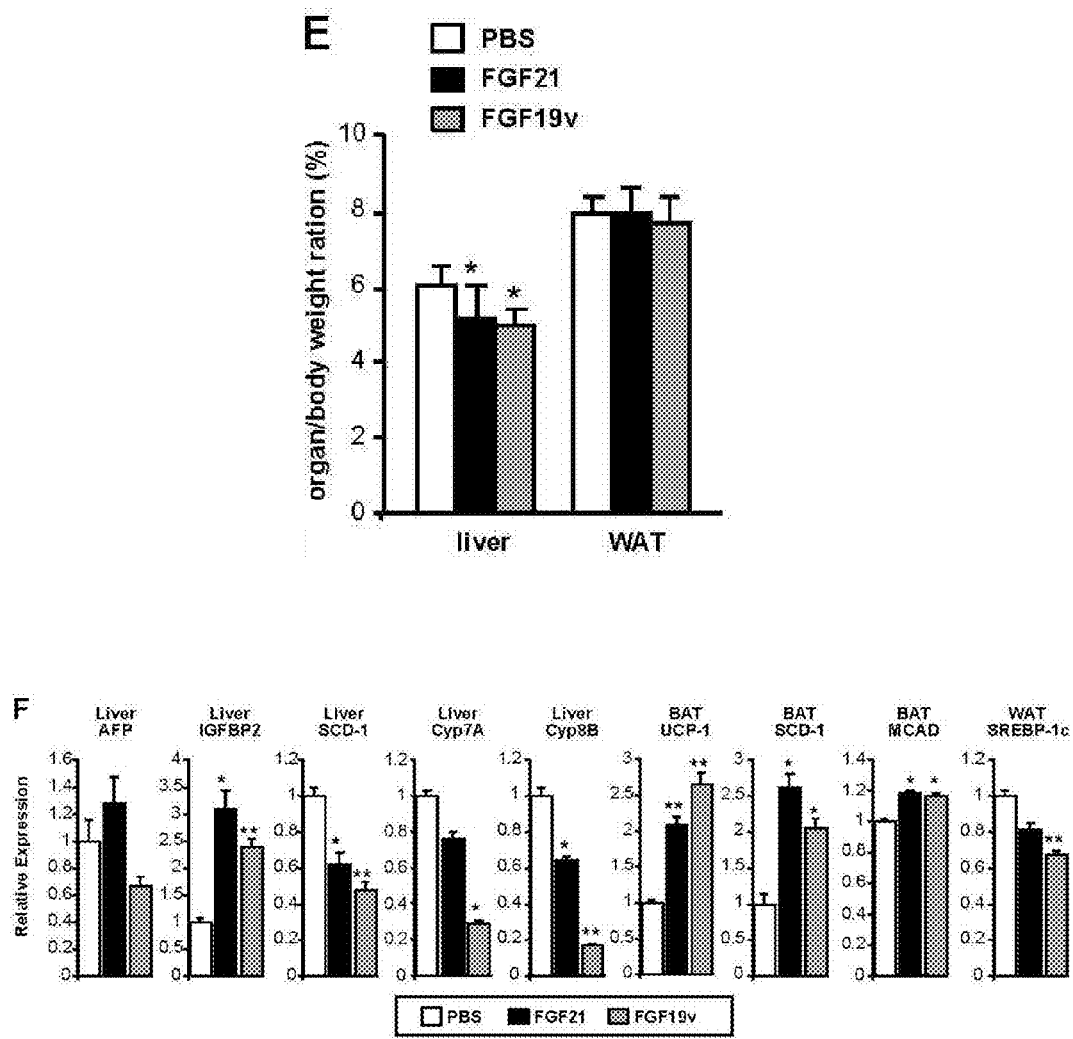
FIG. 22 shows that FGF19v and FGF21 had similar metabolic effects and ameliorate hyperglycemia in ob/ob mice. 11-week-old ob/ob mice were subcutaneously implanted with an osmotic pump to infuse 1 ng/hr FGF protein (0.4 mg/kg/day) or PBS control (N=7).

By examining individual serum BA, recombinant FGF19, acting through Fgfr4, was demonstrated to suppress Cyp7a1 causing bile acid synthesis to proceed by the Cyp7a1-independent alternate (acidic) pathway leading to the production of CDCA at the expense of CA. Cyp8b1 expression increased several-fold in Fgfr4 knockout mice and that FGF19 treatment suppresses Cyp8b1, an obligatory enzymatic step for CA synthesis. FGFR4 was a determinant of the ratio of CDCA to CA production, through negative regulation of both Cyp7a1 and Cyp8b1. FGFR4 activation shifts BA production towards CDCA, while its abrogation leads to CA formation. In addition, FGF19 increased hepatic AFP expression in an Fgfr4 dependent manner. FGF19 improved glucose tolerance in HFD-fed FGFR4 KO mice (FIG. 17) and FGF19v, a protein specifically impaired for FGFR4 binding and activation, ameliorates hyperglycemia in ob/ob mice (FIGS. 18 and 21-22). In addition to the effects in insulin resistance and glucose metabolism, FGF19 increases serum BHB levels even in FGFR4 KO mice (FIG. 17), like FGF21. Both FGF19 and FGF21 can bind and activate FGFR1c, FGFR2c, and FGFR3c in the presence of KLB. Thus FGFR1c, FGFR2c, or FGFR3c, in cooperation with KLB, may mediate the common metabolic effects of FGF19 and FGF21.

What is claimed is:

1. A chimeric FGF19 polypeptide comprising the sequence of SEQ ID NO:5.

2. The chimeric FGF19 polypeptide of claim 1, wherein the chimeric hFGF19 polypeptide is fused to a second polypeptide, the second polypeptide is selected from the group consisting of: the Fc portion of an immunoglobulin, an analog of the Fc portion of an immunoglobulin and one or more fragments of the Fc portion of an immunoglobulin.

3. The chimeric FGF19 polypeptide of claim 2, wherein the immunoglobulin is selected from the group consisting of: IgG-1, IgG-2, IgG-3, IgG-4, IgA-1, IgA-2, IgE, IgD and IgM.

4. The chimeric FGF19 polypeptide of claim 2 or 3, wherein the Fc portion is human or humanized.

5. The chimeric FGF19 polypeptide of claim 2, wherein the C-terminus of the chimeric hFGF19 polypeptide is fused to the N-terminus of the second polypeptide.

6. The chimeric FGF19 polypeptide of claim 5, wherein the C-terminus of the chimeric hFGF19 polypeptide is fused to the N-terminus of the second polypeptide via a linker, the linker is selected from the group consisting of: a [Gly]n linker, a [Gly3Ser]m linker and a [Gly4Ser]m linker, wherein n is an integer from 1-30 and m is an integer from 1-6.

7. The chimeric FGF19 polypeptide of claim 1, wherein the chimeric hFGF19 polypeptide does not substantially activate FGFR4 in either a Klotho-beta independent or Klotho-beta dependent manner.

8. The chimeric FGF19 polypeptide of claim 1, wherein the chimeric FGF19 polypeptide activates FGFR1c in a Klotho-beta dependent manner.

9. The chimeric FGF19 polypeptide of claim 1, wherein the chimeric FGF19 polypeptide when administered to an individual does not reduce the level of phosphorylated STATS polypeptide in the individual.

10. The chimeric FGF19 polypeptide of claim 1, wherein the chimeric FGF19 polypeptide when administered to an individual reduces the amount of phosphorylated STATS polypeptide in the individual but this amount of phosphorylated STATS polypeptide is greater than the amount of phosphorylated STATS polypeptide upon administration of native hFGF21 to the individual.

11. The chimeric FGF19 polypeptide of claim 1, wherein the chimeric FGF19 polypeptide when administered to an individual reduces the amount of phosphorylated STATS polypeptide to an amount that is any of: from 100% to 5%, from 100% to 10%, from 100% to 20%, from 100% to 30%, from 100% to 40%, from 100% to 50%, from 100% to 60%, from 100% to 70%, from 100% to 80%, from 100% to 90% or from 100% to 95%, of the amount of phosphorylated STATS polypeptide in the individual without such administration.

12. The chimeric FGF19 polypeptide of claim 1, wherein the chimeric FGF19 polypeptide when administered to an individual, the reduction in the amount of phosphorylated STATS polypeptide is less than reduction in the amount of phosphorylated STATS polypeptide upon administration of native hFGF21.

13. The chimeric FGF19 polypeptide of claim 12, wherein the reduction of the phosphorylated STATS polypeptide when the chimeric hFGF19 polypeptide is administered to the individual is by any of: from 0% to 5%, from 0% to 10%, from 0% to 20%, from 0% to 30%, from 0% to 40%, from 0% to 50%, from 0% to 60%, from 0% to 70%, from 0% to 80%, from 0% to 90% or from 0% to 95%, of the reduction in the amount of phosphorylated STATS polypeptide upon administration of native hFGF21.

14. The chimeric FGF19 polypeptide of claim 1, wherein the chimeric FGF19 polypeptide when administered to an individual does not induce growth hormone resistance.

15. The chimeric FGF19 polypeptide of claim 1, wherein the in vivo physiological half-life of the chimeric FGF19 polypeptide is at least or about the same as FGF19.

16. The chimeric FGF19 polypeptide of claim 1, wherein the in vivo physiological half-life of the chimeric FGF19 polypeptide is at least or about the same as FGF21.

17. A pharmaceutical composition comprising:
(a) a therapeutically effective amount of the chimeric FGF19 polypeptide of claim 1; and
(b) an acceptable pharmaceutical carrier.

18. A method of lowering the blood glucose of an individual in need of such treatment, the method comprising administering to the individual a therapeutically effective amount of the pharmaceutical composition of claim 17.

19. The method of claim 18, wherein the individual is a human.

20. An isolated nucleic acid molecule comprising (a) a DNA molecule encoding a polypeptide comprising the amino acid sequence of SEQ ID NO:5, or (b) the complement of the DNA molecule of (a).

21. The isolated nucleic acid molecule of claim 20 comprising the nucleic acid sequence with SEQ ID NO:7.

22. The isolated nucleic acid of claim 20, wherein the encoded polypeptide further comprises the amino acid residues corresponding to the Fc portion of an immunoglobulin.

23. An expression system comprising the nucleic acid molecule of claim 20.

24. A host cell comprising the expression system of claim 23.

25. A host cell comprising the nucleic acid molecule of claim 20.

26. A process for producing an isolated polypeptide comprising: culturing the host cell of claim 25 under conditions suitable for expression of the encoded polypeptide; and recovering the encoded polypeptide from the cell culture.

27. An isolated polypeptide produced by the process of claim 26.

28. An antibody that binds specifically to a chimeric FGF19 polypeptide consisting of the sequence of SEQ ID NO:5, wherein the antibody does not bind to a native FGF19 polypeptide or a native FGF21 polypeptide.

29. The antibody of claim 28, wherein the antibody is monoclonal.

* * * * *

UNITED STATES PATENT AND TRADEMARK OFFICE
CERTIFICATE OF CORRECTION

| | | |
|---|---|---|
| PATENT NO. | : 8,535,912 B2 | Page 1 of 1 |
| APPLICATION NO. | : 12/905776 | |
| DATED | : September 17, 2013 | |
| INVENTOR(S) | : Sonoda | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 72 days.

Signed and Sealed this
Tenth Day of February, 2015

Michelle K. Lee
*Deputy Director of the United States Patent and Trademark Office*

SEQUENCE LISTING

```
<160> NUMBER OF SEQ ID NOS: 317

<210> SEQ ID NO 1
<211> LENGTH: 194
<212> TYPE: PRT
<213> ORGANISM: Homo sapiens

<400> SEQUENCE: 1

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80
```

```
Met Gly Ala Asp Gly Lys Met Gln Gly Leu Leu Gln Tyr Ser Glu Glu
                85                  90                  95
Asp Cys Ala Phe Glu Glu Ile Arg Pro Asp Gly Tyr Asn Val Tyr
                100                 105                 110
Arg Ser Glu Lys His Arg Leu Pro Val Ser Leu Ser Ser Ala Lys Gln
                115                 120                 125
Arg Gln Leu Tyr Lys Asn Arg Gly Phe Leu Pro Leu Ser His Phe Leu
                130                 135                 140
Pro Met Leu Pro Met Val Pro Glu Glu Pro Glu Asp Leu Arg Gly His
145                 150                 155                 160
Leu Glu Ser Asp Met Phe Ser Ser Pro Leu Glu Thr Asp Ser Met Asp
                165                 170                 175
Pro Phe Gly Leu Val Thr Gly Leu Glu Ala Val Arg Ser Pro Ser Phe
                180                 185                 190
Glu Lys

<210> SEQ ID NO 2
<211> LENGTH: 181
<212> TYPE: PRT
<213> ORGANISM: Homo sapiens

<400> SEQUENCE: 2

His Pro Ile Pro Asp Ser Ser Pro Leu Leu Gln Phe Gly Gly Gln Val
1               5                   10                  15
Arg Gln Arg Tyr Leu Tyr Thr Asp Asp Ala Gln Gln Thr Glu Ala His
                20                  25                  30
Leu Glu Ile Arg Glu Asp Gly Thr Val Gly Gly Ala Ala Asp Gln Ser
                35                  40                  45
Pro Glu Ser Leu Leu Gln Leu Lys Ala Leu Lys Pro Gly Val Ile Gln
                50                  55                  60
Ile Leu Gly Val Lys Thr Ser Arg Phe Leu Cys Gln Arg Pro Asp Gly
65                  70                  75                  80
Ala Leu Tyr Gly Ser Leu His Phe Asp Pro Glu Ala Cys Ser Phe Arg
                85                  90                  95
Glu Leu Leu Leu Glu Asp Gly Tyr Asn Val Tyr Gln Ser Glu Ala His
                100                 105                 110
Gly Leu Pro Leu His Leu Pro Gly Asn Lys Ser Pro His Arg Asp Pro
                115                 120                 125
Ala Pro Arg Gly Pro Ala Arg Phe Leu Pro Leu Pro Gly Leu Pro Pro
                130                 135                 140
Ala Leu Pro Glu Pro Pro Gly Ile Leu Ala Pro Gln Pro Pro Asp Val
145                 150                 155                 160
Gly Ser Ser Asp Pro Leu Ser Met Val Gly Pro Ser Gln Gly Arg Ser
                165                 170                 175
Pro Ser Tyr Ala Ser
                180

<210> SEQ ID NO 3
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Arg Ser Gly Cys Val Val Val His Val Trp Ile Leu Ala Gly Leu
1               5                   10                  15
```

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215

<210> SEQ ID NO 4
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

```
Pro Ala Arg Phe Leu Pro Leu Pro Gly Leu Pro Pro Ala Leu Pro Glu
            165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
            195                 200                 205

Ser

<210> SEQ ID NO 5
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

His Pro Ile Pro Asp Ser Ser Pro Leu Leu Gln Phe Gly Gly Gln Val
1               5                   10                  15

Arg Gln Arg Tyr Leu Tyr Thr Ser Gly Pro His Gly Leu Ser Ser Cys
            20                  25                  30

Phe Leu Arg Ile Arg Ala Asp Gly Val Val Asp Cys Ala Arg Gly Gln
        35                  40                  45

Ser Ala His Ser Leu Leu Glu Ile Lys Ala Val Ala Leu Arg Thr Val
    50                  55                  60

Ala Ile Lys Gly Val His Ser Val Arg Tyr Leu Cys Met Gly Ala Asp
65                  70                  75                  80

Gly Lys Met Gln Gly Leu Leu Gln Tyr Ser Glu Glu Asp Cys Ala Phe
                85                  90                  95

Glu Glu Glu Ile Arg Pro Asp Gly Tyr Asn Val Tyr Arg Ser Glu Lys
            100                 105                 110

His Arg Leu Pro Val Ser Leu Ser Ser Ala Lys Gln Arg Gln Leu Tyr
        115                 120                 125

Lys Asn Arg Gly Phe Leu Pro Leu Ser His Phe Leu Pro Met Leu Pro
130                 135                 140

Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
                165                 170                 175

Val Thr Gly Leu Glu Ala Val Arg Ser Pro Ser Phe Glu Lys
            180                 185                 190

<210> SEQ ID NO 6

<400> SEQUENCE: 6

000

<210> SEQ ID NO 7
<211> LENGTH: 570
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7 cacccatcc ctgactccag tcctctcctg caattcgggg gccaagtccg gcagcggtac    60
ctctacacct ccggcccca cgggctctcc agctgcttcc tgcgcatccg tgccgacggc   120
```

-continued

```
gtcgtggact gcgcgcgggg ccagagcgcg cacagtttgc tggagatcaa ggcagtcgct      180
ctgcggaccg tggccatcaa gggcgtgcac agcgtgcggt acctctgcat gggcgccgac      240
ggcaagatgc aggggctgct tcagtactcg gaggaagact gtgctttcga ggaggagatc      300
cgcccagatg gctacaatgt gtaccgatcc gagaagcacc gcctcccggt ctccctgagc      360
agtgccaaac agcggcagct gtacaagaac agaggctttc ttccactctc tcatttcctg      420
cccatgctgc ccatggtccc agaggagcct gaggacctca gggccactt ggaatctgac       480 atgttctctt cgcccctgga gaccgacagc atggacccat ttgggcttgt caccggactg      540
gaggccgtga ggagtcccag ctttgagaag                                       570
```

<210> SEQ ID NO 8
<211> LENGTH: 185
<212> TYPE: PRT
<213> ORGANISM: Homo sapiens

<400> SEQUENCE: 8

```
Pro His Val His Tyr Gly Trp Gly Asp Pro Ile Arg Leu Arg His Leu
1               5                   10                  15

Tyr Thr Ser Gly Pro His Gly Leu Ser Ser Cys Phe Leu Arg Ile Arg
            20                  25                  30

Ala Asp Gly Val Val Asp Cys Ala Arg Gly Gln Ser Ala His Ser Leu
        35                  40                  45

Leu Glu Ile Lys Ala Val Ala Leu Arg Thr Val Ala Ile Lys Gly Val
    50                  55                  60

His Ser Val Arg Tyr Leu Cys Met Gly Ala Asp Gly Lys Met Gln Gly
65                  70                  75                  80

Leu Leu Gln Tyr Ser Glu Glu Asp Cys Ala Phe Glu Glu Glu Ile Arg
                85                  90                  95

Pro Asp Gly Tyr Asn Val Tyr Arg Ser Glu Lys His Arg Leu Pro Val
            100                 105                 110

Ser Leu Ser Ser Ala Lys Gln Arg Gln Leu Tyr Lys Asn Arg Gly Phe
        115                 120                 125

Leu Pro Leu Ser His Phe Leu Pro Met Leu Pro Met Val Pro Glu Glu
    130                 135                 140

Pro Glu Asp Leu Arg Gly His Leu Glu Ser Asp Met Phe Ser Ser Pro
145                 150                 155                 160

Leu Glu Thr Asp Ser Met Asp Pro Phe Gly Leu Val Thr Gly Leu Glu
                165                 170                 175

Ala Val Arg Ser Pro Ser Phe Glu Lys
            180                 185
```

<210> SEQ ID NO 9
<211> LENGTH: 184
<212> TYPE: PRT
<213> ORGANISM: Homo sapiens

<400> SEQUENCE: 9

```
His Val His Tyr Gly Trp Gly Asp Pro Ile Arg Leu Arg His Leu Tyr
1               5                   10                  15

Thr Ser Gly Pro His Gly Leu Ser Ser Cys Phe Leu Arg Ile Arg Ala
            20                  25                  30

Asp Gly Val Val Asp Cys Ala Arg Gly Gln Ser Ala His Ser Leu Leu
        35                  40                  45

Glu Ile Lys Ala Val Ala Leu Arg Thr Val Ala Ile Lys Gly Val His
    50                  55                  60
```

```
Ser Val Arg Tyr Leu Cys Met Gly Ala Asp Gly Lys Met Gln Gly Leu
 65                  70                  75                  80

Leu Gln Tyr Ser Glu Glu Asp Cys Ala Phe Glu Glu Ile Arg Pro
                 85                  90                  95

Asp Gly Tyr Asn Val Tyr Arg Ser Glu Lys His Arg Leu Pro Val Ser
                100                 105                 110

Leu Ser Ser Ala Lys Gln Arg Gln Leu Tyr Lys Asn Arg Gly Phe Leu
            115                 120                 125

Pro Leu Ser His Phe Leu Pro Met Leu Pro Met Val Pro Glu Glu Pro
        130                 135                 140

Glu Asp Leu Arg Gly His Leu Glu Ser Asp Met Phe Ser Ser Pro Leu
145                 150                 155                 160

Glu Thr Asp Ser Met Asp Pro Phe Gly Leu Val Thr Gly Leu Glu Ala
                165                 170                 175

Val Arg Ser Pro Ser Phe Glu Lys
                180

<210> SEQ ID NO 10
<211> LENGTH: 170
<212> TYPE: PRT
<213> ORGANISM: Homo sapiens

<400> SEQUENCE: 10

Leu Tyr Thr Ser Gly Pro His Gly Leu Ser Ser Cys Phe Leu Arg Ile
  1               5                  10                  15

Arg Ala Asp Gly Val Val Asp Cys Ala Arg Gly Gln Ser Ala His Ser
             20                  25                  30

Leu Leu Glu Ile Lys Ala Val Ala Leu Arg Thr Val Ala Ile Lys Gly
         35                  40                  45

Val His Ser Val Arg Tyr Leu Cys Met Gly Ala Asp Gly Lys Met Gln
     50                  55                  60

Gly Leu Leu Gln Tyr Ser Glu Glu Asp Cys Ala Phe Glu Glu Glu Ile
 65                  70                  75                  80

Arg Pro Asp Gly Tyr Asn Val Tyr Arg Ser Glu Lys His Arg Leu Pro
                 85                  90                  95

Val Ser Leu Ser Ser Ala Lys Gln Arg Gln Leu Tyr Lys Asn Arg Gly
                100                 105                 110

Phe Leu Pro Leu Ser His Phe Leu Pro Met Leu Pro Met Val Pro Glu
            115                 120                 125

Glu Pro Glu Asp Leu Arg Gly His Leu Glu Ser Asp Met Phe Ser Ser
        130                 135                 140

Pro Leu Glu Thr Asp Ser Met Asp Pro Phe Gly Leu Val Thr Gly Leu
145                 150                 155                 160

Glu Ala Val Arg Ser Pro Ser Phe Glu Lys
                165                 170

<210> SEQ ID NO 11
<211> LENGTH: 169
<212> TYPE: PRT
<213> ORGANISM: Homo sapiens

<400> SEQUENCE: 11

Tyr Thr Ser Gly Pro His Gly Leu Ser Ser Cys Phe Leu Arg Ile Arg
  1               5                  10                  15

Ala Asp Gly Val Val Asp Cys Ala Arg Gly Gln Ser Ala His Ser Leu
             20                  25                  30
```

```
Leu Glu Ile Lys Ala Val Ala Leu Arg Thr Val Ala Ile Lys Gly Val
            35                  40                  45

His Ser Val Arg Tyr Leu Cys Met Gly Ala Asp Gly Lys Met Gln Gly
 50                  55                  60

Leu Leu Gln Tyr Ser Glu Glu Asp Cys Ala Phe Glu Glu Ile Arg
 65                  70                  75                  80

Pro Asp Gly Tyr Asn Val Tyr Arg Ser Glu Lys His Arg Leu Pro Val
                    85                  90                  95

Ser Leu Ser Ser Ala Lys Gln Arg Gln Leu Tyr Lys Asn Arg Gly Phe
                100                 105                 110

Leu Pro Leu Ser His Phe Leu Pro Met Leu Pro Met Val Pro Glu Glu
                115                 120                 125

Pro Glu Asp Leu Arg Gly His Leu Glu Ser Asp Met Phe Ser Ser Pro
130                 135                 140

Leu Glu Thr Asp Ser Met Asp Pro Phe Gly Leu Val Thr Gly Leu Glu
145                 150                 155                 160

Ala Val Arg Ser Pro Ser Phe Glu Lys
                165

<210> SEQ ID NO 12
<211> LENGTH: 168
<212> TYPE: PRT
<213> ORGANISM: Homo sapiens

<400> SEQUENCE: 12

Thr Ser Gly Pro His Gly Leu Ser Ser Cys Phe Leu Arg Ile Arg Ala
  1               5                  10                  15

Asp Gly Val Val Asp Cys Ala Arg Gly Gln Ser Ala His Ser Leu Leu
                 20                  25                  30

Glu Ile Lys Ala Val Ala Leu Arg Thr Val Ala Ile Lys Gly Val His
             35                  40                  45

Ser Val Arg Tyr Leu Cys Met Gly Ala Asp Gly Lys Met Gln Gly Leu
 50                  55                  60

Leu Gln Tyr Ser Glu Glu Asp Cys Ala Phe Glu Glu Ile Arg Pro
 65                  70                  75                  80

Asp Gly Tyr Asn Val Tyr Arg Ser Glu Lys His Arg Leu Pro Val Ser
                 85                  90                  95

Leu Ser Ser Ala Lys Gln Arg Gln Leu Tyr Lys Asn Arg Gly Phe Leu
                100                 105                 110

Pro Leu Ser His Phe Leu Pro Met Leu Pro Met Val Pro Glu Glu Pro
                115                 120                 125

Glu Asp Leu Arg Gly His Leu Glu Ser Asp Met Phe Ser Ser Pro Leu
            130                 135                 140

Glu Thr Asp Ser Met Asp Pro Phe Gly Leu Val Thr Gly Leu Glu Ala
145                 150                 155                 160

Val Arg Ser Pro Ser Phe Glu Lys
                165

<210> SEQ ID NO 13
<211> LENGTH: 167
<212> TYPE: PRT
<213> ORGANISM: Homo sapiens

<400> SEQUENCE: 13

Ser Gly Pro His Gly Leu Ser Ser Cys Phe Leu Arg Ile Arg Ala Asp
  1               5                  10                  15

Gly Val Val Asp Cys Ala Arg Gly Gln Ser Ala His Ser Leu Leu Glu
```

```
                    20                  25                  30
Ile Lys Ala Val Ala Leu Arg Thr Val Ala Ile Lys Gly Val His Ser
            35                  40                  45

Val Arg Tyr Leu Cys Met Gly Ala Asp Gly Lys Met Gln Gly Leu Leu
 50                  55                  60

Gln Tyr Ser Glu Glu Asp Cys Ala Phe Glu Glu Ile Arg Pro Asp
 65                  70                  75                  80

Gly Tyr Asn Val Tyr Arg Ser Glu Lys His Arg Leu Pro Val Ser Leu
                85                  90                  95

Ser Ser Ala Lys Gln Arg Gln Leu Tyr Lys Asn Arg Gly Phe Leu Pro
            100                 105                 110

Leu Ser His Phe Leu Pro Met Leu Pro Met Val Pro Glu Glu Pro Glu
            115                 120                 125

Asp Leu Arg Gly His Leu Glu Ser Asp Met Phe Ser Ser Pro Leu Glu
            130                 135                 140

Thr Asp Ser Met Asp Pro Phe Gly Leu Val Thr Gly Leu Glu Ala Val
145                 150                 155                 160

Arg Ser Pro Ser Phe Glu Lys
                165

<210> SEQ ID NO 14
<211> LENGTH: 165
<212> TYPE: PRT
<213> ORGANISM: Homo sapiens

<400> SEQUENCE: 14

Pro His Gly Leu Ser Ser Cys Phe Leu Arg Ile Arg Ala Asp Gly Val
 1               5                  10                  15

Val Asp Cys Ala Arg Gly Gln Ser Ala His Ser Leu Leu Glu Ile Lys
            20                  25                  30

Ala Val Ala Leu Arg Thr Val Ala Ile Lys Gly Val His Ser Val Arg
            35                  40                  45

Tyr Leu Cys Met Gly Ala Asp Gly Lys Met Gln Gly Leu Leu Gln Tyr
 50                  55                  60

Ser Glu Glu Asp Cys Ala Phe Glu Glu Ile Arg Pro Asp Gly Tyr
 65                  70                  75                  80

Asn Val Tyr Arg Ser Glu Lys His Arg Leu Pro Val Ser Leu Ser Ser
                85                  90                  95

Ala Lys Gln Arg Gln Leu Tyr Lys Asn Arg Gly Phe Leu Pro Leu Ser
            100                 105                 110

His Phe Leu Pro Met Leu Pro Met Val Pro Glu Glu Pro Glu Asp Leu
            115                 120                 125

Arg Gly His Leu Glu Ser Asp Met Phe Ser Ser Pro Leu Glu Thr Asp
            130                 135                 140

Ser Met Asp Pro Phe Gly Leu Val Thr Gly Leu Glu Ala Val Arg Ser
145                 150                 155                 160

Pro Ser Phe Glu Lys
                165

<210> SEQ ID NO 15
<211> LENGTH: 162
<212> TYPE: PRT
<213> ORGANISM: Homo sapiens

<400> SEQUENCE: 15

Leu Ser Ser Cys Phe Leu Arg Ile Arg Ala Asp Gly Val Val Asp Cys
 1               5                  10                  15
```

Ala Arg Gly Gln Ser Ala His Ser Leu Leu Glu Ile Lys Ala Val Ala
            20                  25                  30

Leu Arg Thr Val Ala Ile Lys Gly Val His Ser Val Arg Tyr Leu Cys
        35                  40                  45

Met Gly Ala Asp Gly Lys Met Gln Gly Leu Leu Gln Tyr Ser Glu Glu
50                  55                  60

Asp Cys Ala Phe Glu Glu Ile Arg Pro Asp Gly Tyr Asn Val Tyr
65                  70                  75                  80

Arg Ser Glu Lys His Arg Leu Pro Val Ser Leu Ser Ser Ala Lys Gln
                85                  90                  95

Arg Gln Leu Tyr Lys Asn Arg Gly Phe Leu Pro Leu Ser His Phe Leu
            100                 105                 110

Pro Met Leu Pro Met Val Pro Glu Glu Pro Asp Leu Arg Gly His
            115                 120                 125

Leu Glu Ser Asp Met Phe Ser Ser Pro Leu Glu Thr Asp Ser Met Asp
130                 135                 140

Pro Phe Gly Leu Val Thr Gly Leu Glu Ala Val Arg Ser Pro Ser Phe
145                 150                 155                 160

Glu Lys

<210> SEQ ID NO 16
<211> LENGTH: 160
<212> TYPE: PRT
<213> ORGANISM: Homo sapiens

<400> SEQUENCE: 16

Ser Cys Phe Leu Arg Ile Arg Ala Asp Gly Val Val Asp Cys Ala Arg
1               5                   10                  15

Gly Gln Ser Ala His Ser Leu Leu Glu Ile Lys Ala Val Ala Leu Arg
            20                  25                  30

Thr Val Ala Ile Lys Gly Val His Ser Val Arg Tyr Leu Cys Met Gly
        35                  40                  45

Ala Asp Gly Lys Met Gln Gly Leu Leu Gln Tyr Ser Glu Glu Asp Cys
50                  55                  60

Ala Phe Glu Glu Ile Arg Pro Asp Gly Tyr Asn Val Tyr Arg Ser
65                  70                  75                  80

Glu Lys His Arg Leu Pro Val Ser Leu Ser Ser Ala Lys Gln Arg Gln
                85                  90                  95

Leu Tyr Lys Asn Arg Gly Phe Leu Pro Leu Ser His Phe Leu Pro Met
            100                 105                 110

Leu Pro Met Val Pro Glu Glu Pro Asp Leu Arg Gly His Leu Glu
            115                 120                 125

Ser Asp Met Phe Ser Ser Pro Leu Glu Thr Asp Ser Met Asp Pro Phe
130                 135                 140

Gly Leu Val Thr Gly Leu Glu Ala Val Arg Ser Pro Ser Phe Glu Lys
145                 150                 155                 160

<210> SEQ ID NO 17
<211> LENGTH: 158
<212> TYPE: PRT
<213> ORGANISM: Homo sapiens

<400> SEQUENCE: 17

Phe Leu Arg Ile Arg Ala Asp Gly Val Val Asp Cys Ala Arg Gly Gln
1               5                   10                  15

Ser Ala His Ser Leu Leu Glu Ile Lys Ala Val Ala Leu Arg Thr Val

```
                20                  25                  30
Ala Ile Lys Gly Val His Ser Val Arg Tyr Leu Cys Met Gly Ala Asp
                35                  40                  45

Gly Lys Met Gln Gly Leu Leu Gln Tyr Ser Glu Glu Asp Cys Ala Phe
                50                  55                  60

Glu Glu Glu Ile Arg Pro Asp Gly Tyr Asn Val Tyr Arg Ser Glu Lys
 65                  70                  75                  80

His Arg Leu Pro Val Ser Leu Ser Ser Ala Lys Gln Arg Gln Leu Tyr
                85                  90                  95

Lys Asn Arg Gly Phe Leu Pro Leu Ser His Phe Leu Pro Met Leu Pro
                100                 105                 110

Met Val Pro Glu Glu Pro Glu Asp Leu Arg Gly His Leu Glu Ser Asp
                115                 120                 125

Met Phe Ser Ser Pro Leu Glu Thr Asp Ser Met Asp Pro Phe Gly Leu
                130                 135                 140

Val Thr Gly Leu Glu Ala Val Arg Ser Pro Ser Phe Glu Lys
145                 150                 155

<210> SEQ ID NO 18
<211> LENGTH: 155
<212> TYPE: PRT
<213> ORGANISM: Homo sapiens

<400> SEQUENCE: 18

Ile Arg Ala Asp Gly Val Val Asp Cys Ala Arg Gly Gln Ser Ala His
 1               5                   10                  15

Ser Leu Leu Glu Ile Lys Ala Val Ala Leu Arg Thr Val Ala Ile Lys
                20                  25                  30

Gly Val His Ser Val Arg Tyr Leu Cys Met Gly Ala Asp Gly Lys Met
                35                  40                  45

Gln Gly Leu Leu Gln Tyr Ser Glu Glu Asp Cys Ala Phe Glu Glu Glu
                50                  55                  60

Ile Arg Pro Asp Gly Tyr Asn Val Tyr Arg Ser Glu Lys His Arg Leu
 65                  70                  75                  80

Pro Val Ser Leu Ser Ser Ala Lys Gln Arg Gln Leu Tyr Lys Asn Arg
                85                  90                  95

Gly Phe Leu Pro Leu Ser His Phe Leu Pro Met Leu Pro Met Val Pro
                100                 105                 110

Glu Glu Pro Glu Asp Leu Arg Gly His Leu Glu Ser Asp Met Phe Ser
                115                 120                 125

Ser Pro Leu Glu Thr Asp Ser Met Asp Pro Phe Gly Leu Val Thr Gly
                130                 135                 140

Leu Glu Ala Val Arg Ser Pro Ser Phe Glu Lys
145                 150                 155

<210> SEQ ID NO 19
<211> LENGTH: 154
<212> TYPE: PRT
<213> ORGANISM: Homo sapiens

<400> SEQUENCE: 19

Arg Ala Asp Gly Val Val Asp Cys Ala Arg Gly Gln Ser Ala His Ser
 1               5                   10                  15

Leu Leu Glu Ile Lys Ala Val Ala Leu Arg Thr Val Ala Ile Lys Gly
                20                  25                  30

Val His Ser Val Arg Tyr Leu Cys Met Gly Ala Asp Gly Lys Met Gln
                35                  40                  45
```

```
Gly Leu Leu Gln Tyr Ser Glu Glu Asp Cys Ala Phe Glu Glu Glu Ile
 50                  55                  60

Arg Pro Asp Gly Tyr Asn Val Tyr Arg Ser Glu Lys His Arg Leu Pro
 65                  70                  75                  80

Val Ser Leu Ser Ser Ala Lys Gln Arg Gln Leu Tyr Lys Asn Arg Gly
                 85                  90                  95

Phe Leu Pro Leu Ser His Phe Leu Pro Met Leu Pro Met Val Pro Glu
                100                 105                 110

Glu Pro Glu Asp Leu Arg Gly His Leu Glu Ser Asp Met Phe Ser Ser
                115                 120                 125

Pro Leu Glu Thr Asp Ser Met Asp Pro Phe Gly Leu Val Thr Gly Leu
130                 135                 140

Glu Ala Val Arg Ser Pro Ser Phe Glu Lys
145                 150

<210> SEQ ID NO 20
<211> LENGTH: 153
<212> TYPE: PRT
<213> ORGANISM: Homo sapiens

<400> SEQUENCE: 20

Ala Asp Gly Val Val Asp Cys Ala Arg Gly Gln Ser Ala His Ser Leu
 1               5                  10                  15

Leu Glu Ile Lys Ala Val Ala Leu Arg Thr Val Ala Ile Lys Gly Val
                 20                  25                  30

His Ser Val Arg Tyr Leu Cys Met Gly Ala Asp Gly Lys Met Gln Gly
             35                  40                  45

Leu Leu Gln Tyr Ser Glu Glu Asp Cys Ala Phe Glu Glu Glu Ile Arg
 50                  55                  60

Pro Asp Gly Tyr Asn Val Tyr Arg Ser Glu Lys His Arg Leu Pro Val
 65                  70                  75                  80

Ser Leu Ser Ser Ala Lys Gln Arg Gln Leu Tyr Lys Asn Arg Gly Phe
                 85                  90                  95

Leu Pro Leu Ser His Phe Leu Pro Met Leu Pro Met Val Pro Glu Glu
                100                 105                 110

Pro Glu Asp Leu Arg Gly His Leu Glu Ser Asp Met Phe Ser Ser Pro
                115                 120                 125

Leu Glu Thr Asp Ser Met Asp Pro Phe Gly Leu Val Thr Gly Leu Glu
130                 135                 140

Ala Val Arg Ser Pro Ser Phe Glu Lys
145                 150

<210> SEQ ID NO 21
<211> LENGTH: 152
<212> TYPE: PRT
<213> ORGANISM: Homo sapiens

<400> SEQUENCE: 21

Asp Gly Val Val Asp Cys Ala Arg Gly Gln Ser Ala His Ser Leu Leu
 1               5                  10                  15

Glu Ile Lys Ala Val Ala Leu Arg Thr Val Ala Ile Lys Gly Val His
                 20                  25                  30

Ser Val Arg Tyr Leu Cys Met Gly Ala Asp Gly Lys Met Gln Gly Leu
             35                  40                  45

Leu Gln Tyr Ser Glu Glu Asp Cys Ala Phe Glu Glu Glu Ile Arg Pro
 50                  55                  60
```

```
Asp Gly Tyr Asn Val Tyr Arg Ser Glu Lys His Arg Leu Pro Val Ser
 65                  70                  75                  80

Leu Ser Ser Ala Lys Gln Arg Gln Leu Tyr Lys Asn Arg Gly Phe Leu
                 85                  90                  95

Pro Leu Ser His Phe Leu Pro Met Leu Pro Met Val Pro Glu Glu Pro
            100                 105                 110

Glu Asp Leu Arg Gly His Leu Glu Ser Asp Met Phe Ser Ser Pro Leu
            115                 120                 125

Glu Thr Asp Ser Met Asp Pro Phe Gly Leu Val Thr Gly Leu Glu Ala
            130                 135                 140

Val Arg Ser Pro Ser Phe Glu Lys
145                 150

<210> SEQ ID NO 22
<211> LENGTH: 151
<212> TYPE: PRT
<213> ORGANISM: Homo sapiens

<400> SEQUENCE: 22

Gly Val Val Asp Cys Ala Arg Gly Gln Ser Ala His Ser Leu Leu Glu
  1               5                  10                  15

Ile Lys Ala Val Ala Leu Arg Thr Val Ala Ile Lys Gly Val His Ser
                 20                  25                  30

Val Arg Tyr Leu Cys Met Gly Ala Asp Gly Lys Met Gln Gly Leu Leu
             35                  40                  45

Gln Tyr Ser Glu Glu Asp Cys Ala Phe Glu Glu Glu Ile Arg Pro Asp
         50                  55                  60

Gly Tyr Asn Val Tyr Arg Ser Glu Lys His Arg Leu Pro Val Ser Leu
 65                  70                  75                  80

Ser Ser Ala Lys Gln Arg Gln Leu Tyr Lys Asn Arg Gly Phe Leu Pro
                 85                  90                  95

Leu Ser His Phe Leu Pro Met Leu Pro Met Val Pro Glu Glu Pro Glu
            100                 105                 110

Asp Leu Arg Gly His Leu Glu Ser Asp Met Phe Ser Ser Pro Leu Glu
            115                 120                 125

Thr Asp Ser Met Asp Pro Phe Gly Leu Val Thr Gly Leu Glu Ala Val
            130                 135                 140

Arg Ser Pro Ser Phe Glu Lys
145                 150

<210> SEQ ID NO 23
<211> LENGTH: 150
<212> TYPE: PRT
<213> ORGANISM: Homo sapiens

<400> SEQUENCE: 23

Val Val Asp Cys Ala Arg Gly Gln Ser Ala His Ser Leu Leu Glu Ile
  1               5                  10                  15

Lys Ala Val Ala Leu Arg Thr Val Ala Ile Lys Gly Val His Ser Val
                 20                  25                  30

Arg Tyr Leu Cys Met Gly Ala Asp Gly Lys Met Gln Gly Leu Leu Gln
             35                  40                  45

Tyr Ser Glu Glu Asp Cys Ala Phe Glu Glu Glu Ile Arg Pro Asp Gly
         50                  55                  60

Tyr Asn Val Tyr Arg Ser Glu Lys His Arg Leu Pro Val Ser Leu Ser
 65                  70                  75                  80

Ser Ala Lys Gln Arg Gln Leu Tyr Lys Asn Arg Gly Phe Leu Pro Leu
```

```
                85                  90                  95
Ser His Phe Leu Pro Met Leu Pro Met Val Pro Glu Glu Pro Glu Asp
            100                 105                 110

Leu Arg Gly His Leu Glu Ser Asp Met Phe Ser Ser Pro Leu Glu Thr
        115                 120                 125

Asp Ser Met Asp Pro Phe Gly Leu Val Thr Gly Leu Glu Ala Val Arg
130                 135                 140

Ser Pro Ser Phe Glu Lys
145                 150

<210> SEQ ID NO 24
<211> LENGTH: 143
<212> TYPE: PRT
<213> ORGANISM: Homo sapiens

<400> SEQUENCE: 24

Gln Ser Ala His Ser Leu Leu Glu Ile Lys Ala Val Ala Leu Arg Thr
1               5                   10                  15

Val Ala Ile Lys Gly Val His Ser Val Arg Tyr Leu Cys Met Gly Ala
            20                  25                  30

Asp Gly Lys Met Gln Gly Leu Leu Gln Tyr Ser Glu Glu Asp Cys Ala
        35                  40                  45

Phe Glu Glu Glu Ile Arg Pro Asp Gly Tyr Asn Val Tyr Arg Ser Glu
50                  55                  60

Lys His Arg Leu Pro Val Ser Leu Ser Ser Ala Lys Gln Arg Gln Leu
65                  70                  75                  80

Tyr Lys Asn Arg Gly Phe Leu Pro Leu Ser His Phe Leu Pro Met Leu
                85                  90                  95

Pro Met Val Pro Glu Glu Pro Glu Asp Leu Arg Gly His Leu Glu Ser
            100                 105                 110

Asp Met Phe Ser Ser Pro Leu Glu Thr Asp Ser Met Asp Pro Phe Gly
        115                 120                 125

Leu Val Thr Gly Leu Glu Ala Val Arg Ser Pro Ser Phe Glu Lys
130                 135                 140

<210> SEQ ID NO 25
<211> LENGTH: 142
<212> TYPE: PRT
<213> ORGANISM: Homo sapiens

<400> SEQUENCE: 25

Ser Ala His Ser Leu Leu Glu Ile Lys Ala Val Ala Leu Arg Thr Val
1               5                   10                  15

Ala Ile Lys Gly Val His Ser Val Arg Tyr Leu Cys Met Gly Ala Asp
            20                  25                  30

Gly Lys Met Gln Gly Leu Leu Gln Tyr Ser Glu Glu Asp Cys Ala Phe
        35                  40                  45

Glu Glu Glu Ile Arg Pro Asp Gly Tyr Asn Val Tyr Arg Ser Glu Lys
50                  55                  60

His Arg Leu Pro Val Ser Leu Ser Ser Ala Lys Gln Arg Gln Leu Tyr
65                  70                  75                  80

Lys Asn Arg Gly Phe Leu Pro Leu Ser His Phe Leu Pro Met Leu Pro
                85                  90                  95

Met Val Pro Glu Glu Pro Glu Asp Leu Arg Gly His Leu Glu Ser Asp
            100                 105                 110

Met Phe Ser Ser Pro Leu Glu Thr Asp Ser Met Asp Pro Phe Gly Leu
        115                 120                 125
```

Val Thr Gly Leu Glu Ala Val Arg Ser Pro Ser Phe Glu Lys
    130                 135                 140

<210> SEQ ID NO 26
<211> LENGTH: 141
<212> TYPE: PRT
<213> ORGANISM: Homo sapiens

<400> SEQUENCE: 26

Ala His Ser Leu Leu Glu Ile Lys Ala Val Ala Leu Arg Thr Val Ala
1               5                   10                  15

Ile Lys Gly Val His Ser Val Arg Tyr Leu Cys Met Gly Ala Asp Gly
                20                  25                  30

Lys Met Gln Gly Leu Leu Gln Tyr Ser Glu Glu Asp Cys Ala Phe Glu
            35                  40                  45

Glu Glu Ile Arg Pro Asp Gly Tyr Asn Val Tyr Arg Ser Glu Lys His
        50                  55                  60

Arg Leu Pro Val Ser Leu Ser Ser Ala Lys Gln Arg Gln Leu Tyr Lys
65                  70                  75                  80

Asn Arg Gly Phe Leu Pro Leu Ser His Phe Leu Pro Met Leu Pro Met
                85                  90                  95

Val Pro Glu Glu Pro Glu Asp Leu Arg Gly His Leu Glu Ser Asp Met
            100                 105                 110

Phe Ser Ser Pro Leu Glu Thr Asp Ser Met Asp Pro Phe Gly Leu Val
        115                 120                 125

Thr Gly Leu Glu Ala Val Arg Ser Pro Ser Phe Glu Lys
    130                 135                 140

<210> SEQ ID NO 27
<211> LENGTH: 139
<212> TYPE: PRT
<213> ORGANISM: Homo sapiens

<400> SEQUENCE: 27

Ser Leu Leu Glu Ile Lys Ala Val Ala Leu Arg Thr Val Ala Ile Lys
1               5                   10                  15

Gly Val His Ser Val Arg Tyr Leu Cys Met Gly Ala Asp Gly Lys Met
                20                  25                  30

Gln Gly Leu Leu Gln Tyr Ser Glu Glu Asp Cys Ala Phe Glu Glu Glu
            35                  40                  45

Ile Arg Pro Asp Gly Tyr Asn Val Tyr Arg Ser Glu Lys His Arg Leu
        50                  55                  60

Pro Val Ser Leu Ser Ser Ala Lys Gln Arg Gln Leu Tyr Lys Asn Arg
65                  70                  75                  80

Gly Phe Leu Pro Leu Ser His Phe Leu Pro Met Leu Pro Met Val Pro
                85                  90                  95

Glu Glu Pro Glu Asp Leu Arg Gly His Leu Glu Ser Asp Met Phe Ser
            100                 105                 110

Ser Pro Leu Glu Thr Asp Ser Met Asp Pro Phe Gly Leu Val Thr Gly
        115                 120                 125

Leu Glu Ala Val Arg Ser Pro Ser Phe Glu Lys
    130                 135

<210> SEQ ID NO 28
<211> LENGTH: 138
<212> TYPE: PRT
<213> ORGANISM: Homo sapiens -continued

<400> SEQUENCE: 28

Leu Leu Glu Ile Lys Ala Val Ala Leu Arg Thr Val Ala Ile Lys Gly
1               5                   10                  15

Val His Ser Val Arg Tyr Leu Cys Met Gly Ala Asp Gly Lys Met Gln
            20                  25                  30

Gly Leu Leu Gln Tyr Ser Glu Glu Asp Cys Ala Phe Glu Glu Ile
        35                  40                  45

Arg Pro Asp Gly Tyr Asn Val Tyr Arg Ser Glu Lys His Arg Leu Pro
    50                  55                  60

Val Ser Leu Ser Ser Ala Lys Gln Arg Gln Leu Tyr Lys Asn Arg Gly
65                  70                  75                  80

Phe Leu Pro Leu Ser His Phe Leu Pro Met Leu Pro Met Val Pro Glu
                85                  90                  95

Glu Pro Glu Asp Leu Arg Gly His Leu Glu Ser Asp Met Phe Ser Ser
            100                 105                 110

Pro Leu Glu Thr Asp Ser Met Asp Pro Phe Gly Leu Val Thr Gly Leu
        115                 120                 125

Glu Ala Val Arg Ser Pro Ser Phe Glu Lys
    130                 135

<210> SEQ ID NO 29
<211> LENGTH: 137
<212> TYPE: PRT
<213> ORGANISM: Homo sapiens

<400> SEQUENCE: 29

Leu Glu Ile Lys Ala Val Ala Leu Arg Thr Val Ala Ile Lys Gly Val
1               5                   10                  15

His Ser Val Arg Tyr Leu Cys Met Gly Ala Asp Gly Lys Met Gln Gly
            20                  25                  30

Leu Leu Gln Tyr Ser Glu Glu Asp Cys Ala Phe Glu Glu Ile Arg
        35                  40                  45

Pro Asp Gly Tyr Asn Val Tyr Arg Ser Glu Lys His Arg Leu Pro Val
    50                  55                  60

Ser Leu Ser Ser Ala Lys Gln Arg Gln Leu Tyr Lys Asn Arg Gly Phe
65                  70                  75                  80

Leu Pro Leu Ser His Phe Leu Pro Met Leu Pro Met Val Pro Glu Glu
                85                  90                  95

Pro Glu Asp Leu Arg Gly His Leu Glu Ser Asp Met Phe Ser Ser Pro
            100                 105                 110

Leu Glu Thr Asp Ser Met Asp Pro Phe Gly Leu Val Thr Gly Leu Glu
        115                 120                 125

Ala Val Arg Ser Pro Ser Phe Glu Lys
    130                 135

<210> SEQ ID NO 30
<211> LENGTH: 136
<212> TYPE: PRT
<213> ORGANISM: Homo sapiens

<400> SEQUENCE: 30

Glu Ile Lys Ala Val Ala Leu Arg Thr Val Ala Ile Lys Gly Val His
1               5                   10                  15

Ser Val Arg Tyr Leu Cys Met Gly Ala Asp Gly Lys Met Gln Gly Leu
            20                  25                  30

Leu Gln Tyr Ser Glu Glu Asp Cys Ala Phe Glu Glu Ile Arg Pro
        35                  40                  45

```
Asp Gly Tyr Asn Val Tyr Arg Ser Glu Lys His Arg Leu Pro Val Ser
        50                  55                  60

Leu Ser Ser Ala Lys Gln Arg Gln Leu Tyr Lys Asn Arg Gly Phe Leu
65                  70                  75                  80

Pro Leu Ser His Phe Leu Pro Met Leu Pro Met Val Pro Glu Glu Pro
                85                  90                  95

Glu Asp Leu Arg Gly His Leu Glu Ser Asp Met Phe Ser Ser Pro Leu
            100                 105                 110

Glu Thr Asp Ser Met Asp Pro Phe Gly Leu Val Thr Gly Leu Glu Ala
        115                 120                 125

Val Arg Ser Pro Ser Phe Glu Lys
    130                 135

<210> SEQ ID NO 31
<211> LENGTH: 123
<212> TYPE: PRT
<213> ORGANISM: Homo sapiens

<400> SEQUENCE: 31

Gly Val His Ser Val Arg Tyr Leu Cys Met Gly Ala Asp Gly Lys Met
1               5                   10                  15

Gln Gly Leu Leu Gln Tyr Ser Glu Glu Asp Cys Ala Phe Glu Glu Glu
            20                  25                  30

Ile Arg Pro Asp Gly Tyr Asn Val Tyr Arg Ser Glu Lys His Arg Leu
        35                  40                  45

Pro Val Ser Leu Ser Ser Ala Lys Gln Arg Gln Leu Tyr Lys Asn Arg
    50                  55                  60

Gly Phe Leu Pro Leu Ser His Phe Leu Pro Met Leu Pro Met Val Pro
65                  70                  75                  80

Glu Glu Pro Glu Asp Leu Arg Gly His Leu Glu Ser Asp Met Phe Ser
                85                  90                  95

Ser Pro Leu Glu Thr Asp Ser Met Asp Pro Phe Gly Leu Val Thr Gly
            100                 105                 110

Leu Glu Ala Val Arg Ser Pro Ser Phe Glu Lys
        115                 120

<210> SEQ ID NO 32
<211> LENGTH: 122
<212> TYPE: PRT
<213> ORGANISM: Homo sapiens

<400> SEQUENCE: 32

Val His Ser Val Arg Tyr Leu Cys Met Gly Ala Asp Gly Lys Met Gln
1               5                   10                  15

Gly Leu Leu Gln Tyr Ser Glu Glu Asp Cys Ala Phe Glu Glu Glu Ile
            20                  25                  30

Arg Pro Asp Gly Tyr Asn Val Tyr Arg Ser Glu Lys His Arg Leu Pro
        35                  40                  45

Val Ser Leu Ser Ser Ala Lys Gln Arg Gln Leu Tyr Lys Asn Arg Gly
    50                  55                  60

Phe Leu Pro Leu Ser His Phe Leu Pro Met Leu Pro Met Val Pro Glu
65                  70                  75                  80

Glu Pro Glu Asp Leu Arg Gly His Leu Glu Ser Asp Met Phe Ser Ser
                85                  90                  95

Pro Leu Glu Thr Asp Ser Met Asp Pro Phe Gly Leu Val Thr Gly Leu
            100                 105                 110
```

```
Glu Ala Val Arg Ser Pro Ser Phe Glu Lys
        115                 120

<210> SEQ ID NO 33
<211> LENGTH: 121
<212> TYPE: PRT
<213> ORGANISM: Homo sapiens

<400> SEQUENCE: 33

His Ser Val Arg Tyr Leu Cys Met Gly Ala Asp Gly Lys Met Gln Gly
1               5                   10                  15

Leu Leu Gln Tyr Ser Glu Glu Asp Cys Ala Phe Glu Glu Glu Ile Arg
            20                  25                  30

Pro Asp Gly Tyr Asn Val Tyr Arg Ser Glu Lys His Arg Leu Pro Val
        35                  40                  45

Ser Leu Ser Ser Ala Lys Gln Arg Gln Leu Tyr Lys Asn Arg Gly Phe
    50                  55                  60

Leu Pro Leu Ser His Phe Leu Pro Met Leu Pro Met Val Pro Glu Glu
65                  70                  75                  80

Pro Glu Asp Leu Arg Gly His Leu Glu Ser Asp Met Phe Ser Ser Pro
                85                  90                  95

Leu Glu Thr Asp Ser Met Asp Pro Phe Gly Leu Val Thr Gly Leu Glu
            100                 105                 110

Ala Val Arg Ser Pro Ser Phe Glu Lys
        115                 120

<210> SEQ ID NO 34
<211> LENGTH: 116
<212> TYPE: PRT
<213> ORGANISM: Homo sapiens

<400> SEQUENCE: 34

Leu Cys Met Gly Ala Asp Gly Lys Met Gln Gly Leu Leu Gln Tyr Ser
1               5                   10                  15

Glu Glu Asp Cys Ala Phe Glu Glu Glu Ile Arg Pro Asp Gly Tyr Asn
            20                  25                  30

Val Tyr Arg Ser Glu Lys His Arg Leu Pro Val Ser Leu Ser Ser Ala
        35                  40                  45

Lys Gln Arg Gln Leu Tyr Lys Asn Arg Gly Phe Leu Pro Leu Ser His
    50                  55                  60

Phe Leu Pro Met Leu Pro Met Val Pro Glu Glu Pro Glu Asp Leu Arg
65                  70                  75                  80

Gly His Leu Glu Ser Asp Met Phe Ser Ser Pro Leu Glu Thr Asp Ser
                85                  90                  95

Met Asp Pro Phe Gly Leu Val Thr Gly Leu Glu Ala Val Arg Ser Pro
            100                 105                 110

Ser Phe Glu Lys
        115

<210> SEQ ID NO 35
<211> LENGTH: 115
<212> TYPE: PRT
<213> ORGANISM: Homo sapiens

<400> SEQUENCE: 35

Cys Met Gly Ala Asp Gly Lys Met Gln Gly Leu Leu Gln Tyr Ser Glu
1               5                   10                  15

Glu Asp Cys Ala Phe Glu Glu Glu Ile Arg Pro Asp Gly Tyr Asn Val
            20                  25                  30
```

```
Tyr Arg Ser Glu Lys His Arg Leu Pro Val Ser Leu Ser Ala Lys
            35                  40                  45

Gln Arg Gln Leu Tyr Lys Asn Arg Gly Phe Leu Pro Leu Ser His Phe
 50                  55                  60

Leu Pro Met Leu Pro Met Val Pro Glu Glu Pro Glu Asp Leu Arg Gly
 65                  70                  75                  80

His Leu Glu Ser Asp Met Phe Ser Ser Pro Leu Glu Thr Asp Ser Met
                 85                  90                  95

Asp Pro Phe Gly Leu Val Thr Gly Leu Glu Ala Val Arg Ser Pro Ser
                100                 105                 110

Phe Glu Lys
        115

<210> SEQ ID NO 36
<211> LENGTH: 114
<212> TYPE: PRT
<213> ORGANISM: Homo sapiens

<400> SEQUENCE: 36

Met Gly Ala Asp Gly Lys Met Gln Gly Leu Leu Gln Tyr Ser Glu Glu
 1               5                  10                  15

Asp Cys Ala Phe Glu Glu Glu Ile Arg Pro Asp Gly Tyr Asn Val Tyr
                 20                  25                  30

Arg Ser Glu Lys His Arg Leu Pro Val Ser Leu Ser Ser Ala Lys Gln
            35                  40                  45

Arg Gln Leu Tyr Lys Asn Arg Gly Phe Leu Pro Leu Ser His Phe Leu
 50                  55                  60

Pro Met Leu Pro Met Val Pro Glu Glu Pro Glu Asp Leu Arg Gly His
 65                  70                  75                  80

Leu Glu Ser Asp Met Phe Ser Ser Pro Leu Glu Thr Asp Ser Met Asp
                 85                  90                  95

Pro Phe Gly Leu Val Thr Gly Leu Glu Ala Val Arg Ser Pro Ser Phe
                100                 105                 110

Glu Lys

<210> SEQ ID NO 37
<211> LENGTH: 52
<212> TYPE: PRT
<213> ORGANISM: Homo sapiens

<400> SEQUENCE: 37

Phe Leu Pro Met Leu Pro Met Val Pro Glu Glu Pro Glu Asp Leu Arg
 1               5                  10                  15

Gly His Leu Glu Ser Asp Met Phe Ser Ser Pro Leu Glu Thr Asp Ser
                 20                  25                  30

Met Asp Pro Phe Gly Leu Val Thr Gly Leu Glu Ala Val Arg Ser Pro
                 35                  40                  45

Ser Phe Glu Lys
     50

<210> SEQ ID NO 38
<211> LENGTH: 51
<212> TYPE: PRT
<213> ORGANISM: Homo sapiens

<400> SEQUENCE: 38

Leu Pro Met Leu Pro Met Val Pro Glu Glu Pro Glu Asp Leu Arg Gly
 1               5                  10                  15
```

```
His Leu Glu Ser Asp Met Phe Ser Ser Pro Leu Glu Thr Asp Ser Met
            20                  25                  30

Asp Pro Phe Gly Leu Val Thr Gly Leu Glu Ala Val Arg Ser Pro Ser
            35                  40                  45

Phe Glu Lys
    50

<210> SEQ ID NO 39
<211> LENGTH: 50
<212> TYPE: PRT
<213> ORGANISM: Homo sapiens

<400> SEQUENCE: 39

Pro Met Leu Pro Met Val Pro Glu Glu Pro Glu Asp Leu Arg Gly His
1               5                   10                  15

Leu Glu Ser Asp Met Phe Ser Ser Pro Leu Glu Thr Asp Ser Met Asp
            20                  25                  30

Pro Phe Gly Leu Val Thr Gly Leu Glu Ala Val Arg Ser Pro Ser Phe
            35                  40                  45

Glu Lys
    50

<210> SEQ ID NO 40
<211> LENGTH: 49
<212> TYPE: PRT
<213> ORGANISM: Homo sapiens

<400> SEQUENCE: 40

Met Leu Pro Met Val Pro Glu Glu Pro Glu Asp Leu Arg Gly His Leu
1               5                   10                  15

Glu Ser Asp Met Phe Ser Ser Pro Leu Glu Thr Asp Ser Met Asp Pro
            20                  25                  30

Phe Gly Leu Val Thr Gly Leu Glu Ala Val Arg Ser Pro Ser Phe Glu
            35                  40                  45

Lys

<210> SEQ ID NO 41
<211> LENGTH: 7
<212> TYPE: PRT
<213> ORGANISM: Homo sapiens

<400> SEQUENCE: 41

His Pro Ile Pro Asp Ser Ser
1               5

<210> SEQ ID NO 42
<211> LENGTH: 8
<212> TYPE: PRT
<213> ORGANISM: Homo sapiens

<400> SEQUENCE: 42

His Pro Ile Pro Asp Ser Ser Pro
1               5

<210> SEQ ID NO 43
<211> LENGTH: 20
<212> TYPE: PRT
<213> ORGANISM: Homo sapiens

<400> SEQUENCE: 43

His Pro Ile Pro Asp Ser Ser Pro Leu Leu Gln Phe Gly Gly Gln Val
```

-continued

```
                1               5                  10                 15
Arg Gln Arg Tyr
            20

<210> SEQ ID NO 44
<211> LENGTH: 21
<212> TYPE: PRT
<213> ORGANISM: Homo sapiens

<400> SEQUENCE: 44

His Pro Ile Pro Asp Ser Ser Pro Leu Leu Gln Phe Gly Gly Gln Val
1               5                  10                 15

Arg Gln Arg Tyr Leu
            20

<210> SEQ ID NO 45
<211> LENGTH: 22
<212> TYPE: PRT
<213> ORGANISM: Homo sapiens

<400> SEQUENCE: 45

His Pro Ile Pro Asp Ser Ser Pro Leu Leu Gln Phe Gly Gly Gln Val
1               5                  10                 15

Arg Gln Arg Tyr Leu Tyr
            20

<210> SEQ ID NO 46
<211> LENGTH: 23
<212> TYPE: PRT
<213> ORGANISM: Homo sapiens

<400> SEQUENCE: 46

His Pro Ile Pro Asp Ser Ser Pro Leu Leu Gln Phe Gly Gly Gln Val
1               5                  10                 15

Arg Gln Arg Tyr Leu Tyr Thr
            20

<210> SEQ ID NO 47
<211> LENGTH: 25
<212> TYPE: PRT
<213> ORGANISM: Homo sapiens

<400> SEQUENCE: 47

His Pro Ile Pro Asp Ser Ser Pro Leu Leu Gln Phe Gly Gly Gln Val
1               5                  10                 15

Arg Gln Arg Tyr Leu Tyr Thr Asp Asp
            20                  25

<210> SEQ ID NO 48
<211> LENGTH: 27
<212> TYPE: PRT
<213> ORGANISM: Homo sapiens

<400> SEQUENCE: 48

His Pro Ile Pro Asp Ser Ser Pro Leu Leu Gln Phe Gly Gly Gln Val
1               5                  10                 15

Arg Gln Arg Tyr Leu Tyr Thr Asp Asp Ala Gln
            20                  25

<210> SEQ ID NO 49
<211> LENGTH: 29
<212> TYPE: PRT
<213> ORGANISM: Homo sapiens
```

<400> SEQUENCE: 49

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr
            20                  25

<210> SEQ ID NO 50
<211> LENGTH: 31
<212> TYPE: PRT
<213> ORGANISM: Homo sapiens

<400> SEQUENCE: 50

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala
            20                  25                  30

<210> SEQ ID NO 51
<211> LENGTH: 34
<212> TYPE: PRT
<213> ORGANISM: Homo sapiens

<400> SEQUENCE: 51

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu

<210> SEQ ID NO 52
<211> LENGTH: 35
<212> TYPE: PRT
<213> ORGANISM: Homo sapiens

<400> SEQUENCE: 52

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile
        35

<210> SEQ ID NO 53
<211> LENGTH: 36
<212> TYPE: PRT
<213> ORGANISM: Homo sapiens

<400> SEQUENCE: 53

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg
        35

<210> SEQ ID NO 54
<211> LENGTH: 37
<212> TYPE: PRT
<213> ORGANISM: Homo sapiens

<400> SEQUENCE: 54

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu
            35

<210> SEQ ID NO 55
<211> LENGTH: 38
<212> TYPE: PRT
<213> ORGANISM: Homo sapiens

<400> SEQUENCE: 55

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp
            35

<210> SEQ ID NO 56
<211> LENGTH: 39
<212> TYPE: PRT
<213> ORGANISM: Homo sapiens

<400> SEQUENCE: 56

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly
            35

<210> SEQ ID NO 57
<211> LENGTH: 46
<212> TYPE: PRT
<213> ORGANISM: Homo sapiens

<400> SEQUENCE: 57

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp
            35                  40                  45

<210> SEQ ID NO 58
<211> LENGTH: 47
<212> TYPE: PRT
<213> ORGANISM: Homo sapiens

<400> SEQUENCE: 58

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln
            35                  40                  45

<210> SEQ ID NO 59

```
<211> LENGTH: 48
<212> TYPE: PRT
<213> ORGANISM: Homo sapiens

<400> SEQUENCE: 59

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

<210> SEQ ID NO 60
<211> LENGTH: 50
<212> TYPE: PRT
<213> ORGANISM: Homo sapiens

<400> SEQUENCE: 60

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu
    50

<210> SEQ ID NO 61
<211> LENGTH: 51
<212> TYPE: PRT
<213> ORGANISM: Homo sapiens

<400> SEQUENCE: 61

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser
    50

<210> SEQ ID NO 62
<211> LENGTH: 52
<212> TYPE: PRT
<213> ORGANISM: Homo sapiens

<400> SEQUENCE: 62

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu
    50

<210> SEQ ID NO 63
<211> LENGTH: 53
<212> TYPE: PRT
<213> ORGANISM: Homo sapiens
```

<400> SEQUENCE: 63

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu
    50

<210> SEQ ID NO 64
<211> LENGTH: 66
<212> TYPE: PRT
<213> ORGANISM: Homo sapiens

<400> SEQUENCE: 64

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu
65

<210> SEQ ID NO 65
<211> LENGTH: 67
<212> TYPE: PRT
<213> ORGANISM: Homo sapiens

<400> SEQUENCE: 65

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly
65

<210> SEQ ID NO 66
<211> LENGTH: 68
<212> TYPE: PRT
<213> ORGANISM: Homo sapiens

<400> SEQUENCE: 66

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val
65

<210> SEQ ID NO 67
<211> LENGTH: 73
<212> TYPE: PRT
<213> ORGANISM: Homo sapiens

<400> SEQUENCE: 67

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe
65                  70

<210> SEQ ID NO 68
<211> LENGTH: 74
<212> TYPE: PRT
<213> ORGANISM: Homo sapiens

<400> SEQUENCE: 68

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu
65                  70

<210> SEQ ID NO 69
<211> LENGTH: 75
<212> TYPE: PRT
<213> ORGANISM: Homo sapiens

<400> SEQUENCE: 69

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys
65                  70                  75

<210> SEQ ID NO 70
<211> LENGTH: 135
<212> TYPE: PRT
<213> ORGANISM: Homo sapiens

<400> SEQUENCE: 70

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg
    130                 135

<210> SEQ ID NO 71
<211> LENGTH: 136
<212> TYPE: PRT
<213> ORGANISM: Homo sapiens

<400> SEQUENCE: 71

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe
    130                 135

<210> SEQ ID NO 72
<211> LENGTH: 137
<212> TYPE: PRT
<213> ORGANISM: Homo sapiens

<400> SEQUENCE: 72

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

```
Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
 65                 70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu
    130                 135

<210> SEQ ID NO 73
<211> LENGTH: 138
<212> TYPE: PRT
<213> ORGANISM: Homo sapiens

<400> SEQUENCE: 73

His Pro Ile Pro Asp Ser Ser Pro Leu Leu Gln Phe Gly Gly Gln Val
  1               5                  10                  15

Arg Gln Arg Tyr Leu Tyr Thr Asp Asp Ala Gln Gln Thr Glu Ala His
                 20                  25                  30

Leu Glu Ile Arg Glu Asp Gly Thr Val Gly Gly Ala Ala Asp Gln Ser
             35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
 65                 70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro
    130                 135

<210> SEQ ID NO 74
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

His Pro Ile Pro Asp Ser Ser Pro His Val His Tyr Gly Trp Gly Asp
  1               5                  10                  15

Pro Ile Arg Leu Arg His Leu Tyr Thr Ser Gly Pro His Gly Leu Ser
                 20                  25                  30

Ser Cys Phe Leu Arg Ile Arg Ala Asp Gly Val Val Asp Cys Ala Arg
             35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
 65                 70                  75                  80

Ala Asp Gly Lys Met Gln Gly Leu Leu Gln Tyr Ser Glu Glu Asp Cys
```

```
                        85                  90                  95
Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 75
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

His Pro Ile Pro Asp Ser Ser Pro Leu Leu Gln Phe Gly Gly Gln Val
1               5                   10                  15

Arg Gln Arg Tyr Leu Tyr Thr Asp Asp Pro His Gly Leu Ser Ser Cys
            20                  25                  30

Phe Leu Arg Ile Arg Ala Asp Gly Val Val Asp Cys Ala Arg Gly Gln
        35                  40                  45

Ser Ala His Ser Leu Leu Glu Ile Lys Ala Val Ala Leu Arg Thr Val
    50                  55                  60

Ala Ile Lys Gly Val His Ser Val Arg Tyr Leu Cys Met Gly Ala Asp
65                  70                  75                  80

Gly Lys Met Gln Gly Leu Leu Gln Tyr Ser Glu Glu Asp Cys Ala Phe
                85                  90                  95

Glu Glu Glu Ile Arg Pro Asp Gly Tyr Asn Val Tyr Arg Ser Glu Lys
            100                 105                 110

His Arg Leu Pro Val Ser Leu Ser Ser Ala Lys Gln Arg Gln Leu Tyr
        115                 120                 125

Lys Asn Arg Gly Phe Leu Pro Leu Ser His Phe Leu Pro Met Leu Pro
    130                 135                 140

Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
                165                 170                 175

Val Thr Gly Leu Glu Ala Val Arg Ser Pro Ser Phe Glu Lys
            180                 185                 190

<210> SEQ ID NO 76
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

His Pro Ile Pro Asp Ser Ser Pro Leu Leu Gln Phe Gly Gly Gln Val
1               5                   10                  15
```

Arg Gln Arg Tyr Leu Tyr Thr Asp Asp Ala Gln Leu Ser Ser Cys Phe
            20                  25                  30

Leu Arg Ile Arg Ala Asp Gly Val Val Asp Cys Ala Arg Gly Gln Ser
        35                  40                  45

Ala His Ser Leu Leu Glu Ile Lys Ala Val Ala Leu Arg Thr Val Ala
    50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
            100                 105                 110

Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met
    130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys
            180                 185

<210> SEQ ID NO 77
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

His Pro Ile Pro Asp Ser Ser Pro Leu Leu Gln Phe Gly Gly Gln Val
1               5                   10                  15

Arg Gln Arg Tyr Leu Tyr Thr Asp Ala Gln Thr Ser Cys Phe
            20                  25                  30

Leu Arg Ile Arg Ala Asp Gly Val Val Asp Cys Ala Arg Gly Gln Ser
        35                  40                  45

Ala His Ser Leu Leu Glu Ile Lys Ala Val Ala Leu Arg Thr Val Ala
    50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
            100                 105                 110

Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met
    130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys
            180                 185

<210> SEQ ID NO 78
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala Phe
            20                  25                  30

Leu Arg Ile Arg Ala Asp Gly Val Val Asp Cys Ala Arg Gly Gln Ser
        35                  40                  45

Ala His Ser Leu Leu Glu Ile Lys Ala Val Ala Leu Arg Thr Val Ala
    50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
            100                 105                 110

Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met
    130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys
            180                 185

<210> SEQ ID NO 79
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Ala Asp Gly Val Val Asp Cys Ala Arg Gly Gln Ser
        35                  40                  45

Ala His Ser Leu Leu Glu Ile Lys Ala Val Ala Leu Arg Thr Val Ala
    50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
            100                 105                 110

```
Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met
    130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys
            180                 185

<210> SEQ ID NO 80
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Val Val Asp Cys Ala Arg Gly Gln Ser
        35                  40                  45

Ala His Ser Leu Leu Glu Ile Lys Ala Val Ala Leu Arg Thr Val Ala
    50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
            100                 105                 110

Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met
    130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys
            180                 185

<210> SEQ ID NO 81
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
```

```
                 35                  40                  45
Ala His Ser Leu Leu Glu Ile Lys Ala Val Ala Leu Arg Thr Val Ala
 50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                 85                  90                  95

Glu Glu Ile Arg Pro Asp Gly Tyr Asn Val Tyr Arg Ser Glu Lys His
                100                 105                 110

Arg Leu Pro Val Ser Leu Ser Ser Ala Lys Gln Arg Gln Leu Tyr Lys
            115                 120                 125

Asn Arg Gly Phe Leu Pro Leu Ser His Phe Leu Pro Met Leu Pro Met
        130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys
            180                 185

<210> SEQ ID NO 82
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

His Pro Ile Pro Asp Ser Ser Pro Leu Leu Gln Phe Gly Gly Gln Val
1               5                  10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Glu Ile Lys Ala Val Ala Leu Arg Thr Val Ala
 50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                 85                  90                  95

Glu Glu Ile Arg Pro Asp Gly Tyr Asn Val Tyr Arg Ser Glu Lys His
                100                 105                 110

Arg Leu Pro Val Ser Leu Ser Ser Ala Lys Gln Arg Gln Leu Tyr Lys
            115                 120                 125

Asn Arg Gly Phe Leu Pro Leu Ser His Phe Leu Pro Met Leu Pro Met
        130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys
            180                 185

<210> SEQ ID NO 83
<211> LENGTH: 189
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 83

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
            100                 105                 110

Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met
    130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys
            180                 185

<210> SEQ ID NO 84
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
            100                 105                 110

Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met
    130                 135                 140

Val Pro Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys
            180                 185

<210> SEQ ID NO 85
<211> LENGTH: 187
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

His Pro Ile Pro Asp Ser Ser Pro Leu Leu Gln Phe Gly Gly Gln Val
1               5                   10                  15

Arg Gln Arg Tyr Leu Tyr Thr Asp Ala Gln Gln Thr Glu Ala His
            20                  25                  30

Leu Glu Ile Arg Glu Asp Gly Thr Val Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Met Leu Pro Met Val Pro
130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 86
<211> LENGTH: 9
<212> TYPE: PRT
<213> ORGANISM: Homo sapiens

<400> SEQUENCE: 86

Arg Pro Leu Ala Phe Ser Asp Ala Gly
1               5

<210> SEQ ID NO 87
<211> LENGTH: 10
<212> TYPE: PRT
<213> ORGANISM: Homo sapiens

<400> SEQUENCE: 87

Arg Pro Leu Ala Phe Ser Asp Ala Gly Pro
1               5                   10

```
<210> SEQ ID NO 88
<211> LENGTH: 24
<212> TYPE: PRT
<213> ORGANISM: Homo sapiens

<400> SEQUENCE: 88

Arg Pro Leu Ala Phe Ser Asp Ala Gly Pro His Val His Tyr Gly Trp
1               5                   10                  15

Gly Asp Pro Ile Arg Leu Arg His
            20

<210> SEQ ID NO 89
<211> LENGTH: 25
<212> TYPE: PRT
<213> ORGANISM: Homo sapiens

<400> SEQUENCE: 89

Arg Pro Leu Ala Phe Ser Asp Ala Gly Pro His Val His Tyr Gly Trp
1               5                   10                  15

Gly Asp Pro Ile Arg Leu Arg His Leu
            20                  25

<210> SEQ ID NO 90
<211> LENGTH: 26
<212> TYPE: PRT
<213> ORGANISM: Homo sapiens

<400> SEQUENCE: 90

Arg Pro Leu Ala Phe Ser Asp Ala Gly Pro His Val His Tyr Gly Trp
1               5                   10                  15

Gly Asp Pro Ile Arg Leu Arg His Leu Tyr
            20                  25

<210> SEQ ID NO 91
<211> LENGTH: 27
<212> TYPE: PRT
<213> ORGANISM: Homo sapiens

<400> SEQUENCE: 91

Arg Pro Leu Ala Phe Ser Asp Ala Gly Pro His Val His Tyr Gly Trp
1               5                   10                  15

Gly Asp Pro Ile Arg Leu Arg His Leu Tyr Thr
            20                  25

<210> SEQ ID NO 92
<211> LENGTH: 39
<212> TYPE: PRT
<213> ORGANISM: Homo sapiens

<400> SEQUENCE: 92

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg
        35

<210> SEQ ID NO 93
<211> LENGTH: 40
<212> TYPE: PRT
<213> ORGANISM: Homo sapiens

<400> SEQUENCE: 93
```

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile
        35                  40

<210> SEQ ID NO 94
<211> LENGTH: 41
<212> TYPE: PRT
<213> ORGANISM: Homo sapiens

<400> SEQUENCE: 94

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg
        35                  40

<210> SEQ ID NO 95
<211> LENGTH: 42
<212> TYPE: PRT
<213> ORGANISM: Homo sapiens

<400> SEQUENCE: 95

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala
        35                  40

<210> SEQ ID NO 96
<211> LENGTH: 43
<212> TYPE: PRT
<213> ORGANISM: Homo sapiens

<400> SEQUENCE: 96

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp
        35                  40

<210> SEQ ID NO 97
<211> LENGTH: 44
<212> TYPE: PRT
<213> ORGANISM: Homo sapiens

<400> SEQUENCE: 97

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly
        35                  40

<210> SEQ ID NO 98
<211> LENGTH: 51

```
<212> TYPE: PRT
<213> ORGANISM: Homo sapiens

<400> SEQUENCE: 98

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly
    50

<210> SEQ ID NO 99
<211> LENGTH: 52
<212> TYPE: PRT
<213> ORGANISM: Homo sapiens

<400> SEQUENCE: 99

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln
    50

<210> SEQ ID NO 100
<211> LENGTH: 53
<212> TYPE: PRT
<213> ORGANISM: Homo sapiens

<400> SEQUENCE: 100

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser
    50

<210> SEQ ID NO 101
<211> LENGTH: 55
<212> TYPE: PRT
<213> ORGANISM: Homo sapiens

<400> SEQUENCE: 101

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His
    50                  55

<210> SEQ ID NO 102
<211> LENGTH: 56
```

```
<212> TYPE: PRT
<213> ORGANISM: Homo sapiens

<400> SEQUENCE: 102

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser
    50                  55

<210> SEQ ID NO 103
<211> LENGTH: 57
<212> TYPE: PRT
<213> ORGANISM: Homo sapiens

<400> SEQUENCE: 103

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu
    50                  55

<210> SEQ ID NO 104
<211> LENGTH: 58
<212> TYPE: PRT
<213> ORGANISM: Homo sapiens

<400> SEQUENCE: 104

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu
    50                  55

<210> SEQ ID NO 105
<211> LENGTH: 71
<212> TYPE: PRT
<213> ORGANISM: Homo sapiens

<400> SEQUENCE: 105

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys
65                  70
```

-continued

<210> SEQ ID NO 106
<211> LENGTH: 72
<212> TYPE: PRT
<213> ORGANISM: Homo sapiens

<400> SEQUENCE: 106

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly
65                  70

<210> SEQ ID NO 107
<211> LENGTH: 73
<212> TYPE: PRT
<213> ORGANISM: Homo sapiens

<400> SEQUENCE: 107

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val
65                  70

<210> SEQ ID NO 108
<211> LENGTH: 78
<212> TYPE: PRT
<213> ORGANISM: Homo sapiens

<400> SEQUENCE: 108

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr
65                  70                  75

<210> SEQ ID NO 109
<211> LENGTH: 79
<212> TYPE: PRT
<213> ORGANISM: Homo sapiens

<400> SEQUENCE: 109

Arg Pro Leu Ala Phe Ser Asp Ala Gly Pro His Val His Tyr Gly Trp
1               5                   10                  15

```
Gly Asp Pro Ile Arg Leu Arg His Leu Tyr Thr Ser Gly Pro His Gly
         20                  25                  30

Leu Ser Ser Cys Phe Leu Arg Ile Arg Ala Asp Gly Val Val Asp Cys
         35                  40                  45

Ala Arg Gly Gln Ser Ala His Ser Leu Leu Glu Ile Lys Ala Val Ala
 50                  55                  60

Leu Arg Thr Val Ala Ile Lys Gly Val His Ser Val Arg Tyr Leu
 65                  70                  75

<210> SEQ ID NO 110
<211> LENGTH: 80
<212> TYPE: PRT
<213> ORGANISM: Homo sapiens

<400> SEQUENCE: 110

Arg Pro Leu Ala Phe Ser Asp Ala Gly Pro His Val His Tyr Gly Trp
 1               5                  10                  15

Gly Asp Pro Ile Arg Leu Arg His Leu Tyr Thr Ser Gly Pro His Gly
                 20                  25                  30

Leu Ser Ser Cys Phe Leu Arg Ile Arg Ala Asp Gly Val Val Asp Cys
             35                  40                  45

Ala Arg Gly Gln Ser Ala His Ser Leu Leu Glu Ile Lys Ala Val Ala
 50                  55                  60

Leu Arg Thr Val Ala Ile Lys Gly Val His Ser Val Arg Tyr Leu Cys
 65                  70                  75                  80

<210> SEQ ID NO 111
<211> LENGTH: 142
<212> TYPE: PRT
<213> ORGANISM: Homo sapiens

<400> SEQUENCE: 111

Arg Pro Leu Ala Phe Ser Asp Ala Gly Pro His Val His Tyr Gly Trp
 1               5                  10                  15

Gly Asp Pro Ile Arg Leu Arg His Leu Tyr Thr Ser Gly Pro His Gly
                 20                  25                  30

Leu Ser Ser Cys Phe Leu Arg Ile Arg Ala Asp Gly Val Val Asp Cys
             35                  40                  45

Ala Arg Gly Gln Ser Ala His Ser Leu Leu Glu Ile Lys Ala Val Ala
 50                  55                  60

Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                 85                  90                  95

Asp Cys Ala Phe Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
            115                 120                 125

Arg Gln Leu Tyr Lys Asn Arg Gly Phe Leu Pro Leu Ser His
        130                 135                 140

<210> SEQ ID NO 112
<211> LENGTH: 143
<212> TYPE: PRT
<213> ORGANISM: Homo sapiens

<400> SEQUENCE: 112

Arg Pro Leu Ala Phe Ser Asp Ala Gly Pro His Val His Tyr Gly Trp
 1               5                  10                  15
```

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe
    130                 135                 140

<210> SEQ ID NO 113
<211> LENGTH: 144
<212> TYPE: PRT
<213> ORGANISM: Homo sapiens

<400> SEQUENCE: 113

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

<210> SEQ ID NO 114
<211> LENGTH: 145
<212> TYPE: PRT
<213> ORGANISM: Homo sapiens

<400> SEQUENCE: 114

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

```
Leu Arg Thr Val Ala Ile Lys Gly Val His Ser Val Arg Tyr Leu Cys
 65                  70                  75                  80

Met Gly Ala Asp Gly Lys Met Gln Gly Leu Gln Tyr Ser Glu
                 85                  90                  95

Asp Cys Ala Phe Glu Glu Ile Arg Pro Asp Gly Tyr Asn Val Tyr
                100                 105                 110

Arg Ser Glu Lys His Arg Leu Pro Val Ser Leu Ser Ser Ala Lys Gln
            115                 120                 125

Arg Gln Leu Tyr Lys Asn Arg Gly Phe Leu Pro Leu Ser His Phe Leu
130                 135                 140

Pro
145

<210> SEQ ID NO 115
<211> LENGTH: 174
<212> TYPE: PRT
<213> ORGANISM: Homo sapiens

<400> SEQUENCE: 115

Pro Leu Leu Gln Phe Gly Gly Gln Val Arg Gln Arg Tyr Leu Tyr Thr
1               5                   10                  15

Asp Asp Ala Gln Gln Thr Glu Ala His Leu Glu Ile Arg Glu Asp Gly
            20                  25                  30

Thr Val Gly Gly Ala Ala Asp Gln Ser Pro Glu Ser Leu Leu Gln Leu
        35                  40                  45

Lys Ala Leu Lys Pro Gly Val Ile Gln Ile Leu Gly Val Lys Thr Ser
 50                  55                  60

Arg Phe Leu Cys Gln Arg Pro Asp Gly Ala Leu Tyr Gly Ser Leu His
 65                  70                  75                  80

Phe Asp Pro Glu Ala Cys Ser Phe Arg Glu Leu Leu Leu Glu Asp Gly
                 85                  90                  95

Tyr Asn Val Tyr Gln Ser Glu Ala His Gly Leu Pro Leu His Leu Pro
                100                 105                 110

Gly Asn Lys Ser Pro His Arg Asp Pro Ala Pro Arg Gly Pro Ala Arg
            115                 120                 125

Phe Leu Pro Leu Pro Gly Leu Pro Pro Ala Leu Pro Glu Pro Pro Gly
130                 135                 140

Ile Leu Ala Pro Gln Pro Pro Asp Val Gly Ser Ser Asp Pro Leu Ser
145                 150                 155                 160

Met Val Gly Pro Ser Gln Gly Arg Ser Pro Ser Tyr Ala Ser
                165                 170

<210> SEQ ID NO 116
<211> LENGTH: 173
<212> TYPE: PRT
<213> ORGANISM: Homo sapiens

<400> SEQUENCE: 116

Leu Leu Gln Phe Gly Gly Gln Val Arg Gln Arg Tyr Leu Tyr Thr Asp
1               5                   10                  15

Asp Ala Gln Gln Thr Glu Ala His Leu Glu Ile Arg Glu Asp Gly Thr
            20                  25                  30

Val Gly Gly Ala Ala Asp Gln Ser Pro Glu Ser Leu Leu Gln Leu Lys
        35                  40                  45

Ala Leu Lys Pro Gly Val Ile Gln Ile Leu Gly Val Lys Thr Ser Arg
 50                  55                  60

Phe Leu Cys Gln Arg Pro Asp Gly Ala Leu Tyr Gly Ser Leu His Phe
```

```
                    65                  70                  75                  80
Asp Pro Glu Ala Cys Ser Phe Arg Glu Leu Leu Leu Glu Asp Gly Tyr
                85                  90                  95

Asn Val Tyr Gln Ser Glu Ala His Gly Leu Pro Leu His Leu Pro Gly
                100                 105                 110

Asn Lys Ser Pro His Arg Asp Pro Ala Pro Arg Gly Pro Ala Arg Phe
                115                 120                 125

Leu Pro Leu Pro Gly Leu Pro Pro Ala Leu Pro Glu Pro Pro Gly Ile
            130                 135                 140

Leu Ala Pro Gln Pro Pro Asp Val Gly Ser Ser Asp Pro Leu Ser Met
145                 150                 155                 160

Val Gly Pro Ser Gln Gly Arg Ser Pro Ser Tyr Ala Ser
                165                 170

<210> SEQ ID NO 117
<211> LENGTH: 161
<212> TYPE: PRT
<213> ORGANISM: Homo sapiens

<400> SEQUENCE: 117

Leu Tyr Thr Asp Asp Ala Gln Gln Thr Glu Ala His Leu Glu Ile Arg
1               5                   10                  15

Glu Asp Gly Thr Val Gly Gly Ala Ala Asp Gln Ser Pro Glu Ser Leu
                20                  25                  30

Leu Gln Leu Lys Ala Leu Lys Pro Gly Val Ile Gln Ile Leu Gly Val
            35                  40                  45

Lys Thr Ser Arg Phe Leu Cys Gln Arg Pro Asp Gly Ala Leu Tyr Gly
    50                  55                  60

Ser Leu His Phe Asp Pro Glu Ala Cys Ser Phe Arg Glu Leu Leu Leu
65                  70                  75                  80

Glu Asp Gly Tyr Asn Val Tyr Gln Ser Glu Ala His Gly Leu Pro Leu
                85                  90                  95

His Leu Pro Gly Asn Lys Ser Pro His Arg Asp Pro Ala Pro Arg Gly
                100                 105                 110

Pro Ala Arg Phe Leu Pro Leu Pro Gly Leu Pro Pro Ala Leu Pro Glu
            115                 120                 125

Pro Pro Gly Ile Leu Ala Pro Gln Pro Pro Asp Val Gly Ser Ser Asp
    130                 135                 140

Pro Leu Ser Met Val Gly Pro Ser Gln Gly Arg Ser Pro Ser Tyr Ala
145                 150                 155                 160

Ser

<210> SEQ ID NO 118
<211> LENGTH: 160
<212> TYPE: PRT
<213> ORGANISM: Homo sapiens

<400> SEQUENCE: 118

Tyr Thr Asp Asp Ala Gln Gln Thr Glu Ala His Leu Glu Ile Arg Glu
1               5                   10                  15

Asp Gly Thr Val Gly Gly Ala Ala Asp Gln Ser Pro Glu Ser Leu Leu
                20                  25                  30

Gln Leu Lys Ala Leu Lys Pro Gly Val Ile Gln Ile Leu Gly Val Lys
            35                  40                  45

Thr Ser Arg Phe Leu Cys Gln Arg Pro Asp Gly Ala Leu Tyr Gly Ser
    50                  55                  60
```

```
Leu His Phe Asp Pro Glu Ala Cys Ser Phe Arg Glu Leu Leu Leu Glu
 65                  70                  75                  80

Asp Gly Tyr Asn Val Tyr Gln Ser Glu Ala His Gly Leu Pro Leu His
                 85                  90                  95

Leu Pro Gly Asn Lys Ser Pro His Arg Asp Pro Ala Pro Arg Gly Pro
            100                 105                 110

Ala Arg Phe Leu Pro Leu Pro Gly Leu Pro Pro Ala Leu Pro Glu Pro
        115                 120                 125

Pro Gly Ile Leu Ala Pro Gln Pro Pro Asp Val Gly Ser Ser Asp Pro
    130                 135                 140

Leu Ser Met Val Gly Pro Ser Gln Gly Arg Ser Pro Ser Tyr Ala Ser
145                 150                 155                 160

<210> SEQ ID NO 119
<211> LENGTH: 159
<212> TYPE: PRT
<213> ORGANISM: Homo sapiens

<400> SEQUENCE: 119

Thr Asp Asp Ala Gln Gln Thr Glu Ala His Leu Glu Ile Arg Glu Asp
 1               5                  10                  15

Gly Thr Val Gly Gly Ala Ala Asp Gln Ser Pro Glu Ser Leu Leu Gln
                20                  25                  30

Leu Lys Ala Leu Lys Pro Gly Val Ile Gln Ile Leu Gly Val Lys Thr
            35                  40                  45

Ser Arg Phe Leu Cys Gln Arg Pro Asp Gly Ala Leu Tyr Gly Ser Leu
        50                  55                  60

His Phe Asp Pro Glu Ala Cys Ser Phe Arg Glu Leu Leu Leu Glu Asp
 65                  70                  75                  80

Gly Tyr Asn Val Tyr Gln Ser Glu Ala His Gly Leu Pro Leu His Leu
                 85                  90                  95

Pro Gly Asn Lys Ser Pro His Arg Asp Pro Ala Pro Arg Gly Pro Ala
            100                 105                 110

Arg Phe Leu Pro Leu Pro Gly Leu Pro Pro Ala Leu Pro Glu Pro Pro
        115                 120                 125

Gly Ile Leu Ala Pro Gln Pro Pro Asp Val Gly Ser Ser Asp Pro Leu
    130                 135                 140

Ser Met Val Gly Pro Ser Gln Gly Arg Ser Pro Ser Tyr Ala Ser
145                 150                 155

<210> SEQ ID NO 120
<211> LENGTH: 158
<212> TYPE: PRT
<213> ORGANISM: Homo sapiens

<400> SEQUENCE: 120

Asp Asp Ala Gln Gln Thr Glu Ala His Leu Glu Ile Arg Glu Asp Gly
 1               5                  10                  15

Thr Val Gly Gly Ala Ala Asp Gln Ser Pro Glu Ser Leu Leu Gln Leu
                20                  25                  30

Lys Ala Leu Lys Pro Gly Val Ile Gln Ile Leu Gly Val Lys Thr Ser
            35                  40                  45

Arg Phe Leu Cys Gln Arg Pro Asp Gly Ala Leu Tyr Gly Ser Leu His
        50                  55                  60

Phe Asp Pro Glu Ala Cys Ser Phe Arg Glu Leu Leu Leu Glu Asp Gly
 65                  70                  75                  80

Tyr Asn Val Tyr Gln Ser Glu Ala His Gly Leu Pro Leu His Leu Pro
```

```
                85                  90                  95
Gly Asn Lys Ser Pro His Arg Asp Pro Ala Pro Arg Gly Pro Ala Arg
            100                 105                 110
Phe Leu Pro Leu Pro Gly Leu Pro Ala Leu Pro Glu Pro Pro Gly
            115                 120                 125
Ile Leu Ala Pro Gln Pro Pro Asp Val Gly Ser Ser Asp Pro Leu Ser
            130                 135                 140
Met Val Gly Pro Ser Gln Gly Arg Ser Pro Ser Tyr Ala Ser
145                 150                 155

<210> SEQ ID NO 121
<211> LENGTH: 147
<212> TYPE: PRT
<213> ORGANISM: Homo sapiens

<400> SEQUENCE: 121

Ile Arg Glu Asp Gly Thr Val Gly Gly Ala Ala Asp Gln Ser Pro Glu
1               5                   10                  15
Ser Leu Leu Gln Leu Lys Ala Leu Lys Pro Gly Val Ile Gln Ile Leu
                20                  25                  30
Gly Val Lys Thr Ser Arg Phe Leu Cys Gln Arg Pro Asp Gly Ala Leu
            35                  40                  45
Tyr Gly Ser Leu His Phe Asp Pro Glu Ala Cys Ser Phe Arg Glu Leu
        50                  55                  60
Leu Leu Glu Asp Gly Tyr Asn Val Tyr Gln Ser Glu Ala His Gly Leu
65                  70                  75                  80
Pro Leu His Leu Pro Gly Asn Lys Ser Pro His Arg Asp Pro Ala Pro
                85                  90                  95
Arg Gly Pro Ala Arg Phe Leu Pro Leu Pro Gly Leu Pro Ala Leu
            100                 105                 110
Pro Glu Pro Pro Gly Ile Leu Ala Pro Gln Pro Pro Asp Val Gly Ser
            115                 120                 125
Ser Asp Pro Leu Ser Met Val Gly Pro Ser Gln Gly Arg Ser Pro Ser
        130                 135                 140
Tyr Ala Ser
145

<210> SEQ ID NO 122
<211> LENGTH: 146
<212> TYPE: PRT
<213> ORGANISM: Homo sapiens

<400> SEQUENCE: 122

Arg Glu Asp Gly Thr Val Gly Gly Ala Ala Asp Gln Ser Pro Glu Ser
1               5                   10                  15
Leu Leu Gln Leu Lys Ala Leu Lys Pro Gly Val Ile Gln Ile Leu Gly
                20                  25                  30
Val Lys Thr Ser Arg Phe Leu Cys Gln Arg Pro Asp Gly Ala Leu Tyr
            35                  40                  45
Gly Ser Leu His Phe Asp Pro Glu Ala Cys Ser Phe Arg Glu Leu Leu
        50                  55                  60
Leu Glu Asp Gly Tyr Asn Val Tyr Gln Ser Glu Ala His Gly Leu Pro
65                  70                  75                  80
Leu His Leu Pro Gly Asn Lys Ser Pro His Arg Asp Pro Ala Pro Arg
                85                  90                  95
Gly Pro Ala Arg Phe Leu Pro Leu Pro Gly Leu Pro Ala Leu Pro
            100                 105                 110
```

Glu Pro Pro Gly Ile Leu Ala Pro Gln Pro Pro Asp Val Gly Ser Ser
            115                 120                 125

Asp Pro Leu Ser Met Val Gly Pro Ser Gln Gly Arg Ser Pro Ser Tyr
130                 135                 140

Ala Ser
145

<210> SEQ ID NO 123
<211> LENGTH: 145
<212> TYPE: PRT
<213> ORGANISM: Homo sapiens

<400> SEQUENCE: 123

Glu Asp Gly Thr Val Gly Gly Ala Ala Asp Gln Ser Pro Glu Ser Leu
1               5                   10                  15

Leu Gln Leu Lys Ala Leu Lys Pro Gly Val Ile Gln Ile Leu Gly Val
            20                  25                  30

Lys Thr Ser Arg Phe Leu Cys Gln Arg Pro Asp Gly Ala Leu Tyr Gly
        35                  40                  45

Ser Leu His Phe Asp Pro Glu Ala Cys Ser Phe Arg Glu Leu Leu Leu
    50                  55                  60

Glu Asp Gly Tyr Asn Val Tyr Gln Ser Glu Ala His Gly Leu Pro Leu
65                  70                  75                  80

His Leu Pro Gly Asn Lys Ser Pro His Arg Asp Pro Ala Pro Arg Gly
                85                  90                  95

Pro Ala Arg Phe Leu Pro Leu Pro Gly Leu Pro Pro Ala Leu Pro Glu
            100                 105                 110

Pro Pro Gly Ile Leu Ala Pro Gln Pro Pro Asp Val Gly Ser Ser Asp
        115                 120                 125

Pro Leu Ser Met Val Gly Pro Ser Gln Gly Arg Ser Pro Ser Tyr Ala
    130                 135                 140

Ser
145

<210> SEQ ID NO 124
<211> LENGTH: 144
<212> TYPE: PRT
<213> ORGANISM: Homo sapiens

<400> SEQUENCE: 124

Asp Gly Thr Val Gly Gly Ala Ala Asp Gln Ser Pro Glu Ser Leu Leu
1               5                   10                  15

Gln Leu Lys Ala Leu Lys Pro Gly Val Ile Gln Ile Leu Gly Val Lys
            20                  25                  30

Thr Ser Arg Phe Leu Cys Gln Arg Pro Asp Gly Ala Leu Tyr Gly Ser
        35                  40                  45

Leu His Phe Asp Pro Glu Ala Cys Ser Phe Arg Glu Leu Leu Leu Glu
    50                  55                  60

Asp Gly Tyr Asn Val Tyr Gln Ser Glu Ala His Gly Leu Pro Leu His
65                  70                  75                  80

Leu Pro Gly Asn Lys Ser Pro His Arg Asp Pro Ala Pro Arg Gly Pro
                85                  90                  95

Ala Arg Phe Leu Pro Leu Pro Gly Leu Pro Pro Ala Leu Pro Glu Pro
            100                 105                 110

Pro Gly Ile Leu Ala Pro Gln Pro Pro Asp Val Gly Ser Ser Asp Pro
        115                 120                 125

```
Leu Ser Met Val Gly Pro Ser Gln Gly Arg Ser Pro Ser Tyr Ala Ser
    130                 135                 140
```

<210> SEQ ID NO 125
<211> LENGTH: 143
<212> TYPE: PRT
<213> ORGANISM: Homo sapiens

<400> SEQUENCE: 125

```
Gly Thr Val Gly Gly Ala Ala Asp Gln Ser Pro Glu Ser Leu Leu Gln
1               5                   10                  15

Leu Lys Ala Leu Lys Pro Gly Val Ile Gln Ile Leu Gly Val Lys Thr
                20                  25                  30

Ser Arg Phe Leu Cys Gln Arg Pro Asp Gly Ala Leu Tyr Gly Ser Leu
            35                  40                  45

His Phe Asp Pro Glu Ala Cys Ser Phe Arg Glu Leu Leu Leu Glu Asp
    50                  55                  60

Gly Tyr Asn Val Tyr Gln Ser Glu Ala His Gly Leu Pro Leu His Leu
65                  70                  75                  80

Pro Gly Asn Lys Ser Pro His Arg Asp Pro Ala Pro Arg Gly Pro Ala
                85                  90                  95

Arg Phe Leu Pro Leu Pro Gly Leu Pro Pro Ala Leu Pro Glu Pro Pro
            100                 105                 110

Gly Ile Leu Ala Pro Gln Pro Pro Asp Val Gly Ser Ser Asp Pro Leu
        115                 120                 125

Ser Met Val Gly Pro Ser Gln Gly Arg Ser Pro Ser Tyr Ala Ser
    130                 135                 140
```

<210> SEQ ID NO 126
<211> LENGTH: 142
<212> TYPE: PRT
<213> ORGANISM: Homo sapiens

<400> SEQUENCE: 126

```
Thr Val Gly Gly Ala Ala Asp Gln Ser Pro Glu Ser Leu Leu Gln Leu
1               5                   10                  15

Lys Ala Leu Lys Pro Gly Val Ile Gln Ile Leu Gly Val Lys Thr Ser
                20                  25                  30

Arg Phe Leu Cys Gln Arg Pro Asp Gly Ala Leu Tyr Gly Ser Leu His
            35                  40                  45

Phe Asp Pro Glu Ala Cys Ser Phe Arg Glu Leu Leu Leu Glu Asp Gly
    50                  55                  60

Tyr Asn Val Tyr Gln Ser Glu Ala His Gly Leu Pro Leu His Leu Pro
65                  70                  75                  80

Gly Asn Lys Ser Pro His Arg Asp Pro Ala Pro Arg Gly Pro Ala Arg
                85                  90                  95

Phe Leu Pro Leu Pro Gly Leu Pro Pro Ala Leu Pro Glu Pro Pro Gly
            100                 105                 110

Ile Leu Ala Pro Gln Pro Pro Asp Val Gly Ser Ser Asp Pro Leu Ser
        115                 120                 125

Met Val Gly Pro Ser Gln Gly Arg Ser Pro Ser Tyr Ala Ser
    130                 135                 140
```

<210> SEQ ID NO 127
<211> LENGTH: 135
<212> TYPE: PRT
<213> ORGANISM: Homo sapiens

<400> SEQUENCE: 127

Gln Ser Pro Glu Ser Leu Leu Gln Leu Lys Ala Leu Lys Pro Gly Val
1               5                   10                  15

Ile Gln Ile Leu Gly Val Lys Thr Ser Arg Phe Leu Cys Gln Arg Pro
            20                  25                  30

Asp Gly Ala Leu Tyr Gly Ser Leu His Phe Asp Pro Glu Ala Cys Ser
            35                  40                  45

Phe Arg Glu Leu Leu Leu Glu Asp Gly Tyr Asn Val Tyr Gln Ser Glu
50                  55                  60

Ala His Gly Leu Pro Leu His Leu Pro Gly Asn Lys Ser Pro His Arg
65                  70                  75                  80

Asp Pro Ala Pro Arg Gly Pro Ala Arg Phe Leu Pro Leu Pro Gly Leu
                85                  90                  95

Pro Pro Ala Leu Pro Glu Pro Pro Gly Ile Leu Ala Pro Gln Pro Pro
            100                 105                 110

Asp Val Gly Ser Ser Asp Pro Leu Ser Met Val Gly Pro Ser Gln Gly
            115                 120                 125

Arg Ser Pro Ser Tyr Ala Ser
            130                 135

<210> SEQ ID NO 128
<211> LENGTH: 134
<212> TYPE: PRT
<213> ORGANISM: Homo sapiens

<400> SEQUENCE: 128

Ser Pro Glu Ser Leu Leu Gln Leu Lys Ala Leu Lys Pro Gly Val Ile
1               5                   10                  15

Gln Ile Leu Gly Val Lys Thr Ser Arg Phe Leu Cys Gln Arg Pro Asp
            20                  25                  30

Gly Ala Leu Tyr Gly Ser Leu His Phe Asp Pro Glu Ala Cys Ser Phe
            35                  40                  45

Arg Glu Leu Leu Leu Glu Asp Gly Tyr Asn Val Tyr Gln Ser Glu Ala
50                  55                  60

His Gly Leu Pro Leu His Leu Pro Gly Asn Lys Ser Pro His Arg Asp
65                  70                  75                  80

Pro Ala Pro Arg Gly Pro Ala Arg Phe Leu Pro Leu Pro Gly Leu Pro
                85                  90                  95

Pro Ala Leu Pro Glu Pro Pro Gly Ile Leu Ala Pro Gln Pro Pro Asp
            100                 105                 110

Val Gly Ser Ser Asp Pro Leu Ser Met Val Gly Pro Ser Gln Gly Arg
            115                 120                 125

Ser Pro Ser Tyr Ala Ser
            130

<210> SEQ ID NO 129
<211> LENGTH: 133
<212> TYPE: PRT
<213> ORGANISM: Homo sapiens

<400> SEQUENCE: 129

Pro Glu Ser Leu Leu Gln Leu Lys Ala Leu Lys Pro Gly Val Ile Gln
1               5                   10                  15

Ile Leu Gly Val Lys Thr Ser Arg Phe Leu Cys Gln Arg Pro Asp Gly
            20                  25                  30

Ala Leu Tyr Gly Ser Leu His Phe Asp Pro Glu Ala Cys Ser Phe Arg
            35                  40                  45

```
Glu Leu Leu Leu Glu Asp Gly Tyr Asn Val Tyr Gln Ser Glu Ala His
            50                  55                  60

Gly Leu Pro Leu His Leu Pro Gly Asn Lys Ser Pro His Arg Asp Pro
 65                  70                  75                  80

Ala Pro Arg Gly Pro Ala Arg Phe Leu Pro Leu Pro Gly Leu Pro Pro
                85                  90                  95

Ala Leu Pro Glu Pro Pro Gly Ile Leu Ala Pro Gln Pro Pro Asp Val
               100                 105                 110

Gly Ser Ser Asp Pro Leu Ser Met Val Gly Pro Ser Gln Gly Arg Ser
               115                 120                 125

Pro Ser Tyr Ala Ser
           130

<210> SEQ ID NO 130
<211> LENGTH: 131
<212> TYPE: PRT
<213> ORGANISM: Homo sapiens

<400> SEQUENCE: 130

Ser Leu Leu Gln Leu Lys Ala Leu Lys Pro Gly Val Ile Gln Ile Leu
 1               5                  10                  15

Gly Val Lys Thr Ser Arg Phe Leu Cys Gln Arg Pro Asp Gly Ala Leu
                20                  25                  30

Tyr Gly Ser Leu His Phe Asp Pro Glu Ala Cys Ser Phe Arg Glu Leu
            35                  40                  45

Leu Leu Glu Asp Gly Tyr Asn Val Tyr Gln Ser Glu Ala His Gly Leu
        50                  55                  60

Pro Leu His Leu Pro Gly Asn Lys Ser Pro His Arg Asp Pro Ala Pro
 65                  70                  75                  80

Arg Gly Pro Ala Arg Phe Leu Pro Leu Pro Gly Leu Pro Pro Ala Leu
                85                  90                  95

Pro Glu Pro Pro Gly Ile Leu Ala Pro Gln Pro Pro Asp Val Gly Ser
               100                 105                 110

Ser Asp Pro Leu Ser Met Val Gly Pro Ser Gln Gly Arg Ser Pro Ser
               115                 120                 125

Tyr Ala Ser
   130

<210> SEQ ID NO 131
<211> LENGTH: 130
<212> TYPE: PRT
<213> ORGANISM: Homo sapiens

<400> SEQUENCE: 131

Leu Leu Gln Leu Lys Ala Leu Lys Pro Gly Val Ile Gln Ile Leu Gly
 1               5                  10                  15

Val Lys Thr Ser Arg Phe Leu Cys Gln Arg Pro Asp Gly Ala Leu Tyr
                20                  25                  30

Gly Ser Leu His Phe Asp Pro Glu Ala Cys Ser Phe Arg Glu Leu Leu
            35                  40                  45

Leu Glu Asp Gly Tyr Asn Val Tyr Gln Ser Glu Ala His Gly Leu Pro
        50                  55                  60

Leu His Leu Pro Gly Asn Lys Ser Pro His Arg Asp Pro Ala Pro Arg
 65                  70                  75                  80

Gly Pro Ala Arg Phe Leu Pro Leu Pro Gly Leu Pro Pro Ala Leu Pro
                85                  90                  95

Glu Pro Pro Gly Ile Leu Ala Pro Gln Pro Pro Asp Val Gly Ser Ser
```

-continued

```
                100             105             110
Asp Pro Leu Ser Met Val Gly Pro Ser Gln Gly Arg Ser Pro Ser Tyr
        115                 120                 125
Ala Ser
    130
```

<210> SEQ ID NO 132
<211> LENGTH: 129
<212> TYPE: PRT
<213> ORGANISM: Homo sapiens

<400> SEQUENCE: 132

```
Leu Gln Leu Lys Ala Leu Lys Pro Gly Val Ile Gln Ile Leu Gly Val
1               5                   10                  15
Lys Thr Ser Arg Phe Leu Cys Gln Arg Pro Asp Gly Ala Leu Tyr Gly
                20                  25                  30
Ser Leu His Phe Asp Pro Glu Ala Cys Ser Phe Arg Glu Leu Leu Leu
            35                  40                  45
Glu Asp Gly Tyr Asn Val Tyr Gln Ser Glu Ala His Gly Leu Pro Leu
        50                  55                  60
His Leu Pro Gly Asn Lys Ser Pro His Arg Asp Pro Ala Pro Arg Gly
65                  70                  75                  80
Pro Ala Arg Phe Leu Pro Leu Pro Gly Leu Pro Pro Ala Leu Pro Glu
                85                  90                  95
Pro Pro Gly Ile Leu Ala Pro Gln Pro Pro Asp Val Gly Ser Ser Asp
                100                 105                 110
Pro Leu Ser Met Val Gly Pro Ser Gln Gly Arg Ser Pro Ser Tyr Ala
            115                 120                 125
Ser
```

<210> SEQ ID NO 133
<211> LENGTH: 128
<212> TYPE: PRT
<213> ORGANISM: Homo sapiens

<400> SEQUENCE: 133

```
Gln Leu Lys Ala Leu Lys Pro Gly Val Ile Gln Ile Leu Gly Val Lys
1               5                   10                  15
Thr Ser Arg Phe Leu Cys Gln Arg Pro Asp Gly Ala Leu Tyr Gly Ser
                20                  25                  30
Leu His Phe Asp Pro Glu Ala Cys Ser Phe Arg Glu Leu Leu Leu Glu
            35                  40                  45
Asp Gly Tyr Asn Val Tyr Gln Ser Glu Ala His Gly Leu Pro Leu His
        50                  55                  60
Leu Pro Gly Asn Lys Ser Pro His Arg Asp Pro Ala Pro Arg Gly Pro
65                  70                  75                  80
Ala Arg Phe Leu Pro Leu Pro Gly Leu Pro Pro Ala Leu Pro Glu Pro
                85                  90                  95
Pro Gly Ile Leu Ala Pro Gln Pro Pro Asp Val Gly Ser Ser Asp Pro
                100                 105                 110
Leu Ser Met Val Gly Pro Ser Gln Gly Arg Ser Pro Ser Tyr Ala Ser
            115                 120                 125
```

<210> SEQ ID NO 134
<211> LENGTH: 115
<212> TYPE: PRT
<213> ORGANISM: Homo sapiens

<400> SEQUENCE: 134

```
Gly Val Lys Thr Ser Arg Phe Leu Cys Gln Arg Pro Asp Gly Ala Leu
1               5                   10                  15

Tyr Gly Ser Leu His Phe Asp Pro Glu Ala Cys Ser Phe Arg Glu Leu
            20                  25                  30

Leu Leu Glu Asp Gly Tyr Asn Val Tyr Gln Ser Glu Ala His Gly Leu
        35                  40                  45

Pro Leu His Leu Pro Gly Asn Lys Ser Pro His Arg Asp Pro Ala Pro
    50                  55                  60

Arg Gly Pro Ala Arg Phe Leu Pro Leu Pro Gly Leu Pro Pro Ala Leu
65                  70                  75                  80

Pro Glu Pro Pro Gly Ile Leu Ala Pro Gln Pro Pro Asp Val Gly Ser
                85                  90                  95

Ser Asp Pro Leu Ser Met Val Gly Pro Ser Gln Gly Arg Ser Pro Ser
                100                 105                 110

Tyr Ala Ser
        115
```

<210> SEQ ID NO 135
<211> LENGTH: 114
<212> TYPE: PRT
<213> ORGANISM: Homo sapiens

<400> SEQUENCE: 135

```
Val Lys Thr Ser Arg Phe Leu Cys Gln Arg Pro Asp Gly Ala Leu Tyr
1               5                   10                  15

Gly Ser Leu His Phe Asp Pro Glu Ala Cys Ser Phe Arg Glu Leu Leu
            20                  25                  30

Leu Glu Asp Gly Tyr Asn Val Tyr Gln Ser Glu Ala His Gly Leu Pro
        35                  40                  45

Leu His Leu Pro Gly Asn Lys Ser Pro His Arg Asp Pro Ala Pro Arg
    50                  55                  60

Gly Pro Ala Arg Phe Leu Pro Leu Pro Gly Leu Pro Pro Ala Leu Pro
65                  70                  75                  80

Glu Pro Pro Gly Ile Leu Ala Pro Gln Pro Pro Asp Val Gly Ser Ser
                85                  90                  95

Asp Pro Leu Ser Met Val Gly Pro Ser Gln Gly Arg Ser Pro Ser Tyr
                100                 105                 110

Ala Ser
```

<210> SEQ ID NO 136
<211> LENGTH: 113
<212> TYPE: PRT
<213> ORGANISM: Homo sapiens

<400> SEQUENCE: 136

```
Lys Thr Ser Arg Phe Leu Cys Gln Arg Pro Asp Gly Ala Leu Tyr Gly
1               5                   10                  15

Ser Leu His Phe Asp Pro Glu Ala Cys Ser Phe Arg Glu Leu Leu Leu
            20                  25                  30

Glu Asp Gly Tyr Asn Val Tyr Gln Ser Glu Ala His Gly Leu Pro Leu
        35                  40                  45

His Leu Pro Gly Asn Lys Ser Pro His Arg Asp Pro Ala Pro Arg Gly
    50                  55                  60

Pro Ala Arg Phe Leu Pro Leu Pro Gly Leu Pro Pro Ala Leu Pro Glu
65                  70                  75                  80
```

```
Pro Pro Gly Ile Leu Ala Pro Gln Pro Pro Asp Val Gly Ser Ser Asp
                85                  90                  95

Pro Leu Ser Met Val Gly Pro Ser Gln Gly Arg Ser Pro Ser Tyr Ala
            100                 105                 110

Ser

<210> SEQ ID NO 137
<211> LENGTH: 108
<212> TYPE: PRT
<213> ORGANISM: Homo sapiens

<400> SEQUENCE: 137

Leu Cys Gln Arg Pro Asp Gly Ala Leu Tyr Gly Ser Leu His Phe Asp
1               5                   10                  15

Pro Glu Ala Cys Ser Phe Arg Glu Leu Leu Glu Asp Gly Tyr Asn
            20                  25                  30

Val Tyr Gln Ser Glu Ala His Gly Leu Pro Leu His Leu Pro Gly Asn
        35                  40                  45

Lys Ser Pro His Arg Asp Pro Ala Pro Arg Gly Pro Ala Arg Phe Leu
    50                  55                  60

Pro Leu Pro Gly Leu Pro Ala Leu Pro Glu Pro Pro Gly Ile Leu
65                  70                  75                  80

Ala Pro Gln Pro Pro Asp Val Gly Ser Ser Asp Pro Leu Ser Met Val
                85                  90                  95

Gly Pro Ser Gln Gly Arg Ser Pro Ser Tyr Ala Ser
            100                 105

<210> SEQ ID NO 138
<211> LENGTH: 107
<212> TYPE: PRT
<213> ORGANISM: Homo sapiens

<400> SEQUENCE: 138

Cys Gln Arg Pro Asp Gly Ala Leu Tyr Gly Ser Leu His Phe Asp Pro
1               5                   10                  15

Glu Ala Cys Ser Phe Arg Glu Leu Leu Leu Glu Asp Gly Tyr Asn Val
            20                  25                  30

Tyr Gln Ser Glu Ala His Gly Leu Pro Leu His Leu Pro Gly Asn Lys
        35                  40                  45

Ser Pro His Arg Asp Pro Ala Pro Arg Gly Pro Ala Arg Phe Leu Pro
    50                  55                  60

Leu Pro Gly Leu Pro Pro Ala Leu Pro Glu Pro Pro Gly Ile Leu Ala
65                  70                  75                  80

Pro Gln Pro Pro Asp Val Gly Ser Ser Asp Pro Leu Ser Met Val Gly
                85                  90                  95

Pro Ser Gln Gly Arg Ser Pro Ser Tyr Ala Ser
            100                 105

<210> SEQ ID NO 139
<211> LENGTH: 106
<212> TYPE: PRT
<213> ORGANISM: Homo sapiens

<400> SEQUENCE: 139

Gln Arg Pro Asp Gly Ala Leu Tyr Gly Ser Leu His Phe Asp Pro Glu
1               5                   10                  15

Ala Cys Ser Phe Arg Glu Leu Leu Leu Glu Asp Gly Tyr Asn Val Tyr
            20                  25                  30
```

-continued

Gln Ser Glu Ala His Gly Leu Pro Leu His Leu Pro Gly Asn Lys Ser
            35                  40                  45

Pro His Arg Asp Pro Ala Pro Arg Gly Pro Ala Arg Phe Leu Pro Leu
        50                  55                  60

Pro Gly Leu Pro Pro Ala Leu Pro Glu Pro Pro Gly Ile Leu Ala Pro
65                  70                  75                  80

Gln Pro Pro Asp Val Gly Ser Ser Asp Pro Leu Ser Met Val Gly Pro
                85                  90                  95

Ser Gln Gly Arg Ser Pro Ser Tyr Ala Ser
                100                 105

<210> SEQ ID NO 140
<211> LENGTH: 46
<212> TYPE: PRT
<213> ORGANISM: Homo sapiens

<400> SEQUENCE: 140

Phe Leu Pro Leu Pro Gly Leu Pro Pro Ala Leu Pro Glu Pro Pro Gly
1               5                   10                  15

Ile Leu Ala Pro Gln Pro Pro Asp Val Gly Ser Ser Asp Pro Leu Ser
            20                  25                  30

Met Val Gly Pro Ser Gln Gly Arg Ser Pro Ser Tyr Ala Ser
        35                  40                  45

<210> SEQ ID NO 141
<211> LENGTH: 45
<212> TYPE: PRT
<213> ORGANISM: Homo sapiens

<400> SEQUENCE: 141

Leu Pro Leu Pro Gly Leu Pro Pro Ala Leu Pro Glu Pro Pro Gly Ile
1               5                   10                  15

Leu Ala Pro Gln Pro Pro Asp Val Gly Ser Ser Asp Pro Leu Ser Met
            20                  25                  30

Val Gly Pro Ser Gln Gly Arg Ser Pro Ser Tyr Ala Ser
        35                  40                  45

<210> SEQ ID NO 142
<211> LENGTH: 44
<212> TYPE: PRT
<213> ORGANISM: Homo sapiens

<400> SEQUENCE: 142

Pro Leu Pro Gly Leu Pro Pro Ala Leu Pro Glu Pro Pro Gly Ile Leu
1               5                   10                  15

Ala Pro Gln Pro Pro Asp Val Gly Ser Ser Asp Pro Leu Ser Met Val
            20                  25                  30

Gly Pro Ser Gln Gly Arg Ser Pro Ser Tyr Ala Ser
        35                  40

<210> SEQ ID NO 143
<211> LENGTH: 43
<212> TYPE: PRT
<213> ORGANISM: Homo sapiens

<400> SEQUENCE: 143

Leu Pro Gly Leu Pro Pro Ala Leu Pro Glu Pro Pro Gly Ile Leu Ala
1               5                   10                  15

Pro Gln Pro Pro Asp Val Gly Ser Ser Asp Pro Leu Ser Met Val Gly
            20                  25                  30

Pro Ser Gln Gly Arg Ser Pro Ser Tyr Ala Ser
            35                  40

<210> SEQ ID NO 144
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Ala Gln Gln Thr Glu
            20                  25                  30

Ala His Leu Glu Ile Arg Glu Asp Gly Thr Val Gly Gly Ala Ala Asp
        35                  40                  45

Gln Ser Pro Glu Ser Leu Leu Gln Leu Lys Ala Leu Lys Pro Gly Val
    50                  55                  60

Ile Gln Ile Leu Gly Val Lys Thr Ser Arg Phe Leu Cys Gln Arg Pro
65                  70                  75                  80

Asp Gly Ala Leu Tyr Gly Ser Leu His Phe Asp Pro Glu Ala Cys Ser
                85                  90                  95

Phe Arg Glu Leu Leu Leu Glu Asp Gly Tyr Asn Val Tyr Gln Ser Glu
            100                 105                 110

Ala His Gly Leu Pro Leu His Leu Pro Gly Asn Lys Ser Pro His Arg
        115                 120                 125

Asp Pro Ala Pro Arg Gly Pro Ala Arg Phe Leu Pro Leu Pro Gly Leu
    130                 135                 140

Pro Pro Ala Leu Pro Glu Pro Pro Gly Ile Leu Ala Pro Gln Pro Pro
145                 150                 155                 160

Asp Val Gly Ser Ser Asp Pro Leu Ser Met Val Gly Pro Ser Gln Gly
                165                 170                 175

Arg Ser Pro Ser Tyr Ala Ser
            180

<210> SEQ ID NO 145
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Arg Pro Leu Ala Phe Ser Asp Ala Gly Pro His Val His Tyr Gly Trp
1               5                   10                  15

Gly Asp Pro Ile Arg Leu Arg His Leu Tyr Thr Asp Ala Gln Gln
            20                  25                  30

Thr Glu Ala His Leu Glu Ile Arg Glu Asp Gly Thr Val Gly Gly Ala
        35                  40                  45

Ala Asp Gln Ser Pro Glu Ser Leu Leu Gln Leu Lys Ala Leu Lys Pro
    50                  55                  60

Gly Val Ile Gln Ile Leu Gly Val Lys Thr Ser Arg Phe Leu Cys Gln
65                  70                  75                  80

Arg Pro Asp Gly Ala Leu Tyr Gly Ser Leu His Phe Asp Pro Glu Ala
                85                  90                  95

Cys Ser Phe Arg Glu Leu Leu Leu Glu Asp Gly Tyr Asn Val Tyr Gln

```
                    100                 105                 110
Ser Glu Ala His Gly Leu Pro Leu His Leu Pro Gly Asn Lys Ser Pro
            115                 120                 125

His Arg Asp Pro Ala Pro Arg Gly Pro Ala Arg Phe Leu Pro Leu Pro
        130                 135                 140

Gly Leu Pro Pro Ala Leu Pro Glu Pro Pro Gly Ile Leu Ala Pro Gln
145                 150                 155                 160

Pro Pro Asp Val Gly Ser Ser Asp Pro Leu Ser Met Val Gly Pro Ser
                165                 170                 175

Gln Gly Arg Ser Pro Ser Tyr Ala Ser
            180                 185

<210> SEQ ID NO 146
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Glu Asp Gly Thr Val Gly Gly
        35                  40                  45

Ala Ala Asp Gln Ser Pro Glu Ser Leu Leu Gln Leu Lys Ala Leu Lys
    50                  55                  60

Pro Gly Val Ile Gln Ile Leu Gly Val Lys Thr Ser Arg Phe Leu Cys
65                  70                  75                  80

Gln Arg Pro Asp Gly Ala Leu Tyr Gly Ser Leu His Phe Asp Pro Glu
                85                  90                  95

Ala Cys Ser Phe Arg Glu Leu Leu Leu Glu Asp Gly Tyr Asn Val Tyr
            100                 105                 110

Gln Ser Glu Ala His Gly Leu Pro Leu His Leu Pro Gly Asn Lys Ser
        115                 120                 125

Pro His Arg Asp Pro Ala Pro Arg Gly Pro Ala Arg Phe Leu Pro Leu
    130                 135                 140

Pro Gly Leu Pro Pro Ala Leu Pro Glu Pro Pro Gly Ile Leu Ala Pro
145                 150                 155                 160

Gln Pro Pro Asp Val Gly Ser Ser Asp Pro Leu Ser Met Val Gly Pro
                165                 170                 175

Ser Gln Gly Arg Ser Pro Ser Tyr Ala Ser
            180                 185

<210> SEQ ID NO 147
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30
```

```
Leu Ser Ser Cys Phe Leu Arg Ile Arg Ala Asp Gly Thr Val Gly Gly
            35                  40                  45

Ala Ala Asp Gln Ser Pro Glu Ser Leu Leu Gln Leu Lys Ala Leu Lys
 50                  55                  60

Pro Gly Val Ile Gln Ile Leu Gly Val Lys Thr Ser Arg Phe Leu Cys
 65                  70                  75                  80

Gln Arg Pro Asp Gly Ala Leu Tyr Gly Ser Leu His Phe Asp Pro Glu
                 85                  90                  95

Ala Cys Ser Phe Arg Glu Leu Leu Glu Asp Gly Tyr Asn Val Tyr
                100                 105                 110

Gln Ser Glu Ala His Gly Leu Pro Leu His Leu Pro Gly Asn Lys Ser
                115                 120                 125

Pro His Arg Asp Pro Ala Pro Arg Gly Pro Ala Arg Phe Leu Pro Leu
                130                 135                 140

Pro Gly Leu Pro Pro Ala Leu Pro Glu Pro Pro Gly Ile Leu Ala Pro
145                 150                 155                 160

Gln Pro Pro Asp Val Gly Ser Ser Asp Pro Leu Ser Met Val Gly Pro
                165                 170                 175

Ser Gln Gly Arg Ser Pro Ser Tyr Ala Ser
                180                 185

<210> SEQ ID NO 148
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Arg Pro Leu Ala Phe Ser Asp Ala Gly Pro His Val His Tyr Gly Trp
 1               5                  10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Pro Glu Ser Leu Leu Gln Leu Lys Ala Leu Lys
 50                  55                  60

Pro Gly Val Ile Gln Ile Leu Gly Val Lys Thr Ser Arg Phe Leu Cys
 65                  70                  75                  80

Gln Arg Pro Asp Gly Ala Leu Tyr Gly Ser Leu His Phe Asp Pro Glu
                 85                  90                  95

Ala Cys Ser Phe Arg Glu Leu Leu Leu Glu Asp Gly Tyr Asn Val Tyr
                100                 105                 110

Gln Ser Glu Ala His Gly Leu Pro Leu His Leu Pro Gly Asn Lys Ser
                115                 120                 125

Pro His Arg Asp Pro Ala Pro Arg Gly Pro Ala Arg Phe Leu Pro Leu
                130                 135                 140

Pro Gly Leu Pro Pro Ala Leu Pro Glu Pro Pro Gly Ile Leu Ala Pro
145                 150                 155                 160

Gln Pro Pro Asp Val Gly Ser Ser Asp Pro Leu Ser Met Val Gly Pro
                165                 170                 175

Ser Gln Gly Arg Ser Pro Ser Tyr Ala Ser
                180                 185

<210> SEQ ID NO 149
```

```
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Gln Leu Lys Ala Leu Lys
    50                  55                  60

Pro Gly Val Ile Gln Ile Leu Gly Val Lys Thr Ser Arg Phe Leu Cys
65                  70                  75                  80

Gln Arg Pro Asp Gly Ala Leu Tyr Gly Ser Leu His Phe Asp Pro Glu
                85                  90                  95

Ala Cys Ser Phe Arg Glu Leu Leu Leu Glu Asp Gly Tyr Asn Val Tyr
            100                 105                 110

Gln Ser Glu Ala His Gly Leu Pro Leu His Leu Pro Gly Asn Lys Ser
        115                 120                 125

Pro His Arg Asp Pro Ala Pro Arg Gly Pro Ala Arg Phe Leu Pro Leu
    130                 135                 140

Pro Gly Leu Pro Pro Ala Leu Pro Glu Pro Pro Gly Ile Leu Ala Pro
145                 150                 155                 160

Gln Pro Pro Asp Val Gly Ser Ser Asp Pro Leu Ser Met Val Gly Pro
                165                 170                 175

Ser Gln Gly Arg Ser Pro Ser Tyr Ala Ser
            180                 185

<210> SEQ ID NO 150
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val Lys Thr Ser Arg Phe Leu Cys
65                  70                  75                  80

Gln Arg Pro Asp Gly Ala Leu Tyr Gly Ser Leu His Phe Asp Pro Glu
                85                  90                  95

Ala Cys Ser Phe Arg Glu Leu Leu Leu Glu Asp Gly Tyr Asn Val Tyr
            100                 105                 110

Gln Ser Glu Ala His Gly Leu Pro Leu His Leu Pro Gly Asn Lys Ser
        115                 120                 125
```

```
Pro His Arg Asp Pro Ala Pro Arg Gly Pro Ala Arg Phe Leu Pro Leu
        130                 135                 140

Pro Gly Leu Pro Pro Ala Leu Pro Glu Pro Pro Gly Ile Leu Ala Pro
145                 150                 155                 160

Gln Pro Pro Asp Val Gly Ser Ser Asp Pro Leu Ser Met Val Gly Pro
                165                 170                 175

Ser Gln Gly Arg Ser Pro Ser Tyr Ala Ser
        180                 185

<210> SEQ ID NO 151
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
        50                  55                  60

Leu Arg Thr Val Ala Ile Lys Gly Val His Ser Val Arg Tyr Leu Cys
65                  70                  75                  80

Gln Arg Pro Asp Gly Ala Leu Tyr Gly Ser Leu His Phe Asp Pro Glu
                85                  90                  95

Ala Cys Ser Phe Arg Glu Leu Leu Glu Asp Gly Tyr Asn Val Tyr
            100                 105                 110

Gln Ser Glu Ala His Gly Leu Pro Leu His Leu Pro Gly Asn Lys Ser
        115                 120                 125

Pro His Arg Asp Pro Ala Pro Arg Gly Pro Ala Arg Phe Leu Pro Leu
    130                 135                 140

Pro Gly Leu Pro Pro Ala Leu Pro Glu Pro Pro Gly Ile Leu Ala Pro
145                 150                 155                 160

Gln Pro Pro Asp Val Gly Ser Ser Asp Pro Leu Ser Met Val Gly Pro
                165                 170                 175

Ser Gln Gly Arg Ser Pro Ser Tyr Ala Ser
        180                 185

<210> SEQ ID NO 152
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
```

```
                50                  55                  60
Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                 85                  90                  95

Asp Cys Ala Phe Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
            115                 120                 125

Arg Gln Leu Tyr Lys Asn Arg Gly Phe Leu Pro Leu Ser His Phe Leu
            130                 135                 140

Pro Leu Pro Gly Leu Pro Pro Ala Leu Pro Glu Pro Pro Gly Ile Leu
145                 150                 155                 160

Ala Pro Gln Pro Pro Asp Val Gly Ser Ser Asp Pro Leu Ser Met Val
                165                 170                 175

Gly Pro Ser Gln Gly Arg Ser Pro Ser Tyr Ala Ser
            180                 185

<210> SEQ ID NO 153
<211> LENGTH: 18
<212> TYPE: PRT
<213> ORGANISM: Homo sapiens

<400> SEQUENCE: 153

Pro His Val His Tyr Gly Trp Gly Asp Pro Ile Arg Leu Arg His Leu
 1               5                   10                  15

Tyr Thr

<210> SEQ ID NO 154
<211> LENGTH: 20
<212> TYPE: PRT
<213> ORGANISM: Homo sapiens

<400> SEQUENCE: 154

Pro His Val His Tyr Gly Trp Gly Asp Pro Ile Arg Leu Arg His Leu
 1               5                   10                  15

Tyr Thr Ser Gly
         20

<210> SEQ ID NO 155
<211> LENGTH: 22
<212> TYPE: PRT
<213> ORGANISM: Homo sapiens

<400> SEQUENCE: 155

Pro His Val His Tyr Gly Trp Gly Asp Pro Ile Arg Leu Arg His Leu
 1               5                   10                  15

Tyr Thr Ser Gly Pro His
         20

<210> SEQ ID NO 156
<211> LENGTH: 23
<212> TYPE: PRT
<213> ORGANISM: Homo sapiens

<400> SEQUENCE: 156

Pro His Val His Tyr Gly Trp Gly Asp Pro Ile Arg Leu Arg His Leu
 1               5                   10                  15

Tyr Thr Ser Gly Pro His Gly
         20
```

<210> SEQ ID NO 157
<211> LENGTH: 25
<212> TYPE: PRT
<213> ORGANISM: Homo sapiens

<400> SEQUENCE: 157

Pro His Val His Tyr Gly Trp Gly Asp Pro Ile Arg Leu Arg His Leu
1               5                   10                  15

Tyr Thr Ser Gly Pro His Gly Leu Ser
            20                  25

<210> SEQ ID NO 158
<211> LENGTH: 27
<212> TYPE: PRT
<213> ORGANISM: Homo sapiens

<400> SEQUENCE: 158

Pro His Val His Tyr Gly Trp Gly Asp Pro Ile Arg Leu Arg His Leu
1               5                   10                  15

Tyr Thr Ser Gly Pro His Gly Leu Ser Ser Cys
            20                  25

<210> SEQ ID NO 159
<211> LENGTH: 32
<212> TYPE: PRT
<213> ORGANISM: Homo sapiens

<400> SEQUENCE: 159

Pro His Val His Tyr Gly Trp Gly Asp Pro Ile Arg Leu Arg His Leu
1               5                   10                  15

Tyr Thr Ser Gly Pro His Gly Leu Ser Ser Cys Phe Leu Arg Ile Arg
            20                  25                  30

<210> SEQ ID NO 160
<211> LENGTH: 35
<212> TYPE: PRT
<213> ORGANISM: Homo sapiens

<400> SEQUENCE: 160

Pro His Val His Tyr Gly Trp Gly Asp Pro Ile Arg Leu Arg His Leu
1               5                   10                  15

Tyr Thr Ser Gly Pro His Gly Leu Ser Ser Cys Phe Leu Arg Ile Arg
            20                  25                  30

Ala Asp Gly
        35

<210> SEQ ID NO 161
<211> LENGTH: 44
<212> TYPE: PRT
<213> ORGANISM: Homo sapiens

<400> SEQUENCE: 161

Pro His Val His Tyr Gly Trp Gly Asp Pro Ile Arg Leu Arg His Leu
1               5                   10                  15

Tyr Thr Ser Gly Pro His Gly Leu Ser Ser Cys Phe Leu Arg Ile Arg
            20                  25                  30

Ala Asp Gly Val Val Asp Cys Ala Arg Gly Gln Ser
        35                  40

<210> SEQ ID NO 162
<211> LENGTH: 49

```
<212> TYPE: PRT
<213> ORGANISM: Homo sapiens

<400> SEQUENCE: 162

Pro His Val His Tyr Gly Trp Gly Asp Pro Ile Arg Leu Arg His Leu
1               5                   10                  15

Tyr Thr Ser Gly Pro His Gly Leu Ser Ser Cys Phe Leu Arg Ile Arg
            20                  25                  30

Ala Asp Gly Val Val Asp Cys Ala Arg Gly Gln Ser Ala His Ser Leu
        35                  40                  45

Leu

<210> SEQ ID NO 163
<211> LENGTH: 64
<212> TYPE: PRT
<213> ORGANISM: Homo sapiens

<400> SEQUENCE: 163

Pro His Val His Tyr Gly Trp Gly Asp Pro Ile Arg Leu Arg His Leu
1               5                   10                  15

Tyr Thr Ser Gly Pro His Gly Leu Ser Ser Cys Phe Leu Arg Ile Arg
            20                  25                  30

Ala Asp Gly Val Val Asp Cys Ala Arg Gly Gln Ser Ala His Ser Leu
        35                  40                  45

Leu Glu Ile Lys Ala Val Ala Leu Arg Thr Val Ala Ile Lys Gly Val
    50                  55                  60

<210> SEQ ID NO 164
<211> LENGTH: 11
<212> TYPE: PRT
<213> ORGANISM: Homo sapiens

<400> SEQUENCE: 164

Gly Asp Pro Ile Arg Leu Arg His Leu Tyr Thr
1               5                   10

<210> SEQ ID NO 165
<211> LENGTH: 13
<212> TYPE: PRT
<213> ORGANISM: Homo sapiens

<400> SEQUENCE: 165

Gly Asp Pro Ile Arg Leu Arg His Leu Tyr Thr Ser Gly
1               5                   10

<210> SEQ ID NO 166
<211> LENGTH: 15
<212> TYPE: PRT
<213> ORGANISM: Homo sapiens

<400> SEQUENCE: 166

Gly Asp Pro Ile Arg Leu Arg His Leu Tyr Thr Ser Gly Pro His
1               5                   10                  15

<210> SEQ ID NO 167
<211> LENGTH: 16
<212> TYPE: PRT
<213> ORGANISM: Homo sapiens

<400> SEQUENCE: 167

Gly Asp Pro Ile Arg Leu Arg His Leu Tyr Thr Ser Gly Pro His Gly
1               5                   10                  15
```

```
<210> SEQ ID NO 168
<211> LENGTH: 18
<212> TYPE: PRT
<213> ORGANISM: Homo sapiens

<400> SEQUENCE: 168

Gly Asp Pro Ile Arg Leu Arg His Leu Tyr Thr Ser Gly Pro His Gly
1               5                   10                  15

Leu Ser

<210> SEQ ID NO 169
<211> LENGTH: 20
<212> TYPE: PRT
<213> ORGANISM: Homo sapiens

<400> SEQUENCE: 169

Gly Asp Pro Ile Arg Leu Arg His Leu Tyr Thr Ser Gly Pro His Gly
1               5                   10                  15

Leu Ser Ser Cys
            20

<210> SEQ ID NO 170
<211> LENGTH: 7
<212> TYPE: PRT
<213> ORGANISM: Homo sapiens

<400> SEQUENCE: 170

Arg Leu Arg His Leu Tyr Thr
1               5

<210> SEQ ID NO 171
<211> LENGTH: 9
<212> TYPE: PRT
<213> ORGANISM: Homo sapiens

<400> SEQUENCE: 171

Arg Leu Arg His Leu Tyr Thr Ser Gly
1               5

<210> SEQ ID NO 172
<211> LENGTH: 11
<212> TYPE: PRT
<213> ORGANISM: Homo sapiens

<400> SEQUENCE: 172

Arg Leu Arg His Leu Tyr Thr Ser Gly Pro His
1               5                   10

<210> SEQ ID NO 173
<211> LENGTH: 12
<212> TYPE: PRT
<213> ORGANISM: Homo sapiens

<400> SEQUENCE: 173

Arg Leu Arg His Leu Tyr Thr Ser Gly Pro His Gly
1               5                   10

<210> SEQ ID NO 174
<211> LENGTH: 14
<212> TYPE: PRT
<213> ORGANISM: Homo sapiens

<400> SEQUENCE: 174

Arg Leu Arg His Leu Tyr Thr Ser Gly Pro His Gly Leu Ser
```

<210> SEQ ID NO 175
<211> LENGTH: 16
<212> TYPE: PRT
<213> ORGANISM: Homo sapiens

<400> SEQUENCE: 175

Arg Leu Arg His Leu Tyr Thr Ser Gly Pro His Gly Leu Ser Ser Cys
1               5                   10                  15

<210> SEQ ID NO 176
<211> LENGTH: 17
<212> TYPE: PRT
<213> ORGANISM: Homo sapiens

<400> SEQUENCE: 176

Leu Tyr Thr Ser Gly Pro His Gly Leu Ser Ser Cys Phe Leu Arg Ile
1               5                   10                  15

Arg

<210> SEQ ID NO 177
<211> LENGTH: 20
<212> TYPE: PRT
<213> ORGANISM: Homo sapiens

<400> SEQUENCE: 177

Leu Tyr Thr Ser Gly Pro His Gly Leu Ser Ser Cys Phe Leu Arg Ile
1               5                   10                  15

Arg Ala Asp Gly
            20

<210> SEQ ID NO 178
<211> LENGTH: 29
<212> TYPE: PRT
<213> ORGANISM: Homo sapiens

<400> SEQUENCE: 178

Leu Tyr Thr Ser Gly Pro His Gly Leu Ser Ser Cys Phe Leu Arg Ile
1               5                   10                  15

Arg Ala Asp Gly Val Val Asp Cys Ala Arg Gly Gln Ser
            20                  25

<210> SEQ ID NO 179
<211> LENGTH: 34
<212> TYPE: PRT
<213> ORGANISM: Homo sapiens

<400> SEQUENCE: 179

Leu Tyr Thr Ser Gly Pro His Gly Leu Ser Ser Cys Phe Leu Arg Ile
1               5                   10                  15

Arg Ala Asp Gly Val Val Asp Cys Ala Arg Gly Gln Ser Ala His Ser
            20                  25                  30

Leu Leu

<210> SEQ ID NO 180
<211> LENGTH: 49
<212> TYPE: PRT
<213> ORGANISM: Homo sapiens

<400> SEQUENCE: 180

Leu Tyr Thr Ser Gly Pro His Gly Leu Ser Ser Cys Phe Leu Arg Ile
1               5                   10                  15

Arg Ala Asp Gly Val Val Asp Cys Ala Arg Gly Gln Ser Ala His Ser
            20                  25                  30

Leu Leu Glu Ile Lys Ala Val Ala Leu Arg Thr Val Ala Ile Lys Gly
        35                  40                  45

Val

<210> SEQ ID NO 181
<211> LENGTH: 4
<212> TYPE: PRT
<213> ORGANISM: Homo sapiens

<400> SEQUENCE: 181

Val Ala Leu Arg
1

<210> SEQ ID NO 182
<211> LENGTH: 16
<212> TYPE: PRT
<213> ORGANISM: Homo sapiens

<400> SEQUENCE: 182

Pro Leu Leu Gln Phe Gly Gly Gln Val Arg Gln Arg Tyr Leu Tyr Thr
1               5                   10                  15

<210> SEQ ID NO 183
<211> LENGTH: 18
<212> TYPE: PRT
<213> ORGANISM: Homo sapiens

<400> SEQUENCE: 183

Pro Leu Leu Gln Phe Gly Gly Gln Val Arg Gln Arg Tyr Leu Tyr Thr
1               5                   10                  15

Asp Asp

<210> SEQ ID NO 184
<211> LENGTH: 20
<212> TYPE: PRT
<213> ORGANISM: Homo sapiens

<400> SEQUENCE: 184

Pro Leu Leu Gln Phe Gly Gly Gln Val Arg Gln Arg Tyr Leu Tyr Thr
1               5                   10                  15

Asp Asp Ala Gln
            20

<210> SEQ ID NO 185
<211> LENGTH: 22
<212> TYPE: PRT
<213> ORGANISM: Homo sapiens

<400> SEQUENCE: 185

Pro Leu Leu Gln Phe Gly Gly Gln Val Arg Gln Arg Tyr Leu Tyr Thr
1               5                   10                  15

Asp Asp Ala Gln Gln Thr
            20

<210> SEQ ID NO 186
<211> LENGTH: 24
<212> TYPE: PRT
<213> ORGANISM: Homo sapiens

<400> SEQUENCE: 186

```
Pro Leu Leu Gln Phe Gly Gly Gln Val Arg Gln Arg Tyr Leu Tyr Thr
1               5                   10                  15

Asp Asp Ala Gln Gln Thr Glu Ala
            20
```

<210> SEQ ID NO 187
<211> LENGTH: 29
<212> TYPE: PRT
<213> ORGANISM: Homo sapiens

<400> SEQUENCE: 187

```
Pro Leu Leu Gln Phe Gly Gly Gln Val Arg Gln Arg Tyr Leu Tyr Thr
1               5                   10                  15

Asp Asp Ala Gln Gln Thr Glu Ala His Leu Glu Ile Arg
            20                  25
```

<210> SEQ ID NO 188
<211> LENGTH: 32
<212> TYPE: PRT
<213> ORGANISM: Homo sapiens

<400> SEQUENCE: 188

```
Pro Leu Leu Gln Phe Gly Gly Gln Val Arg Gln Arg Tyr Leu Tyr Thr
1               5                   10                  15

Asp Asp Ala Gln Gln Thr Glu Ala His Leu Glu Ile Arg Glu Asp Gly
            20                  25                  30
```

<210> SEQ ID NO 189
<211> LENGTH: 41
<212> TYPE: PRT
<213> ORGANISM: Homo sapiens

<400> SEQUENCE: 189

```
Pro Leu Leu Gln Phe Gly Gly Gln Val Arg Gln Arg Tyr Leu Tyr Thr
1               5                   10                  15

Asp Asp Ala Gln Gln Thr Glu Ala His Leu Glu Ile Arg Glu Asp Gly
            20                  25                  30

Thr Val Gly Gly Ala Ala Asp Gln Ser
            35                  40
```

<210> SEQ ID NO 190
<211> LENGTH: 46
<212> TYPE: PRT
<213> ORGANISM: Homo sapiens

<400> SEQUENCE: 190

```
Pro Leu Leu Gln Phe Gly Gly Gln Val Arg Gln Arg Tyr Leu Tyr Thr
1               5                   10                  15

Asp Asp Ala Gln Gln Thr Glu Ala His Leu Glu Ile Arg Glu Asp Gly
            20                  25                  30

Thr Val Gly Gly Ala Ala Asp Gln Ser Pro Glu Ser Leu Leu
            35                  40                  45
```

<210> SEQ ID NO 191
<211> LENGTH: 55
<212> TYPE: PRT
<213> ORGANISM: Homo sapiens

<400> SEQUENCE: 191

```
Pro Leu Leu Gln Phe Gly Gly Gln Val Arg Gln Arg Tyr Leu Tyr Thr
1               5                   10                  15

Asp Asp Ala Gln Gln Thr Glu Ala His Leu Glu Ile Arg Glu Asp Gly
```

```
                20                  25                  30
Thr Val Gly Gly Ala Ala Asp Gln Ser Pro Glu Ser Leu Leu Gln Leu
            35                  40                  45

Lys Ala Leu Lys Pro Gly Val
        50                  55
```

<210> SEQ ID NO 192
<211> LENGTH: 11
<212> TYPE: PRT
<213> ORGANISM: Homo sapiens

<400> SEQUENCE: 192

```
Gly Gly Gln Val Arg Gln Arg Tyr Leu Tyr Thr
1               5                   10
```

<210> SEQ ID NO 193
<211> LENGTH: 13
<212> TYPE: PRT
<213> ORGANISM: Homo sapiens

<400> SEQUENCE: 193

```
Gly Gly Gln Val Arg Gln Arg Tyr Leu Tyr Thr Asp Asp
1               5                   10
```

<210> SEQ ID NO 194
<211> LENGTH: 15
<212> TYPE: PRT
<213> ORGANISM: Homo sapiens

<400> SEQUENCE: 194

```
Gly Gly Gln Val Arg Gln Arg Tyr Leu Tyr Thr Asp Asp Ala Gln
1               5                   10                  15
```

<210> SEQ ID NO 195
<211> LENGTH: 17
<212> TYPE: PRT
<213> ORGANISM: Homo sapiens

<400> SEQUENCE: 195

```
Gly Gly Gln Val Arg Gln Arg Tyr Leu Tyr Thr Asp Asp Ala Gln Gln
1               5                   10                  15

Thr
```

<210> SEQ ID NO 196
<211> LENGTH: 19
<212> TYPE: PRT
<213> ORGANISM: Homo sapiens

<400> SEQUENCE: 196

```
Gly Gly Gln Val Arg Gln Arg Tyr Leu Tyr Thr Asp Asp Ala Gln Gln
1               5                   10                  15

Thr Glu Ala
```

<210> SEQ ID NO 197
<211> LENGTH: 7
<212> TYPE: PRT
<213> ORGANISM: Homo sapiens

<400> SEQUENCE: 197

```
Arg Gln Arg Tyr Leu Tyr Thr
1               5
```

<210> SEQ ID NO 198

```
<211> LENGTH: 9
<212> TYPE: PRT
<213> ORGANISM: Homo sapiens

<400> SEQUENCE: 198

Arg Gln Arg Tyr Leu Tyr Thr Asp Asp
1               5

<210> SEQ ID NO 199
<211> LENGTH: 11
<212> TYPE: PRT
<213> ORGANISM: Homo sapiens

<400> SEQUENCE: 199

Arg Gln Arg Tyr Leu Tyr Thr Asp Asp Ala Gln
1               5                   10

<210> SEQ ID NO 200
<211> LENGTH: 13
<212> TYPE: PRT
<213> ORGANISM: Homo sapiens

<400> SEQUENCE: 200

Arg Gln Arg Tyr Leu Tyr Thr Asp Asp Ala Gln Gln Thr
1               5                   10

<210> SEQ ID NO 201
<211> LENGTH: 15
<212> TYPE: PRT
<213> ORGANISM: Homo sapiens

<400> SEQUENCE: 201

Arg Gln Arg Tyr Leu Tyr Thr Asp Asp Ala Gln Gln Thr Glu Ala
1               5                   10                  15

<210> SEQ ID NO 202
<211> LENGTH: 16
<212> TYPE: PRT
<213> ORGANISM: Homo sapiens

<400> SEQUENCE: 202

Leu Tyr Thr Asp Asp Ala Gln Gln Thr Glu Ala His Leu Glu Ile Arg
1               5                   10                  15

<210> SEQ ID NO 203
<211> LENGTH: 19
<212> TYPE: PRT
<213> ORGANISM: Homo sapiens

<400> SEQUENCE: 203

Leu Tyr Thr Asp Asp Ala Gln Gln Thr Glu Ala His Leu Glu Ile Arg
1               5                   10                  15

Glu Asp Gly

<210> SEQ ID NO 204
<211> LENGTH: 28
<212> TYPE: PRT
<213> ORGANISM: Homo sapiens

<400> SEQUENCE: 204

Leu Tyr Thr Asp Asp Ala Gln Gln Thr Glu Ala His Leu Glu Ile Arg
1               5                   10                  15

Glu Asp Gly Thr Val Gly Gly Ala Ala Asp Gln Ser
            20                  25
```

<210> SEQ ID NO 205
<211> LENGTH: 33
<212> TYPE: PRT
<213> ORGANISM: Homo sapiens

<400> SEQUENCE: 205

Leu Tyr Thr Asp Asp Ala Gln Gln Thr Glu Ala His Leu Glu Ile Arg
1               5                   10                  15

Glu Asp Gly Thr Val Gly Gly Ala Ala Asp Gln Ser Pro Glu Ser Leu
            20                  25                  30

Leu

<210> SEQ ID NO 206
<211> LENGTH: 42
<212> TYPE: PRT
<213> ORGANISM: Homo sapiens

<400> SEQUENCE: 206

Leu Tyr Thr Asp Asp Ala Gln Gln Thr Glu Ala His Leu Glu Ile Arg
1               5                   10                  15

Glu Asp Gly Thr Val Gly Gly Ala Ala Asp Gln Ser Pro Glu Ser Leu
            20                  25                  30

Leu Gln Leu Lys Ala Leu Lys Pro Gly Val
        35                  40

<210> SEQ ID NO 207
<211> LENGTH: 4
<212> TYPE: PRT
<213> ORGANISM: Homo sapiens

<400> SEQUENCE: 207

Leu Lys Pro Gly
1

<210> SEQ ID NO 208
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Arg Pro Leu Ala Phe Ser Asp Ala Gly Pro Leu Leu Gln Phe Gly Gly
1               5                   10                  15

Gln Val Arg Gln Arg Tyr Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met

```
                130                 135                 140
Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
                180                 185                 190

<210> SEQ ID NO 209
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Pro His Gly Leu Ser
                20                  25                  30

Ser Cys Phe Leu Arg Ile Arg Ala Asp Gly Val Val Asp Cys Ala Arg
            35                  40                  45

Gly Gln Ser Ala His Ser Leu Leu Glu Ile Lys Ala Val Ala Leu Arg
50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
                180                 185                 190

<210> SEQ ID NO 210
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Asp Ala Gln Gly Leu Ser
                20                  25                  30

Ser Cys Phe Leu Arg Ile Arg Ala Asp Gly Val Val Asp Cys Ala Arg
            35                  40                  45

Gly Gln Ser Ala His Ser Leu Leu Glu Ile Lys Ala Val Ala Leu Arg
50                  55                  60
```

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 211
<211> LENGTH: 191
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Asp Ala Gln Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 212
<211> LENGTH: 191
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Asp Ala Gln Thr Ser
            20                  25                  30

Cys Phe Leu Arg Ile Arg Ala Asp Gly Val Val Asp Cys Ala Arg Gly
                35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 213
<211> LENGTH: 191
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Asp Ala Gln Thr Glu
            20                  25                  30

Ala Phe Leu Arg Ile Arg Ala Asp Gly Val Val Asp Cys Ala Arg Gly
                35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

```
Asp Met Phe Ser Ser Pro Leu Glu Thr Asp Ser Met Asp Pro Phe Gly
            165                 170                 175

Leu Val Thr Gly Leu Glu Ala Val Arg Ser Pro Ser Phe Glu Lys
            180                 185                 190
```

<210> SEQ ID NO 214
<211> LENGTH: 191
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 214

```
Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Asp Ala Gln Gln Thr Glu
            20                  25                  30

Ala His Leu Glu Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
            165                 170                 175

Leu Val Thr Gly Leu Glu Ala Val Arg Ser Pro Ser Phe Glu Lys
            180                 185                 190
```

<210> SEQ ID NO 215
<211> LENGTH: 191
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 215

```
Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Asp Ala Gln Gln Thr Glu
            20                  25                  30

Ala His Leu Glu Ile Arg Glu Asp Gly Val Val Asp Cys Ala Arg Gly
        35                  40                  45

Gln Ser Ala His Ser Leu Leu Glu Ile Lys Ala Val Ala Leu Arg Thr
50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
```

```
                 85                  90                  95
Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
        130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 216
<211> LENGTH: 191
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Ala Gln Gln Thr Glu
            20                  25                  30

Ala His Leu Glu Ile Arg Glu Asp Gly Thr Val Gly Gly Ala Ala Asp
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
        130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 217
<211> LENGTH: 191
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Arg Pro Leu Ala Phe Ser Asp Ala Gly Pro Leu Leu Gln Phe Gly Gly
1               5                   10                  15
```

```
Gln Val Arg Gln Arg Tyr Leu Tyr Thr Asp Asp Ala Gln Gln Thr Glu
             20                  25                  30

Ala His Leu Glu Ile Arg Glu Asp Gly Thr Val Gly Gly Ala Ala Asp
         35                  40                  45

Gln Ser Pro Glu Ser Leu Leu Glu Ile Lys Ala Val Ala Leu Arg Thr
     50                  55                  60

Val Ala Ile Lys Gly Val His Ser Val Arg Tyr Leu Cys Met Gly Ala
 65                  70                  75                  80

Asp Gly Lys Met Gln Gly Leu Leu Gln Tyr Ser Glu Glu Asp Cys Ala
                 85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
        130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 218
<211> LENGTH: 191
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Arg Pro Leu Ala Phe Ser Asp Ala Gly Pro Leu Leu Gln Phe Gly Gly
 1               5                  10                  15

Gln Val Arg Gln Arg Tyr Leu Tyr Thr Asp Asp Ala Gln Gln Thr Glu
             20                  25                  30

Ala His Leu Glu Ile Arg Glu Asp Gly Thr Val Gly Gly Ala Ala Asp
         35                  40                  45

Gln Ser Pro Glu Ser Leu Leu Gln Leu Lys Ala Leu Lys Pro Gly Val
     50                  55                  60

Ile Gln Ile Leu Gly Val His Ser Val Arg Tyr Leu Cys Met Gly Ala
 65                  70                  75                  80

Asp Gly Lys Met Gln Gly Leu Leu Gln Tyr Ser Glu Glu Asp Cys Ala
                 85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
        130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190
```

<210> SEQ ID NO 219
<211> LENGTH: 194
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 219

Arg Pro Leu Ala Phe Ser Asp Ala Gly Pro His Val His Tyr Gly Trp
1               5                   10                  15

Gly Gly Gln Val Arg Gln Arg Tyr Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 220
<211> LENGTH: 194
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 220

Arg Pro Leu Ala Phe Ser Asp Ala Gly Pro His Val His Tyr Gly Trp
1               5                   10                  15

Gly Gly Gln Val Arg Gln Arg Tyr Leu Tyr Thr Asp Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr

```
                100                 105                 110
Arg Ser Glu Lys His Arg Leu Pro Val Ser Leu Ser Ser Ala Lys Gln
            115                 120                 125

Arg Gln Leu Tyr Lys Asn Arg Gly Phe Leu Pro Leu Ser His Phe Leu
        130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 221
<211> LENGTH: 194
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Arg Pro Leu Ala Phe Ser Asp Ala Gly Pro His Val His Tyr Gly Trp
1               5                   10                  15

Gly Gly Gln Val Arg Gln Arg Tyr Leu Tyr Thr Asp Asp Ala Gln Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 222
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Arg Pro Leu Ala Phe Ser Asp Ala Gly Pro His Val His Tyr Gly Trp
```

```
                1               5                   10                  15
Gly Gly Gln Val Arg Gln Arg Tyr Leu Tyr Thr Asp Asp Ala Gln Leu
                20                  25                  30

Ser Ser Cys Phe Leu Arg Ile Arg Ala Asp Gly Val Val Asp Cys Ala
            35                  40                  45

Arg Gly Gln Ser Ala His Ser Leu Leu Glu Ile Lys Ala Val Ala Leu
        50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
            115                 120                 125

Gln Leu Tyr Lys Asn Arg Gly Phe Leu Pro Leu Ser His Phe Leu Pro
        130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
            180                 185                 190

Lys

<210> SEQ ID NO 223
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Arg Pro Leu Ala Phe Ser Asp Ala Gly Pro His Val His Tyr Gly Trp
1               5                   10                  15

Gly Gly Gln Val Arg Gln Arg Tyr Leu Tyr Thr Asp Asp Ala Gln Gln
                20                  25                  30

Thr Ser Cys Phe Leu Arg Ile Arg Ala Asp Gly Val Val Asp Cys Ala
            35                  40                  45

Arg Gly Gln Ser Ala His Ser Leu Leu Glu Ile Lys Ala Val Ala Leu
        50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
            115                 120                 125

Gln Leu Tyr Lys Asn Arg Gly Phe Leu Pro Leu Ser His Phe Leu Pro
        130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175
```

```
Phe Gly Leu Val Thr Gly Leu Glu Ala Val Arg Ser Pro Ser Phe Glu
            180                 185                 190

Lys

<210> SEQ ID NO 224
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Arg Pro Leu Ala Phe Ser Asp Ala Gly Pro His Val His Tyr Gly Trp
1               5                   10                  15

Gly Gly Gln Val Arg Gln Arg Tyr Leu Tyr Thr Asp Asp Ala Gln Gln
            20                  25                  30

Thr Glu Ala Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
        115                 120                 125

Gln Leu Tyr Lys Asn Arg Gly Phe Leu Pro Leu Ser His Phe Leu Pro
    130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
            180                 185                 190

Lys

<210> SEQ ID NO 225
<211> LENGTH: 194
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Arg Pro Leu Ala Phe Ser Asp Ala Gly Pro His Val His Tyr Gly Trp
1               5                   10                  15

Gly Asp Pro Ile Arg Gln Arg Tyr Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80
```

```
Met Gly Ala Asp Gly Lys Met Gln Gly Leu Leu Gln Tyr Ser Glu Glu
                85                  90                  95

Asp Cys Ala Phe Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
            115                 120                 125

Arg Gln Leu Tyr Lys Asn Arg Gly Phe Leu Pro Leu Ser His Phe Leu
        130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 226
<211> LENGTH: 194
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Arg Pro Leu Ala Phe Ser Asp Ala Gly Pro His Val His Tyr Gly Trp
1               5                   10                  15

Gly Asp Pro Ile Arg Gln Arg Tyr Leu Tyr Thr Asp Asp Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
            115                 120                 125

Arg Gln Leu Tyr Lys Asn Arg Gly Phe Leu Pro Leu Ser His Phe Leu
        130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 227
<211> LENGTH: 194
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 227

Arg Pro Leu Ala Phe Ser Asp Ala Gly Pro His Val His Tyr Gly Trp
1               5                   10                  15

Gly Asp Pro Ile Arg Gln Arg Tyr Leu Tyr Thr Asp Asp Ala Gln Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 228
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Arg Pro Leu Ala Phe Ser Asp Ala Gly Pro His Val His Tyr Gly Trp
1               5                   10                  15

Gly Asp Pro Ile Arg Gln Arg Tyr Leu Tyr Thr Asp Asp Ala Gln Leu
            20                  25                  30

Ser Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
        115                 120                 125

Gln Leu Tyr Lys Asn Arg Gly Phe Leu Pro Leu Ser His Phe Leu Pro
    130                 135                 140

```
Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
            165                 170                 175

Phe Gly Leu Val Thr Gly Leu Glu Ala Val Arg Ser Pro Ser Phe Glu
        180                 185                 190

Lys
```

<210> SEQ ID NO 229
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

```
Arg Pro Leu Ala Phe Ser Asp Ala Gly Pro His Val His Tyr Gly Trp
1               5                   10                  15

Gly Asp Pro Ile Arg Gln Arg Tyr Leu Tyr Thr Asp Ala Gln Gln
            20                  25                  30

Thr Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
            85                  90                  95

Cys Ala Phe Glu Glu Glu Ile Arg Pro Asp Gly Tyr Asn Val Tyr Arg
        100                 105                 110

Ser Glu Lys His Arg Leu Pro Val Ser Leu Ser Ser Ala Lys Gln Arg
    115                 120                 125

Gln Leu Tyr Lys Asn Arg Gly Phe Leu Pro Leu Ser His Phe Leu Pro
130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
            165                 170                 175

Phe Gly Leu Val Thr Gly Leu Glu Ala Val Arg Ser Pro Ser Phe Glu
        180                 185                 190

Lys
```

<210> SEQ ID NO 230
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

```
Arg Pro Leu Ala Phe Ser Asp Ala Gly Pro His Val His Tyr Gly Trp
1               5                   10                  15

Gly Asp Pro Ile Arg Gln Arg Tyr Leu Tyr Thr Asp Ala Gln Gln
            20                  25                  30

Thr Glu Ala Phe Leu Arg Ile Arg Ala Asp Gly Val Val Asp Cys Ala
        35                  40                  45
```

```
Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Asp
                85                  90                  95

Cys Ala Phe Glu Glu Glu Ile Arg Pro Asp Gly Tyr Asn Val Tyr Arg
                100                 105                 110

Ser Glu Lys His Arg Leu Pro Val Ser Leu Ser Ser Ala Lys Gln Arg
            115                 120                 125

Gln Leu Tyr Lys Asn Arg Gly Phe Leu Pro Leu Ser His Phe Leu Pro
    130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
                180                 185                 190

Lys

<210> SEQ ID NO 231
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Arg Pro Leu Ala Phe Ser Asp Ala Gly Pro His Val His Tyr Gly Trp
1               5                   10                  15

Gly Asp Pro Ile Arg Leu Arg His Leu Tyr Thr Asp Asp Ala Gln Gln
                20                  25                  30

Thr Glu Ala His Leu Glu Ile Arg Ala Asp Gly Val Val Asp Cys Ala
            35                  40                  45

Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Asp
                85                  90                  95

Cys Ala Phe Glu Glu Glu Ile Arg Pro Asp Gly Tyr Asn Val Tyr Arg
                100                 105                 110

Ser Glu Lys His Arg Leu Pro Val Ser Leu Ser Ser Ala Lys Gln Arg
            115                 120                 125

Gln Leu Tyr Lys Asn Arg Gly Phe Leu Pro Leu Ser His Phe Leu Pro
    130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
                180                 185                 190

Lys

<210> SEQ ID NO 232
```

```
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Arg Pro Leu Ala Phe Ser Asp Ala Gly Pro His Val His Tyr Gly Trp
1               5                   10                  15

Gly Asp Pro Ile Arg Leu Arg His Leu Tyr Thr Asp Ala Gln Gln
            20                  25                  30

Thr Glu Ala His Leu Glu Ile Arg Glu Asp Gly Val Val Asp Cys Ala
        35                  40                  45

Arg Gly Gln Ser Ala His Ser Leu Leu Glu Ile Lys Ala Val Ala Leu
50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
        115                 120                 125

Gln Leu Tyr Lys Asn Arg Gly Phe Leu Pro Leu Ser His Phe Leu Pro
130                 135                 140

Met Leu Pro Met Val Pro Glu Glu Pro Gly Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
            180                 185                 190

Lys

<210> SEQ ID NO 233
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Arg Pro Leu Ala Phe Ser Asp Ala Gly Pro His Val His Tyr Gly Trp
1               5                   10                  15

Gly Asp Pro Ile Arg Leu Arg His Leu Tyr Thr Asp Ala Gln Gln
            20                  25                  30

Thr Glu Ala His Leu Glu Ile Arg Glu Asp Gly Thr Val Gly Gly Ala
        35                  40                  45

Ala Asp Gln Ser Ala His Ser Leu Leu Glu Ile Lys Ala Val Ala Leu
50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
```

```
            115                 120                 125
Gln Leu Tyr Lys Asn Arg Gly Phe Leu Pro Leu Ser His Phe Leu Pro
    130                 135                 140
Met Leu Pro Met Val Pro Glu Glu Pro Glu Asp Leu Arg Gly His Leu
145                 150                 155                 160
Glu Ser Asp Met Phe Ser Ser Pro Leu Glu Thr Asp Ser Met Asp Pro
                165                 170                 175
Phe Gly Leu Val Thr Gly Leu Glu Ala Val Arg Ser Pro Ser Phe Glu
            180                 185                 190
Lys

<210> SEQ ID NO 234
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Arg Pro Leu Ala Phe Ser Asp Ala Gly Pro His Val His Tyr Gly Trp
1               5                   10                  15
Gly Asp Pro Ile Arg Leu Arg His Leu Tyr Thr Asp Asp Ala Gln Gln
            20                  25                  30
Thr Glu Ala His Leu Glu Ile Arg Glu Asp Gly Thr Val Gly Gly Ala
        35                  40                  45
Ala Asp Gln Ser Pro Glu Ser Leu Leu Glu Ile Lys Ala Val Ala Leu
    50                  55                  60
Arg Thr Val Ala Ile Lys Gly Val His Ser Val Arg Tyr Leu Cys Met
65                  70                  75                  80
Gly Ala Asp Gly Lys Met Gln Gly Leu Leu Gln Tyr Ser Glu Glu Asp
                85                  90                  95
Cys Ala Phe Glu Glu Glu Ile Arg Pro Asp Gly Tyr Asn Val Tyr Arg
            100                 105                 110
Ser Glu Lys His Arg Leu Pro Val Ser Leu Ser Ser Ala Lys Gln Arg
        115                 120                 125
Gln Leu Tyr Lys Asn Arg Gly Phe Leu Pro Leu Ser His Phe Leu Pro
    130                 135                 140
Met Leu Pro Met Val Pro Glu Glu Pro Glu Asp Leu Arg Gly His Leu
145                 150                 155                 160
Glu Ser Asp Met Phe Ser Ser Pro Leu Glu Thr Asp Ser Met Asp Pro
                165                 170                 175
Phe Gly Leu Val Thr Gly Leu Glu Ala Val Arg Ser Pro Ser Phe Glu
            180                 185                 190
Lys

<210> SEQ ID NO 235
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Arg Pro Leu Ala Phe Ser Asp Ala Gly Pro His Val His Tyr Gly Trp
1               5                   10                  15
Gly Asp Pro Ile Arg Leu Arg His Leu Tyr Thr Asp Asp Ala Gln Gln
```

```
                    20                  25                  30
Thr Glu Ala His Leu Glu Ile Arg Glu Asp Gly Thr Val Gly Gly Ala
                35                  40                  45
Ala Asp Gln Ser Pro Glu Ser Leu Leu Gln Leu Lys Ala Leu Lys Pro
         50                  55                  60
Gly Val Ile Gln Ile Leu Gly Val His Ser Val Arg Tyr Leu Cys Met
 65                  70                  75                  80
Gly Ala Asp Gly Lys Met Gln Gly Leu Leu Gln Tyr Ser Glu Glu Asp
                 85                  90                  95
Cys Ala Phe Glu Glu Glu Ile Arg Pro Asp Gly Tyr Asn Val Tyr Arg
                100                 105                 110
Ser Glu Lys His Arg Leu Pro Val Ser Leu Ser Ser Ala Lys Gln Arg
                115                 120                 125
Gln Leu Tyr Lys Asn Arg Gly Phe Leu Pro Leu Ser His Phe Leu Pro
                130                 135                 140
Met Leu Pro Met Val Pro Glu Glu Pro Glu Asp Leu Arg Gly His Leu
145                 150                 155                 160
Glu Ser Asp Met Phe Ser Ser Pro Leu Glu Thr Asp Ser Met Asp Pro
                165                 170                 175
Phe Gly Leu Val Thr Gly Leu Glu Ala Val Arg Ser Pro Ser Phe Glu
                180                 185                 190
Lys

<210> SEQ ID NO 236
<211> LENGTH: 194
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Arg Pro Leu Ala Phe Ser Asp Ala Gly Pro His Val His Tyr Gly Trp
 1               5                  10                  15
Gly Asp Pro Ile Arg Leu Arg His Leu Tyr Thr Ser Gly Pro His Gly
                20                  25                  30
Leu Ser Ser Cys Phe Leu Arg Ile Arg Ala Asp Gly Val Val Asp Cys
                35                  40                  45
Ala Arg Gly Gln Ser Ala His Ser Leu Leu Glu Ile Lys Ala Leu Lys
         50                  55                  60
Pro Gly Thr Val Ala Ile Lys Gly Val His Ser Val Arg Tyr Leu Cys
 65                  70                  75                  80
Met Gly Ala Asp Gly Lys Met Gln Gly Leu Leu Gln Tyr Ser Glu Glu
                 85                  90                  95
Asp Cys Ala Phe Glu Glu Glu Ile Arg Pro Asp Gly Tyr Asn Val Tyr
                100                 105                 110
Arg Ser Glu Lys His Arg Leu Pro Val Ser Leu Ser Ser Ala Lys Gln
                115                 120                 125
Arg Gln Leu Tyr Lys Asn Arg Gly Phe Leu Pro Leu Ser His Phe Leu
                130                 135                 140
Pro Met Leu Pro Met Val Pro Glu Glu Pro Glu Asp Leu Arg Gly His
145                 150                 155                 160
Leu Glu Ser Asp Met Phe Ser Ser Pro Leu Glu Thr Asp Ser Met Asp
                165                 170                 175
Pro Phe Gly Leu Val Thr Gly Leu Glu Ala Val Arg Ser Pro Ser Phe
                180                 185                 190
```

Glu Lys

<210> SEQ ID NO 237
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys Asp Tyr Lys Asp Asp Asp Lys
195                 200

<210> SEQ ID NO 238
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

His His His His His His Pro Ile Pro Asp Ser Ser Pro Leu Leu Gln
1               5                   10                  15

Phe Gly Gly Gln Val Arg Gln Arg Tyr Leu Tyr Thr Asp Asp Ala Gln
                20                  25                  30

Gln Thr Glu Ala His Leu Glu Ile Arg Glu Asp Gly Thr Val Gly Gly
            35                  40                  45

Ala Ala Asp Gln Ser Pro Glu Ser Leu Leu Gln Leu Lys Ala Leu Lys
    50                  55                  60

Pro Gly Val Ile Gln Ile Leu Gly Val Lys Thr Ser Arg Phe Leu Cys
65                  70                  75                  80

Gln Arg Pro Asp Gly Ala Leu Tyr Gly Ser Leu His Phe Asp Pro Glu

```
                    85                  90                  95
Ala Cys Ser Phe Arg Glu Leu Leu Leu Glu Asp Gly Tyr Asn Val Tyr
                100                 105                 110

Gln Ser Glu Ala His Gly Leu Pro Leu His Leu Pro Gly Asn Lys Ser
            115                 120                 125

Pro His Arg Asp Pro Ala Pro Arg Gly Pro Ala Arg Phe Leu Pro Leu
        130                 135                 140

Pro Gly Leu Pro Pro Ala Leu Pro Glu Pro Pro Gly Ile Leu Ala Pro
145                 150                 155                 160

Gln Pro Pro Asp Val Gly Ser Ser Asp Pro Leu Ser Met Val Gly Pro
                165                 170                 175

Ser Gln Gly Arg Ser Pro Ser Tyr Ala Ser
            180                 185

<210> SEQ ID NO 239
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser Asp Tyr Lys Asp Asp Asp Asp Lys
            180                 185

<210> SEQ ID NO 240
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Lys Asp Tyr Lys Asp Asp Asp Asp Lys Leu Glu His Pro Ile Pro Asp
1               5                   10                  15
```

Ser Ser Pro Leu Leu Gln Phe Gly Gly Gln Val Arg Gln Arg Tyr Leu
            20                  25                  30

Tyr Thr Asp Asp Ala Gln Gln Thr Glu Ala His Leu Glu Ile Arg Glu
        35                  40                  45

Asp Gly Thr Val Gly Gly Ala Ala Asp Gln Ser Pro Glu Ser Leu Leu
    50                  55                  60

Gln Leu Lys Ala Leu Lys Pro Gly Val Ile Gln Ile Leu Gly Val Lys
65                  70                  75                  80

Thr Ser Arg Phe Leu Cys Gln Arg Pro Asp Gly Ala Leu Tyr Gly Ser
                85                  90                  95

Leu His Phe Asp Pro Glu Ala Cys Ser Phe Arg Glu Leu Leu Leu Glu
            100                 105                 110

Asp Gly Tyr Asn Val Tyr Gln Ser Glu Ala His Gly Leu Pro Leu His
            115                 120                 125

Leu Pro Gly Asn Lys Ser Pro His Arg Asp Pro Ala Pro Arg Gly Pro
    130                 135                 140

Ala Arg Phe Leu Pro Leu Pro Gly Leu Pro Pro Ala Leu Pro Glu Pro
145                 150                 155                 160

Pro Gly Ile Leu Ala Pro Gln Pro Pro Asp Val Gly Ser Ser Asp Pro
                165                 170                 175

Leu Ser Met Val Gly Pro Ser Gln Gly Arg Ser Pro Ser Tyr Ala Ser
            180                 185                 190

<210> SEQ ID NO 241
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

His Pro Ile Pro Asp Ser Ser Pro His Val His Tyr Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

```
Asp Tyr Lys Asp Asp Asp Lys
        195             200

<210> SEQ ID NO 242
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

His Pro Ile Pro Asp Ser Ser Pro Leu Leu Gln Phe Gly Gly Gln Val
1               5                   10                  15

Arg Gln Arg Tyr Leu Tyr Thr Ser Gly Pro His Gly Leu Ser Ser Cys
            20                  25                  30

Phe Leu Arg Ile Arg Ala Asp Gly Val Val Asp Cys Ala Arg Gly Gln
        35                  40                  45

Ser Ala His Ser Leu Leu Glu Ile Lys Ala Val Ala Leu Arg Thr Val
    50                  55                  60

Ala Ile Lys Gly Val His Ser Val Arg Tyr Leu Cys Met Gly Ala Asp
65                  70                  75                  80

Gly Lys Met Gln Gly Leu Leu Gln Tyr Ser Glu Glu Asp Cys Ala Phe
                85                  90                  95

Glu Glu Glu Ile Arg Pro Asp Gly Tyr Asn Val Tyr Arg Ser Glu Lys
            100                 105                 110

His Arg Leu Pro Val Ser Leu Ser Ser Ala Lys Gln Arg Gln Leu Tyr
        115                 120                 125

Lys Asn Arg Gly Phe Leu Pro Leu Ser His Phe Leu Pro Met Leu Pro
    130                 135                 140

Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
                165                 170                 175

Val Thr Gly Leu Glu Ala Val Arg Ser Pro Ser Phe Glu Lys Asp Tyr
            180                 185                 190

Lys Asp Asp Asp Asp Lys
        195

<210> SEQ ID NO 243
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

His Pro Ile Pro Asp Ser Ser Pro Leu Leu Gln Phe Gly Gly Gln Val
1               5                   10                  15

Arg Gln Arg Tyr Leu Tyr Thr Asp Asp Pro His Gly Leu Ser Ser Cys
            20                  25                  30

Phe Leu Arg Ile Arg Ala Asp Gly Val Val Asp Cys Ala Arg Gly Gln
        35                  40                  45

Ser Ala His Ser Leu Leu Glu Ile Lys Ala Val Ala Leu Arg Thr Val
    50                  55                  60

Ala Ile Lys Gly Val His Ser Val Arg Tyr Leu Cys Met Gly Ala Asp
65                  70                  75                  80
```

```
Gly Lys Met Gln Gly Leu Leu Gln Tyr Ser Glu Glu Asp Cys Ala Phe
                85                  90                  95

Glu Glu Glu Ile Arg Pro Asp Gly Tyr Asn Val Tyr Arg Ser Glu Lys
            100                 105                 110

His Arg Leu Pro Val Ser Leu Ser Ser Ala Lys Gln Arg Gln Leu Tyr
        115                 120                 125

Lys Asn Arg Gly Phe Leu Pro Leu Ser His Phe Leu Pro Met Leu Pro
    130                 135                 140

Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
                165                 170                 175

Val Thr Gly Leu Glu Ala Val Arg Ser Pro Ser Phe Glu Lys Asp Tyr
            180                 185                 190

Lys Asp Asp Asp Asp Lys
        195

<210> SEQ ID NO 244
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Leu Ser Ser Cys Phe
            20                  25                  30

Leu Arg Ile Arg Ala Asp Gly Val Val Asp Cys Ala Arg Gly Gln Ser
        35                  40                  45

Ala His Ser Leu Leu Glu Ile Lys Ala Val Ala Leu Arg Thr Val Ala
    50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
            100                 105                 110

Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met
    130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys Asp Tyr Lys
            180                 185                 190

Asp Asp Asp Asp Lys
        195

<210> SEQ ID NO 245
<211> LENGTH: 197
<212> TYPE: PRT
<213> ORGANISM: Artificial Sequence
<220> FEATURE:
```

-continued

<223> OTHER INFORMATION: Description of Artificial Sequence: Synthetic
      polypeptide

<400> SEQUENCE: 245

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Ser Cys Phe
            20                  25                  30

Leu Arg Ile Arg Ala Asp Gly Val Val Asp Cys Ala Arg Gly Gln Ser
        35                  40                  45

Ala His Ser Leu Leu Glu Ile Lys Ala Val Ala Leu Arg Thr Val Ala
    50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
            100                 105                 110

Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met
    130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys Asp Tyr Lys
            180                 185                 190

Asp Asp Asp Asp Lys
            195

<210> SEQ ID NO 246
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala Phe
            20                  25                  30

Leu Arg Ile Arg Ala Asp Gly Val Val Asp Cys Ala Arg Gly Gln Ser
        35                  40                  45

Ala His Ser Leu Leu Glu Ile Lys Ala Val Ala Leu Arg Thr Val Ala
    50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
            100                 105                 110

Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met

```
                130                 135                 140
Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys Asp Tyr Lys
                180                 185                 190

Asp Asp Asp Asp Lys
            195

<210> SEQ ID NO 247
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

His Pro Ile Pro Asp Ser Ser Pro Leu Leu Gln Phe Gly Gly Gln Val
1               5                   10                  15

Arg Gln Arg Tyr Leu Tyr Thr Asp Ala Gln Gln Thr Glu Ala His
                20                  25                  30

Leu Glu Ile Arg Ala Asp Gly Val Val Asp Cys Ala Arg Gly Gln Ser
                35                  40                  45

Ala His Ser Leu Leu Glu Ile Lys Ala Val Ala Leu Arg Thr Val Ala
            50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
                100                 105                 110

Arg Leu Pro Val Ser Leu Ser Ser Ala Lys Gln Arg Gln Leu Tyr Lys
            115                 120                 125

Asn Arg Gly Phe Leu Pro Leu Ser His Phe Leu Pro Met Leu Pro Met
        130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys Asp Tyr Lys
                180                 185                 190

Asp Asp Asp Asp Lys
            195

<210> SEQ ID NO 248
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

His Pro Ile Pro Asp Ser Ser Pro Leu Leu Gln Phe Gly Gly Gln Val
1               5                   10                  15

Arg Gln Arg Tyr Leu Tyr Thr Asp Ala Gln Gln Thr Glu Ala His
                20                  25                  30
```

Leu Glu Ile Arg Glu Asp Gly Val Val Asp Cys Ala Arg Gly Gln Ser
            35                  40                  45

Ala His Ser Leu Leu Glu Ile Lys Ala Val Ala Leu Arg Thr Val Ala
    50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
            100                 105                 110

Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met
    130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys Asp Tyr Lys
            180                 185                 190

Asp Asp Asp Asp Lys
        195

<210> SEQ ID NO 249
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

His Pro Ile Pro Asp Ser Ser Pro Leu Leu Gln Phe Gly Gly Gln Val
1               5                   10                  15

Arg Gln Arg Tyr Leu Tyr Thr Asp Ala Gln Thr Glu Ala His
        20                  25                  30

Leu Glu Ile Arg Glu Asp Gly Thr Val Gly Gly Ala Ala Asp Gln Ser
            35                  40                  45

Ala His Ser Leu Leu Glu Ile Lys Ala Val Ala Leu Arg Thr Val Ala
    50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
            100                 105                 110

Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met
    130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys Asp Tyr Lys
            180                 185                 190

Asp Asp Asp Asp Lys
        195

<210> SEQ ID NO 250
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Glu Ile Lys Ala Val Ala Leu Arg Thr Val Ala
    50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
            100                 105                 110

Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met
    130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys Asp Tyr Lys
            180                 185                 190

Asp Asp Asp Asp Lys
        195

<210> SEQ ID NO 251
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val His Ser Val Arg Tyr Leu Cys Met Gly Ala Asp Gly
65                  70                  75                  80

```
Lys Met Gln Gly Leu Leu Gln Tyr Ser Glu Glu Asp Cys Ala Phe Glu
                 85                  90                  95

Glu Glu Ile Arg Pro Asp Gly Tyr Asn Val Tyr Arg Ser Glu Lys His
                100                 105                 110

Arg Leu Pro Val Ser Leu Ser Ser Ala Lys Gln Arg Gln Leu Tyr Lys
                115                 120                 125

Asn Arg Gly Phe Leu Pro Leu Ser His Phe Leu Pro Met Leu Pro Met
            130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys Asp Tyr Lys
                180                 185                 190

Asp Asp Asp Asp Lys
            195
```

<210> SEQ ID NO 252
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
                35                  40                  45

Pro Glu Ser Leu Leu Gln Leu Lys Ala Leu Lys Pro Gly Val Ile Gln
            50                  55                  60

Ile Leu Gly Val Lys Thr Ser Arg Phe Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
                100                 105                 110

Arg Leu Pro Val Ser Leu Ser Ser Ala Lys Gln Arg Gln Leu Tyr Lys
                115                 120                 125

Asn Arg Gly Phe Leu Pro Leu Ser His Phe Leu Pro Met Leu Pro Met
            130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys Asp Tyr Lys
                180                 185                 190

Asp Asp Asp Asp Lys
            195
```

<210> SEQ ID NO 253
<211> LENGTH: 195
<212> TYPE: PRT
<213> ORGANISM: Artificial Sequence
<220> FEATURE:

-continued

<223> OTHER INFORMATION: Description of Artificial Sequence: Synthetic
      polypeptide

<400> SEQUENCE: 253

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Met Leu Pro Met Val Pro
    130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys Asp Tyr Lys Asp Asp
            180                 185                 190

Asp Asp Lys
        195

<210> SEQ ID NO 254
<211> LENGTH: 191
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Asp Ala Gln Gln Thr Glu
            20                  25                  30

Ala His Leu Glu Ile Arg Glu Asp Gly Thr Val Gly Gly Ala Ala Asp
        35                  40                  45

Gln Ser Pro Glu Ser Leu Leu Gln Leu Lys Ala Leu Lys Pro Gly Val
    50                  55                  60

Ile Gln Ile Leu Gly Val Lys Thr Ser Arg Phe Leu Cys Gln Arg Pro
65                  70                  75                  80

Asp Gly Ala Leu Tyr Gly Ser Leu His Phe Asp Pro Glu Ala Cys Ser
                85                  90                  95

Phe Arg Glu Leu Leu Leu Glu Asp Gly Tyr Asn Val Tyr Gln Ser Glu
            100                 105                 110

Ala His Gly Leu Pro Leu His Leu Pro Gly Asn Lys Ser Pro His Arg
        115                 120                 125

Asp Pro Ala Pro Arg Gly Pro Ala Arg Phe Leu Pro Leu Pro Gly Leu

```
                130                 135                 140
Pro Pro Ala Leu Pro Glu Pro Gly Ile Leu Ala Pro Gln Pro Pro
145                 150                 155                 160

Asp Val Gly Ser Ser Asp Pro Leu Ser Met Val Gly Pro Ser Gln Gly
                165                 170                 175

Arg Ser Pro Ser Tyr Ala Ser Asp Tyr Lys Asp Asp Asp Lys
                180                 185                 190
```

<210> SEQ ID NO 255
<211> LENGTH: 193
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 255

```
Arg Pro Leu Ala Phe Ser Asp Ala Gly Pro His Val His Tyr Gly Trp
1               5                   10                  15

Gly Asp Pro Ile Arg Leu Arg His Leu Tyr Thr Asp Ala Gln Gln
                20                  25                  30

Thr Glu Ala His Leu Glu Ile Arg Glu Asp Gly Thr Val Gly Gly Ala
        35                  40                  45

Ala Asp Gln Ser Pro Glu Ser Leu Leu Gln Leu Lys Ala Leu Lys Pro
50                  55                  60

Gly Val Ile Gln Ile Leu Gly Val Lys Thr Ser Arg Phe Leu Cys Gln
65                  70                  75                  80

Arg Pro Asp Gly Ala Leu Tyr Gly Ser Leu His Phe Asp Pro Glu Ala
                85                  90                  95

Cys Ser Phe Arg Glu Leu Leu Leu Glu Asp Gly Tyr Asn Val Tyr Gln
                100                 105                 110

Ser Glu Ala His Gly Leu Pro Leu His Leu Pro Gly Asn Lys Ser Pro
                115                 120                 125

His Arg Asp Pro Ala Pro Arg Gly Pro Ala Arg Phe Leu Pro Leu Pro
130                 135                 140

Gly Leu Pro Pro Ala Leu Pro Glu Pro Pro Gly Ile Leu Ala Pro Gln
145                 150                 155                 160

Pro Pro Asp Val Gly Ser Ser Asp Pro Leu Ser Met Val Gly Pro Ser
                165                 170                 175

Gln Gly Arg Ser Pro Ser Tyr Ala Ser Asp Tyr Lys Asp Asp Asp
                180                 185                 190

Lys
```

<210> SEQ ID NO 256
<211> LENGTH: 194
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 256

```
Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Glu Asp Gly Thr Val Gly Gly
        35                  40                  45
```

Ala Ala Asp Gln Ser Pro Glu Ser Leu Leu Gln Leu Lys Ala Leu Lys
    50                  55                  60

Pro Gly Val Ile Gln Ile Leu Gly Val Lys Thr Ser Arg Phe Leu Cys
65                  70                  75                  80

Gln Arg Pro Asp Gly Ala Leu Tyr Gly Ser Leu His Phe Asp Pro Glu
                85                  90                  95

Ala Cys Ser Phe Arg Glu Leu Leu Glu Asp Gly Tyr Asn Val Tyr
            100                 105                 110

Gln Ser Glu Ala His Gly Leu Pro Leu His Leu Pro Gly Asn Lys Ser
            115                 120                 125

Pro His Arg Asp Pro Ala Pro Arg Gly Pro Ala Arg Phe Leu Pro Leu
    130                 135                 140

Pro Gly Leu Pro Pro Ala Leu Pro Glu Pro Pro Gly Ile Leu Ala Pro
145                 150                 155                 160

Gln Pro Pro Asp Val Gly Ser Ser Asp Pro Leu Ser Met Val Gly Pro
                165                 170                 175

Ser Gln Gly Arg Ser Pro Ser Tyr Ala Ser Asp Tyr Lys Asp Asp Asp
            180                 185                 190

Asp Lys

<210> SEQ ID NO 257
<211> LENGTH: 194
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Thr Val Gly Gly
            35                  40                  45

Ala Ala Asp Gln Ser Pro Glu Ser Leu Leu Gln Leu Lys Ala Leu Lys
    50                  55                  60

Pro Gly Val Ile Gln Ile Leu Gly Val Lys Thr Ser Arg Phe Leu Cys
65                  70                  75                  80

Gln Arg Pro Asp Gly Ala Leu Tyr Gly Ser Leu His Phe Asp Pro Glu
                85                  90                  95

Ala Cys Ser Phe Arg Glu Leu Leu Glu Asp Gly Tyr Asn Val Tyr
            100                 105                 110

Gln Ser Glu Ala His Gly Leu Pro Leu His Leu Pro Gly Asn Lys Ser
            115                 120                 125

Pro His Arg Asp Pro Ala Pro Arg Gly Pro Ala Arg Phe Leu Pro Leu
    130                 135                 140

Pro Gly Leu Pro Pro Ala Leu Pro Glu Pro Pro Gly Ile Leu Ala Pro
145                 150                 155                 160

Gln Pro Pro Asp Val Gly Ser Ser Asp Pro Leu Ser Met Val Gly Pro
                165                 170                 175

Ser Gln Gly Arg Ser Pro Ser Tyr Ala Ser Asp Tyr Lys Asp Asp Asp
            180                 185                 190

Asp Lys

<210> SEQ ID NO 258

<211> LENGTH: 194
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Pro Glu Ser Leu Leu Gln Leu Lys Ala Leu Lys
    50                  55                  60

Pro Gly Val Ile Gln Ile Leu Gly Val Lys Thr Ser Arg Phe Leu Cys
65                  70                  75                  80

Gln Arg Pro Asp Gly Ala Leu Tyr Gly Ser Leu His Phe Asp Pro Glu
                85                  90                  95

Ala Cys Ser Phe Arg Glu Leu Leu Leu Glu Asp Gly Tyr Asn Val Tyr
            100                 105                 110

Gln Ser Glu Ala His Gly Leu Pro Leu His Leu Pro Gly Asn Lys Ser
        115                 120                 125

Pro His Arg Asp Pro Ala Pro Arg Gly Pro Ala Arg Phe Leu Pro Leu
130                 135                 140

Pro Gly Leu Pro Pro Ala Leu Pro Glu Pro Pro Gly Ile Leu Ala Pro
145                 150                 155                 160

Gln Pro Pro Asp Val Gly Ser Ser Asp Pro Leu Ser Met Val Gly Pro
                165                 170                 175

Ser Gln Gly Arg Ser Pro Ser Tyr Ala Ser Asp Tyr Lys Asp Asp Asp
            180                 185                 190

Asp Lys

<210> SEQ ID NO 259
<211> LENGTH: 194
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Gln Leu Lys Ala Leu Lys
    50                  55                  60

Pro Gly Val Ile Gln Ile Leu Gly Val Lys Thr Ser Arg Phe Leu Cys
65                  70                  75                  80

Gln Arg Pro Asp Gly Ala Leu Tyr Gly Ser Leu His Phe Asp Pro Glu
                85                  90                  95

Ala Cys Ser Phe Arg Glu Leu Leu Leu Glu Asp Gly Tyr Asn Val Tyr
            100                 105                 110

Gln Ser Glu Ala His Gly Leu Pro Leu His Leu Pro Gly Asn Lys Ser

-continued

```
                115                 120                 125
Pro His Arg Asp Pro Ala Pro Arg Gly Pro Ala Arg Phe Leu Pro Leu
        130                 135                 140

Pro Gly Leu Pro Pro Ala Leu Pro Glu Pro Pro Gly Ile Leu Ala Pro
145                 150                 155                 160

Gln Pro Pro Asp Val Gly Ser Ser Asp Pro Leu Ser Met Val Gly Pro
                165                 170                 175

Ser Gln Gly Arg Ser Pro Ser Tyr Ala Ser Asp Tyr Lys Asp Asp Asp
        180                 185                 190

Asp Lys

<210> SEQ ID NO 260
<211> LENGTH: 194
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val Lys Thr Ser Arg Phe Leu Cys
65                  70                  75                  80

Gln Arg Pro Asp Gly Ala Leu Tyr Gly Ser Leu His Phe Asp Pro Glu
                85                  90                  95

Ala Cys Ser Phe Arg Glu Leu Leu Glu Asp Gly Tyr Asn Val Tyr
                100                 105                 110

Gln Ser Glu Ala His Gly Leu Pro Leu His Leu Pro Gly Asn Lys Ser
        115                 120                 125

Pro His Arg Asp Pro Ala Pro Arg Gly Pro Ala Arg Phe Leu Pro Leu
    130                 135                 140

Pro Gly Leu Pro Pro Ala Leu Pro Glu Pro Pro Gly Ile Leu Ala Pro
145                 150                 155                 160

Gln Pro Pro Asp Val Gly Ser Ser Asp Pro Leu Ser Met Val Gly Pro
                165                 170                 175

Ser Gln Gly Arg Ser Pro Ser Tyr Ala Ser Asp Tyr Lys Asp Asp Asp
        180                 185                 190

Asp Lys

<210> SEQ ID NO 261
<211> LENGTH: 194
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
```

```
               20                  25                  30
Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
         50                  55                  60

Leu Arg Thr Val Ala Ile Lys Gly Val His Ser Val Arg Tyr Leu Cys
 65                  70                  75                  80

Gln Arg Pro Asp Gly Ala Leu Tyr Gly Ser Leu His Phe Asp Pro Glu
                 85                  90                  95

Ala Cys Ser Phe Arg Glu Leu Leu Glu Asp Gly Tyr Asn Val Tyr
                100                 105                 110

Gln Ser Glu Ala His Gly Leu Pro Leu His Leu Pro Gly Asn Lys Ser
            115                 120                 125

Pro His Arg Asp Pro Ala Pro Arg Gly Pro Ala Arg Phe Leu Pro Leu
        130                 135                 140

Pro Gly Leu Pro Pro Ala Leu Pro Glu Pro Pro Gly Ile Leu Ala Pro
145                 150                 155                 160

Gln Pro Pro Asp Val Gly Ser Ser Asp Pro Leu Ser Met Val Gly Pro
                165                 170                 175

Ser Gln Gly Arg Ser Pro Ser Tyr Ala Ser Asp Tyr Lys Asp Asp Asp
            180                 185                 190

Asp Lys

<210> SEQ ID NO 262
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Arg Pro Leu Ala Phe Ser Asp Ala Gly Pro His Val His Tyr Gly Trp
1               5                  10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
         50                  55                  60

Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                 85                  90                  95

Asp Cys Ala Phe Glu Glu Glu Ile Arg Pro Asp Gly Tyr Asn Val Tyr
                100                 105                 110

Arg Ser Glu Lys His Arg Leu Pro Val Ser Leu Ser Ser Ala Lys Gln
            115                 120                 125

Arg Gln Leu Tyr Lys Asn Arg Gly Phe Leu Pro Leu Ser His Phe Leu
        130                 135                 140

Pro Leu Pro Gly Leu Pro Pro Ala Leu Pro Glu Pro Pro Gly Ile Leu
145                 150                 155                 160

Ala Pro Gln Pro Pro Asp Val Gly Ser Ser Asp Pro Leu Ser Met Val
                165                 170                 175

Gly Pro Ser Gln Gly Arg Ser Pro Ser Tyr Ala Ser Asp Tyr Lys Asp
            180                 185                 190
```

Asp Asp Asp Lys
        195

<210> SEQ ID NO 263
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Arg Pro Leu Ala Phe Ser Asp Ala Gly Pro Leu Gln Phe Gly Gly
1               5                   10                  15

Gln Val Arg Gln Arg Tyr Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Leu Thr Asp Ser Met Asp Pro Phe
                165                 170                 175

Gly Leu Val Thr Gly Leu Glu Ala Val Arg Ser Pro Ser Phe Glu Lys
            180                 185                 190

Asp Tyr Lys Asp Asp Asp Asp Lys
        195                 200

<210> SEQ ID NO 264
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Arg Pro Leu Ala Phe Ser Asp Ala Gly Pro Leu Gln Phe Gly Gly
1               5                   10                  15

Gln Val Arg Gln Arg Tyr Leu Tyr Thr Asp Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
            85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Ser Met Asp Pro Phe
            165                 170                 175

Gly Leu Val Thr Gly Leu Glu Ala Val Arg Ser Pro Ser Phe Glu Lys
            180                 185                 190

Asp Tyr Lys Asp Asp Asp Asp Lys
        195                 200

<210> SEQ ID NO 265
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Asp Ala Gln Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
            85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Ser Met Asp Pro Phe
            165                 170                 175

Gly Leu Val Thr Gly Leu Glu Ala Val Arg Ser Pro Ser Phe Glu Lys
            180                 185                 190

Asp Tyr Lys Asp Asp Asp Asp Lys
        195                 200

<210> SEQ ID NO 266
<211> LENGTH: 199
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 266

Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Asp Ala Gln Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys Asp
            180                 185                 190

Tyr Lys Asp Asp Asp Asp Lys
        195

<210> SEQ ID NO 267
<211> LENGTH: 199
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Asp Ala Gln Gln Thr Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu

```
                130                 135                 140
Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys Asp
                180                 185                 190

Tyr Lys Asp Asp Asp Asp Lys
        195

<210> SEQ ID NO 268
<211> LENGTH: 199
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Asp Ala Gln Gln Thr Glu
                20                  25                  30

Ala Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
        50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
        130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys Asp
                180                 185                 190

Tyr Lys Asp Asp Asp Asp Lys
        195

<210> SEQ ID NO 269
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
                20                  25                  30
```

```
Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Leu Lys
 50                  55                  60

Pro Gly Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                 85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys Asp Tyr Lys Asp Asp Asp Lys
        195                 200

<210> SEQ ID NO 270
<211> LENGTH: 194
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Arg Pro Leu Ala Phe Ser Asp Ala Gly Pro His Val His Tyr Gly Trp
 1               5                  10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Leu Lys
 50                  55                  60

Pro Gly Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                 85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190
```

Glu Lys

<210> SEQ ID NO 271
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Leu Pro Gly Leu Pro Pro Ala Leu Pro Glu Pro Gly Ile Leu
145                 150                 155                 160

Ala Pro Gln Pro Pro Asp Val Gly Ser Ser Asp Pro Leu Ser Met Val
                165                 170                 175

Gly Pro Ser Gln Gly Arg Ser Pro Ser Tyr Ala Ser
            180                 185

<210> SEQ ID NO 272
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val Lys Thr Ser Arg Phe Leu Cys
65                  70                  75                  80

Gln Arg Pro Asp Gly Ala Leu Tyr Gly Ser Leu His Phe Asp Pro Glu
                85                  90                  95

Ala Cys Ser Phe Arg Glu Leu Leu Leu Glu Asp Gly Tyr Asn Val Tyr

```
                    100                 105                 110
Gln Ser Glu Ala His Gly Leu Pro Leu His Leu Pro Gly Asn Lys Ser
        115                 120                 125
Pro His Arg Asp Pro Ala Pro Arg Gly Pro Ala Arg Phe Leu Pro Leu
    130                 135                 140
Pro Gly Leu Pro Pro Ala Leu Pro Glu Pro Pro Gly Ile Leu Ala Pro
145                 150                 155                 160
Gln Pro Pro Asp Val Gly Ser Ser Asp Pro Leu Ser Met Val Gly Pro
                165                 170                 175
Ser Gln Gly Arg Ser Pro Ser Tyr Ala Ser
            180                 185

<210> SEQ ID NO 273
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Arg Pro Leu Ala Phe Ser Asp Ala Gly Pro His Val His Tyr Gly Trp
1               5                   10                  15
Gly Asp Pro Ile Arg Leu Arg His Leu Tyr Thr Ser Gly Pro His Gly
            20                  25                  30
Leu Ser Ser Cys Phe Leu Arg Ile Arg Ala Asp Gly Val Val Asp Cys
        35                  40                  45
Ala Arg Gly Gln Ser Ala His Ser Leu Leu Gln Leu Lys Ala Leu Lys
    50                  55                  60
Pro Gly Val Ile Gln Ile Leu Gly Val Lys Thr Ser Arg Phe Leu Cys
65                  70                  75                  80
Gln Arg Pro Asp Gly Ala Leu Tyr Gly Ser Leu His Phe Asp Pro Glu
                85                  90                  95
Ala Cys Ser Phe Arg Glu Leu Leu Leu Glu Asp Gly Tyr Asn Val Tyr
            100                 105                 110
Gln Ser Glu Ala His Gly Leu Pro Leu His Leu Pro Gly Asn Lys Ser
        115                 120                 125
Pro His Arg Asp Pro Ala Pro Arg Gly Pro Ala Arg Phe Leu Pro Leu
    130                 135                 140
Pro Gly Leu Pro Pro Ala Leu Pro Glu Pro Pro Gly Ile Leu Ala Pro
145                 150                 155                 160
Gln Pro Pro Asp Val Gly Ser Ser Asp Pro Leu Ser Met Val Gly Pro
                165                 170                 175
Ser Gln Gly Arg Ser Pro Ser Tyr Ala Ser
            180                 185

<210> SEQ ID NO 274
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Arg Pro Leu Ala Phe Ser Asp Ala Gly Pro His Val His Tyr Gly Trp
1               5                   10                  15
Gly Asp Pro Ile Arg Leu Arg His Leu Tyr Thr Ser Gly Pro His Gly
            20                  25                  30
```

```
Leu Ser Ser Cys Phe Leu Arg Ile Arg Ala Asp Gly Val Val Asp Cys
            35                  40                  45

Ala Arg Gly Gln Ser Pro Glu Ser Leu Leu Gln Leu Lys Ala Leu Lys
 50                  55                  60

Pro Gly Val Ile Gln Ile Leu Gly Val Lys Thr Ser Arg Phe Leu Cys
 65                  70                  75                  80

Gln Arg Pro Asp Gly Ala Leu Tyr Gly Ser Leu His Phe Asp Pro Glu
                85                  90                  95

Ala Cys Ser Phe Arg Glu Leu Leu Glu Asp Gly Tyr Asn Val Tyr
                100                 105                 110

Gln Ser Glu Ala His Gly Leu Pro Leu His Leu Pro Gly Asn Lys Ser
                115                 120                 125

Pro His Arg Asp Pro Ala Pro Arg Gly Pro Ala Arg Phe Leu Pro Leu
                130                 135                 140

Pro Gly Leu Pro Pro Ala Leu Pro Glu Pro Pro Gly Ile Leu Ala Pro
145                 150                 155                 160

Gln Pro Pro Asp Val Gly Ser Ser Asp Pro Leu Ser Met Val Gly Pro
                165                 170                 175

Ser Gln Gly Arg Ser Pro Ser Tyr Ala Ser
                180                 185

<210> SEQ ID NO 275
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Arg Pro Leu Ala Phe Ser Asp Ala Gly Pro His Val His Tyr Gly Trp
  1               5                  10                  15

Gly Asp Pro Ile Arg Leu Arg His Leu Tyr Thr Ser Gly Pro His Gly
                 20                  25                  30

Leu Ser Ser Cys Phe Leu Arg Ile Arg Ala Asp Gly Thr Val Gly Gly
            35                  40                  45

Ala Ala Asp Gln Ser Pro Glu Ser Leu Leu Gln Leu Lys Ala Leu Lys
 50                  55                  60

Pro Gly Val Ile Gln Ile Leu Gly Val Lys Thr Ser Arg Phe Leu Cys
 65                  70                  75                  80

Gln Arg Pro Asp Gly Ala Leu Tyr Gly Ser Leu His Phe Asp Pro Glu
                85                  90                  95

Ala Cys Ser Phe Arg Glu Leu Leu Leu Glu Asp Gly Tyr Asn Val Tyr
                100                 105                 110

Gln Ser Glu Ala His Gly Leu Pro Leu His Leu Pro Gly Asn Lys Ser
                115                 120                 125

Pro His Arg Asp Pro Ala Pro Arg Gly Pro Ala Arg Phe Leu Pro Leu
                130                 135                 140

Pro Gly Leu Pro Pro Ala Leu Pro Glu Pro Pro Gly Ile Leu Ala Pro
145                 150                 155                 160

Gln Pro Pro Asp Val Gly Ser Ser Asp Pro Leu Ser Met Val Gly Pro
                165                 170                 175

Ser Gln Gly Arg Ser Pro Ser Tyr Ala Ser
                180                 185

<210> SEQ ID NO 276
```

```
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Glu Asp Gly Thr Val Gly Gly
            35                  40                  45

Ala Ala Asp Gln Ser Pro Glu Ser Leu Leu Gln Leu Lys Ala Leu Lys
    50                  55                  60

Pro Gly Val Ile Gln Ile Leu Gly Val Lys Thr Ser Arg Phe Leu Cys
65                  70                  75                  80

Gln Arg Pro Asp Gly Ala Leu Tyr Gly Ser Leu His Phe Asp Pro Glu
                85                  90                  95

Ala Cys Ser Phe Arg Glu Leu Leu Leu Glu Asp Gly Tyr Asn Val Tyr
            100                 105                 110

Gln Ser Glu Ala His Gly Leu Pro Leu His Leu Pro Gly Asn Lys Ser
        115                 120                 125

Pro His Arg Asp Pro Ala Pro Arg Gly Pro Ala Arg Phe Leu Pro Leu
    130                 135                 140

Pro Gly Leu Pro Pro Ala Leu Pro Glu Pro Pro Gly Ile Leu Ala Pro
145                 150                 155                 160

Gln Pro Pro Asp Val Gly Ser Ser Asp Pro Leu Ser Met Val Gly Pro
                165                 170                 175

Ser Gln Gly Arg Ser Pro Ser Tyr Ala Ser
            180                 185

<210> SEQ ID NO 277
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Arg Pro Leu Ala Phe Ser Asp Ala Gly Pro His Val His Tyr Gly Trp
1               5                   10                  15

Gly Asp Pro Ile Arg Leu Arg His Leu Tyr Thr Asp Ala Gln Gln
                20                  25                  30

Thr Glu Ala His Leu Glu Ile Arg Glu Asp Gly Thr Val Gly Gly Ala
        35                  40                  45

Ala Asp Gln Ser Pro Glu Ser Leu Leu Gln Leu Lys Ala Leu Lys Pro
    50                  55                  60

Gly Val Ile Gln Ile Leu Gly Val Lys Thr Ser Arg Phe Leu Cys Gln
65                  70                  75                  80

Arg Pro Asp Gly Ala Leu Tyr Gly Ser Leu His Phe Asp Pro Glu Ala
                85                  90                  95

Cys Ser Phe Arg Glu Leu Leu Leu Glu Asp Gly Tyr Asn Val Tyr Gln
            100                 105                 110

Ser Glu Ala His Gly Leu Pro Leu His Leu Pro Gly Asn Lys Ser Pro
        115                 120                 125
```

His Arg Asp Pro Ala Pro Arg Gly Pro Ala Arg Phe Leu Pro Leu Pro
            130                 135                 140

Gly Leu Pro Pro Ala Leu Pro Glu Pro Pro Gly Ile Leu Ala Pro Gln
145                 150                 155                 160

Pro Pro Asp Val Gly Ser Ser Asp Pro Leu Ser Met Val Gly Pro Ser
                165                 170                 175

Gln Gly Arg Ser Pro Ser Tyr Ala Ser
            180                 185

<210> SEQ ID NO 278
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Asp Ala Gln Gln Thr Glu
            20                  25                  30

Ala His Leu Glu Ile Arg Glu Asp Gly Thr Val Gly Gly Ala Ala Asp
        35                  40                  45

Gln Ser Pro Glu Ser Leu Leu Gln Leu Lys Ala Leu Lys Pro Gly Val
    50                  55                  60

Ile Gln Ile Leu Gly Val Lys Thr Ser Arg Phe Leu Cys Gln Arg Pro
65                  70                  75                  80

Asp Gly Ala Leu Tyr Gly Ser Leu His Phe Asp Pro Glu Ala Cys Ser
                85                  90                  95

Phe Arg Glu Leu Leu Leu Glu Asp Gly Tyr Asn Val Tyr Gln Ser Glu
            100                 105                 110

Ala His Gly Leu Pro Leu His Leu Pro Gly Asn Lys Ser Pro His Arg
        115                 120                 125

Asp Pro Ala Pro Arg Gly Pro Ala Arg Phe Leu Pro Leu Pro Gly Leu
    130                 135                 140

Pro Pro Ala Leu Pro Glu Pro Pro Gly Ile Leu Ala Pro Gln Pro Pro
145                 150                 155                 160

Asp Val Gly Ser Ser Asp Pro Leu Ser Met Val Gly Pro Ser Gln Gly
                165                 170                 175

Arg Ser Pro Ser Tyr Ala Ser
            180

<210> SEQ ID NO 279
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Asp Tyr Lys Asp Asp Asp Asp Lys
1               5

<210> SEQ ID NO 280
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 280

Asp Tyr Lys Asp Asp Asp Lys
1               5

<210> SEQ ID NO 281
<211> LENGTH: 681
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 281

| | | | | | |
|---|---|---|---|---|---|
| atggactcgg | acgagaccgg | gttcgagcac | tcagggctgt | gggtttctgt | gctggctggt | 60 |
| cttctgctgg | gagcctgcca | ggcacacccc | atccctgact | ccagtcctct | cctgcaattc | 120 |
| gggggccaag | tccggcagcg | gtacctctac | acctccggcc | ccacgggct | ctccagctgc | 180 |
| ttcctgcgca | tccgtgccga | cggcgtcgtg | gactgcgcgc | ggggccagag | cgcgcacagt | 240 |
| ttgctggaga | tcaaggcagt | cgctctgcgg | accgtggcca | tcaagggcgt | gcacagcgtg | 300 |
| cggtacctct | gcatgggcgc | cgacggcaag | atgcaggggc | tgcttcagta | ctcggaggaa | 360 |
| gactgtgctt | cgaggagga | gatccgccca | gatggctaca | atgtgtaccg | atccgagaag | 420 |
| caccgcctcc | cggtctccct | gagcagtgcc | aaacagcggc | agctgtacaa | gaacagaggc | 480 |
| tttcttccac | tctctcattt | cctgcccatg | ctgcccatgg | tcccagagga | gcctgaggac | 540 |
| ctcaggggcc | acttggaatc | tgacatgttc | tcttcgcccc | tggagaccga | cagcatggac | 600 |
| ccatttgggc | ttgtcaccgg | actggaggcc | gtgaggagtc | ccagctttga | gaaggactac | 660 |
| aaagacgatg | acgacaagtg | a | | | | 681 |

<210> SEQ ID NO 282
<211> LENGTH: 28
<212> TYPE: PRT
<213> ORGANISM: Homo sapiens

<400> SEQUENCE: 282

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala
            20                  25

<210> SEQ ID NO 283
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 283

| | | | | | |
|---|---|---|---|---|---|
| atgcggagcg | ggtgtgtggt | ggtccacgta | tggatcctgg | ccggcctctg | gctggccgtg | 60 |
| gccgggcgcc | ccctcgcctt | ctcggacgcg | gggcccacg | tgcactacgg | ctggggcgac | 120 |
| cccatccgcc | tgcggcacct | gtacacagat | gatgcccagc | agacagaagc | ccacctggag | 180 |
| atcagggagg | atgggacggt | gggggggcgct | gctgaccaga | gccccgaaag | tctcctgcag | 240 |
| ctgaaagcct | tgaagccggg | agttattcaa | atcttgggag | tcaagacatc | caggttcctg | 300 |
| tgccagcggc | cagatggggc | cctgtatgga | tcgctccact | tgaccctga | ggcctgcagc | 360 |
| ttccgggagc | tgcttcttga | ggacggatac | aatgtttacc | agtccgaagc | ccacggcctc | 420 |

| | |
|---|---|
| ccgctgcacc tgccagggaa caagtcccca caccgggacc ctgcacccg aggaccagct | 480 |
| cgcttcctgc cactaccagg cctgccccc gcactcccgg agccaccgg aatcctggcc | 540 |
| ccccagcccc ccgatgtggg ctcctcggac cctctgagca tggtgggacc ttcccagggc | 600 |
| cgaagcccca gctacgcttc cgactacaag gacgacgatg acaagtga | 648 |

<210> SEQ ID NO 284
<211> LENGTH: 22
<212> TYPE: PRT
<213> ORGANISM: Homo sapiens

<400> SEQUENCE: 284

Met Arg Ser Gly Cys Val Val His Val Trp Ile Leu Ala Gly Leu
1               5                   10                  15

Trp Leu Ala Val Ala Gly
            20

<210> SEQ ID NO 285
<211> LENGTH: 690
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 285

| | |
|---|---|
| atggactcgg acgagaccgg gttcgagcac tcagggctgt gggtttctgt gctggctggt | 60 |
| cttctgctgg gagcctgcca ggcacacccc atccctgact ccagtcctct cctgcaattc | 120 |
| gggggccaag tccggcagcg gtacctctac acagatgatg cccagcagac agaagcccac | 180 |
| ctggagatca ggaggatgg gacggtgggg ggcgctgctg accagagccc cgaaagtctc | 240 |
| ctgcagctga aagccttgaa gccgggagtt attcaaatct gggagtcaa gacatccagg | 300 |
| ttcctgtgcc agcggccaga tggggccctg tatggatcgc tccactttga ccctgaggcc | 360 |
| tgcagcttcc gggagctgct tcttgaggac ggatacaatg tttaccagtc gaagcccac | 420 |
| ggcctcccgc tgcacctgcc agggaacaag tccccacacc gggaccctgc accccgagga | 480 |
| ccagctcgct tccttccact ctctcatttc ctgcccatgc tgcccatggt cccagaggag | 540 |
| cctgaggacc tcaggggcca cttggaatct gacatgttct cttcgcccct ggagaccgac | 600 |
| agcatggacc catttgggct tgtcaccgga ctggaggccg tgaggagtcc agctttgag | 660 |
| aaggactaca agacgatga cgacaagtga | 690 |

<210> SEQ ID NO 286
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Gly Gly Gly Gly Ser Gly Gly Gly Gly Ser Asp Tyr Lys Asp Asp
1               5                   10                  15

Asp Lys Gly Arg Ala Gln Val Thr
            20

<210> SEQ ID NO 287
<211> LENGTH: 5
<212> TYPE: PRT
<213> ORGANISM: Homo sapiens

<400> SEQUENCE: 287

Trp Gly Asp Pro Ile
1               5

<210> SEQ ID NO 288
<211> LENGTH: 8
<212> TYPE: PRT
<213> ORGANISM: Homo sapiens

<400> SEQUENCE: 288

Ser Gly Pro His Gly Leu Ser Ser
1               5

<210> SEQ ID NO 289
<211> LENGTH: 7
<212> TYPE: PRT
<213> ORGANISM: Homo sapiens

<400> SEQUENCE: 289

Asp Asp Ala Gln Gln Thr Glu
1               5

<210> SEQ ID NO 290
<211> LENGTH: 17
<212> TYPE: PRT
<213> ORGANISM: Homo sapiens

<400> SEQUENCE: 290

Ser Ser Ala Lys Gln Arg Gln Leu Tyr Lys Asn Arg Gly Phe Leu Pro
1               5                   10                  15

Leu

<210> SEQ ID NO 291
<211> LENGTH: 15
<212> TYPE: PRT
<213> ORGANISM: Homo sapiens

<400> SEQUENCE: 291

Pro Gly Asn Lys Ser Pro His Arg Asp Pro Ala Pro Arg Gly Pro
1               5                   10                  15

<210> SEQ ID NO 292
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(30)
<223> OTHER INFORMATION: This sequence may encompass 1 to 30 repeating
      "Gly" residues

<400> SEQUENCE: 292

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly
            20                  25                  30

<210> SEQ ID NO 293
<211> LENGTH: 24
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: misc_feature
<222> LOCATION: (1)..(24)
<223> OTHER INFORMATION: This sequence may encompass 1 to 6 'Gly Gly
      Gly Ser' repeating units

<400> SEQUENCE: 293

Gly Gly Gly Ser Gly Gly Gly Ser Gly Gly Gly Ser Gly Gly Gly Ser
1               5                   10                  15

Gly Gly Gly Ser Gly Gly Gly Ser
            20

<210> SEQ ID NO 294
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(30)
<223> OTHER INFORMATION: This sequence may encompass 1 to 6 'Gly Gly Gly
      Gly Ser' repeating units

<400> SEQUENCE: 294

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 295
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Leu Glu Asp Tyr Lys Asp Asp Asp Asp Lys
1               5                   10

<210> SEQ ID NO 296
<211> LENGTH: 39
<212> TYPE: PRT
<213> ORGANISM: Homo sapiens

<400> SEQUENCE: 296

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly
        35

<210> SEQ ID NO 297
<211> LENGTH: 44
<212> TYPE: PRT
<213> ORGANISM: Homo sapiens

<400> SEQUENCE: 297

Arg Pro Leu Ala Phe Ser Asp Ala Gly Pro His Val His Tyr Gly Trp
1               5                   10                  15
```

-continued

```
Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly
        35                  40

<210> SEQ ID NO 298
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

His Pro Ile Pro Asp Ser Ser Pro His Val His Tyr Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly
        35                  40

<210> SEQ ID NO 299
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

His Pro Ile Pro Asp Ser Ser Pro Leu Leu Gln Phe Gly Gly Gln Val
1               5                   10                  15

Arg Gln Arg Tyr Leu Tyr Thr Ser Gly Pro His Gly Leu Ser Ser Cys
            20                  25                  30

Phe Leu Arg Ile Arg Ala Asp Gly
        35                  40

<210> SEQ ID NO 300
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

His Pro Ile Pro Asp Ser Ser Pro Leu Leu Gln Phe Gly Gly Gln Val
1               5                   10                  15

Arg Gln Arg Tyr Leu Tyr Thr Asp Asp Pro His Gly Leu Ser Ser Cys
            20                  25                  30

Phe Leu Arg Ile Arg Ala Asp Gly
        35                  40

<210> SEQ ID NO 301
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

His Pro Ile Pro Asp Ser Ser Pro Leu Leu Gln Phe Gly Gly Gln Val
1               5                   10                  15
```

Arg Gln Arg Tyr Leu Tyr Thr Asp Asp Ala Gln Leu Ser Ser Cys Phe
            20                  25                  30

Leu Arg Ile Arg Ala Asp Gly
        35

<210> SEQ ID NO 302
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

His Pro Ile Pro Asp Ser Ser Pro Leu Leu Gln Phe Gly Gly Gln Val
1               5                   10                  15

Arg Gln Arg Tyr Leu Tyr Thr Asp Ala Gln Gln Thr Ser Cys Phe
            20                  25                  30

Leu Arg Ile Arg Ala Asp Gly
        35

<210> SEQ ID NO 303
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

His Pro Ile Pro Asp Ser Ser Pro Leu Leu Gln Phe Gly Gly Gln Val
1               5                   10                  15

Arg Gln Arg Tyr Leu Tyr Thr Asp Ala Gln Thr Glu Ala Phe
            20                  25                  30

Leu Arg Ile Arg Ala Asp Gly
        35

<210> SEQ ID NO 304
<211> LENGTH: 39
<212> TYPE: PRT
<213> ORGANISM: Homo sapiens

<400> SEQUENCE: 304

His Pro Ile Pro Asp Ser Ser Pro Leu Leu Gln Phe Gly Gly Gln Val
1               5                   10                  15

Arg Gln Arg Tyr Leu Tyr Thr Asp Ala Gln Thr Glu Ala His
            20                  25                  30

Leu Glu Ile Arg Glu Asp Gly
        35

<210> SEQ ID NO 305
<211> LENGTH: 44
<212> TYPE: PRT
<213> ORGANISM: Homo sapiens

<400> SEQUENCE: 305

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly
        35                  40

-continued

<210> SEQ ID NO 306
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

His Pro Ile Pro Asp Ser Ser Pro Leu Leu Gln Phe Gly Gly Gln Val
1               5                   10                  15

Arg Gln Arg Tyr Leu Tyr Thr Ser Gly Pro His Gly Leu Ser Ser Cys
            20                  25                  30

Phe Leu Arg Ile Arg Ala Asp Gly
        35                  40

<210> SEQ ID NO 307
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

His Pro Ile Pro Asp Ser Ser Pro Leu Leu Gln Phe Gly Gly Gln Val
1               5                   10                  15

Arg Gln Arg Tyr Leu Tyr Thr Asp Asp Pro His Gly Leu Ser Ser Cys
            20                  25                  30

Phe Leu Arg Ile Arg Ala Asp Gly
        35                  40

<210> SEQ ID NO 308
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Leu Ser Ser Cys Phe
            20                  25                  30

Leu Arg Ile Arg Ala Asp Gly
        35

<210> SEQ ID NO 309
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Ser Cys Phe
            20                  25                  30

Leu Arg Ile Arg Ala Asp Gly
        35

```
<210> SEQ ID NO 310
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala Phe
            20                  25                  30

Leu Arg Ile Arg Ala Asp Gly
        35

<210> SEQ ID NO 311
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Arg Pro Leu Ala Phe Ser Asp Ala Gly Pro Leu Leu Gln Phe Gly Gly
1               5                   10                  15

Gln Val Arg Gln Arg Tyr Leu Tyr Thr Ser Gly Pro His Gly Leu Ser
            20                  25                  30

Ser Cys Phe Leu Arg Ile Arg Ala Asp Gly
        35                  40

<210> SEQ ID NO 312
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Pro His Gly Leu Ser
            20                  25                  30

Ser Cys Phe Leu Arg Ile Arg Ala Asp Gly
        35                  40

<210> SEQ ID NO 313
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Asp Ala Gln Gly Leu Ser
            20                  25                  30

Ser Cys Phe Leu Arg Ile Arg Ala Asp Gly
        35                  40
```

```
<210> SEQ ID NO 314
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Asp Ala Gln Leu Ser Ser
            20                  25                  30

Cys Phe Leu Arg Ile Arg Ala Asp Gly
        35                  40

<210> SEQ ID NO 315
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Asp Ala Gln Gln Thr Ser
            20                  25                  30

Cys Phe Leu Arg Ile Arg Ala Asp Gly
        35                  40

<210> SEQ ID NO 316
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Asp Ala Gln Gln Thr Glu
            20                  25                  30

Ala Phe Leu Arg Ile Arg Ala Asp Gly
        35                  40

<210> SEQ ID NO 317
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Arg Pro Leu Ala Phe Ser Asp Ala Gly Pro Leu Leu Gln Phe Gly Gly
1               5                   10                  15

Gln Val Arg Gln Arg Tyr Leu Tyr Thr Asp Asp Ala Gln Gln Thr Glu
            20                  25                  30

Ala His Leu Glu Ile Arg Glu Asp Gly
        35                  40
```